US011173190B2

(12) United States Patent
Heartlein et al.

(10) Patent No.: US 11,173,190 B2
(45) **Date of Patent: *Nov. 16, 2021**

(54) TREATMENT OF CYSTIC FIBROSIS BY DELIVERY OF CODON-OPTIMIZED MRNA ENCODING CFTR

(71) Applicant: Translate Bio, Inc., Lexington, MA (US)

(72) Inventors: Michael Heartlein, Lexington, MA (US); Frank DeRosa, Lexington, MA (US); Alan Kimura, Lexington, MA (US); Jonathan Abysalh, Lexington, MA (US); Anusha Dias, Lexington, MA (US); Shrirang Karve, Lexington, MA (US); Zarna Patel, Lexington, MA (US)

(73) Assignee: TRANSLATE BIO, INC., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/981,757

(22) Filed: May 16, 2018

(65) Prior Publication Data

US 2018/0333457 A1 Nov. 22, 2018

Related U.S. Application Data

(60) Provisional application No. 62/507,061, filed on May 16, 2017, provisional application No. 62/532,301, filed on Jul. 13, 2017, provisional application No. 62/580,782, filed on Nov. 2, 2017, provisional application No. 62/592,238, filed on Nov. 29, 2017, provisional application No. 62/659,053, filed on Apr. 17, 2018.

(51) Int. Cl.

| | |
|---|---|
| ***A61K 48/00*** | (2006.01) |
| ***A61K 38/17*** | (2006.01) |
| ***A61P 11/12*** | (2006.01) |
| ***A61K 9/127*** | (2006.01) |
| ***A61K 9/00*** | (2006.01) |
| *C12N 15/88* | (2006.01) |

(52) U.S. Cl.

CPC ........ *A61K 38/1709* (2013.01); *A61K 9/0078* (2013.01); *A61K 9/127* (2013.01); *A61K 48/0075* (2013.01); *A61P 11/12* (2018.01); *C12N 15/88* (2013.01)

(58) Field of Classification Search

CPC ............ A61K 38/1709; A61K 48/0075; A61K 9/127; A61K 9/0078; A61P 11/12; C12N 15/88

See application file for complete search history.

(56) References Cited

U.S. PATENT DOCUMENTS

| | | | |
|---|---|---|---|
| 2,647,121 | A | 7/1953 | Jacoby |
| 2,717,909 | A | 9/1955 | Kosmin |
| 2,819,718 | A | 1/1958 | Goldman |
| 2,844,629 | A | 7/1958 | William et al. |
| 3,096,560 | A | 7/1963 | Liebig |
| 3,535,289 | A | 10/1970 | Yoshihara et al. |
| 3,614,954 | A | 10/1971 | Mirowski et al. |
| 3,614,955 | A | 10/1971 | Mirowski |
| 3,656,185 | A | 4/1972 | Carpentier |
| 3,805,301 | A | 4/1974 | Liebig |
| 3,945,052 | A | 3/1976 | Liebig |
| 3,995,623 | A | 12/1976 | Blake et al. |
| 4,013,507 | A | 3/1977 | Rembaum |
| 4,072,146 | A | 2/1978 | Howes |
| 4,096,860 | A | 6/1978 | McLaughlin |
| 4,099,528 | A | 7/1978 | Sorenson et al. |
| 4,106,129 | A | 8/1978 | Carpentier et al. |
| 4,134,402 | A | 1/1979 | Mahurkar |
| 4,140,126 | A | 2/1979 | Choudhury |
| 4,180,068 | A | 12/1979 | Jacobsen et al. |
| 4,182,833 | A | 1/1980 | Hicks |
| 4,227,533 | A | 10/1980 | Godfrey |
| 4,284,459 | A | 8/1981 | Patel et al. |
| 4,308,085 | A | 12/1981 | Horhold et al. |
| 4,323,525 | A | 4/1982 | Bornat |
| 4,335,723 | A | 6/1982 | Patel |

(Continued)

FOREIGN PATENT DOCUMENTS

| | | | |
|---|---|---|---|
| CA | 2518132 | A1 | 3/2006 |
| CA | 2807552 | A1 | 2/2012 |

(Continued)

OTHER PUBLICATIONS

McLachlan et al., "Pre-clinical evaluation of three non-viral gene transfer agents for cystic fibrosis after aerosol delivery to the ovine lung", Gene Ther., 18(10): 996-1005 (2011).
Robinson et al., "Lipid Nanoparticle-Delivered Chemically Modified mRNA Restores Chloride Secretion in Cystic Fibrosis", Molecular Therapy, 26(8): 1-13 (2018).
Ruiz et al., "A clinical inflammatory syndrome attributable to aerosolized lipid-DNA administration in cystic fibrosis", Hum Gene Ther., 12(7): 751-61 (2001).
U.S. Appl. No. 60/083,294, filed Apr. 28, 1998, Chen et al.
U.S. Appl. No. 61/494,714, filed Jun. 8, 2011, Guild.

(Continued)

*Primary Examiner* — J. E. Angell
(74) *Attorney, Agent, or Firm* — Proskauer Rose LLP; Fangli Chen

(57) ABSTRACT

The present invention provides, among other things, methods of treating cystic fibrosis, comprising a step of administering to a subject in need of treatment a composition comprising an mRNA encoding a Cystic Fibrosis Transmembrane Conductance Regulator (CFTR) protein, wherein the mRNA encoding the CFTR protein comprises a polynucleotide sequence at least 80% identical to SEQ ID NO: 1, wherein the mRNA is at a concentration of at least 0.4 mg/mL, and wherein the step of administering comprises inhalation.

17 Claims, 16 Drawing Sheets

Specification includes a Sequence Listing.

(56) References Cited

U.S. PATENT DOCUMENTS

| | | | |
|---|---|---|---|
| 4,339,369 | A | 7/1982 | Hicks et al. |
| 4,355,426 | A | 10/1982 | MacGregor |
| 4,375,817 | A | 3/1983 | Engle et al. |
| 4,385,631 | A | 5/1983 | Uthmann |
| 4,401,472 | A | 8/1983 | Gerber |
| 4,406,656 | A | 9/1983 | Hattler et al. |
| 4,475,972 | A | 10/1984 | Wong |
| 4,530,113 | A | 7/1985 | Matterson |
| 4,550,447 | A | 11/1985 | Seiler, Jr. et al. |
| 4,562,596 | A | 1/1986 | Kornberg |
| 4,568,329 | A | 2/1986 | Mahurkar |
| 4,571,241 | A | 2/1986 | Christopher |
| 4,601,718 | A | 7/1986 | Possis et al. |
| 4,647,416 | A | 3/1987 | Seiler, Jr. et al. |
| 4,662,382 | A | 5/1987 | Sluetz et al. |
| 4,701,162 | A | 10/1987 | Rosenberg |
| 4,710,169 | A | 12/1987 | Christopher |
| 4,720,517 | A | 1/1988 | Ravichandran et al. |
| 4,737,323 | A | 4/1988 | Martin et al. |
| 4,762,915 | A | 8/1988 | Kung et al. |
| 4,782,836 | A | 11/1988 | Alt |
| 4,856,521 | A | 8/1989 | Irnich |
| 4,860,751 | A | 8/1989 | Callaghan |
| 4,878,908 | A | 11/1989 | Martin et al. |
| 4,892,540 | A | 1/1990 | Vallana |
| 4,897,355 | A | 1/1990 | Eppstein et al. |
| 4,920,016 | A | 4/1990 | Allen et al. |
| 4,946,683 | A | 8/1990 | Forssen |
| 4,946,857 | A | 8/1990 | Kanehira et al. |
| 4,960,409 | A | 10/1990 | Catalano |
| 4,966,945 | A | 10/1990 | Drawert et al. |
| 5,024,671 | A | 6/1991 | Tu et al. |
| 5,025,005 | A | 6/1991 | Nomura et al. |
| 5,047,540 | A | 9/1991 | Kamata et al. |
| 5,101,824 | A | 4/1992 | Lekholm |
| 5,104,399 | A | 4/1992 | Lazarus |
| 5,116,360 | A | 5/1992 | Pinchuk et al. |
| 5,138,067 | A | 8/1992 | Kamata et al. |
| 5,151,105 | A | 9/1992 | Kwan-Gett |
| 5,171,678 | A | 12/1992 | Behr et al. |
| 5,176,661 | A | 1/1993 | Evard et al. |
| 5,194,654 | A | 3/1993 | Hostetler et al. |
| 5,200,395 | A | 4/1993 | Eto et al. |
| 5,223,263 | A | 6/1993 | Hostetler et al. |
| 5,261,419 | A | 11/1993 | Osypka |
| 5,264,618 | A | 11/1993 | Felgner et al. |
| 5,279,833 | A | 1/1994 | Rose |
| 5,282,824 | A | 2/1994 | Gianturco |
| 5,284,491 | A | 2/1994 | Sutton et al. |
| 5,300,022 | A | 4/1994 | Klapper et al. |
| 5,314,430 | A | 5/1994 | Bardy |
| 5,330,768 | A | 7/1994 | Park et al. |
| 5,334,761 | A | 8/1994 | Gebeyehu et al. |
| 5,395,619 | A | 3/1995 | Zalipsky et al. |
| 5,405,363 | A | 4/1995 | Kroll et al. |
| 5,405,379 | A | 4/1995 | Lane |
| 5,455,352 | A | 10/1995 | Huellmann et al. |
| 5,464,924 | A | 11/1995 | Silvis et al. |
| 5,503,852 | A | 4/1996 | Steiner et al. |
| 5,528,023 | A | 6/1996 | Butturini et al. |
| 5,552,155 | A | 9/1996 | Bailey et al. |
| 5,595,756 | A | 1/1997 | Bally et al. |
| 5,607,385 | A | 3/1997 | Francischelli et al. |
| 5,609,624 | A | 3/1997 | Kalis |
| 5,610,283 | A | 3/1997 | Buechler |
| 5,614,548 | A | 3/1997 | Piantadosi et al. |
| 5,626,869 | A | 5/1997 | Nyqvist et al. |
| 5,631,018 | A | 5/1997 | Zalipsky et al. |
| 5,677,124 | A | 10/1997 | DuBois et al. |
| 5,693,088 | A | 12/1997 | Lazarus |
| 5,697,953 | A | 12/1997 | Kroll et al. |
| 5,700,437 | A | 12/1997 | Fujii et al. |
| 5,705,188 | A | 1/1998 | Junichi et al. |
| 5,705,385 | A | 1/1998 | Bally et al. |
| 5,736,573 | A | 4/1998 | Galat |
| 5,744,335 | A | 4/1998 | Wolff et al. |
| 5,772,694 | A | 6/1998 | Bokros et al. |
| 5,776,165 | A | 7/1998 | Ripart |
| 5,776,747 | A | 7/1998 | Schinstine et al. |
| 5,783,383 | A | 7/1998 | Kondo et al. |
| 5,844,107 | A | 12/1998 | Hanson et al. |
| 5,874,105 | A | 2/1999 | Watkins et al. |
| 5,885,613 | A | 3/1999 | Holland et al. |
| 5,910,168 | A | 6/1999 | Myers et al. |
| 5,916,208 | A | 6/1999 | Luther et al. |
| 5,965,434 | A | 10/1999 | Wolff et al. |
| 5,976,567 | A | 11/1999 | Wheeler et al. |
| 5,976,569 | A | 11/1999 | Milstein |
| 5,981,501 | A | 11/1999 | Wheeler et al. |
| 6,055,454 | A | 4/2000 | Heemels |
| 6,067,471 | A | 5/2000 | Warren |
| 6,090,384 | A | 7/2000 | Ra et al. |
| 6,096,070 | A | 8/2000 | Ragheb et al. |
| 6,096,075 | A | 8/2000 | Bokros et al. |
| 6,120,799 | A | 9/2000 | McDonald et al. |
| 6,147,055 | A | 11/2000 | Hobart et al. |
| 6,152,955 | A | 11/2000 | KenKnight et al. |
| 6,165,763 | A | 12/2000 | Brown et al. |
| 6,169,923 | B1 | 1/2001 | Kroll |
| 6,176,877 | B1 | 1/2001 | Buchanan et al. |
| 6,204,297 | B1 | 3/2001 | Tracy et al. |
| 6,210,892 | B1 | 4/2001 | Bennett et al. |
| 6,214,804 | B1 | 4/2001 | Felgner et al. |
| 6,271,208 | B1 | 8/2001 | Bischoff |
| 6,271,209 | B1 | 8/2001 | Smith et al. |
| 6,287,591 | B1 | 9/2001 | Semple et al. |
| 6,299,604 | B1 | 10/2001 | Ragheb et al. |
| 6,335,199 | B1 | 1/2002 | Bischoff et al. |
| 6,358,278 | B1 | 3/2002 | Brendzel et al. |
| 6,370,434 | B1 | 4/2002 | Zhang et al. |
| 6,371,983 | B1 | 4/2002 | Lane |
| 6,417,326 | B1 | 7/2002 | Cullis et al. |
| 6,485,726 | B1 | 11/2002 | Blumberg et al. |
| 6,534,484 | B1 | 3/2003 | Wheeler et al. |
| 6,585,410 | B1 | 7/2003 | Ryan |
| 6,586,410 | B1 | 7/2003 | Wheeler et al. |
| 6,670,178 | B1 | 12/2003 | Selden et al. |
| 6,696,424 | B1 | 2/2004 | Wheeler |
| 6,733,777 | B2 | 5/2004 | Erbacher et al. |
| 6,743,823 | B1 | 6/2004 | Summar et al. |
| 6,756,055 | B2 | 6/2004 | McDonald et al. |
| 6,790,838 | B2 | 9/2004 | Alison et al. |
| 6,815,432 | B2 | 11/2004 | Wheeler et al. |
| 6,821,530 | B2 | 11/2004 | Koob et al. |
| 6,835,395 | B1 | 12/2004 | Semple et al. |
| 6,858,224 | B2 | 2/2005 | Wheeler et al. |
| 6,858,225 | B2 | 2/2005 | Semple et al. |
| 6,887,665 | B2 | 5/2005 | Trulson et al. |
| 6,998,115 | B2 | 2/2006 | Langer et al. |
| 7,022,214 | B2 | 4/2006 | Olech |
| 7,067,697 | B2 | 6/2006 | Gao |
| 7,084,303 | B2 | 8/2006 | Watanabe et al. |
| 7,341,738 | B2 | 3/2008 | Semple et al. |
| 7,422,902 | B1 | 9/2008 | Wheeler et al. |
| 7,427,394 | B2 | 9/2008 | Anderson et al. |
| 7,507,859 | B2 | 3/2009 | Grinstaff et al. |
| 7,556,684 | B2 | 7/2009 | Bury et al. |
| 7,745,651 | B2 | 6/2010 | Heyes et al. |
| 7,799,565 | B2 | 9/2010 | MacLachlan et al. |
| 7,803,397 | B2 | 9/2010 | Heyes et al. |
| 7,901,708 | B2 | 3/2011 | MacLachlan et al. |
| 7,972,435 | B2 | 7/2011 | Bury et al. |
| 8,021,686 | B2 | 9/2011 | Semple et al. |
| 8,071,082 | B2 | 12/2011 | Zugates et al. |
| 8,101,741 | B2 | 1/2012 | MacLachlan et al. |
| 8,106,022 | B2 | 1/2012 | Manoharan et al. |
| 8,158,601 | B2 | 4/2012 | Chen et al. |
| 8,188,263 | B2 | 5/2012 | MacLachlan et al. |
| RE43,612 | E | 8/2012 | Anderson et al. |
| 8,236,943 | B2 | 8/2012 | Lee et al. |
| 8,278,036 | B2 | 10/2012 | Kariko et al. |
| 8,287,849 | B2 | 10/2012 | Langer et al. |
| 8,329,070 | B2 | 12/2012 | MacLachlan et al. |
| 8,389,238 | B2 | 3/2013 | Cooper et al. |

(56) References Cited

U.S. PATENT DOCUMENTS 8,450,298 B2 5/2013 Mahon et al.
8,450,467 B2 5/2013 Manoharan et al.
8,513,403 B2 8/2013 MacLachlan et al.
8,557,231 B2 10/2013 Langer et al.
8,562,966 B2 10/2013 Zugates et al.
8,569,256 B2 10/2013 Heyes et al.
8,652,512 B2 2/2014 Schmehl et al.
8,691,966 B2 4/2014 Kariko et al.
8,710,200 B2 4/2014 Schrum et al.
8,748,089 B2 6/2014 Kariko et al.
8,802,644 B2 8/2014 Chen et al.
8,808,681 B2 8/2014 Anderson et al.
8,808,982 B2 8/2014 Dahl et al.
8,822,663 B2 9/2014 Schrum et al.
8,828,956 B2 9/2014 Manoharan et al.
8,835,108 B2 9/2014 Kariko et al.
8,846,348 B2 9/2014 Jendrisak et al.
8,853,377 B2 10/2014 Guild et al.
8,859,229 B2 10/2014 Rabinovich et al.
8,883,202 B2 11/2014 Manoharan et al.
8,936,942 B2 1/2015 Heyes et al.
8,969,353 B2 3/2015 Mahon et al.
8,980,864 B2 3/2015 Hoge et al.
8,999,351 B2 4/2015 Manoharan et al.
8,999,950 B2 4/2015 MacLachlan et al.
9,005,930 B2 4/2015 Jendrisak et al.
9,012,219 B2 4/2015 Kariko et al.
9,012,498 B2 4/2015 Manoharan et al.
9,018,187 B2 4/2015 Heyes et al.
9,040,256 B2 5/2015 Grunenwald et al.
9,051,567 B2 6/2015 Fitzgerald et al.
9,061,021 B2 6/2015 Guild et al.
9,061,059 B2 6/2015 Chakraborty et al.
9,074,208 B2 7/2015 MacLachlan et al.
9,080,211 B2 7/2015 Grunenwald et al.
9,085,801 B2 7/2015 Grunenwald et al.
9,089,604 B2 7/2015 Chakraborty et al.
9,095,552 B2 8/2015 Chakraborty et al.
9,107,886 B2 8/2015 Chakraborty et al.
9,114,113 B2 8/2015 Chakraborty et al.
9,181,319 B2 11/2015 Schrum et al.
9,181,321 B2 11/2015 Heartlein et al.
9,186,325 B2 11/2015 Manoharan et al.
9,186,372 B2 11/2015 de Fougerolles et al.
9,187,748 B2 11/2015 Geisbert et al.
9,192,651 B2 11/2015 Chakraborty et al.
9,220,682 B2 12/2015 Manoharan et al.
9,220,683 B2 12/2015 Manoharan et al.
9,220,755 B2 12/2015 Chakraborty et al.
9,220,792 B2 12/2015 Chakraborty et al.
9,233,141 B2 1/2016 Chakraborty et al.
9,254,311 B2 2/2016 Bancel et al.
9,295,689 B2 3/2016 de Fougerolles et al.
9,301,993 B2 4/2016 Chakraborty et al.
9,303,079 B2 4/2016 Chakraborty et al.
9,334,328 B2 5/2016 Schrum et al.
9,345,780 B2 5/2016 Manoharan et al.
9,352,042 B2 5/2016 Heyes et al.
9,352,048 B2 5/2016 Manoharan et al.
9,364,435 B2 6/2016 Yaworski et al.
9,394,234 B2 7/2016 Chen et al.
9,404,127 B2 8/2016 Yaworski et al.
9,428,751 B2 8/2016 MacDonald et al.
9,464,124 B2 10/2016 Bancel et al.
9,492,386 B2 11/2016 MacLachlan et al.
9,504,651 B2 11/2016 MacLachlan et al.
9,504,734 B2 11/2016 Bancel et al.
9,518,272 B2 12/2016 Yaworksi et al.
9,572,874 B2 2/2017 Fotin-Mleczek et al.
9,587,003 B2 3/2017 Bancel et al.
9,616,084 B2 4/2017 Mutzke
10,471,153 B2 * 11/2019 DeRosa ............. A61K 48/0033
2002/0022721 A1 2/2002 Trulson et al.
2002/0094528 A1 7/2002 Salafsky
2002/0192651 A1 12/2002 Wheeler et al.
2002/0192721 A1 12/2002 Rizzuto et al.
2002/0193622 A1 12/2002 Watanabe et al.
2003/0082154 A1 5/2003 Leamon
2003/0083272 A1 5/2003 Wiederholt et al.
2003/0104044 A1 6/2003 Semple et al.
2003/0181410 A1 9/2003 Wheeler et al.
2003/0215395 A1 11/2003 Yu et al.
2004/0110709 A1 6/2004 Li et al.
2004/0132683 A1 7/2004 Felgner et al.
2004/0142025 A1 7/2004 MacLachlan et al.
2004/0224912 A1 11/2004 Dobie et al.
2004/0235982 A1 11/2004 Rabasco et al.
2005/0004058 A1 1/2005 Benoit et al.
2005/0008689 A1 1/2005 Semple et al.
2005/0032730 A1 2/2005 Von Der Mulbe et al.
2005/0054026 A1 3/2005 Atsushi et al.
2005/0059005 A1 3/2005 Tuschl et al.
2005/0059624 A1 3/2005 Hoerr et al.
2005/0065107 A1 3/2005 Hobart et al.
2005/0069590 A1 3/2005 Buehler et al.
2005/0079212 A1 4/2005 Wheeler et al.
2005/0143332 A1 6/2005 Monahan et al.
2005/0148786 A1 7/2005 Ikeda et al.
2005/0158302 A1 7/2005 Faustman et al.
2005/0244961 A1 11/2005 Short et al.
2005/0250723 A1 11/2005 Hoerr et al.
2006/0008910 A1 1/2006 MacLachlan et al.
2006/0059576 A1 3/2006 Pasinetti et al.
2006/0069225 A1 3/2006 Wintermantel et al.
2006/0083780 A1 4/2006 Heyes et al.
2006/0172003 A1 8/2006 Meers et al.
2006/0204566 A1 9/2006 Smyth-Templeton et al.
2006/0216343 A1 9/2006 Panzner et al.
2006/0223939 A1 10/2006 Lange et al.
2006/0228404 A1 10/2006 Anderson et al.
2006/0241071 A1 10/2006 Grinstaff et al.
2007/0135372 A1 6/2007 MacLachlan et al.
2007/0142628 A1 6/2007 Ghoshal et al.
2007/0172950 A1 7/2007 Wheeler et al.
2007/0252295 A1 11/2007 Panzner et al.
2007/0275923 A1 11/2007 Chen et al.
2007/0281336 A1 12/2007 Jendrisak et al.
2008/0145338 A1 6/2008 Anderson et al.
2008/0160048 A1 7/2008 Fuller
2008/0242626 A1 10/2008 Zugates et al.
2008/0260706 A1 10/2008 Rabinovich et al.
2009/0023673 A1 1/2009 Manoharan et al.
2009/0093433 A1 4/2009 Woolf et al.
2009/0163705 A1 6/2009 Manoharan et al.
2009/0186805 A1 7/2009 Tabor et al.
2009/0221684 A1 9/2009 Grinstaff et al.
2009/0263407 A1 10/2009 Dande et al.
2009/0270481 A1 10/2009 MacLachlan et al.
2009/0286852 A1 11/2009 Kariko et al.
2009/0326051 A1 12/2009 Corey et al.
2010/0028943 A1 2/2010 Thomas et al.
2010/0035249 A1 2/2010 Hayashizaki et al.
2010/0036084 A1 2/2010 Langer et al.
2010/0041152 A1 2/2010 Wheeler et al.
2010/0047261 A1 2/2010 Hoerr et al.
2010/0120129 A1 5/2010 Amshey et al.
2010/0178699 A1 7/2010 Gao et al.
2010/0189729 A1 7/2010 Hoerr et al.
2010/0267806 A1 10/2010 Bumcrot et al.
2010/0323356 A1 12/2010 Inoue et al.
2010/0331234 A1 12/2010 Mahon et al.
2011/0009641 A1 1/2011 Anderson et al.
2011/0035819 A1 2/2011 Cooper et al.
2011/0038941 A1 2/2011 Lee et al.
2011/0092739 A1 4/2011 Chen et al.
2011/0143397 A1 6/2011 Kariko et al.
2011/0200582 A1 8/2011 Baryza et al.
2011/0244026 A1 10/2011 Guild et al.
2011/0256175 A1 10/2011 Hope et al.
2011/0287435 A1 11/2011 Grunenwald et al.
2011/0293703 A1 12/2011 Mahon et al.
2011/0311583 A1 12/2011 Manoharan et al.
2012/0007803 A1 1/2012 Takatsuka
2012/0009222 A1 1/2012 Nguyen et al.

(56) References Cited

U.S. PATENT DOCUMENTS

| | | | |
|---|---|---|---|
| 2012/0065252 | A1 | 3/2012 | Schrum et al. |
| 2012/0065358 | A1 | 3/2012 | Langer et al. |
| 2012/0114831 | A1 | 5/2012 | Semple et al. |
| 2012/0128760 | A1 | 5/2012 | Manoharan et al. |
| 2012/0129910 | A1 | 5/2012 | Thompson et al. |
| 2012/0142756 | A1 | 6/2012 | Guild et al. |
| 2012/0195936 | A1 | 8/2012 | Rudolph et al. |
| 2012/0202871 | A1 | 8/2012 | Heyes et al. |
| 2012/0237975 | A1 | 9/2012 | Schrum et al. |
| 2012/0251560 | A1 | 10/2012 | Dahlman et al. |
| 2012/0251618 | A1 | 10/2012 | Schrum et al. |
| 2012/0328668 | A1 | 12/2012 | MacLachlan et al. |
| 2013/0017223 | A1 | 1/2013 | Hope et al. |
| 2013/0158021 | A1 | 6/2013 | Dong et al. |
| 2013/0195967 | A1 | 8/2013 | Guild et al. |
| 2013/0237594 | A1 | 9/2013 | de Fougerolles et al. |
| 2013/0259923 | A1 | 10/2013 | Bancel et al. |
| 2013/0259924 | A1 | 10/2013 | Bancel et al. |
| 2013/0266640 | A1 | 10/2013 | de Fougerolles et al. |
| 2013/0302401 | A1 | 11/2013 | Ma et al. |
| 2014/0010861 | A1 | 1/2014 | Bancel et al. |
| 2014/0044772 | A1 | 2/2014 | MacLachlan et al. |
| 2014/0094399 | A1 | 4/2014 | Langer et al. |
| 2014/0105964 | A1 | 4/2014 | Bancel et al. |
| 2014/0105965 | A1 | 4/2014 | Bancel et al. |
| 2014/0147432 | A1 | 5/2014 | Bancel et al. |
| 2014/0147454 | A1 | 5/2014 | Chakraborty et al. |
| 2014/0148502 | A1 | 5/2014 | Bancel et al. |
| 2014/0155472 | A1 | 6/2014 | Bancel et al. |
| 2014/0155473 | A1 | 6/2014 | Bancel et al. |
| 2014/0155474 | A1 | 6/2014 | Bancel et al. |
| 2014/0155475 | A1 | 6/2014 | Bancel et al. |
| 2014/0161830 | A1 | 6/2014 | Anderson et al. |
| 2014/0162897 | A1 | 6/2014 | Grunenwald et al. |
| 2014/0171485 | A1 | 6/2014 | Bancel et al. |
| 2014/0179756 | A1 | 6/2014 | MacLachlan et al. |
| 2014/0179771 | A1 | 6/2014 | Bancel et al. |
| 2014/0186432 | A1 | 7/2014 | Bancel et al. |
| 2014/0193482 | A1 | 7/2014 | Bancel et al. |
| 2014/0194494 | A1 | 7/2014 | Bancel et al. |
| 2014/0199371 | A1 | 7/2014 | Bancel et al. |
| 2014/0200163 | A1 | 7/2014 | Mikkelsen et al. |
| 2014/0200261 | A1 | 7/2014 | Hoge et al. |
| 2014/0200262 | A1 | 7/2014 | Bancel et al. |
| 2014/0200263 | A1 | 7/2014 | Bancel et al. |
| 2014/0200264 | A1 | 7/2014 | Bancel et al. |
| 2014/0206752 | A1 | 7/2014 | Afeyan et al. |
| 2014/0206753 | A1 | 7/2014 | Guild et al. |
| 2014/0206755 | A1 | 7/2014 | Bancel et al. |
| 2014/0206852 | A1 | 7/2014 | Hoge et al. |
| 2014/0221248 | A1 | 8/2014 | Jendrisak et al. |
| 2014/0221465 | A1 | 8/2014 | Bancel et al. |
| 2014/0227300 | A1 | 8/2014 | Chin et al. |
| 2014/0243399 | A1 | 8/2014 | Schrum et al. |
| 2014/0249208 | A1 | 9/2014 | Bancel et al. |
| 2014/0255467 | A1 | 9/2014 | Bancel et al. |
| 2014/0255468 | A1 | 9/2014 | Bancel et al. |
| 2014/0275227 | A1 | 9/2014 | Hoge et al. |
| 2014/0275229 | A1 | 9/2014 | Bancel et al. |
| 2014/0288160 | A1 | 9/2014 | Guild et al. |
| 2014/0294937 | A1 | 10/2014 | MacLachlan et al. |
| 2014/0294938 | A1 | 10/2014 | Guild et al. |
| 2014/0294939 | A1 | 10/2014 | Guild et al. |
| 2014/0294940 | A1 | 10/2014 | Guild et al. |
| 2014/0329884 | A1 | 11/2014 | Dong et al. |
| 2014/0343129 | A1 | 11/2014 | de Fougerolles et al. |
| 2014/0363876 | A1 | 12/2014 | Jendrisak et al. |
| 2015/0004217 | A1 | 1/2015 | Guild et al. |
| 2015/0005372 | A1 | 1/2015 | Hoge et al. |
| 2015/0011615 | A1 | 1/2015 | Manoharan et al. |
| 2015/0011633 | A1 | 1/2015 | Shorr et al. |
| 2015/0017211 | A1 | 1/2015 | de Fougerolles et al. |
| 2015/0038556 | A1 | 2/2015 | Heartlein et al. |
| 2015/0038558 | A1 | 2/2015 | Kariko et al. |
| 2015/0044277 | A1 | 2/2015 | Bancel et al. |
| 2015/0050354 | A1 | 2/2015 | Bouchon et al. |
| 2015/0051268 | A1 | 2/2015 | Bancel et al. |
| 2015/0056253 | A1 | 2/2015 | Bancel et al. |
| 2015/0064235 | A1 | 3/2015 | Bancel et al. |
| 2015/0064236 | A1 | 3/2015 | Bancel et al. |
| 2015/0064242 | A1 | 3/2015 | Heyes et al. |
| 2015/0064725 | A1 | 3/2015 | Schrum et al. |
| 2015/0086614 | A1 | 3/2015 | Bancel et al. |
| 2015/0110857 | A1 | 4/2015 | DeRosa et al. |
| 2015/0110858 | A1 | 4/2015 | DeRosa et al. |
| 2015/0110859 | A1 | 4/2015 | Heartlein et al. |
| 2015/0111248 | A1 | 4/2015 | Bancel et al. |
| 2015/0111945 | A1 | 4/2015 | Geisbert et al. |
| 2015/0119444 | A1 | 4/2015 | Manoharan et al. |
| 2015/0119445 | A1 | 4/2015 | Manoharan et al. |
| 2015/0157565 | A1 | 6/2015 | Heartlein et al. |
| 2015/0166465 | A1 | 6/2015 | Chen et al. |
| 2015/0190515 | A1 | 7/2015 | Manoharan et al. |
| 2015/0191760 | A1 | 7/2015 | Jendrisak et al. |
| 2015/0265708 | A1 | 9/2015 | Manoharan et al. |
| 2015/0267192 | A1 | 9/2015 | Heartlein et al. |
| 2015/0315541 | A1 | 11/2015 | Bancel et al. |
| 2015/0315584 | A1 | 11/2015 | MacDonald et al. |
| 2015/0366997 | A1 | 12/2015 | Guild et al. |
| 2016/0095924 | A1 | 4/2016 | Hope et al. |
| 2016/0114011 | A1 | 4/2016 | Bancel et al. |
| 2016/0115477 | A1 | 4/2016 | MacLachlan et al. |
| 2016/0115483 | A1 | 4/2016 | MacLachlan et al. |
| 2016/0136236 | A1 | 5/2016 | Hoge et al. |
| 2016/0151284 | A1 | 6/2016 | Heyes et al. |
| 2016/0158385 | A1 | 6/2016 | Bancel et al. |
| 2016/0193299 | A1 | 7/2016 | de Fougerolles et al. |
| 2016/0194368 | A1 | 7/2016 | Hoge et al. |
| 2016/0194625 | A1 | 7/2016 | Hoge et al. |
| 2016/0199485 | A1 | 7/2016 | Manoharan et al. |
| 2016/0213785 | A1 | 7/2016 | Manoharan et al. |
| 2016/0237108 | A1 | 8/2016 | Fraley et al. |
| 2016/0237134 | A1 | 8/2016 | Hoge et al. |
| 2016/0250354 | A1 | 9/2016 | Manoharan et al. |
| 2016/0251681 | A1 | 9/2016 | Yaworski et al. |
| 2016/0256567 | A1 | 9/2016 | Heyes et al. |
| 2016/0256568 | A1 | 9/2016 | Heyes et al. |
| 2016/0256573 | A1 | 9/2016 | de Fougerolles et al. |
| 2016/0264971 | A1 | 9/2016 | Geisbert et al. |
| 2016/0264975 | A1 | 9/2016 | Schrum et al. |
| 2016/0274089 | A1 | 9/2016 | Ciufolini et al. |
| 2016/0304552 | A1 | 10/2016 | Roy et al. |
| 2016/0317647 | A1 | 11/2016 | Ciaramella et al. |
| 2016/0317676 | A1 | 11/2016 | Hope et al. |
| 2016/0331828 | A1 | 11/2016 | Ciaramella et al. |
| 2016/0348099 | A1 | 12/2016 | Roy et al. |
| 2016/0354490 | A1 | 12/2016 | Roy et al. |
| 2016/0354491 | A1 | 12/2016 | Roy et al. |
| 2016/0354492 | A1 | 12/2016 | Roy et al. |
| 2016/0354493 | A1 | 12/2016 | Roy et al. |
| 2016/0367687 | A1 | 12/2016 | Manoharan et al. |
| 2016/0367702 | A1 | 12/2016 | Hoge et al. |
| 2016/0375134 | A1 | 12/2016 | Bancel et al. |
| 2016/0375137 | A9 | 12/2016 | Manoharan et al. |
| 2017/0000858 | A1 | 1/2017 | Fotin-Mleczek et al. |
| 2017/0000870 | A1 | 1/2017 | Hoerr et al. |
| 2017/0000871 | A1 | 1/2017 | Probst et al. |
| 2017/0002060 | A1 | 1/2017 | Bolen et al. |
| 2017/0007702 | A1 | 1/2017 | Heyes et al. |
| 2017/0014496 | A1 | 1/2017 | Fotin-Mleczek et al. |
| 2017/0028059 | A1 | 2/2017 | Baumhoff et al. |
| 2017/0029847 | A1 | 2/2017 | Thess |
| 2017/0056528 | A1 | 3/2017 | De Fougerolles et al. |
| 2017/0056529 | A1 | 3/2017 | Thess et al. |
| 2017/0065727 | A1 | 3/2017 | Fotin-Mleczek et al. |
| 2018/0161451 | A1 | 1/2018 | Fotin-Mleczek et al. |

FOREIGN PATENT DOCUMENTS

| | | | |
|---|---|---|---|
| CN | 100569877 | C | 12/2009 |
| CN | 101863544 | A | 10/2010 |
| DE | 24 30 998 | A1 | 1/1975 |
| DE | 2520814 | A1 | 11/1976 |
| DE | 3728917 | A1 | 3/1989 |

(56) References Cited

FOREIGN PATENT DOCUMENTS

| | | | |
|---|---|---|---|
| EP | 6 73 637 | A1 | 9/1995 |
| EP | 0783297 | A1 | 7/1997 |
| EP | 0853123 | A1 | 7/1998 |
| EP | 0959092 | A1 | 11/1999 |
| EP | 1519714 | B1 | 4/2005 |
| EP | 1979364 | A2 | 10/2008 |
| EP | 2045251 | A1 | 4/2009 |
| EP | 2338478 | B1 | 6/2011 |
| EP | 2338520 | A1 | 6/2011 |
| EP | 2449106 | A1 | 5/2012 |
| EP | 2532649 | A1 | 12/2012 |
| EP | 2578685 | A2 | 4/2013 |
| EP | 2823809 | A1 | 1/2015 |
| FR | 1 378 382 | A | 11/1964 |
| FR | 2 235 112 | A1 | 1/1975 |
| GB | 1072118 | A | 6/1967 |
| GB | 1602085 | A | 11/1981 |
| JP | H07-053535 | | 2/1955 |
| JP | S48-022365 | | 3/1973 |
| JP | S49-127908 | A | 12/1974 |
| JP | S51-023537 | | 2/1976 |
| JP | 51-125144 | | 11/1976 |
| JP | S52-010847 | | 1/1977 |
| JP | S63125144 | A | 5/1988 |
| JP | 63-154788 | | 6/1988 |
| JP | H09-505593 | A | 6/1997 |
| JP | H10-197978 | A | 7/1998 |
| JP | 11-005786 | A | 1/1999 |
| JP | 11-080142 | | 3/1999 |
| JP | 2001-523215 | A | 11/2001 |
| JP | 2002-167368 | A | 6/2002 |
| JP | 2003-519199 | A | 6/2003 |
| JP | 4-108173 | B2 | 6/2008 |
| JP | 2008-247749 | A | 10/2008 |
| JP | 50-24216 | B2 | 9/2012 |
| WO | WO-90/11092 | A1 | 10/1990 |
| WO | WO-93/18229 | A1 | 9/1993 |
| WO | WO-93/18754 | A1 | 9/1993 |
| WO | WO-95/11004 | A1 | 4/1995 |
| WO | WO-95/14651 | A1 | 6/1995 |
| WO | WO-95/27478 | A1 | 10/1995 |
| WO | WO-96/18372 | A2 | 6/1996 |
| WO | WO-96/26179 | A1 | 8/1996 |
| WO | WO-96/37211 | A1 | 11/1996 |
| WO | WO-96/40964 | A2 | 12/1996 |
| WO | WO-97/46223 | A1 | 12/1997 |
| WO | WO-98/10748 | A1 | 3/1998 |
| WO | WO-98/16202 | A2 | 4/1998 |
| WO | WO-98/51278 | A2 | 11/1998 |
| WO | WO-99/14346 | A2 | 3/1999 |
| WO | WO-00/03044 | A1 | 1/2000 |
| WO | WO-00/62813 | A2 | 10/2000 |
| WO | WO-00/64484 | A2 | 11/2000 |
| WO | WO-00/69913 | A1 | 11/2000 |
| WO | WO-01/05375 | A1 | 1/2001 |
| WO | WO-01/07599 | A1 | 2/2001 |
| WO | WO-02/00870 | A2 | 1/2002 |
| WO | WO-02/22709 | A1 | 3/2002 |
| WO | WO-02/31025 | A2 | 4/2002 |
| WO | WO-02/34236 | A2 | 5/2002 |
| WO | WO-02/42317 | A2 | 5/2002 |
| WO | WO-03/040288 | A2 | 5/2003 |
| WO | WO-03/070735 | A2 | 8/2003 |
| WO | WO-2004/043588 | A2 | 5/2004 |
| WO | WO-2004/048345 | A2 | 6/2004 |
| WO | WO-2004/106411 | A2 | 12/2004 |
| WO | WO-2005/026372 | A1 | 3/2005 |
| WO | WO-2005/028619 | A2 | 3/2005 |
| WO | WO-2005/037226 | A2 | 4/2005 |
| WO | WO-2005/121348 | A1 | 12/2005 |
| WO | WO-2006/000448 | A2 | 1/2006 |
| WO | WO-2006/016097 | A2 | 2/2006 |
| WO | WO-2006/082088 | A1 | 8/2006 |
| WO | WO-2006/105043 | A2 | 10/2006 |
| WO | WO-2006/138380 | A2 | 12/2006 |
| WO | WO-2007/024708 | A2 | 3/2007 |
| WO | WO-2007/031091 | A2 | 3/2007 |
| WO | WO-2007/120863 | A2 | 10/2007 |
| WO | WO-2007/126386 | A1 | 11/2007 |
| WO | WO-2007/143659 | A2 | 12/2007 |
| WO | WO-2008/011561 | A2 | 1/2008 |
| WO | 2008/045548 | A2 | 4/2008 |
| WO | WO-2008/042973 | A2 | 4/2008 |
| WO | WO-2008/045548 | A2 | 4/2008 |
| WO | WO-2008/083949 | A2 | 7/2008 |
| WO | WO-2008/113364 | A2 | 9/2008 |
| WO | WO-2009/046220 | A2 | 4/2009 |
| WO | WO-2009/127060 | A1 | 10/2009 |
| WO | WO-2009/127230 | A1 | 10/2009 |
| WO | WO-2010/037408 | A1 | 4/2010 |
| WO | WO-2010/042877 | A1 | 4/2010 |
| WO | WO-2010/045512 | A2 | 4/2010 |
| WO | WO-2010/053572 | A2 | 5/2010 |
| WO | WO-2010/054401 | A1 | 5/2010 |
| WO | WO-2010/054405 | A1 | 5/2010 |
| WO | WO-2010/056403 | A1 | 5/2010 |
| WO | WO-2010/099387 | A1 | 9/2010 |
| WO | WO-2010/114789 | A1 | 10/2010 |
| WO | WO-2010/119256 | A1 | 10/2010 |
| WO | WO-2010/129709 | A1 | 11/2010 |
| WO | WO-2010/144740 | A1 | 12/2010 |
| WO | WO-2010/147992 | A1 | 12/2010 |
| WO | WO-2010/148013 | A2 | 12/2010 |
| WO | WO-2011/012316 | A2 | 2/2011 |
| WO | WO-2011/012746 | A2 | 2/2011 |
| WO | WO-2011/039144 | A1 | 4/2011 |
| WO | WO-2011/068810 | A1 | 6/2011 |
| WO | WO-2011/075656 | A1 | 6/2011 |
| WO | WO-2011/141705 | A1 | 11/2011 |
| WO | WO-2012/019168 | A2 | 2/2012 |
| WO | WO-2012/019630 | A1 | 2/2012 |
| WO | WO-2012/019780 | A1 | 2/2012 |
| WO | WO-2012/027675 | A2 | 3/2012 |
| WO | WO-2012/045075 | A1 | 4/2012 |
| WO | WO-2012/045082 | A2 | 4/2012 |
| WO | WO-2012/075040 | A2 | 6/2012 |
| WO | WO-2012/133737 | A1 | 10/2012 |
| WO | WO-2012/135025 | A2 | 10/2012 |
| WO | WO-2012/135805 | A2 | 10/2012 |
| WO | WO-2012/170889 | A1 | 12/2012 |
| WO | WO-2012/170930 | A1 | 12/2012 |
| WO | WO-2013/039857 | A1 | 3/2013 |
| WO | WO-2013/039861 | A2 | 3/2013 |
| WO | WO-2013/063468 | A1 | 5/2013 |
| WO | WO2013/090186 | | 6/2013 |
| WO | WO-2013/101690 | A1 | 7/2013 |
| WO | WO-2013/102203 | A1 | 7/2013 |
| WO | WO-2013/126803 | A1 | 8/2013 |
| WO | WO-2013/130161 | A1 | 9/2013 |
| WO | WO-2013/149140 | A1 | 10/2013 |
| WO | WO-2013/149141 | A1 | 10/2013 |
| WO | WO-2013/151663 | A1 | 10/2013 |
| WO | WO-2013/151664 | A1 | 10/2013 |
| WO | WO-2013/151666 | A2 | 10/2013 |
| WO | WO-2013/151667 | A1 | 10/2013 |
| WO | WO-2013/151668 | A2 | 10/2013 |
| WO | WO-2013/151670 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2013/182683 | A1 | 12/2013 |
| WO | WO-2013/185067 | A1 | 12/2013 |
| WO | WO-2013/185069 | A1 | 12/2013 |
| WO | WO-2014/028487 | A1 | 2/2014 |
| WO | WO-2014/089486 | A1 | 6/2014 |
| WO | WO-2014/113089 | A2 | 7/2014 |
| WO | WO-2014/144039 | A1 | 9/2014 |
| WO | WO-2014/144196 | A1 | 9/2014 |
| WO | WO-2014/144711 | A1 | 9/2014 |
| WO | WO-2014/144767 | A1 | 9/2014 |
| WO | WO-2014/152027 | A1 | 9/2014 |
| WO | WO-2014/152030 | A1 | 9/2014 |
| WO | WO-2014/152031 | A1 | 9/2014 |
| WO | WO-2014/152211 | A1 | 9/2014 |

(56) References Cited

FOREIGN PATENT DOCUMENTS

| | | |
|---|---|---|
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 10/2014 |
| WO | WO-2014/159813 A1 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO2015/085318 | 6/2015 |
| WO | WO2015/089511 | 6/2015 |
| WO | WO2016/054421 | 4/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2017/019891 A2 | 2/2017 |
| WO | WO2017/049074 A1 | 3/2017 |
| WO | WO2017/049275 A2 | 3/2017 |
| WO | WO2017/049286 A1 | 3/2017 |
| WO | 2018/089790 A1 | 5/2018 |

OTHER PUBLICATIONS

Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).
Anderson, D.G. et al., Structure/property studies of polymeric gene delivery using a library of poly(beta-amino esters). Molecular Therapy 11(3):426-434 (2005).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Anderson, J. Biological Responses to Materials. Annual Review of Materials Research 31:81-110 (2001).
Anderson, W. French, Human gene therapy, Nature, 392, 25-30 (1998).
Andries, O. et al., Comparison of the Gene Transfer Efficiency of mRNA/GL67 and pDNA/GL67 Complexes in Respiratory Cells, Mol. Pharmaceut., 9: 2136-2145 (2012).
Auffray, C. et al., Purification of Mouse Immunoglubulin Heavy-Chain Messenger RNAs from Total Myeloma Tumor RNA, European Journal of Biochemistry, 107(2):303-314 (1980).
Author Unknown, Blood Proteins, published by WikiPedia, San Francisco, CA, 2 pages, <http://en.wikipedia.org/wiki/Biood_proteins> downloaded May 17, 2015.

Bajaj, A. et al., Synthesis and gene transfection efficacies of PEI-cholesterol-based lipopolymers. Bioconjugate Chemistry 19(8):1640-516511 (2008).
Barreau, C. et al., Liposome-mediated RNA transfection should be used with caution, RNA, 12:1790-1793 (2006).
Behlke, M.A. et al., Progress towards in vivo use of siRNAs, Molecular Therapy, 13:644-670 (2006).
Behr, J. et al., Efficient Gene Transfer into Mammalian Primary Endocrine Cells with Lipo Polyamine-Coated DNA, Proc. Nat'l Acad. Sci., 86: 6982-6986 (1989).
Bennett, J. Immune response following intraocular delivery of recombinant viral vectors, Gene Therapy, 10: 977-982 (2003).
Bhaduri, S. et al., Procedure for the preparation of milligram quantities of adenovirus messenger ribonucleic acid, J. Virol., 10(6): 1126-1129 (1972).
Bloomfield, V.A., Quasi-Elastic Light Scattering Applications in Biochemistry and Biology, Ann. Rev. Biophys. Bioeng. 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., ucture/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23: 139-147 (1997).
Burger, G. et al., Sequencing complete mitochondrial and plastid genomes, Nature Protocols, 2: 603-614 (2007).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).

(56) References Cited

OTHER PUBLICATIONS

Chiou, H.C. et al., Enhanced resistance to nuclease degradation of nucleic acids complexed to; asialoglycoprotein-polylysine carriers, Nucleic Acids Research, 22(24):5439-5446 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Conese, M. et al., Gene and Cell Therapy for Cystic Fibrosis: From Bench to Bedside, J. Cyst. Fibros., 10 Suppl 2:S114-s128 (2011).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N",N"-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(541 7):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Driscoll, K.E. et al., Intratracheal instillation as an exposure technique for the evaluation of respiratory tract toxicity: uses and limitations, Toxicol. Sci., 55(1): 24-35 (2000).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).
Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (14 pages) 2011.
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).
Felgner, P.L. et al., Lipofection: A Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(I-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Galipon, J. et al., Stress-induced 1 ncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).

(56) References Cited

OTHER PUBLICATIONS

Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, ILAR J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(25):346S (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin—Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).
Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Sequence NM_000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-based lipids for ordered assembly of bioresponsive gene carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (dated Jun. 14, 2012).
International Search Report for PCT/US15/27563, 5 pages (dated Sep. 18, 2015).
International Search Report for PCT/US2010/058457, 4 pages (dated May 6, 2011).
International Search Report for PCT/US2011/062459, 3 pages (dated Apr. 11, 2012).
International Search Report for PCT/US2012/041663, 4 pages (dated Oct. 8, 2012).
International Search Report for PCT/US2012/041724, 5 pages (dated Oct. 25, 2012).
International Search Report for PCT/US2013/034602, 2 pages (dated Jun. 17, 2013).
International Search Report for PCT/US2013/034604, 4 pages (dated Jun. 17, 2013).
International Search Report for PCT/US2013/044769, 4 pages (dated Nov. 12, 2013).
International Search Report for PCT/US2013/044771, 6 pages (dated Nov. 1, 2013).
International Search Report for PCT/US2013/073672, 6 pages (dated Mar. 3, 2014).
International Search Report for PCT/US2014/027422, 5 pages (dated Jul. 31, 2014).
International Search Report for PCT/US2014/027585, 3 pages (dated Jul. 14, 2014).
International Search Report for PCT/US2014/027587, 6 pages (dated Jul. 24, 2014).
International Search Report for PCT/US2014/027602, 6 pages (dated Jul. 28, 2014).
International Search Report for PCT/US2014/027717, 5 pages (dated Jul. 16, 2014).
International Search Report for PCT/US2014/028330, 5 pages (dated Jul. 22, 2014).
International Search Report for PCT/US2014/028441, 6 pages (dated Jul. 22, 2014).
International Search Report for PCT/US2014/028498, 5 pages (dated Jul. 28, 2014).
International Search Report for PCT/US2014/028849, 6 pages (dated Jul. 17, 2015).

(56) References Cited

OTHER PUBLICATIONS

International Search Report for PCT/US2014/061786, 6 pages (dated Feb. 6, 2015).
International Search Report for PCT/US2014/061793, 4 pages (dated Feb. 6, 2015).
International Search Report for PCT/US2014/061830, 5 pages (dated Feb. 4, 2015).
International Search Report for PCT/US2014/061841, 6 pages (dated Feb. 24, 2015).
International Search Report for PCT/US2015/039004, 4 pages (dated Oct. 6, 2015).
International Search Report for PCT/US2015/21403 (4 pages) dated Jun. 15, 2015.
Jakobsen, K. et al., Purification of MRNA Directly From Crude Plant Tissues in 15 Minutes Using Magnetic Oligo DT Microsheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jemielity, J. et al., Novel "anti-reverse" cap analogs with superior translational properties, Cold Spring Harbor Laboratory Press, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying *Phaseolus vulgaris* Agglutinin-$L_4$ Isolectin to Malignant Tumors Overexpressing *N*-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kore, A. and Charles, I., Synthesis and evaluation of 2'-*O*-allyl substituted dinucleotide cap analog for mRNA translation, Bioorganics & Medicinal Chemistry, 18:8061-8065 (2010).
Kore, A. and Shanmugasundaram, M., Synthesis and biological evaluation of trimethyl-substituted cap analogs, Bioorganic & Medicinal Chemistry, 18:880-884 (2008).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-l-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing, PNAS, 107(5):1864-1869 (2010).

(56) References Cited

OTHER PUBLICATIONS

Lu, D. et al., Optimization of methods to achieve mRNA-mediated transfection of tumor cells in vitro and in vivo employing cationic liposome vectors, Cancer Gene Therapy, 1(4):245-252 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters):? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123 (33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Developlment of Cationic Polymer Coatings to Regulate Foreign Body Responses. Advanced Healthcare Materials 23: H189-H194. Reviews (2011).
MacLachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R. et al., In vivo gene delivery by cationic tetraamino; fullerene. Proceedings of National Academy of Sciences USA, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
McIvor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter, H. et al, Topical Delivery of mRNA to the Murine Lung and Nasal Epithelium, Gene Medicine Group and the Medical Informatics Unit, Nuffield Department of Clinical Laboratory Sciences, University of Oxford, 1 page.
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Gene Medicine Research Group Nuffield Department of Clinical Laboratory Sciences and Merton College, University of Oxford, 1-282 (2007).
Painter, H., An Investigation of mRNA as a Gene Transfer Agent, Oxford University GeneMedicine, Abstract Only, 1 page (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Pearson, H., One Gene, Twenty Years, Nature 460:165-169 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).

(56) References Cited

OTHER PUBLICATIONS

Pons, M. et al., Liposomes obtained by the ethanol injection method, Int. J. Pharm., 95: 5156. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).
Putnam, D. and Langer, R., Poly(4-hydroxy-I-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Rowe, S.M. et al., Cystic Fibrosis, New Engl. J. Med. 352:1992-2001 (2005).
Rudolph, C. et al., Aerosolized Nanogram Quantities of Plasmid DNA Mediate Highly Efficient Gene Delivery to Mouse Airway Epithelium, Molecular Therapy, 12(3): 493-501 (2005).
Rudolph, C. et al., Methodological optimization of polyethylenimine (PEI)-based gene delivery to the lungs of mice via aerosol application, Journal of Gene Medicine, 7(1): 59-66 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated via Electrostatic Surface Binding of mRNA to Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Tcherepanova, I. et al., Ectopic expression of a truncated CD40L protein from synthetic post-transcriptionally capped RNA in dendritic cells induces high levels of IL-12 secretion, BMC Molecular Biology, 9(1):pp. 1-13 (2008).
Theus, S. and Liarakos, C., A Simple Assay for Determining the Capping Efficiencies of RNA Polymerases Used for In Vitro Transcription, BioChromatography, 9(5):610-614 (1990).
Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-1653 (2002).

(56) References Cited

OTHER PUBLICATIONS

Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US15/27563, 12 pages (dated Sep. 18, 2015).
Written Opinion for PCT/US2010/058457, 14 pages (dated May 6, 2011).
Written Opinion for PCT/US2011/062459, 9 pages (dated Apr. 11, 2012).
Written Opinion for PCT/US2012/041663, 7 pages (dated Oct. 8, 2012).
Written Opinion for PCT/US2012/041724, 11 pages (dated Oct. 25, 2012).
Written Opinion for PCT/US2013/034602, 4 pages (dated Jun. 17, 2013).
Written Opinion for PCT/US2013/034604, 9 pages (dated Jun. 17, 2013).
Written Opinion for PCT/US2013/044769, 8 pages (dated Nov. 12, 2013).
Written Opinion for PCT/US2013/044771, 7 pages (dated Nov. 1, 2013).
Written Opinion for PCT/US2013/073672, 7 pages (dated Mar. 3, 2014).
Written Opinion for PCT/US2014/027422, 6 pages (dated Jul. 31, 2014).
Written Opinion for PCT/US2014/027587, 5 pages (dated Jul. 24, 2014).
Written Opinion for PCT/US2014/027717, 5 pages (dated Jul. 16, 2014).
Written Opinion for PCT/US2014/028330, 7 pages (dated Jul. 22, 2014).
Written Opinion for PCT/US2014/028441, 6 pages (dated Jul. 22, 2014).
Written Opinion for PCT/US2014/028498, 6 pages (dated Jul. 28, 2014).
Written Opinion for PCT/US2014/028849, 7 pages (dated Jul. 17, 2015).
Written Opinion for PCT/US2014/061786, 5 pages (dated Feb. 6, 2015).
Written Opinion for PCT/US2014/061793, 4 pages (dated Feb. 6, 2015).
Written Opinion for PCT/US2014/061830, 7 pages (dated Feb. 4, 2015).
Written Opinion for PCT/US2014/061841, 8 pages (dated Feb. 24, 2015).
Written Opinion for PCT/US2015/039004, 8 pages (dated Oct. 6, 2015).
Written Opinion for PCT/US2015/21403 (7 pages) dated Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).
Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).

(56) References Cited

OTHER PUBLICATIONS

Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chern. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry, 26(1):184-88. Russian (1990).
Zaugg, H.E. et al., 3-Carboxy-2,5-piperazinedione and Derivatives. Journal of American Chemical Society 78(11):2626-2631 (1956).
Zauner, W.et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).
Zou, S. et al., Lipid-mediated delivery of RNA is more efficient than delivery of DNA in non-dividing cells, International Journal of Pharmaceutics, 389(1-2):232-243 (2010).
Brown, M.D. et al., Gene Delivery with synthetic (non viral) carriers, Int. J. Pharm., 1-21 (2001).
Eck, et al., Goodman & Gilman's The Pharmacological Basis of Therapeutics, McGraw-Hill, New York, 77-101 (1996).
Gorecki, et al., Prospects and problems of gene therapy: an update, Expert Opin. Emerging Drugs, 6(2): 187-198 (2001).
Lechardeur, et al., Metabolic instability of plasmid DNA in the cytosol: a potential barrier to gene transfer, Gene Therapy, 6: 482-497 (1999).

* cited by examiner

Upper bronchial epithelial cells
Group 1, 10% Trehalose

CFTR ZO1 MERGED

Upper bronchial epithelial cells
Group 3, CFTR mRNA 500μg/kg
60 Minutes Exposure Upper bronchial epithelial cells
Group 5, CFTR mRNA 1000μg/kg
120 Minutes Exposure

CFTR ZO1 MERGED

Lower bronchial epithelial cells
Group 1, 10% Trehalose

Lower bronchial epithelial cells
Group 3, CFTR mRNA 500µg/kg
60 Minutes Exposure

CFTR ZO1 MERGED

Lower bronchial epithelial cells
Group 5, CFTR mRNA 1000µg/kg
120 Minutes Exposure

CFTR ZO1 MERGED

Alveolar region
Group 1, 10% Trehalose

Alveolar region
Group 3, CFTR mRNA 500µg/kg
60 Minutes Exposure

Alveolar region
Group 5, CFTR mRNA1000μg/kg
120 Minutes Exposure

CFTR ZO1 MERGED

TREATMENT OF CYSTIC FIBROSIS BY DELIVERY OF CODON-OPTIMIZED MRNA ENCODING CFTR

RELATED APPLICATIONS

This application claims priority to U.S. Provisional Application Ser. No. 62/507,061, filed May 16, 2017; Ser. No. 62/532,301, filed on Jul. 13, 2017; Ser. No. 62/580,782, filed Nov. 2, 2017; Ser. No. 62/592,238, filed Nov. 29, 2017; and Ser. No. 62/659,053, filed Apr. 17, 2018, the disclosures in their entirety of all of which are hereby incorporated by reference.

SEQUENCE LISTING

The present specification makes reference to a Sequence Listing (submitted electronically as a .txt file named "SL_MRT-2005PCT-US" on May 16, 2018. The .txt file was generated May 15, 2018 and is 152,577 bytes in size. The entire contents of the Sequence Listing are herein incorporated by reference.

BACKGROUND

Cystic fibrosis is an autosomal inherited disorder resulting from mutation of the CFTR gene, which encodes a chloride ion channel believed to be involved in regulation of multiple other ion channels and transport systems in epithelial cells. Loss of function of CFTR results in chronic lung disease, aberrant mucus production, and dramatically reduced life expectancy. See generally Rowe et al., New Engl. J. Med. 352, 1992-2001 (2005).

Currently there is no cure for cystic fibrosis (CF). The literature has documented numerous difficulties encountered in attempting to induce expression of CFTR in the lung. For example, viral vectors comprising CFTR DNA triggered immune responses and CF symptoms persisted after administration. Conese et al., J. Cyst. Fibros. 10 Suppl 2, S114-28 (2011); Rosenecker et al., Curr. Opin. Mol. Ther. 8, 439-45 (2006). Non-viral delivery of DNA, including CFTR DNA, has also been reported to trigger immune responses. Alton et al., Lancet 353, 947-54 (1999); Rosenecker et al., J Gene Med. 5, 49-60 (2003). Furthermore, non-viral DNA vectors encounter the additional problem that the machinery of the nuclear pore complex does not ordinarily import DNA into the nucleus, where transcription would occur. Pearson, Nature 460, 164-69 (2009).

SUMMARY OF THE INVENTION

The present invention provides, among other things, methods of treating cystic fibrosis with an mRNA encoding a Cystic Fibrosis Transmembrane Conductance Regulator (CFTR) protein. In one aspect, the present invention provides methods of treating cystic fibrosis, comprising a step of administering to a subject in need of treatment a composition comprising an mRNA encoding a Cystic Fibrosis Transmembrane Conductance Regulator (CFTR) protein, wherein the mRNA encoding the CFTR protein comprises a polynucleotide sequence at least 80% identical to SEQ ID NO: 1. In some embodiments, the mRNA encoding CFTR is at a concentration of at least 0.4 mg/mL and the step of administering comprises inhalation. In some embodiments, the mRNA encoding CFTR is at a concentration of at least 0.5 mg/mL. In some embodiments, the mRNA encoding CFTR is at a concentration of at least 0.6 mg/mL. In some embodiments, the mRNA encoding CFTR is at a concentration ranging from 0.4 mg/mL to 0.8 mg/mL. In some embodiments, the dose is 24 mg or less per week of mRNA encoding CFTR. In some embodiments, the dose is 16 mg or less per week of mRNA encoding CFTR. In some embodiments, the dose is 8 mg or less per week of mRNA encoding CFTR.

In some embodiments, the mRNA encoding the CFTR protein comprises a polynucleotide sequence at least 85% identical to SEQ ID NO: 1. In some embodiments, the mRNA encoding the CFTR protein comprises a polynucleotide sequence at least 90% identical to SEQ ID NO: 1. In some embodiments, the mRNA encoding the CFTR protein comprises a polynucleotide sequence at least 95% identical to SEQ ID NO: 1. In some embodiments, the mRNA encoding the CFTR protein comprises a polynucleotide sequence at least 99% identical to SEQ ID NO: 1. In some embodiments, the mRNA encoding the CFTR protein comprises a polynucleotide sequence identical to SEQ ID NO: 1.

In some embodiments, the composition is nebulized prior to inhalation. In some embodiments, the composition is stored as a frozen, sterile suspension prior to administering. In some embodiments, the composition is stored in a single-use vial prior to administering. In some embodiments, the single-use vial comprises less than 5.0 mL of the composition. In some embodiments, the mRNA encoding the CFTR protein is at a dosage ranging from 8 mg to 24 mg.

In some embodiments, the mRNA encoding the CFTR protein further comprises a 5' untranslated region (UTR) sequence of SEQ ID NO: 3. In some embodiments, the mRNA encoding the CFTR protein further comprises a 3' untranslated region (UTR) sequence of SEQ ID NO: 4 or SEQ ID NO: 5.

In some embodiments, the mRNA encoding the CFTR protein is encapsulated within a nanoparticle. In some embodiments, the nanoparticle is a liposome. In some embodiments, the liposome comprises one or more cationic lipids, one or more non-cationic lipids, and one or more PEG-modified lipids. In some embodiments, the liposome comprises no more than three distinct lipid components. In some embodiments, one distinct lipid component is a sterol-based cationic lipid. In some embodiments, the liposome has a size less than about 100 nm. In some embodiments, the liposome has a size ranging from 40 nm to 60 nm. In some embodiments, the no more than three distinct lipid components are a cationic lipid, a non-cationic lipid and a PEG-modified lipid. In some embodiments, the liposome comprises imidazole cholesterol ester (ICE), 1,2-dioleoyl-sn-glycero-3-phosphoethanolamine (DOPE), and 1,2-dimyristoyl-sn-glycerol, methoxypolyethylene glycol (DMG-PEG-2K). In some embodiments, ICE and DOPE are present at a molar ratio of >1:1. In some embodiments, ICE and DMG-PEG-2K are present at a molar ratio of >10:1. In some embodiments, DOPE and DMG-PEG-2K are present at a molar ratio of >5:1.

In some embodiments, the single-use vial comprises between 3.0 and 4.0 mL of the composition. In some embodiments, the single-use vial comprises between 3.2 mL of the composition.

It is to be understood that all embodiments as described above are applicable to all aspects of the present invention. Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

FIG. 8A depicts microscopic immunostaining images of upper bronchial epithelial cells from a primate treated with buffer (10% trehalose) as a control; showing mRNA-derived CFTR protein staining (left), endogenous ZO1 protein staining (middle) and optical merge of mRNA-derived CFTR protein staining and endogenous ZO1 protein staining (right), with no visible mRNA-derived CFTR protein present in the cell membranes of upper bronchial epithelial cells. FIG. 8B depicts microscopic immunostaining images of upper bronchial epithelial cells from a primate treated with nebulized CFTR mRNA (500 μg/kg); showing mRNA-derived CFTR protein staining (left), endogenous ZO1 protein staining (middle) and optical merge of mRNA-derived CFTR protein staining and endogenous ZO1 protein staining (right), with mRNA-derived CFTR protein present in the cell membranes of upper bronchial epithelial cells. FIG. 8C depicts representative microscopic immunostaining images of upper bronchial epithelial cells from a primate treated with nebulized CFTR mRNA (1000 μg/kg); showing mRNA-derived CFTR protein staining (left), endogenous ZO1 protein staining (middle) and optical merge of mRNA-derived CFTR protein staining and endogenous ZO1 protein staining (right) with mRNA-derived CFTR protein present in the cell membranes of upper bronchial epithelial cells.

FIG. 9A depicts microscopic immunostaining images of lower airway epithelial cells from a primate treated with buffer (10% trehalose) as a control; showing mRNA-derived CFTR protein staining (left), endogenous ZO1 protein staining (middle) and optical merge of mRNA-derived CFTR protein and endogenous ZO1 protein staining (right), with no visible mRNA-derived CFTR protein present in the cell membranes of lower bronchial epithelial cells. FIG. 9B depicts microscopic immunostaining images of lower airway epithelial cells from a primate treated with nebulized CFTR mRNA (500 μg/kg); showing mRNA-derived CFTR protein staining (left), endogenous ZO1 protein staining (middle) and optical merge of mRNA-derived CFTR protein staining and endogenous ZO1 protein staining (right), with mRNA-derived CFTR protein present in the cell membranes of the lower bronchial epithelial cells. FIG. 9C depicts representative microscopic immunostaining images of lower airway epithelial cells from a primate treated with nebulized CFTR mRNA (1000 μg/kg); showing mRNA-derived CFTR protein staining (left), endogenous ZO1 protein staining (middle) and optical merge of mRNA-derived CFTR protein staining and endogenous ZO1 protein staining (right), with mRNA-derived CFTR protein present in the cell membranes of lower bronchial epithelial cells.

FIG. 10A depicts microscopic immunostaining images from a primate treated with buffer (10% trehalose) as a control; showing mRNA-derived CFTR protein staining (left), endogenous ZO1 protein staining (middle) and optical merge of mRNA-derived CFTR protein and endogenous ZO1 protein staining (right), with no mRNA-derived CFTR protein present in the cell membranes of alveolar cells. FIG. 10B depicts microscopic immunostaining images from a primate treated with nebulized CFTR mRNA (500 μg/kg); showing mRNA-derived CFTR protein staining (left), endogenous ZO1 protein staining (middle) and optical merge of mRNA-derived CFTR protein and endogenous ZO1 protein staining (right), with mRNA-derived CFTR protein present in the cell membranes of alveolar cells. FIG. 10C shows representative microscopic immunostaining images from a primate treated with nebulized CFTR mRNA (1000 μg/kg); showing mRNA-derived CFTR protein staining (left), endogenous ZO1 protein staining (middle) and optical merge of mRNA-derived CFTR protein staining and endogenous ZO1 protein staining (right), with mRNA-derived CFTR protein present in the cell membranes of alveolar cells.

DEFINITIONS

Figure 1:
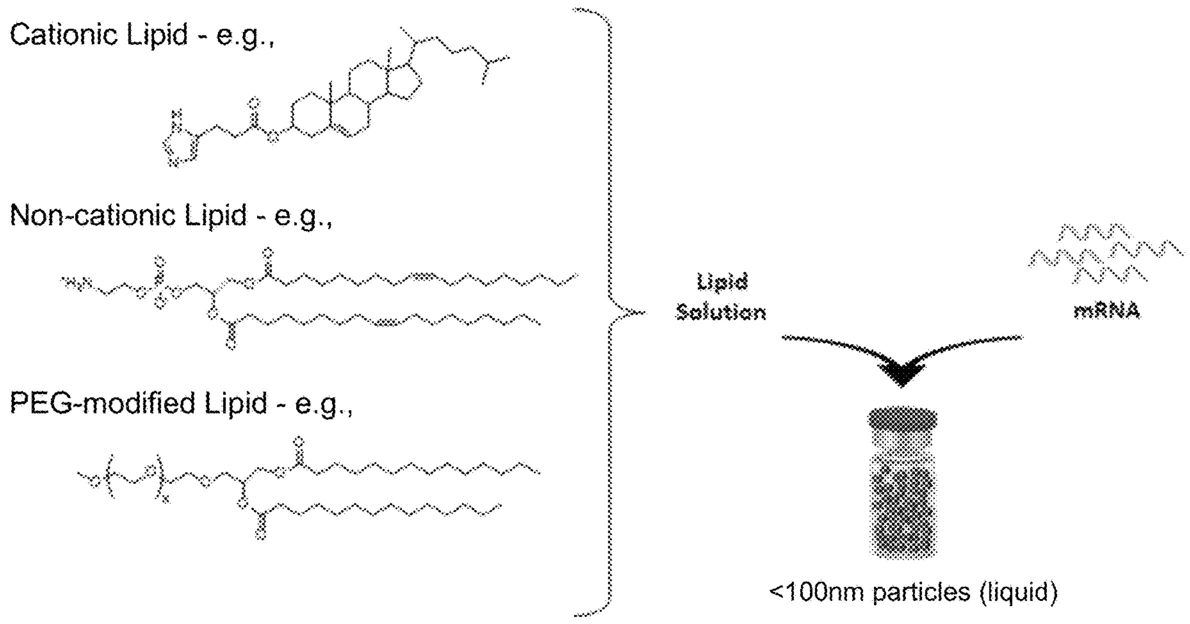
FIG. 1 depicts the general structure of the composition comprising an mRNA encoding a CFTR protein and a simplified formulation process.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term “delivery” encompasses both local and systemic delivery. For example, delivery of mRNA encompasses situations in which an mRNA is delivered to a target tissue and the encoded protein is expressed and retained within the target tissue (also referred to as “local distribution” or “local delivery”), and situations in which an mRNA is delivered to a target tissue and the encoded protein is expressed and secreted into patient's circulation system (e.g., serum) and systematically distributed and taken up by other tissues (also referred to as “systemic distribution” or “systemic delivery). In some embodiments, delivery is pulmonary delivery, e.g., comprising nebulization.

Encapsulation: As used herein, the term “encapsulation,” or grammatical equivalent, refers to the process of confining an mRNA molecule within a nanoparticle.

Expression: As used herein, “expression” of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms “expression” and “production,” and grammatical equivalents, are used interchangeably.

Functional: As used herein, a “functional” biological molecule is a biological molecule in a form in which it exhibits a property and/or activity by which it is characterized.

Half-life: As used herein, the term “half-life” is the time required for a quantity such as nucleic acid or protein concentration or activity to fall to half of its value as measured at the beginning of a time period.

Improve, increase, or reduce: As used herein, the terms “improve,” “increase” or “reduce,” or grammatical equivalents, indicate values that are relative to a baseline measurement, such as a measurement in the same individual prior to initiation of the treatment described herein, or a measurement in a control subject (or multiple control subject) in the absence of the treatment described herein. A “control subject” is a subject afflicted with the same form of disease as the subject being treated, who is about the same age as the subject being treated.

In Vitro: As used herein, the term “in vitro” refers to events that occur in an artificial environment, e.g., in a test tube or reaction vessel, in cell culture, etc., rather than within a multi-cellular organism.

In Vivo: As used herein, the term “in vivo” refers to events that occur within a multi-cellular organism, such as a human and a non-human animal. In the context of cell-based systems, the term may be used to refer to events that occur within a living cell (as opposed to, for example, in vitro systems).

Isolated: As used herein, the term “isolated” refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is “pure” if it is substantially free of other components. As used herein, calculation of percent purity of isolated substances and/or entities should not include excipients (e.g., buffer, solvent, water, etc.).

messenger RNA (mRNA): As used herein, the term “messenger RNA (mRNA)” refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated.

Nucleic acid: As used herein, the term “nucleic acid,” in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, “nucleic acid” refers to individual nucleic acid residues (e.g., nucleotides and/or nucleosides). In some embodiments, “nucleic acid” refers to a polynucleotide chain comprising individual nucleic acid residues. In some embodiments, “nucleic acid” encompasses RNA as well as single and/or double-stranded DNA and/or cDNA. Furthermore, the terms “nucleic acid,” “DNA,” “RNA,” and/or similar terms include nucleic acid analogs, i.e., analogs having other than a phosphodiester backbone. For example, the so-called “peptide nucleic acids,” which are known in the art and have peptide bonds instead of phosphodiester bonds in the backbone, are considered within the scope of the present invention. The term “nucleotide sequence encoding an amino acid sequence” includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases;

modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods of treating cystic fibrosis comprising a step of administering to a subject in need of treatment a composition comprising an mRNA encoding a Cystic Fibrosis Transmembrane Conductance Regulator (CFTR) protein, wherein the mRNA encoding the CFTR protein comprises a polynucleotide sequence at least 80% identical to SEQ ID NO: 1, wherein the mRNA is at a concentration of at least 0.4 mg/mL, and wherein the step of administering comprises inhalation.

Various aspects of the invention are described in detail in the following sections. The use of sections is not meant to limit the invention. Each section can apply to any aspect of the invention. In this application, the use of "or" means "and/or" unless stated otherwise.

Cystic Fibrosis

Cystic fibrosis, also known as mucoviscidosis, is an autosomal recessive genetic disorder that affects most critically the lungs, and also the pancreas, liver, and intestine (Gibson et al., *Am J Respir Crit Care Med.* (2003) 168(8): 918-951; Ratjen et al., *Lancet Lond Engl.* (2003) 361(9358): 681-689; O'Sullivan et al., *Lancet Lond Engl.* (2009) 373 (9678):1891-1904). Cystic fibrosis is caused by mutations in the gene encoding for the cystic fibrosis transmembrane conductance regulator (CFTR) protein. This protein functions as a channel that transports chloride ions across the membrane of cells and is required to regulate the components of mucus, sweat, saliva, tears, and digestive enzymes. Disease-causing mutations in the CFTR protein cause dysfunction of its channel activity resulting in abnormal transport of chloride and sodium ions across the epithelium, leading to the thick, viscous secretions in the lung, pancreas and other organs characteristic of CF disease (O'Sulliven et al., *Lancet Lond Engl.* (2009) 373(9678):1891-1904; Rowe et al., *N Engl J Med.* (2005) 352(19):1992-2001). Most CF patients develop severe, chronic lung disease related to airway obstruction partly due to increased levels of sulfated mucins, inflammation, and recurrent infections that are eventually lethal; the median predicted survival age in the US is 40.7 years. Cystic fibrosis is the most frequent lethal genetic disease in the white population.

Symptoms often appear in infancy and childhood, with respiratory symptoms the most frequent followed by failure to thrive, steatorrhea, and meconium ileus (Gibson et al., *Am J Respir Crit Care Med.* (2003) 168(8):918-951). The most common complications of CF are pulmonary related and include blockages of the narrow passages of affected organs with thickened secretions. These blockages lead to remodeling and infection in the lung, cause damage in the pancreas due to accumulated digestive enzymes, and blockages of the intestines. Diabetes is the most common non-pulmonary complication and is a distinct entity known as CF-related diabetes.

The lungs of individuals with CF are colonized and infected by bacteria from an early age. This leads to chronic airway infection and inflammation, progressing to bronchiectasis, gas trapping, hypoxemia, and hypercarbia. Pulmonary insufficiency is responsible for 68.1% of CF-related deaths in the US. In the initial stage, common bacteria such as *Staphylococcus aureus* and *Hemophilus influenzae* colonize and infect the lungs. Eventually, *Pseudomonas aeruginosa* (and sometimes *Burkholderia cepacia*) dominates. By 18 years of age, 80% of patients with classic CF harbor *P. aeruginosa*, and 3.5% harbor *B. cepacia*. Once within the lungs, these bacteria adapt to the environment and develop resistance to commonly used antibiotics.

The underlying defect causing CF is abnormal epithelial anion transport due to the lack of expression or dysfunction of the CFTR protein. The CFTR protein primarily functions as a chloride channel in epithelial cell membranes; however, it also involved in a number of other cellular membrane functions such as inhibition of sodium transport through the epithelial sodium channel, regulation of the outwardly rectifying chloride channel, and regulation of adenosine triphosphate (ATP) channels (O'Sullivan et al., *Lancet Lond Engl.* (2009) 373(9678):1891-1904). CF is caused by mutations in the gene encoding for the CFTR protein, of which more than 1,500 disease-causing mutations have been identified (O'Sullivan et al., *Lancet Lond Engl.* (2009) 373 (9678):1891-1904). The more common gene mutations result in the lack of synthesis of the CFTR protein (class I), defective processing and maturation of the CFTR protein (class II), or the expression of a CFTR protein defective in regulation, e.g., diminished ATP binding and hydrolysis (class III) (Rowe et al., *N Engl J Med.* (2005) 352(19):1992-2001). A deletion of phenylalanine at position 508 (F508del) is the most common CFTR mutation worldwide and is a class II defect in which the misfolded protein is rapidly degraded by the cell soon after synthesis (Rowe et al., *N Engl J Med.* (2005) 352(19):1992-2001). The lack of a functional CFTR protein causes mucosal obstruction of exocrine glands in CF patients secondary to abnormal transport of chloride and sodium across the epithelium. In the lung, this leads to the development of thick, tenacious secretions that obstruct the airways and submucosal glands, which in turn leads to chronic bacterial infection and inflammation, as described above.

Respiratory symptoms of cystic fibrosis include: a persistent cough that produces thick mucus (sputum), wheezing, breathlessness, exercise intolerance, repeated lung infections and inflamed nasal passages or a stuffy nose. Digestive symptoms of cystic fibrosis include: foul-smelling, greasy stools, poor weight gain and growth, intestinal blockage, particularly in newborns (meconium ileus), and severe constipation.

There are several different methods for assessing symptoms of cystic fibrosis. In one embodiment, one or more symptoms of cystic fibrosis are assessed by forced expiratory volume (FEV), which measures how much air a person can exhale during a forced breath. In one embodiment, the amount of air exhaled in the first second of the forced breath is measured ($FEV_1$). In one embodiment, the amount of air exhaled in the second of the forced breath is measured ($FEV_2$). In one embodiment, the amount of air exhaled in the third second of the forced breath is measured ($FEV_3$). In one embodiment, the forced vital capacity (FVC), which is the total amount of air exhaled during a FEV test, is measured. In one embodiment, one or more symptoms of cystic fibrosis are assessed by Cystic Fibrosis Questionnaire Revise (CFQ-R) respiratory domain score. CFQ-R respiratory domain score is a measure of respiratory symptoms relevant to patients with CF such as cough, sputum production, and difficulty breathing. In one embodiment, one or more symptoms of cystic fibrosis are assessed by relative risk of pulmonary exacerbation. In one embodiment, one or more symptoms of cystic fibrosis are assessed by change in body weight. In one embodiment, one or more symptoms of cystic fibrosis are assessed by change in sweat chloride (mmol/L).

Patient Selection

The present invention is suitable for treatment of patients with various CFTR defects including, but not limited to, patients with different CFTR symptoms, mutations or classes described herein.

In some embodiments, the present invention may be used to treat patients carrying one or more, two or more, three or more, four or more, or five or more mutations from Class I (Defective Protein Synthesis) shown in Table 1. In some embodiments, the present invention may be used to treat patients carrying one or more, two or more, three or more, four or more, or five or more mutations from Class II (Abnormal Processing and Trafficking) shown in Table 1. In some embodiments, the present invention may be used to treat patients carrying one or more, two or more, three or more, four or more, or five or more mutations from Class III (Defective Chanel Regulation/Gating) shown in Table 1. In some embodiments, the present invention may be used to treat patients carrying one or more, two or more, three or more, four or more, or five or more mutations from Class IV (Decreased Channel Conductance) shown in Table 1. In some embodiments, the present invention may be used to treat patients carrying one or more, two or more, three or more, four or more, or five or more mutations from Class V (Reduced Synthesis and/or Trafficking) shown in Table 1. In some embodiments, the present invention may be used to treat patients carrying any combination of specific mutations selected from Table 1 (e.g., one or more, two or more, three or more, four or more, five or more, six or more, seven or more, eight or more, nine or more, or ten or more mutations from different classes shown in Table 1).

TABLE 1

Classification of CFTR Gene Mutations

| Category | Mutation | Specific mutations |
|---|---|---|
| Class I | Defective Protein Synthesis (nonsense, frameshift, aberrant splicing) | 1078delT, 1154 insTC, 1525-2A > G, 1717-1G > A, 1898 + 1G > A, 2184delA, 2184 insA, 3007delG, 3120 + 1G > A, 3659delC, 3876delA, 3905insT, 394delTT, 4010del4, 4016insT, 4326delTC, 4374 + 1G > T, 441delA, 556delA, 621 + 1G > T, 621-1G > T, 711 + 1G > T, 875 + 1G > C, E1104X, E585X, E60X, E822X, G542X, G551D/R553X, Q493X, Q552X, Q814X, R1066C, R1162X, R553X, V520F, W1282X, Y1092X |
| Class II | Abnormal Processing and Trafficking | A559T, D979A, ΔF508, ΔI507, G480C, G85E, N1303K, S549I, S549N, S549R |
| Class III | Defective Chanel Regulation/Gating | G1244E, G1349D, G551D, G551S, G85E, H199R, I1072T, I48T, L1077P, R560T, S1255P, S549N (R75Q) |
| Class IV | Decreased Channel Conductance | A800G, D1152H, D1154G, D614G, delM1140, E822K, G314E, G576A, G622D, G85E, H620Q, I1139V, I1234V, L1335P, M1137V, P67L, R117C, R117P, |

TABLE 1-continued

| Classification of CFTR Gene Mutations | | |
|---|---|---|
| Category | Mutation | Specific mutations |
| | | R117H, R334W, R347H, R347P, R347P/R347H, R792G, S1251N, V232D |
| Class V | Reduced Synthesis and/or Trafficking | 2789 + 5G > A, 3120G > A, 3272-26A > G, 3849 + 10kbC > T, 5T variant, 621 + 3A > G, 711 + 3A > G, A445E, A455E, IVS8 poly T, P574H, 875 + 1G > C |

In some embodiments, a patient in need of treatment is a male or female of 2 years or older, or of 3 years or older, or of 6 years or older, or of 7 years or older, or of 12 years or older, or of 13 years or older, or of 18 years or older, or of 19 years or older, or of 25 years or older, or of 25 years or older, or of 30 years or older, or of 35 years or older, or of 40 years or older, or of 45 years or older, or of 50 years or older. In some embodiments, a patient in need of treatment is less than 50 years old, or less than 45 years old, or less than 40 years old, or less than 35 years old, or less than 30 years old, or less than 25 years old, or less than 20 years old, or less than 19 years old, or less than 18 years old, or less than 13 years old, or less than 12 years old, or less than 7 years old, or less than 6 years old, or less than 3 years old, or less than 2 years old. In some embodiments, a patient in need of treatment is a male or female from 2 to 18 years old, or from 2 to 12 years old, or from 2 to 6 years old, or from 6 to 12 years old, or from 6 to 18 years old, or from 12 to 16 years old, or from 2 to 50 years old, or from 6 to 50 years old, or from 12 to 50 years old, or from 18 to 50 years old. In some embodiments, a patient in need of treatment is a female who is pregnant or who may become pregnant.

In some embodiments, a patient in need of treatment has a sweat chloride value of ≥60 mmol/L, ≥65 mmol/L, ≥70 mmol/L, ≥75 mmol/L, ≥80 mmol/L, ≥85 mmol/L, ≥90 mmol/L, ≥95 mmol/L, ≥100 mmol/L, ≥110 mmol/L, ≥120 mmol/L, ≥130 mmol/L, ≥140 mmol/L or ≥150 mmol/L by quantitative pilocarpine iontophoresis (documented in the subject's medical record). In some embodiments, a patient in need of treatment has chronic sinopulmonary disease and/or gastrointestinal/nutritional abnormalities consistent with CF disease. In some embodiments, a patient in need of treatment has chronic sinopulmonary disease and/or gastrointestinal/nutritional abnormalities consistent with CF disease.

In some embodiments, a patient in need of treatment has $FEV_1$≥50% and ≤90% (e.g., ≤85%, ≤80%, ≤75%, ≤70%, ≤65%, ≤60%, or ≤55%) of the predicted normal (i.e., the average FEV of non-CF patients) based on the patient's age, gender, and height. In some embodiments, a patient in need of treatment has resting oxygen saturation ≥92% on room air (pulse oximetry). In some embodiments, a patient in need of treatment has a body mass index ≥17.5 $kg/m^2$ and weight ≥40 kg.

In some embodiments, a patient in need of treatment has received or is concurrently receiving other CF medications. For example, a patient in need of treatment may be receiving lumacaftor/ivacaftor combination drug (Orkambi) or may have been on this treatment for at least 28 days prior to commencement of the treatment according to the present invention. Other CF medications may include, but are not limited to, routine inhaled therapies directed at airway clearance and management of respiratory infections, such as bronchodilators, rhDNase (Pulmozyme), hypertonic saline, antibiotics, and steroids; and other routine CF-related therapies such as systemic antibiotics, pancreatic enzymes, multivitamins, and diabetes and liver medications.

In some embodiments, a patient in need of treatment has been a non-smoker for a minimum of 2 years. In some embodiments, a patient in need of treatment does not receive inhaled rhDNase (Pulmozyme) treatment for 24 hours before and/or after administration of a composition comprising an mRNA encoding a CFTR protein according to the present invention.

In some embodiments, a patient in need of treatment has been treated or is currently being treated with hormone replacement therapies, thyroid hormone replacement therapy, non-steroidal inflammatory drugs, and prescription dronabinol (Marinol) during treatment.

In some embodiments, a patient in need of treatment has discontinued use of one or more other cystic fibrosis treatments described herein. In some embodiments, the patient has discontinued use of one or more other cystic fibrosis treatments for at least 12 hours, at least 24 hours, at least 36 hours, at least 48 hours, at least 72 hours, at least 1 week, at least 2 weeks, at least 3 weeks, at least 4 weeks, at least 5 weeks, at least 6 weeks, at least 7 weeks, or at least 8 weeks prior to administration of a CFTR mRNA according to the present invention. In some embodiments, the patient has discontinued use of one or more other cystic fibrosis treatments for less than 12 hours, less than 24 hours, less than 36 hours, less than 48 hours, less than 72 hours, less than 1 week, less than 2 weeks, less than 3 weeks, less than 4 weeks, less than 5 weeks, less than 6 weeks, less than 7 weeks, less than 8 weeks, less than 9 weeks, or less than 10 weeks prior to administration of a CFTR mRNA according to the present invention.

Formulation and Administration

According to the present invention, a suitable formulation for the treatment contains an mRNA encoding any full length, fragment or portion of a CFTR protein which can be substituted for naturally-occurring CFTR protein activity and/or reduce the intensity, severity, and/or frequency of one or more symptoms associated with cystic fibrosis.

In some embodiments, a suitable mRNA sequence is an mRNA sequence encoding a human CFTR (hCFTR) protein. In some embodiments, a suitable mRNA sequence is codon optimized for efficient expression human cells. An exemplary codon-optimized CFTR mRNA coding sequence and the corresponding amino acid sequence are shown in Table 2:

TABLE 2

| Exemplary CFTR mRNA and Protein Sequences | |
|---|---|
| Codon- | **AUG**CAACGCUCUCCUCUUGAAAAGGCCUCGGUGGUGUCCAAGCUCUU |
| Optimized | CUUCUCGUGGACUAGACCCAUCCUGAGAAAGGGGUACAGACAGCGCU |
| Human | UGGAGCUGUCCGAUAUCUAUCAAAUCCCUUCCGUGGACUCCGCGGAC |
| CFTR | AACCUGUCCGAGAAGCUCGAGAGAGAAUGGGACAGAGAACUCGCCUC |
| mRNA | AAAGAAGAACCCGAAGCUGAUUAAUGCGCUUAGGCGGUGCUUUUUC |
| coding | UGGCGGUUCAUGUUCUACGGCAUCUUCCUCUACCUGGGAGAGGUCAC |
| sequence | CAAGGCCGUGCAGCCCCUGUUGCUGGGACGGAUUAUUGCCUCCUACG |
| | ACCCCGACAACAAGGAAGAAAGAAGCAUCGCUAUCUACUUGGGCAUC |
| | GGUCUGUGCCUGCUUUUCAUCGUCCGGACCCUCUUGUUGCAUCCUGC |
| | UAUUUUCGGCCUGCAUCACAUUGGCAUGCAGAUGAGAAUUGCCAUG |
| | UUUUCCCUGAUCUACAAGAAAACUCUGAAGCUCUCGAGCCGCGUGCU |
| | UGACAAGAUUUCCAUCGGCCAGCUCGUGUCCCUGCUCUCCAACAAUC |
| | UGAACAAGUUCGACGAGGGCCUCGCCCUGGCCCACUUCGUGUGGAUC |
| | GCCCCUCUGCAAGUGGCGCUUCUGAUGGGCCUGAUCUGGGAGCUGCU |
| | GCAAGCCUCGGCAUUCUGUGGGCUUGGAUUCCUGAUCGUGCUGGCAC |
| | UGUUCCAGGCCGGACUGGGGCGGAUGAUGAUGAAGUACAGGGACCA |
| | GAGAGCCGGAAAGAUUUCCGAACGGCUGGUGAUCACUUCGGAAAUG |
| | AUCGAAAACAUCCAGUCAGUGAAGGCCUACUGCUGGGAAGAGGCCAU |
| | GGAAAAGAUGAUUGAAAACCUCCGGCAAACCGAGCUGAAGCUGACCC |
| | GCAAGGCCGCUUACGUGCGCUAUUUCAACUCGUCCGCUUUCUUCUUC |
| | UCCGGGUUCUUCGUGGUGUUUCUCUCCGUGCUCCCCUACGCCCUGAU |
| | UAAGGGAAUCAUCCUCAGGAAGAUCUUCACCACCAUUUCCUUCUGUA |
| | UCGUGCUCCGCAUGGCCGUGACCCGGCAGUUCCCAUGGGCCGUGCAG |
| | ACUUGGUACGACUCCCUGGGAGCCAUUAACAAGAUCCAGGACUUCCU |
| | UCAAAAGCAGGAGUACAAGACCCUCGAGUACAACCUGACUACUACCG |
| | AGGUCGUGAUGGAAAACGUCACCGCCUUUUGGGAGGAGGGAUUUGG |
| | CGAACUGUUCGAGAAGGCCAAGCAGAACAACAACAACCGCAAGACCU |
| | CGAACGGUGACGACUCCCUCUUCUUUUCAAACUUCAGCCUGCUCGGG |
| | ACGCCCGUGCUGAAGGACAUUAACUUCAAGAUCGAAAGAGGACAGCU |
| | CCUGGCGGUGGCCGGAUCGACCGGAGCCGGAAAGACUUCCCUGCUGA |
| | UGGUGAUCAUGGGAGAGCUUGAACCUAGCGAGGGAAAGAUCAAGCA |
| | CUCCGGCCGCAUCAGCUUCUGUAGCCAGUUUUCCUGGAUCAUGCCCG |
| | GAACCAUUAAGGAAAACAUCAUCUUCGGCGUGUCCUACGAUGAAUAC |
| | CGCUACCGGUCCGUGAUCAAAGCCUGCCAGCUGGAAGAGGAUAUUUC |
| | AAAGUUCGCGGAGAAAGAUAACAUCGUGCUGGGCGAAGGGGGUAUU |
| | ACCUUGUCGGGGGGCCAGCGGGCUAGAAUCUCGCUGGCCAGAGCCGU |
| | GUAUAAGGACGCCGACCUGUAUCUCCUGGACUCCCCCUUCGGAUACC |
| | UGGACGUCCUGACCGAAAAGGAGAUCUUCGAAUCGUGCGUGUGCAA |
| | GCUGAUGGCUAACAAGACUCGCAUCCUCGUGACCUCCAAAAUGGAGC |
| | ACCUGAAGAAGGCAGACAAGAUUCUGAUUCUGCAUGAGGGGUCCUCC |
| | UACUUUUACGGCACCUUCUCGGAGUUGCAGAACUUGCAGCCCGACUU |
| | CUCAUCGAAGCUGAUGGGUUGCGACAGCUUCGACCAGUUCUCCGCCG |
| | AAAGAAGGAACUCGAUCCUGACGGAAACCUUGCACCGCUUCUCUUUG |
| | GAAGGCGACGCCCCUGUGUCAUGGACCGAGACUAAGAAGCAGAGCUU |
| | CAAGCAGACCGGGGAAUUCGGCGAAAAGAGGAAGAACAGCAUCUUG |
| | AACCCCAUUAACUCCAUCCGCAAGUUCUCAAUCGUGCAAAAGACGCC |
| | ACUGCAGAUGAACGGCAUUGAGGAGGACUCCGACGAACCCCUUGAGA |
| | GGCGCCUGUCCCUGGUGCCGGACAGCGAGCAGGGAGAAGCCAUCCUG |
| | CCUCGGAUUUCCGUGAUCUCCACUGGUCCGACGCUCCAAGCCCGGCG |
| | GCGGCAGUCCGUGCUGAACCUGAUGACCCACAGCGUGAACCAGGGCC |
| | AAAACAUUCACCGCAAGACUACCGCAUCCACCCGGAAAGUGUCCCUG |
| | GCACCUCAAGCGAAUCUUACCGAGCUCGACAUCUACUCCCGGAGACU |
| | GUCGCAGGAAACCGGGCUCGAAAUUUCCGAAGAAAUCAACGAGGAG |
| | GAUCUGAAAGAGUGCUUCUUCGACGAUAUGGAGUCGAUACCCGCCGU |
| | GACGACUUGGAACACUUAUCUGCGGUACAUCACUGUGCACAAGUCAU |
| | UGAUCUUCGUGCUGAUUUGGUGCCUGGUGAUUUUCCUGGCCGAGGU |
| | CGCGGCCUCACUGGUGGUGCUCUGGCUGUUGGGAAACACGCCUCUGC |
| | AAGACAAGGGAAACUCCACGCACUCGAGAAACAACAGCUAUGCCGUG |
| | AUUAUCACUUCCACCUCCUCUUAUUACGUGUUCUACAUCUACGUCGG |
| | AGUGGCGGAUACCCUGCUCGCGAUGGGUUUCUUCAGAGGACUGCCGC |
| | UGGUCCACACCUUGAUCACCGUCAGCAAGAUUCUUCACCACAAGAUG |
| | UUGCAUAGCGUGCUGCAGGCCCCCAUGUCCACCCUCAACACUCUGAA |
| | GGCCGGAGGCAUUCUGAACAGAUUCUCCAAGGACAUCGCUAUCCUGG |
| | ACGAUCUCCUGCCGCUUACCAUCUUUGACUUCAUCCAGCUGCUGCUG |
| | AUCGUGAUUGGAGCAAUCGCAGUGGUGGCGGUGCUGCAGCCUUACA |
| | UUUUCGUGGCCACUGUGCCGGUCAUUGUGGCGUUCAUCAUGCUGCGG |
| | GCCUACUUCCUCCAAACCAGCCAGCAGCUGAAGCAACUGGAAUCCGA |
| | GGGACGAUCCCCCAUCUUCACUCACCUUGUGACGUCGUUGAAGGGAC |
| | UGUGGACCCUCCGGGCUUUCGGACGGCAGCCCUACUUCGAAACCCUC |
| | UUCCACAAGGCCCUGAACCUCCACACCGCCAAUUGGUUCCUGUACCU |
| | GUCCACCCUGCGGUGGUUCCAGAUGCGCAUCGAGAUGAUUUUCGUCA |
| | UCUUCUUCAUCGCGGUCACAUUCAUCAGCAUCCUGACUACCGGAGAG |
| | GGAGAGGGACGGGUCGGAAUAAUCCUGACCCUCGCCAUGAACAUUAU |
| | GAGCACCCUGCAGUGGGCAGUGAACAGCUCGAUCGACGUGGACAGCC |
| | UGAUGCGAAGCGUCAGCCGCGUGUUCAAGUUCAUCGACAUGCCUACU |
| | GAGGGAAAACCCACUAAGUCCACUAAGCCCUACAAAAAUGGCCAGCU |
| | GAGCAAGGUCAUGAUCAUCGAAAACUCCCACGUGAAGAAGGACGAU |
| | AUUUGGCCCUCCGGAGGUCAAAUGACCGUGAAGGACCUGACCGCAAA |

TABLE 2-continued

| Exemplary CFTR mRNA and Protein Sequences | |
|---|---|
| | GUACACCGAGGGAGGAAACGCCAUUCUCGAAAACAUCAGCUUCUCCA<br>UUUCGCCGGGACAGCGGGUCGGCCUUCUCGGGCGGACCGGUUCCGGG<br>AAGUCAACUCUGCUGUCGGCUUUCCUCCGGCUGCUGAAUACCGAGGG<br>GGAAAUCCAAAUUGACGGCGUGUCUUGGGAUUCCAUUACUCUGCAGC<br>AGUGGCGGAAGGCCUUCGGCGUGAUCCCCCAGAAGGUGUUCAUCUUC<br>UCGGGUACCUUCCGGAAGAACCUGGAUCCUUACGAGCAGUGGAGCGA<br>CCAAGAAAUCUGGAAGGUCGCCGACGAGGUCGGCCUGCGCUCCGUGA<br>UUGAACAAUUUCCUGGAAAGCUGGACUUCGUGCUCGUCGACGGGGG<br>AUGUGUCCUGUCGCACGGACAUAAGCAGCUCAUGUGCCUCGCACGGU<br>CCGUGCUCUCCAAGGCCAAGAUUCUGCUGCUGGACGAACCUUCGGCC<br>CACCUGGAUCCGGUCACCUACCAGAUCAUCAGGAGGACCCUGAAGCA<br>GGCCUUUGCCGAUUGCACCGUGAUUCUCUGCGAGCACCGCAUCGAGG<br>CCAUGCUGGAGUGCCAGCAGUUCCUGGUCAUCGAGGAGAACAAGGUC<br>CGCCAAUACGACUCCAUUCAAAAGCUCCUCAACGAGCGGUCGCUGUU<br>CAGACAAGCUAUUUCACCGUCCGAUAGAGUGAAGCUCUUCCCGCAUC<br>GGAACAGCUCAAAGUGCAAAUCGAAGCCGCAGAUCGCAGCCUUGAAG<br>GAAGAGACUGAGGAAGAGGUGCAGGACACCCGGCUU**UAA** (SEQ ID<br>NO: 1) |
| Human<br>CFTR<br>Protein<br>Sequence | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE<br>KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNSILTETLHR<br>FSLEGDAPVSWTETKKQSFKQTGEFGEKRKNSILNPINSIRKFSIVQKTPLQ<br>MNGIEEDSDEPLERRLSLVPDSEQGEAILPRISVISTGPTLQARRRQSVLNL<br>MTHSVNQGQNIHRKTTASTRKVSLAPQANLTELDIYSRRLSQETGLEISEEI<br>NEEDLKECFFDDMESIPAVTTWNTYLRYITVHKSLIFVLIWCLVIFLAEVAA<br>SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSK<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHKALN<br>LHTANWFLYLSTLRWFQMRIEMIFVIFFIAVTFISILTTGEGEGRVGIILTLA<br>MNIMSTLQWAVNSSIDVDSLMRSVSRVFKFIDMPTEGKPTKSTKPYKNGQ<br>LSKVMIIENSHVKKDDIWPSGGQMTVKDLTAKYTEGGNAILENISFSISPGQ<br>RVGLLGRTGSGKSTLLSAFLRLLNTEGEIQIDGVSWDSITLQQWRKAFGVIP<br>QKVFIFSGTFRKNLDPYEQWSDQEIWKVADEVGLRSVIEQFPGKLDFVLVD<br>GGCVLSHGHKQLMCLARSVLSKAKILLLDEPSAHLDPVTYQIIRRTLKQAF<br>ADCTVILCEHRIEAMLECQQFLVIEENKVRQYDSIQKLLNERSLFRQAISPS<br>DRVKLFPHRNSSKCKSKPQIAALKEETEEEVQDTRL (SEQ ID NO: 2) |

In one embodiment, a codon-optimized CFTR mRNA sequence includes SEQ ID NO: 1. In some embodiments, a codon-optimized CFTR mRNA sequence suitable for the present invention shares at least 60%, 65%, 70%, 75%, 80%, 85%, 90%, 95%, 96%, 97%, 98%, or 99% identity to SEQ ID NO:1 and encodes a CFTR protein having an amino acid sequence of SEQ ID NO:2.

In some embodiments, a CFTR mRNA suitable for the invention also contains 5' and 3' UTR sequences. Exemplary 5' and 3' UTR sequences are shown below:

Exemplary 5' UTR Sequence (SEQ ID NO: 3)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Exemplary 3' UTR Sequence (SEQ ID NO: 4)

CGGGUGGCAUCCCUGUGACCCCUCCCCAGUGCCUCUCCUGGCCCUGGAAG

-continued

UUGCCACUCCAGUGCCCACCAGCCUUGUCCUAAUAAAAUUAAGUUGCAUC

AAGCU

OR (SEQ ID NO: 5)

GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AAGCU

Thus, in one embodiment, an exemplary full-length codon-optimized CFTR mRNA sequence suitable for the invention is:

(SEQ ID NO: 6)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGCAACGCU

CUCCUCUUGAAAAGGCCUCGGUGGUGUCCAAGCUCUUCUUCUCGUGGACU

-continued

AGACCCAUCCUGAGAAAGGGGUACAGACAGCGCUUGGAGCUGUCCGAUAU

CUAUCAAAUCCCUUCCGUGGACUCCGCGGACAACCUGUCCGAGAAGCUCG

AGAGAGAAUGGGACAGAGAACUCGCCUCAAAGAAGAACCCGAAGCUGAUU

AAUGCGCUUAGGCGGUGCUUUUUCUGGCGGUUCAUGUUCUACGGCAUCUU

CCUCUACCUGGGAGAGGUCACCAAGGCCGUGCAGCCCCUGUUGCUGGGAC

GGAUUAUUGCCUCCUACGACCCCGACAACAAGGAAGAAAGAAGCAUCGCU

AUCUACUUGGGCAUCGGUCUGUGCCUGCUUUUCAUCGUCCGGACCCUCUU

GUUGCAUCCUGCUAUUUUCGGCCUGCAUCACAUUGGCAUGCAGAUGAGAA

UUGCCAUGUUUUCCCUGAUCUACAAGAAAACUCUGAAGCUCUCGAGCCGC

GUGCUUGACAAGAUUUCCAUCGGCCAGCUCGUGUCCCUGCUCUCCAACAA

UCUGAACAAGUUCGACGAGGGCCUCGCCCUGGCCCACUUCGUGUGGAUCG

CCCCUCUGCAAGUGGCGCUUCUGAUGGGCCUGAUCUGGGAGCUGCUGCAA

GCCUCGGCAUUCUGUGGGCUUGGAUUCCUGAUCGUGCUGGCACUGUUCCA

GGCCGGACUGGGGCGGAUGAUGAUGAAGUACAGGGACCAGAGAGCCGGAA

AGAUUUCCGAACGGCUGGUGAUCACUUCGGAAAUGAUCGAAAACAUCCAG

UCAGUGAAGGCCUACUGCUGGGAAGAGGCCAUGGAAAAGAUGAUUGAAAA

CCUCCGGCAAACCGAGCUGAAGCUGACCCGCAAGGCCGCUUACGUGCGCU

AUUUCAACUCGUCCGCUUUCUUCUUCUCCGGGUUCUUCGUGGUGUUUCUC

UCCGUGCUCCCCUACGCCCUGAUUAAGGGAAUCAUCCUCAGGAAGAUCUU

CACCACCAUUUCCUUCUGUAUCGUGCUCCGCAUGGCCGUGACCCGGCAGU

UCCCAUGGGCCGUGCAGACUUGGUACGACUCCCUGGGAGCCAUUAACAAG

AUCCAGGACUUCCUUCAAAAGCAGGAGUACAAGACCCUCGAGUACAACCU

GACUACUACCGAGGUCGUGAUGGAAAACGUCACCGCCUUUUGGGAGGAGG

GAUUUGGCGAACUGUUCGAGAAGGCCAAGCAGAACAACAACAACCGCAAG

ACCUCGAACGGUGACGACUCCCUCUUCUUUUCAAACUUCAGCCUGCUCGG

GACGCCCGUGCUGAAGGACAUUAACUUCAAGAUCGAAAGAGGACAGCUCC

UGGCGGUGGCCGGAUCGACCGGAGCCGGAAAGACUUCCCUGCUGAUGGUG

AUCAUGGGAGAGCUUGAACCUAGCGAGGGAAAGAUCAAGCACUCCGGCCG

CAUCAGCUUCUGUAGCCAGUUUUCCUGGAUCAUGCCCGGAACCAUUAAGG

AAAACAUCAUCUUCGGCGUGUCCUACGAUGAAUACCGCUACCGGUCCGUG

AUCAAAGCCUGCCAGCUGGAAGAGGAUAUUUCAAAGUUCGCGGAGAAAGA

UAACAUCGUGCUGGGCGAAGGGGGUAUUACCUUGUCGGGGGGCCAGCGGG

CUAGAAUCUCGCUGGCCAGAGCCGUGUAUAAGGACGCCGACCUGUAUCUC

CUGGACUCCCCCUUCGGAUACCUGGACGUCCUGACCGAAAAGGAGAUCUU

CGAAUCGUGCGUGUGCAAGCUGAUGGCUAACAAGACUCGCAUCCUCGUGA

CCUCCAAAAUGGAGCACCUGAAGAAGGCAGACAAGAUUCUGAUUCUGCAU

GAGGGGUCCUCCUACUUUUACGGCACCUUCUCGGAGUUGCAGAACUUGCA

GCCCGACUUCUCAUCGAAGCUGAUGGGUUGCGACAGCUUCGACCAGUUCU

CCGCCGAAAGAAGGAACUCGAUCCUGACGGAAACCUUGCACCGCUUCUCU

UUGGAAGGCGACGCCCCUGUGUCAUGGACCGAGACUAAGAAGCAGAGCUU

-continued

CAAGCAGACCGGGGAAUUCGGCGAAAAGAGGAAGAACAGCAUCUUGAACC

CCAUUAACUCCAUCCGCAAGUUCUCAAUCGUGCAAAAGACGCCACUGCAG

AUGAACGGCAUUGAGGAGGACUCCGACGAACCCCUUGAGAGGCGCCUGUC

CCUGGUGCCGGACAGCGAGCAGGGAGAAGCCAUCCUGCCUCGGAUUUCCG

UGAUCUCCACUGGUCCGACGCUCCAAGCCCGGCGGCGGCAGUCCGUGCUG

AACCUGAUGACCCACAGCGUGAACCAGGGCCAAAACAUUCACCGCAAGAC

UACCGCAUCCACCCGGAAAGUGUCCCUGGCACCUCAAGCGAAUCUUACCG

AGCUCGACAUCUACUCCCGGAGACUGUCGCAGGAAACCGGGCUCGAAAUU

UCCGAAGAAAUCAACGAGGAGGAUCUGAAAGAGUGCUUCUUCGACGAUAU

GGAGUCGAUACCCGCCGUGACGACUUGGAACACUUAUCUGCGGUACAUCA

CUGUGCACAAGUCAUUGAUCUUCGUGCUGAUUUGGUGCCUGGUGAUUUUC

CUGGCCGAGGUCGCGGCCUCACUGGUGGUGCUCUGGCUGUUGGGAAACAC

GCCUCUGCAAGACAAGGGAAACUCCACGCACUCGAGAAACAACAGCUAUG

CCGUGAUUAUCACUUCCACCUCCUCUUAUUACGUGUUCUACAUCUACGUC

GGAGUGGCGGAUACCCUGCUCGCGAUGGGUUUCUUCAGAGGACUGCCGCU

GGUCCACACCUUGAUCACCGUCAGCAAGAUUCUUCACCACAAGAUGUUGC

AUAGCGUGCUGCAGGCCCCCAUGUCCACCCUCAACACUCUGAAGGCCGGA

GGCAUUCUGAACAGAUUCUCCAAGGACAUCGCUAUCCUGGACGAUCUCCU

GCCGCUUACCAUCUUUGACUUCAUCCAGCUGCUGCUGAUCGUGAUUGGAG

CAAUCGCAGUGGUGGCGGUGCUGCAGCCUUACAUUUUCGUGGCCACUGUG

CCGGUCAUUGUGGCGUUCAUCAUGCUGCGGGCCUACUUCCUCCAAACCAG

CCAGCAGCUGAAGCAACUGGAAUCCGAGGGACGAUCCCCCAUCUUCACUC

ACCUUGUGACGUCGUUGAAGGGACUGUGGACCCUCCGGGCUUUCGGACGG

CAGCCCUACUUCGAAACCCUCUUCCACAAGGCCCUGAACCUCCACACCGC

CAAUUGGUUCCUGUACCUGUCCACCCUGCGGUGGUUCCAGAUGCGCAUCG

AGAUGAUUUUCGUCAUCUUCUUCAUCGCGGUCACAUUCAUCAGCAUCCUG

ACUACCGGAGAGGGAGAGGGACGGGUCGGAAUAAUCCUGACCCUCGCCAU

GAACAUUAUGAGCACCCUGCAGUGGGCAGUGAACAGCUCGAUCGACGUGG

ACAGCCUGAUGCGAAGCGUCAGCCGCGUGUUCAAGUUCAUCGACAUGCCU

ACUGAGGGAAAACCCACUAAGUCCACUAAGCCCUACAAAAAUGGCCAGCU

GAGCAAGGUCAUGAUCAUCGAAAACUCCCACGUGAAGAAGGACGAUAUUU

GGCCCUCCGGAGGUCAAAUGACCGUGAAGGACCUGACCGCAAAGUACACC

GAGGGAGGAAACGCCAUUCUCGAAAACAUCAGCUUCUCCAUUUCGCCGGG

ACAGCGGGUCGGCCUUCUCGGGCGGACCGGUUCCGGGAAGUCAACUCUGC

UGUCGGCUUUCCUCCGGCUGCUGAAUACCGAGGGGGAAAUCCAAAUUGAC

GGCGUGUCUUGGGAUUCCAUUACUCUGCAGCAGUGGCGGAAGGCCUUCGG

CGUGAUCCCCCAGAAGGUGUUCAUCUUCUCGGGUACCUUCCGGAAGAACC

UGGAUCCUUACGAGCAGUGGAGCGACCAAGAAAUCUGGAAGGUCGCCGAC

GAGGUCGGCCUGCGCUCCGUGAUUGAACAAUUUCCUGGAAAGCUGGACUU

CGUGCUCGUCGACGGGGGAUGUGUCCUGUCGCACGGACAUAAGCAGCUCA

UGUGCCUCGCACGGUCCGUGCUCUCCAAGGCCAAGAUUCUGCUGCUGGAC

-continued

GAACCUUCGGCCCACCUGGAUCCGGUCACCUACCAGAUCAUCAGGAGGAC
CCUGAAGCAGGCCUUUGCCGAUUGCACCGUGAUUCUCUGCGAGCACCGCA
UCGAGGCCAUGCUGGAGUGCCAGCAGUUCCUGGUCAUCGAGGAGAACAAG
GUCCGCCAAUACGACUCCAUUCAAAAGCUCCUCAACGAGCGGUCGCUGUU
CAGACAAGCUAUUUCACCGUCCGAUAGAGUGAAGCUCUUCCCGCAUCGGA
ACAGCUCAAAGUGCAAAUCGAAGCCGCAGAUCGCAGCCUUGAAGGAAGAG
ACUGAGGAAGAGGUGCAGGACACCCGGCUUUAACGGGUGGCAUCCCUGUG
ACCCCUCCCCAGUGCCUCUCCUGGCCCUGGAAGUUGCCACUCCAGUGCCC
ACCAGCCUUGUCCUAAUAAAAUUAAGUUGCAUCAAGCU

In another embodiment, an exemplary full-length codon-optimized CFTR mRNA sequence is:

(SEQ ID NO: 7)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACGAUGCAACGCU
CUCCUCUUGAAAAGGCCUCGGUGGUGUCCAAGCUCUUCUUCUCGUGGACU
AGACCCAUCCUGAGAAAGGGGUACAGACAGCGCUUGGAGCUGUCCGAUAU
CUAUCAAAUCCCUUCCGUGGACUCCGCGGACAACCUGUCCGAGAAGCUCG
AGAGAGAAUGGGACAGAGAACUCGCCUCAAAGAAGAACCCGAAGCUGAUU
AAUGCGCUUAGGCGGUGCUUUUUCUGGCGGUUCAUGUUCUACGGCAUCUU
CCUCUACCUGGGAGAGGUCACCAAGGCCGUGCAGCCCCUGUUGCUGGGAC
GGAUUAUUGCCUCCUACGACCCCGACAACAAGGAAGAAAGAAGCAUCGCU
AUCUACUUGGGCAUCGGUCUGUGCCUGCUUUUCAUCGUCCGGACCCUCUU
GUUGCAUCCUGCUAUUUUCGGCCUGCAUCACAUUGGCAUGCAGAUGAGAA
UUGCCAUGUUUUCCCUGAUCUACAAGAAAACUCUGAAGCUCUCGAGCCGC
GUGCUUGACAAGAUUUCCAUCGGCCAGCUCGUGUCCCUGCUCUCCAACAA
UCUGAACAAGUUCGACGAGGGCCUCGCCCUGGCCCACUUCGUGUGGAUCG
CCCCUCUGCAAGUGGCGCUUCUGAUGGGCCUGAUCUGGGAGCUGCUGCAA
GCCUCGGCAUUCUGUGGGCUUGGAUUCCUGAUCGUGCUGGCACUGUUCCA
GGCCGGACUGGGGCGGAUGAUGAUGAAGUACAGGGACCAGAGAGCCGGAA
AGAUUUCCGAACGGCUGGUGAUCACUUCGGAAAUGAUCGAAAACAUCCAG
UCAGUGAAGGCCUACUGCUGGGAAGAGGCCAUGGAAAAGAUGAUUGAAAA
CCUCCGGCAAACCGAGCUGAAGCUGACCCGCAAGGCCGCUUACGUGCGCU
AUUUCAACUCGUCCGCUUUCUUCUUCUCCGGGUUCUUCGUGGUGUUUCUC
UCCGUGCUCCCCUACGCCCUGAUUAAGGGAAUCAUCCUCAGGAAGAUCUU
CACCACCAUUUCCUUCUGUAUCGUGCUCCGCAUGGCCGUGACCCGGCAGU
UCCCAUGGGCCGUGCAGACUUGGUACGACUCCCUGGGAGCCAUUAACAAG
AUCCAGGACUUCCUUCAAAAGCAGGAGUACAAGACCCUCGAGUACAACCU
GACUACUACCGAGGUCGUGAUGGAAAACGUCACCGCCUUUUGGGAGGAGG
GAUUUGGCGAACUGUUCGAGAAGGCCAAGCAGAACAACAACAACCGCAAG

-continued

ACCUCGAACGGUGACGACUCCCUCUUCUUUUCAAACUUCAGCCUGCUCGG
GACGCCCGUGCUGAAGGACAUUAACUUCAAGAUCGAAAGAGGACAGCUCC
UGGCGGUGGCCGGAUCGACCGGAGCCGGAAAGACUUCCCUGCUGAUGGUG
AUCAUGGGAGAGCUUGAACCUAGCGAGGGAAAGAUCAAGCACUCCGGCCG
CAUCAGCUUCUGUAGCCAGUUUUCCUGGAUCAUGCCCGGAACCAUUAAGG
AAAACAUCAUCUUCGGCGUGUCCUACGAUGAAUACCGCUACCGGUCCGUG
AUCAAAGCCUGCCAGCUGGAAGAGGAUAUUUCAAAGUUCGCGGAGAAAGA
UAACAUCGUGCUGGGCGAAGGGGGUAUUACCUUGUCGGGGGGCCAGCGGG
CUAGAAUCUCGCUGGCCAGAGCCGUGUAUAAGGACGCCGACCUGUAUCUC
CUGGACUCCCCCUUCGGAUACCUGGACGUCCUGACCGAAAAGGAGAUCUU
CGAAUCGUGCGUGUGCAAGCUGAUGGCUAACAAGACUCGCAUCCUCGUGA
CCUCCAAAAUGGAGCACCUGAAGAAGGCAGACAAGAUUCUGAUUCUGCAU
GAGGGGUCCUCCUACUUUUACGGCACCUUCUCGGAGUUGCAGAACUUGCA
GCCCGACUUCUCAUCGAAGCUGAUGGGUUGCGACAGCUUCGACCAGUUCU
CCGCCGAAAGAAGGAACUCGAUCCUGACGGAAACCUUGCACCGCUUCUCU
UUGGAAGGCGACGCCCCUGUGUCAUGGACCGAGACUAAGAAGCAGAGCUU
CAAGCAGACCGGGGAAUUCGGCGAAAAGAGGAAGAACAGCAUCUUGAACC
CCAUUAACUCCAUCCGCAAGUUCUCAAUCGUGCAAAAGACGCCACUGCAG
AUGAACGGCAUUGAGGAGGACUCCGACGAACCCCUUGAGAGGCGCCUGUC
CCUGGUGCCGGACAGCGAGCAGGGAGAAGCCAUCCUGCCUCGGAUUUCCG
UGAUCUCCACUGGUCCGACGCUCCAAGCCCGGCGGCGGCAGUCCGUGCUG
AACCUGAUGACCCACAGCGUGAACCAGGGCCAAAACAUUCACCGCAAGAC
UACCGCAUCCACCCGGAAAGUGUCCCUGGCACCUCAAGCGAAUCUUACCG
AGCUCGACAUCUACUCCCGGAGACUGUCGCAGGAAACCGGGCUCGAAAUU
UCCGAAGAAAUCAACGAGGAGGAUCUGAAAGAGUGCUUCUUCGACGAUAU
GGAGUCGAUACCCGCCGUGACGACUUGGAACACUUAUCUGCGGUACAUCA
CUGUGCACAAGUCAUUGAUCUUCGUGCUGAUUUGGUGCCUGGUGAUUUUC
CUGGCCGAGGUCGCGGCCUCACUGGUGGUGCUCUGGCUGUUGGGAAACAC
GCCUCUGCAAGACAAGGGAAACUCCACGCACUCGAGAAACAACAGCUAUG
CCGUGAUUAUCACUUCCACCUCCUCUUAUUACGUGUUCUACAUCUACGUC
GGAGUGGCGGAUACCCUGCUCGCGAUGGGUUUCUUCAGAGGACUGCCGCU
GGUCCACACCUUGAUCACCGUCAGCAAGAUUCUUCACCACAAGAUGUUGC
AUAGCGUGCUGCAGGCCCCCAUGUCCACCCUCAACACUCUGAAGGCCGGA
GGCAUUCUGAACAGAUUCUCCAAGGACAUCGCUAUCCUGGACGAUCUCCU
GCCGCUUACCAUCUUUGACUUCAUCCAGCUGCUGCUGAUCGUGAUUGGAG
CAAUCGCAGUGGUGGCGGUGCUGCAGCCUUACAUUUUCGUGGCCACUGUG
CCGGUCAUUGUGGCGUUCAUCAUGCUGCGGGCCUACUUCCUCCAAACCAG
CCAGCAGCUGAAGCAACUGGAAUCCGAGGGACGAUCCCCCAUCUUCACUC
ACCUUGUGACGUCGUUGAAGGGACUGUGGACCCUCCGGGCUUUCGGACGG
CAGCCCUACUUCGAAACCCUCUUCCACAAGGCCCUGAACCUCCACACCGC
CAAUUGGUUCCUGUACCUGUCCACCCUGCGGUGGUUCCAGAUGCGCAUCG

-continued

AGAUGAUUUUCGUCAUCUUCUUCAUCGCGGUCACAUUCAUCAGCAUCCUG

ACUACCGGAGAGGGAGAGGGACGGGUCGGAAUAAUCCUGACCCUCGCCAU

GAACAUUAUGAGCACCCUGCAGUGGGCAGUGAACAGCUCGAUCGACGUGG

ACAGCCUGAUGCGAAGCGUCAGCCGCGUGUUCAAGUUCAUCGACAUGCCU

ACUGAGGGAAAACCCACUAAGUCCACUAAGCCCUACAAAAAUGGCCAGCU

GAGCAAGGUCAUGAUCAUCGAAAACUCCCACGUGAAGAAGGACGAUAUUU

GGCCCUCCGGAGGUCAAAUGACCGUGAAGGACCUGACCGCAAAGUACACC

GAGGGAGGAAACGCCAUUCUCGAAAACAUCAGCUUCUCCAUUUCGCCGGG

ACAGCGGGUCGGCCUUCUCGGGCGGACCGGUUCCGGGAAGUCAACUCUGC

UGUCGGCUUUCCUCCGGCUGCUGAAUACCGAGGGGGAAAUCCAAAUUGAC

GGCGUGUCUUGGGAUUCCAUUACUCUGCAGCAGUGGCGGAAGGCCUUCGG

CGUGAUCCCCCAGAAGGUGUUCAUCUUCUCGGGUACCUUCCGGAAGAACC

UGGAUCCUUACGAGCAGUGGAGCGACCAAGAAAUCUGGAAGGUCGCCGAC

GAGGUCGGCCUGCGCUCCGUGAUUGAACAAUUUCCUGGAAAGCUGGACUU

CGUGCUCGUCGACGGGGGAUGUGUCCUGUCGCACGGACAUAAGCAGCUCA

UGUGCCUCGCACGGUCCGUGCUCUCCAAGGCCAAGAUUCUGCUGCUGGAC

GAACCUUCGGCCCACCUGGAUCCGGUCACCUACCAGAUCAUCAGGAGGAC

CCUGAAGCAGGCCUUUGCCGAUUGCACCGUGAUUCUCUGCGAGCACCGCA

UCGAGGCCAUGCUGGAGUGCCAGCAGUUCCUGGUCAUCGAGGAGAACAAG

GUCCGCCAAUACGACUCCAUUCAAAAGCUCCUCAACGAGCGGUCGCUGUU

CAGACAAGCUAUUUCACCGUCCGAUAGAGUGAAGCUCUUCCCGCAUCGGA

ACAGCUCAAAGUGCAAAUCGAAGCCGCAGAUCGCAGCCUUGAAGGAAGAG

ACUGAGGAAGAGGUGCAGGACACCCGGCUUUAAGGGUGGCAUCCCUGUGA

CCCCUCCCCAGUGCCUCUCCUGGCCCUGGAAGUUGCCACUCCAGUGCCCA

CCAGCCUUGUCCUAAUAAAAUUAAGUUGCAUCAAAGCU

In another embodiment, an exemplary codon-optimized CFTR mRNA sequence is:

(SEQ ID NO: 8)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

-continued

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATATCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

TATGTTCGCTATTTCAACAGCAGCGCCTTCTTCTTCAGTGGCTTCTTTGT

TGTCTTCCTGTCTGTTCTGCCATATGCACTGATAAAAGGCATTATTTTAC

GAAAGATCTTCACCACCATCAGTTTTTGCATCGTTCTCAGGATGGCCGTC

ACAAGACAGTTCCCCTGGGCTGTGCAGACCTGGTACGATTCCTTGGGGGC

CATCAACAAGATTCAAGATTTCTTGCAAAAACAAGAATATAAAACTTTAG

AATACAACCTCACCACCACTGAAGTGGTCATGGAAAATGTGACAGCCTTT

TGGGAGGAGGGTTTTGGAGAATTGTTCGAGAAGGCAAAGCAGAATAACAA

CAACAGGAAGACGAGCAATGGGGACGACTCTCTCTTCTTCAGCAACTTTT

CACTGCTCGGGACCCCTGTGTTGAAAGATATAAACTTCAAGATCGAGAGG

GGCCAGCTCTTGGCTGTGGCAGGCTCCACTGGAGCTGGTAAAACATCTCT

TCTCATGGTGATCATGGGGGAACTGGAGCCTTCCGAAGGAAAAATCAAGC

ACAGTGGGAGAATCTCATTCTGCAGCCAGTTTTCCTGGATCATGCCCGGC

ACCATTAAGGAAAACATCATATTTGGAGTGTCCTATGATGAGTACCGCTA

CCGGTCAGTCATCAAAGCCTGTCAGTTGGAGGAGGACATCTCCAAGTTTG

CAGAGAAAGACAACATTGTGCTTGGAGAGGGGGGTATCACTCTTTCTGGA

GGACAAAGAGCCAGGATCTCTTTGGCCCGGGCAGTCTACAAGGATGCAGA

CCTCTACTTGTTGGACAGTCCCTTCGGCTACCTCGACGTGCTGACTGAAA

AAGAAATTTTTGAAAGCTGTGTGTGCAAACTGATGGCAAACAAGACCAGG

ATTCTTGTCACCAGCAAGATGGAACATCTGAAGAAAGCGGACAAAATTCT

GATTCTGCATGAAGGGAGCTCCTACTTCTATGGAACATTTAGCGAGCTTC

AGAACCTACAGCCAGACTTCTCCTCCAAATTAATGGGCTGTGACTCCTTC

GACCAGTTCTCTGCAGAAAGAAGAAACTCTATACTCACAGAGACCCTCCA

CCGCTTCTCCCTTGAGGGAGATGCCCCAGTTTCTTGGACAGAAACCAAGA

AGCAGTCCTTTAAGCAGACTGGCGAGTTTGGTGAAAAGAGGAAAAATTCA

ATTCTCAATCCAATTAACAGTATTCGCAAGTTCAGCATTGTCCAGAAGAC

ACCCCTCCAGATGAATGGCATCGAAGAAGATAGTGACGAGCCGCTGGAGA

GACGGCTGAGTCTGGTGCCAGATTCAGAACAGGGGGAGGCCATCCTGCCC

CGGATCAGCGTCATTTCCACAGGCCCCACATTACAAGCACGGCGCCGGCA

GAGTGTTTTAAATCTCATGACCCATTCAGTGAACCAGGGCCAAAATATCC

ACAGGAAGACTACAGCTTCTACCCGGAAAGTGTCTCTGGCCCCTCAGGCC

AATCTGACCGAGCTGGACATCTACAGCAGGAGGCTCTCCCAGGAAACAGG

GCTGGAAATATCTGAAGAGATTAATGAAGAGGATCTTAAAGAGTGCTTCT

TTGATGACATGGAGAGCATCCCCGCGGTGACCACATGGAACACCTACCTT

AGATATATTACTGTCCACAAGAGCCTCATATTTGTCCTCATCTGGTGCCT

GGTTATTTTCCTCGCTGAGGTGGCGGCCAGTCTTGTTGTGCTCTGGCTGC

-continued

TGGGCAACACTCCTCTCCAGGACAAGGGCAATAGTACTCACAGCAGAAAT

AATTCTTATGCCGTCATCATTACAAGCACCTCCAGCTACTACGTGTTCTA

CATCTATGTGGGCGTGGCTGACACCCTCCTGGCCATGGGTTTCTTCCGGG

GCCTGCCTTTGGTGCACACCCTCATCACAGTGTCAAAAATTCTGCACCAT

AAAATGCTTCATTCTGTCCTGCAGGCACCCATGAGCACTTTGAACACATT

GAAGGCTGGCGGCATCCTCAACAGATTTTCTAAAGATATTGCTATCCTGG

ATGATCTCCTCCCCCTGACAATCTTTGACTTTATCCAGCTTCTGCTGATC

GTGATTGGAGCCATAGCAGTGGTTGCTGTCCTGCAGCCCTACATTTTTGT

GGCCACCGTGCCCGTGATTGTTGCCTTTATTATGCTCAGAGCTTACTTCC

TGCAAACTTCTCAACAGCTCAAACAGCTAGAATCTGAGGGCCGGAGCCCC

ATTTTTACCCACCTGGTGACTTCCCTGAAGGGACTGTGGACTCTGAGAGC

ATTCGGGCGACAGCCTTACTTTGAGACACTGTTCCACAAGGCCCTGAACT

TGCACACTGCCAACTGGTTTCTTTACCTGAGCACACTCCGCTGGTTCCAG

ATGCGGATAGAGATGATCTTCGTCATCTTTTTTATAGCTGTAACCTTCAT

TTCTATCCTTACAACAGGAGAAGGAGAGGGCAGGGTGGGAATCATCCTCA

CGCTGGCTATGAACATAATGTCCACCTTGCAGTGGGCCGTGAATTCCAGT

ATAGATGTGGATTCTCTAATGAGGAGTGTCTCCCGGGTGTTTAAATTCAT

TGATATGCCTACTGAGGGGAAACCCACCAAGTCAACAAAACCTTATAAGA

ATGGACAGCTGAGCAAGGTGATGATAATTGAGAACAGCCACGTGAAGAAG

GATGACATTTGGCCCAGCGGGGGCCAGATGACTGTGAAGGACCTGACGGC

CAAGTACACCGAAGGTGGAAATGCCATTTTGGAAAACATCAGCTTCTCAA

TCTCTCCTGGGCAGAGAGTTGGATTGCTGGGTCGCACGGGCAGCGGCAAA

TCAACCCTGCTCAGTGCCTTCCTTCGGCTCCTGAATACAGAAGGCGAAAT

CCAAATTGACGGGGTGAGCTGGGACAGCATCACCCTGCAGCAGTGGAGAA

AAGCATTTGGGGTCATTCCACAGAAAGTTTTCATCTTCTCTGGCACTTTC

AGAAAGAACCTGGACCCCTATGAGCAGTGGAGCGACCAGGAGATCTGGAA

GGTTGCAGATGAAGTTGGCCTGCGGAGTGTGATAGAACAATTTCCTGGCA

AGCTGGATTTTGTGCTGGTAGATGGAGGCTGCGTGCTGTCCCACGGCCAC

AAACAGCTGATGTGCCTCGCCCGCTCCGTTCTTTCAAAGGCCAAAATCTT

GCTTTTGGATGAGCCCAGTGCTCACCTCGACCCAGTGACCTATCAGATAA

TCCGCAGGACCTTAAAGCAAGCTTTTGCCGACTGCACCGTCATACTGTGT

GAGCACCGGATTGAAGCAATGCTGGAATGCCAGCAGTTTCTGGTGATCGA

GGAGAATAAGGTCCGGCAGTACGACAGCATCCAGAAGTTGTTGAATGAGC

GCAGCCTTTTCCGCCAGGCCATCTCCCCATCTGACAGAGTCAAGCTGTTT

CCACATAGGAACTCCTCTAAGTGCAAGTCCAAGCCCCAGATCGCTGCCCT

CAAGGAGGAAACTGAGGAAGAGGTGCAGGATACCCGCCTGTGA

In another embodiment, an exemplary codon-optimized CFTR mRNA sequence is:

(SEQ ID NO: 9)

ATGCAGAGGAGCCCACTGGAGAAAGCCTCCGTGGTGAGTAAACTCTTTTT

-continued

TAGTTGGACCAGACCCATCCTGCGAAAAGGATACAGGCAGCGCCTCGAGT

TGTCTGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATTTCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

TATGTTCGCTATTTCAACAGCAGCGCCTTCTTCTTCAGTGGCTTCTTTGT

TGTCTTCCTGTCTGTTCTGCCATATGCACTGATAAAAGGCATTATTTTAC

GAAAGATCTTCACCACCATCAGTTTTTGCATCGTTCTCAGGATGGCCGTC

ACAAGACAGTTCCCCTGGGCTGTGCAGACCTGGTACGATTCCTTGGGGGC

CATCAACAAGATTCAAGATTTCTTGCAAAAACAAGAATATAAAACTTTAG

AATACAACCTCACCACCACTGAAGTGGTCATGGAAAATGTGACAGCCTTT

TGGGAGGAGGGTTTTGGAGAATTGTTCGAGAAGGCAAAGCAGAATAACAA

CAACAGGAAGACGAGCAATGGGGACGACTCTCTCTTCTTCAGCAACTTTT

CACTGCTCGGGACCCCTGTGTTGAAAGATATAAACTTCAAGATCGAGAGG

GGCCAGCTCTTGGCTGTGGCAGGCTCCACTGGAGCTGGTAAAACATCTCT

TCTCATGGTGATCATGGGGGAACTGGAGCCTTCCGAAGGAAAAATCAAGC

ACAGTGGGAGAATCTCATTCTGCAGCCAGTTTTCCTGGATCATGCCCGGC

ACCATTAAGGAAAACATCATATTTGGAGTGTCCTATGATGAGTACCGCTA

CCGGTCAGTCATCAAAGCCTGTCAGTTGGAGGAGGACATCTCCAAGTTTG

CAGAGAAAGACAACATTGTGCTTGGAGAGGGGGGTATCACTCTTTCTGGA

GGACAAAGAGCCAGGATCTCTTTGGCCCGGGCAGTCTACAAGGATGCAGA

CCTCTACTTGTTGGACAGTCCCTTCGGCTACCTCGACGTGCTGACTGAAA

AAGAAATTTTTGAAAGCTGTGTGTGCAAACTGATGGCAAACAAGACCAGG

ATTCTTGTCACCAGCAAGATGGAACATCTGAAGAAAGCGGACAAAATTCT

GATTCTGCATGAAGGGAGCTCCTACTTCTATGGAACATTTAGCGAGCTTC

AGAACCTACAGCCAGACTTCTCCTCCAAATTAATGGGCTGTGACTCCTTC

GACCAGTTCTCTGCAGAAAGAAGAAACTCTATACTCACAGAGACCCTCCA

CCGCTTCTCCCTTGAGGGAGATGCCCCAGTTTCTTGGACAGAAACCAAGA

AGCAGTCCTTTAAGCAGACTGGCGAGTTTGGTGAAAAGAGGAAAAATTCA

ATTCTCAATCCAATTAACAGTATTCGCAAGTTCAGCATTGTCCAGAAGAC

ACCCCTCCAGATGAATGGCATCGAAGAAGATAGTGACGAGCCGCTGGAGA

GACGGCTGAGTCTGGTGCCAGATTCAGAACAGGGGGAGGCCATCCTGCCC

CGGATCAGCGTCATTTCCACAGGCCCCACATTACAAGCACGGCGCCGGCA

GAGTGTTTTAAATCTCATGACCCATTCAGTGAACCAGGGCCAAAATATCC

ACAGGAAGACTACAGCTTCTACCCGGAAAGTGTCTCTGGCCCCTCAGGCC

AATCTGACCGAGCTGGACATCTACAGCAGGAGGCTCTCCCAGGAAACAGG

GCTGGAAATATCTGAAGAGATTAATGAAGAGGATCTTAAAGAGTGCTTCT

TTGATGACATGGAGAGCATCCCCGCGGTGACCACATGGAACACCTACCTT

AGATATATTACTGTCCACAAGAGCCTCATATTTGTCCTCATCTGGTGCCT

GGTTATTTTCCTCGCTGAGGTGGCGGCCAGTCTTGTTGTGCTCTGGCTGC

TGGGCAACACTCCTCTCCAGGACAAGGGCAATAGTACTCACAGCAGAAAT

AATTCTTATGCCGTCATCATTACAAGCACCTCCAGCTACTACGTGTTCTA

CATCTATGTGGGCGTGGCTGACACCCTCCTGGCCATGGGTTTCTTCCGGG

GCCTGCCTTTGGTGCACACCCTCATCACAGTGTCAAAAATTCTGCACCAT

AAAATGCTTCATTCTGTCCTGCAGGCACCCATGAGCACTTTGAACACATT

GAAGGCTGGCGGCATCCTCAACAGATTTTCTAAAGATATTGCTATCCTGG

ATGATCTCCTCCCCCTGACAATCTTTGACTTTATCCAGCTTCTGCTGATC

GTGATTGGAGCCATAGCAGTGGTTGCTGTCCTGCAGCCCTACATTTTTGT

GGCCACCGTGCCCGTGATTGTTGCCTTTATTATGCTCAGAGCTTACTTCC

TGCAAACTTCTCAACAGCTCAAACAGCTAGAATCTGAGGGCCGGAGCCCC

ATTTTTACCCACCTGGTGACTTCCCTGAAGGGACTGTGGACTCTGAGAGC

ATTCGGGCGACAGCCTTACTTTGAGACACTGTTCCACAAGGCCCTGAACT

TGCACACTGCCAACTGGTTTCTTTACCTGAGCACACTCCGCTGGTTCCAG

ATGCGGATAGAGATGATCTTCGTCATCTTTTTTATAGCTGTAACCTTCAT

TTCTATCCTTACAACAGGAGAAGGAGAGGGCAGGGTGGGAATCATCCTCA

CGCTGGCTATGAACATAATGTCCACCTTGCAGTGGGCCGTGAATTCCAGT

ATAGATGTGGATTCTCTAATGAGGAGTGTCTCCCGGGTGTTTAAATTCAT

TGATATGCCTACTGAGGGGAAACCCACCAAGTCAACAAAACCTTATAAGA

ATGGACAGCTGAGCAAGGTGATGATAATTGAGAACAGCCACGTGAAGAAG

GATGACATTTGGCCCAGCGGGGGCCAGATGACTGTGAAGGACCTGACGGC

CAAGTACACCGAAGGTGGAAATGCCATTTTGGAAAACATCAGCTTCTCAA

TCTCTCCTGGGCAGAGAGTTGGATTGCTGGGTCGCACGGGCAGCGGCAAA

TCAACCCTGCTCAGTGCCTTCCTTCGGCTCCTGAATACAGAAGGCGAAAT

CCAAATTGACGGGGTGAGCTGGGACAGCATCACCCTGCAGCAGTGGAGAA

AAGCATTTGGGGTCATTCCACAGAAAGTTTTCATCTTCTCTGGCACTTTC

AGAAAGAACCTGGACCCCTATGAGCAGTGGAGCGACCAGGAGATCTGGAA

GGTTGCAGATGAAGTTGGCCTGCGGAGTGTGATAGAACAATTTCCTGGCA

AGCTGGATTTTGTGCTGGTAGATGGAGGCTGCGTGCTGTCCCACGGCCAC

AAACAGCTGATGTGCCTCGCCCGCTCCGTTCTTTCAAAGGCCAAAATCTT

GCTTTTGGATGAGCCCAGTGCTCACCTTGACCCAGTGACCTATCAGATAA

TCCGCAGGACCTTAAAGCAAGCTTTTGCCGACTGCACCGTCATACTGTGT

GAGCACCGGATTGAAGCAATGCTGGAATGCCAGCAGTTTCTGGTGATCGA

GGAGAATAAGGTCCGGCAGTACGACAGCATCCAGAAGTTGTTGAATGAGC

GCAGCCTTTTCCGCCAGGCCATCTCCCCATCTGACAGAGTCAAGCTGTTT

CCACATAGGAACTCCTCTAAGTGCAAGTCCAAGCCCCAGATCGCTGCCCT

CAAGGAGGAAACTGAGGAAGAGGTGCAGGATACCCGCCTGTGA

In yet another embodiment, an exemplary codon-optimized CFTR mRNA sequence is:

(SEQ ID NO: 10)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATATCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

TATGTTCGCTATTTCAACAGCAGCGCCTTCTTCTTCAGTGGCTTCTTTGT

TGTCTTCCTGTCTGTTCTGCCATATGCACTGATAAAAGGCATTATTTTAC

GAAAGATCTTCACCACCATCAGTTTTTGCATCGTTCTCAGGATGGCCGTC

ACAAGACAGTTCCCCTGGGCTGTGCAGACCTGGTACGATTCCTTGGGGGC

CATCAACAAGATTCAAGATTTCTTGCAAAAACAAGAATATAAAACTTTAG

AATACAACCTCACCACCACTGAAGTGGTCATGGAAAATGTGACAGCCTTT

TGGGAGGAGGGTTTTGGAGAATTGTTCGAGAAGGCAAAGCAGAATAACAA

CAACAGGAAGACGAGCAATGGGGACGACTCTCTCTTCTTCAGCAACTTTT

CACTGCTCGGGACCCCTGTGTTGAAAGATATAAACTTCAAGATCGAGAGG

GGCCAGCTCTTGGCTGTGGCAGGCTCCACTGGAGCTGGTAAAACATCTCT

TCTCATGGTGATCATGGGGGAACTGGAGCCTTCCGAAGGAAAAATCAAGC

ACAGTGGGAGAATCTCATTCTGCAGCCAGTTTTCCTGGATCATGCCCGGC

ACCATTAAGGAAAACATCATATTTGGAGTGTCCTATGATGAGTACCGCTA

-continued

CCGGTCAGTCATCAAAGCCTGTCAGTTGGAGGAGGACATCTCCAAGTTTG

CAGAGAAAGACAACATTGTGCTTGGAGAGGGGGGTATCACTCTTTCTGGA

GGACAAAGAGCCAGGATCTCTTTGGCCCGGGCAGTCTACAAGGATGCAGA

CCTCTACTTGTTGGACAGTCCCTTCGGCTACCTCGACGTGCTGACTGAAA

AAGAAATTTTTGAAAGCTGTGTGTGCAAACTGATGGCAAACAAGACCAGG

ATTCTTGTCACCAGCAAGATGGAACATCTGAAGAAAGCGGACAAAATTCT

GATTCTGCATGAAGGGAGCTCCTACTTCTATGGAACATTTAGCGAGCTTC

AGAACCTACAGCCAGACTTCTCCTCCAAATTAATGGGCTGTGACTCCTTC

GACCAGTTCTCTGCAGAAAGAAGAAACTCTATACTCACAGAGACCCTCCA

CCGCTTCTCCCTTGAGGGAGATGCCCCAGTTTCTTGGACAGAAACCAAGA

AGCAGTCCTTTAAGCAGACTGGCGAGTTTGGTGAAAAGAGGAAAAATTCA

ATTCTCAATCCAATTAACAGTATTCGCAAGTTCAGCATTGTCCAGAAGAC

ACCCCTCCAGATGAATGGCATCGAAGAAGATAGTGACGAGCCGCTGGAGA

GACGGCTGAGTCTGGTGCCAGATTCAGAACAGGGGGAGGCCATCCTGCCC

CGGATCAGCGTCATTTCCACAGGCCCCACATTACAAGCACGGCGCCGGCA

GAGTGTTTTAAATCTCATGACCCATTCAGTGAACCAGGGCCAAAATATCC

ACAGGAAGACTACAGCTTCTACCCGGAAAGTGTCTCTGGCCCCTCAGGCC

AATCTGACCGAGCTGGACATCTACAGCAGGAGGCTCTCCCAGGAAACAGG

GCTTGAAATATCTGAAGAGATTAATGAAGAGGATCTTAAAGAGTGCTTCT

TTGATGACATGGAGAGCATCCCCGCGGTGACCACATGGAACACCTACCTT

AGATATATTACTGTCCACAAGAGCCTCATATTTGTCCTCATCTGGTGCCT

GGTTATTTTCCTCGCTGAGGTGGCGGCCAGTCTTGTTGTGCTCTGGCTGC

TGGGCAACACTCCTCTCCAGGACAAGGGCAATAGTACACACAGCAGAAAT

AATTCTTATGCCGTCATCATTACAAGCACCTCCAGCTACTACGTGTTCTA

CATCTATGTGGGCGTGGCTGACACCCTCCTGGCCATGGGTTTCTTCCGGG

GCCTGCCTTTGGTGCACACCCTCATCACAGTGTCAAAAATTCTGCACCAT

AAAATGCTTCATTCTGTCCTGCAGGCACCCATGAGCACTTTGAACACATT

GAAGGCTGGCGGCATCCTCAACAGATTTTCTAAAGATATTGCTATCCTGG

ATGATCTCCTCCCCCTGACAATCTTTGACTTTATCCAGCTTCTGCTGATC

GTGATTGGAGCCATAGCAGTGGTTGCTGTCCTGCAGCCCTACATTTTTGT

GGCCACCGTGCCCGTGATTGTTGCCTTTATTATGCTCAGAGCTTACTTCC

TGCAAACTTCTCAACAGCTCAAACAGCTAGAATCTGAGGGCCGGAGCCCC

ATTTTTACCCACCTGGTGACTTCCCTGAAGGGACTGTGGACTCTGAGAGC

ATTCGGGCGACAGCCTTACTTTGAGACACTGTTCCACAAGGCCCTGAACT

TGCACACTGCCAACTGGTTTCTTTACCTGAGCACACTCCGCTGGTTCCAG

ATGCGGATAGAGATGATCTTCGTCATCTTTTTTATAGCTGTAACCTTCAT

TTCTATCCTTACAACAGGAGAAGGAGAGGGCAGGGTGGGAATCATCCTCA

CGCTGGCTATGAACATAATGTCCACCTTGCAGTGGGCCGTGAATTCCAGT

ATAGATGTGGATTCTCTAATGAGGAGTGTCTCCCGGGTGTTTAAATTCAT

TGATATGCCTACTGAGGGGAAACCCACCAAGTCAACAAAACCTTATAAGA

-continued

ATGGACAGCTGAGCAAGGTGATGATAATTGAGAACAGCCACGTGAAGAAG

GATGACATTTGGCCCAGCGGGGGCCAGATGACTGTGAAGGACCTGACGGC

CAAGTACACCGAAGGTGGAAATGCCATTTTGGAAAACATCAGCTTCTCAA

TCTCTCCTGGGCAGAGAGTTGGATTGCTGGGTCGCACGGGCAGCGGCAAA

TCAACCCTGCTCAGTGCCTTCCTTCGGCTCCTGAATACAGAAGGCGAAAT

CCAAATTGACGGGGTGAGCTGGGACAGCATCACCCTGCAGCAGTGGAGAA

AAGCATTTGGGGTCATTCCACAGAAAGTTTTCATCTTCTCTGGCACTTTC

AGAAAGAACCTGGACCCCTATGAGCAGTGGAGCGACCAGGAGATCTGGAA

GGTTGCAGATGAAGTTGGCCTGCGGAGTGTGATAGAACAATTTCCTGGCA

AGCTGGATTTTGTGCTGGTAGATGGAGGCTGCGTGCTGTCCCACGGCCAC

AAACAGCTGATGTGCCTCGCCCGCTCCGTTCTTTCAAAGGCCAAAATCTT

GCTTTTGGATGAGCCCAGTGCTCACCTTGACCCAGTGACCTATCAGATAA

TCCGCAGGACCTTAAAGCAAGCTTTTGCCGACTGCACCGTCATACTGTGT

GAGCACCGGATTGAAGCAATGCTGGAATGCCAGCAGTTTCTGGTGATCGA

GGAGAATAAGGTCCGGCAGTACGACAGCATCCAGAAGTTGTTGAATGAGC

GCAGCCTTTTCCGCCAGGCCATCTCCCCATCTGACAGAGTCAAGCTGTTT

CCACATAGGAACTCCTCTAAGTGCAAGTCCAAGCCCCAGATCGCTGCCCT

CAAGGAGGAAACTGAGGAAGAGGTGCAGGATACCCGCCTGTGA.

In yet another embodiment, an exemplary codon-optimized CFTR mRNA sequence is:

(SEQ ID NO: 11)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATATCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

TATGTTCGCTATTTCAACAGCAGCGCCTTCTTCTTCAGTGGCTTCTTTGT

TGTCTTCCTGTCTGTTCTGCCATATGCACTGATAAAAGGCATTATTTTAC

-continued

GAAAGATCTTCACCACCATCAGTTTTTGCATCGTTCTCAGGATGGCCGTC

ACAAGACAGTTCCCCTGGGCTGTGCAGACCTGGTACGATTCCTTGGGGGC

CATCAACAAGATTCAAGATTTCTTGCAAAAACAAGAATATAAAACTTTAG

AATACAACCTCACCACCACTGAAGTGGTCATGGAAAATGTGACAGCCTTT

TGGGAGGAGGGTTTTGGAGAATTGTTCGAGAAGGCAAAGCAGAATAACAA

CAACAGGAAGACGAGCAATGGGGACGACTCTCTCTTCTTCAGCAACTTTT

CACTGCTCGGGACCCCTGTGTTGAAAGATATAAACTTCAAGATCGAGAGG

GGCCAGCTCTTGGCTGTGGCAGGCTCCACTGGAGCTGGTAAAACATCTCT

TCTCATGGTGATCATGGGGGAACTGGAGCCTTCCGAAGGAAAAATCAAGC

ACAGTGGGAGAATCTCATTCTGCAGCCAGTTTTCCTGGATCATGCCCGGC

ACCATTAAGGAAAACATCATATTTGGAGTGTCCTATGATGAGTACCGCTA

CCGGTCAGTCATCAAAGCCTGTCAGTTGGAGGAGGACATCTCCAAGTTTG

CAGAGAAAGACAACATTGTGCTTGGAGAGGGGGGTATCACTCTTTCTGGA

GGACAAAGAGCCAGGATCTCTTTGGCCCGGGCAGTCTACAAGGATGCAGA

CCTCTACTTGTTGGACAGTCCCTTCGGCTACCTCGACGTGCTGACTGAAA

AAGAAATTTTTGAAAGCTGTGTGTGCAAACTGATGGCAAACAAGACCAGG

ATTCTTGTCACCAGCAAGATGGAACATCTGAAGAAAGCGGACAAAATTCT

GATTCTGCATGAAGGGAGCTCCTACTTCTATGGAACATTTAGCGAGCTTC

AGAACCTACAGCCAGACTTCTCCTCCAAATTAATGGGCTGTGACTCCTTC

GACCAGTTCTCTGCAGAAAGAAGAAACTCTATACTCACAGAGACCCTCCA

CCGCTTCTCCCTTGAGGGAGATGCCCCAGTTTCTTGGACAGAAACCAAGA

AGCAGTCCTTTAAGCAGACTGGCGAGTTTGGTGAAAAGAGGAAAAATTCA

ATTCTCAATCCAATTAACAGTATTCGCAAGTTCAGCATTGTCCAGAAGAC

ACCCCTCCAGATGAATGGCATCGAAGAAGATAGTGACGAGCCGCTGGAGA

GACGGCTGAGTCTGGTGCCAGATTCAGAACAGGGGGAGGCCATCCTGCCC

CGGATCAGCGTCATTTCCACAGGCCCCACATTACAAGCACGGCGCCGGCA

GAGTGTTTTAAATCTCATGACCCATTCAGTGAACCAGGGCCAAAATATCC

ACAGGAAGACTACAGCTTCTACCCGGAAAGTGTCTCTGGCCCCTCAGGCC

AATCTGACCGAGCTGGACATCTACAGCAGGAGGCTCTCCCAGGAAACAGG

GCTGGAAATATCTGAAGAGATTAATGAAGAGGATCTTAAAGAGTGCTTCT

TTGATGACATGGAGAGCATCCCCGCGGTGACCACATGGAACACCTACCTT

AGATATATTACTGTCCACAAGAGCCTCATATTTGTCCTCATCTGGTGCCT

GGTTATTTTCCTCGCTGAGGTGGCGGCCAGTCTTGTTGTGCTCTGGCTGC

TGGGCAACACTCCTCTCCAGGACAAGGGCAATAGTACTCACAGCAGAAAT

AATTCTTATGCCGTCATCATTACAAGCACCTCCAGCTACTACGTGTTCTA

CATCTATGTGGGCGTGGCTGACACCCTCCTGGCCATGGGTTTCTTCCGGG

GCCTGCCTTTGGTGCACACCCTCATCACAGTGTCAAAAATTCTGCACCAT

AAAATGCTTCATTCTGTCCTGCAGGCACCCATGAGCACTTTGAACACATT

GAAGGCTGGCGGCATCCTCAACAGATTTTCTAAAGATATTGCTATCCTGG

ATGATCTCCTCCCCCTGACAATCTTTGACTTTATCCAGCTTCTGCTGATC

-continued

GTGATTGGAGCCATAGCAGTGGTTGCTGTCCTGCAGCCCTACATTTTTGT

GGCCACCGTGCCCGTGATTGTTGCCTTTATTATGCTCAGAGCTTACTTCC

TGCAAACTTCTCAACAGCTCAAACAGCTAGAATCTGAGGGCCGGAGCCCC

ATTTTTACCCACCTGGTGACTTCCCTGAAGGGACTGTGGACTCTGAGAGC

ATTCGGGCGACAGCCTTACTTTGAGACACTGTTCCACAAGGCCCTGAACT

TGCACACTGCCAACTGGTTTCTTTACCTGAGCACACTCCGCTGGTTCCAG

ATGCGGATAGAGATGATCTTCGTCATCTTTTTTATAGCTGTAACCTTCAT

TTCTATCCTTACAACAGGAGAAGGAGAGGGCAGGGTGGGAATCATCCTCA

CGCTGGCTATGAACATAATGTCCACCTTGCAGTGGGCCGTGAATTCCAGT

ATAGATGTGGATTCTCTAATGAGGAGTGTCTCCCGGGTGTTTAAATTCAT

TGATATGCCAACTGAGGGGAAACCCACCAAGTCAACAAAACCTTATAAGA

ATGGACAGCTGAGCAAGGTGATGATAATTGAGAACAGCCACGTGAAGAAG

GATGACATTTGGCCCAGCGGGGGCCAGATGACTGTGAAGGACCTGACGGC

CAAGTACACCGAAGGTGGAAATGCCATTTTGGAAAACATCAGCTTCTCAA

TCTCTCCTGGGCAGAGAGTTGGATTGCTGGGTCGCACGGGCAGCGGCAAA

TCAACCCTGCTCAGTGCCTTCCTTCGGCTCCTGAATACAGAAGGCGAAAT

CCAAATTGACGGGGTGAGCTGGGACAGCATCACCCTGCAGCAGTGGAGAA

AAGCATTTGGGGTCATTCCACAGAAAGTTTTCATCTTCTCTGGCACTTTC

AGAAAGAACCTGGACCCCTATGAGCAGTGGAGCGACCAGGAGATCTGGAA

GGTTGCAGATGAAGTTGGCCTGCGGAGTGTGATAGAACAATTTCCTGGCA

AGCTGGATTTTGTGCTGGTAGATGGAGGCTGCGTGCTGTCCCACGGCCAC

AAACAGCTGATGTGCCTCGCCCGCTCCGTTCTTTCAAAGGCCAAAATCTT

GCTTTTGGATGAGCCCAGTGCTCACCTCGACCCAGTGACCTATCAGATAA

TCCGCAGGACCTTAAAGCAAGCTTTTGCCGACTGCACCGTCATACTGTGT

GAGCACCGGATTGAAGCAATGCTGGAATGCCAGCAGTTTCTGGTGATCGA

GGAGAATAAGGTCCGGCAGTACGACAGCATCCAGAAGTTGTTGAATGAGC

GCAGCCTTTTCCGCCAGGCCATCTCCCCATCTGACAGAGTCAAGCTGTTT

CCACATAGGAACTCCTCTAAGTGCAAGTCCAAGCCCCAGATCGCTGCCCT

CAAGGAGGAAACTGAGGAAGAGGTGCAGGATACCCGCCTGTGA.

In yet another embodiment, an exemplary codon-optimized CFTR mRNA sequence is:

(SEQ ID NO: 12)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

-continued

CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATATCAGAGCGACTTGTGATCACCAGTGAAATGATTGA
AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCAGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCTATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG

-continued

GCTTGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACTCACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA
CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCTACTGAGGGGAAACCCACCAAGTCAACAAAACCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA
TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA
GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC
GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA.

In another embodiment, an exemplary codon-optimized CFTR mRNA sequence is:

(SEQ ID NO: 13)

ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCAGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCTGCTTTTTCTGGAGGTTCATGTTTT
ATGGGATCTTCCTGTACCTGGGGGAGGTCACCAAAGCTGTTCAGCCGCTC
CTTCTTGGCCGCATCATCGCCAGCTATGACCCTGATAATAAAGAAGAAAG
GTCTATTGCTATTTATCTGGGAATTGGCCTCTGCTTGCTCTTCATCGTCC
GCACCCTTCTGCTGCACCCTGCCATTTTTGGCCTTCACCACATCGGCATG
CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATTTCAGAGCGACTTGTGATCACCAGTGAAATGATTGA
AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCAGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC

-continued

AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCAATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG
GCTGGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACTCACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA
CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCAACTGAGGGGAAACCCACCAAGTCAACAAAACCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA
TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA

-continued

GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC
GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA.

In another embodiment, an exemplary codon-optimized CFTR mRNA sequence is:

(SEQ ID NO: 14)

ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCTGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCTGCTTTTTCTGGAGGTTCATGTTTT
ATGGGATCTTCCTGTACCTGGGGGAGGTCACCAAAGCTGTTCAGCCGCTC
CTTCTTGGCCGCATCATCGCCAGCTATGACCCTGATAATAAAGAAGAAAG
GTCTATTGCTATTTATCTGGGAATTGGCCTCTGCTTGCTCTTCATCGTCC
GCACCCTTCTGCTGCACCCTGCCATTTTTGGCCTTCACCACATCGGCATG
CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATATCAGAGCGACTTGTGATCACCAGTGAAATGATTGA
AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG

-continued

GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCCGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCAATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG
GCTTGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACTCACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA

-continued

CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCTACTGAGGGGAAACCCACCAAGTCAACAAAGCCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA
TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA
GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC
GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA.

In another embodiment, an exemplary codon-optimized CFTR mRNA sequence is:

(SEQ ID NO: 15)

ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCAGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCTGCTTTTTCTGGAGGTTCATGTTTT
ATGGGATCTTCCTGTACCTGGGGGAGGTCACCAAAGCTGTTCAGCCGCTC
CTTCTTGGCCGCATCATCGCCAGCTATGACCCTGATAATAAAGAAGAAAG
GTCTATTGCTATTTATCTGGGAATTGGCCTCTGCTTGCTCTTCATCGTCC
GCACCCTTCTGCTGCACCCTGCCATTTTTGGCCTTCACCACATCGGCATG
CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATATCAGAGCGACTTGTGATCACCAGTGAAATGATTGA

-continued

AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCAGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCTATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG
GCTTGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACACACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT

-continued

AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA
CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCTACTGAGGGGAAACCCACCAAGTCAACAAAACCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA
TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA
GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC
GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA.

In yet another embodiment, an exemplary codon-optimized CFTR mRNA sequence is:

(SEQ ID NO: 16)
ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCAGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCTGCTTTTTCTGGAGGTTCATGTTTT

-continued

ATGGGATCTTCCTGTACCTGGGGGAGGTCACCAAAGCTGTTCAGCCGCTC
CTTCTTGGCCGCATCATCGCCAGCTATGACCCTGATAATAAAGAAGAAAG
GTCTATTGCTATTTATCTGGGAATTGGCCTCTGCTTGCTCTTCATCGTCC
GCACCCTTCTGCTGCACCCTGCCATTTTTGGCCTTCACCACATCGGCATG
CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATATCAGAGCGACTTGTGATCACCAGTGAAATGATTGA
AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCCGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCAATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA

-continued

GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG
GCTGGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACTCACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAGTCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA
CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCTACTGAGGGGAAACCCACCAAGTCAACAAAACCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA
TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA
GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC

-continued

GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA.

In another embodiment, an exemplary codon-optimized CFTR mRNA sequence is:

(SEQ ID NO: 17)

ATGCAGAGGAGCCCACTGGAGAAAGCCTCCGTGGTGAGTAAACTCTTTTT
TAGTTGGACCAGACCCATCCTGCGAAAAGGATACAGGCAGCGCCTCGAGT
TGTCTGATATCTACCAGATTCCTTCTGTGGACTCAGCTGACAATTTGAGT
GAGAAGCTGGAGCGGGAGTGGGATAGAGAGCTGGCGAGCAAAAAAAACCC
CAAGCTTATCAATGCTCTGCGCCGCTGCTTTTTCTGGAGGTTCATGTTTT
ATGGGATCTTCCTGTACCTGGGGGAGGTCACCAAAGCTGTTCAGCCGCTC
CTTCTTGGCCGCATCATCGCCAGCTATGACCCTGATAATAAAGAAGAAAG
GTCTATTGCTATTTATCTGGGAATTGGCCTCTGCTTGCTCTTCATCGTCC
GCACCCTTCTGCTGCACCCTGCCATTTTTGGCCTTCACCACATCGGCATG
CAAATGAGAATTGCCATGTTCTCCCTCATTTACAAAAAGACCCTGAAACT
TTCCTCAAGAGTGTTAGATAAAATATCCATTGGTCAGCTGGTCAGCCTGC
TGTCCAACAATCTTAACAAATTTGATGAAGGCTTGGCGCTGGCCCACTTC
GTGTGGATTGCACCTCTGCAGGTGGCCCTGTTGATGGGACTTATATGGGA
GCTGCTTCAAGCCTCTGCTTTCTGTGGGCTGGGCTTTTTGATTGTACTGG
CACTTTTTCAGGCTGGGCTCGGAAGAATGATGATGAAATACAGAGATCAG
CGGGCCGGGAAGATTTCAGAGCGACTTGTGATCACCAGTGAAATGATTGA
AAATATTCAGAGCGTGAAAGCCTACTGCTGGGAAGAAGCCATGGAGAAGA
TGATTGAGAACCTGAGGCAGACAGAGCTCAAGCTCACTCGGAAGGCTGCT
TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCAGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA

-continued

AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCTATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG
GCTGGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACACACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG
ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA
CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCTACTGAGGGGAAACCCACCAAGTCAACAAAACCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA

-continued

TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA
GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC
GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA.

In another embodiment, an exemplary codon-optimized CFTR mRNA sequence is:

(SEQ ID NO: 18)

ATGCAGAGAAGCCCCCTGGAGAAGGCCTCTGTGGTGAGCAAGCTGTTCTT
CAGCTGGACCAGACCCATCCTGAGAAAGGGCTACAGACAGAGACTGGAGC
TGTCTGACATCTACCAGATCCCCTCTGTGGACTCTGCCGACAACCTGTCT
GAGAAGCTGGAGAGAGAGTGGGACAGAGAGCTGGCCAGCAAGAAGAACCC
CAAGCTGATCAATGCCCTGAGAAGATGCTTCTTCTGGAGATTCATGTTCT
ATGGCATCTTCCTGTACCTGGGAGAGGTGACCAAGGCCGTGCAGCCCCTG
CTGCTGGGCAGGATCATTGCCAGCTATGACCCTGACAACAAGGAGGAGAG
AAGCATTGCCATCTACCTGGGCATTGGCCTGTGCCTGCTGTTCATTGTGA
GAACCCTGCTGCTGCACCCTGCCATCTTTGGCCTGCACCACATTGGCATG
CAGATGAGAATTGCCATGTTCAGCCTGATCTACAAGAAGACCCTGAAGCT
GAGCAGCAGAGTGCTGGACAAGATCAGCATTGGCCAGCTGGTGAGCCTGC
TGAGCAACAACCTGAACAAGTTTGATGAGGGCCTGGCCCTGGCCCACTTT
GTGTGGATTGCCCCCCTGCAGGTGGCCCTGCTGATGGGCCTGATCTGGGA
GCTGCTGCAGGCCTCTGCCTTCTGTGGCCTGGGCTTCCTGATTGTGCTGG
CCCTGTTCCAGGCCGGCCTGGGCAGAATGATGATGAAGTACAGAGACCAG
AGAGCCGGCAAGATCTCTGAGAGACTGGTGATCACCTCTGAGATGATTGA
GAACATCCAGTCTGTGAAGGCCTACTGCTGGGAGGAGGCCATGGAGAAGA
TGATTGAGAACCTGAGACAGACAGAGCTGAAGCTGACCAGGAAGGCCGCC
TATGTGAGATACTTCAACAGCTCTGCCTTCTTCTTCTCTGGCTTCTTTGT
GGTGTTCCTGTCTGTGCTGCCCTATGCCCTGATCAAGGGCATCATCCTGA
GGAAGATCTTCACCACCATCAGCTTCTGCATTGTGCTGAGGATGGCCGTG
ACCAGGCAGTTCCCCTGGGCCGTGCAGACCTGGTATGACAGCCTGGGGGC
CATCAACAAGATCCAGGACTTCCTGCAGAAGCAGGAGTACAAGACCCTGG
AGTACAACCTGACCACCACAGAGGTGGTGATGGAGAATGTGACAGCCTTC

-continued

TGGGAGGAGGGCTTTGGAGAGCTGTTTGAGAAGGCCAAGCAGAACAACAA

CAACAGAAAGACCAGCAATGGAGATGACAGCCTGTTCTTCAGCAACTTCA

GCCTGCTGGGCACCCCTGTGCTGAAGGACATCAACTTCAAGATTGAGAGG

GGCCAGCTGCTGGCCGTGGCCGGCAGCACAGGAGCCGGCAAGACCAGCCT

GCTGATGGTGATCATGGGAGAGCTGGAGCCCTCTGAGGGCAAGATCAAGC

ACTCTGGCAGAATCAGCTTCTGCAGCCAGTTCAGCTGGATCATGCCTGGC

ACCATCAAGGAGAACATCATCTTTGGGGTGAGCTATGATGAGTACAGGTA

CAGATCTGTGATCAAGGCCTGCCAGCTGGAGGAGGACATCTCCAAGTTTG

CCGAGAAGGACAACATTGTGCTGGGGGAGGGAGGCATCACCCTGTCTGGG

GGCCAGAGAGCCAGAATCAGCCTGGCCAGAGCCGTGTACAAGGATGCCGA

CCTGTACCTGCTGGACAGCCCCTTTGGCTACCTGGATGTGCTGACAGAGA

AGGAGATCTTTGAGAGCTGTGTGTGCAAGCTGATGGCCAACAAGACCAGG

ATCCTGGTGACCAGCAAGATGGAGCACCTGAAGAAGGCCGACAAGATCCT

GATCCTGCATGAGGGCAGCAGCTACTTCTATGGCACCTTCTCTGAGCTGC

AGAACCTGCAGCCTGACTTCAGCAGCAAGCTGATGGGCTGTGACAGCTTT

GACCAGTTCTCTGCTGAGAGAAGAAACAGCATCCTGACAGAGACCCTGCA

CAGGTTCAGCCTGGAGGGGGATGCCCCTGTGAGCTGGACAGAGACCAAGA

AGCAGAGCTTCAAGCAGACAGGAGAGTTTGGGGAGAAGAGGAAGAACAGC

ATCCTGAACCCCATCAACAGCATCAGGAAGTTCAGCATTGTGCAGAAGAC

CCCCCTGCAGATGAATGGCATTGAGGAGGACTCTGATGAGCCCCTGGAGA

GAAGACTGAGCCTGGTGCCAGACTCTGAGCAGGGAGAGGCCATCCTGCCC

AGGATCTCTGTGATCAGCACAGGCCCCACCCTGCAGGCCAGAAGAAGACA

GTCTGTGCTGAACCTGATGACCCACTCTGTGAACCAGGGCCAGAATATCC

ACAGAAAGACCACAGCCAGCACCAGAAAGGTGAGCCTGGCCCCCCAGGCC

AACCTGACAGAGCTGGACATCTACAGCAGAAGGCTGAGCCAGGAGACAGG

CCTGGAGATCTCTGAGGAGATCAATGAGGAGGACCTGAAGGAGTGCTTCT

TTGATGACATGGAGAGCATCCCTGCCGTGACCACCTGGAACACCTACCTG

AGATACATCACAGTGCACAAGAGCCTGATCTTTGTGCTGATCTGGTGCCT

GGTGATCTTCCTGGCCGAGGTGGCCGCCAGCCTGGTGGTGCTGTGGCTGC

TGGGCAACACCCCCCTGCAGGACAAGGGCAACAGCACCCACAGCAGAAAC

AACAGCTATGCTGTGATCATCACCAGCACCAGCAGCTACTATGTGTTCTA

CATCTATGTGGGAGTGGCTGACACCCTGCTGGCCATGGGCTTCTTCAGAG

GCCTGCCCCTGGTGCACACCCTGATCACAGTGAGCAAGATCCTGCACCAC

AAGATGCTGCACTCTGTGCTGCAGGCCCCCATGAGCACCCTGAACACCCT

GAAGGCTGGAGGCATCCTGAACAGATTCAGCAAGGACATTGCCATCCTGG

ATGACCTGCTGCCCCTGACCATCTTTGACTTCATCCAGCTGCTGCTGATT

GTGATTGGAGCCATTGCCGTGGTGGCCGTGCTGCAGCCCTACATCTTTGT

GGCCACAGTGCCTGTGATTGTGGCCTTCATCATGCTGAGGGCCTACTTCC

TGCAGACCAGCCAGCAGCTGAAGCAGCTGGAGTCTGAGGGCAGAAGCCCC

ATCTTCACCCACCTGGTGACCAGCCTGAAGGGCCTGTGGACCCTGAGGGC

-continued

CTTTGGCAGACAGCCCTACTTTGAGACCCTGTTCCACAAGGCCCTGAACC

TGCACACAGCCAACTGGTTCCTGTACCTGAGCACCCTGAGATGGTTCCAG

ATGAGGATTGAGATGATCTTTGTGATCTTCTTCATTGCCGTGACCTTCAT

CAGCATCCTGACCACAGGGGAGGGCGAGGGCAGAGTGGGCATCATCCTGA

CCCTGGCCATGAACATCATGAGCACCCTGCAGTGGGCCGTGAACAGCAGC

ATTGATGTGGACAGCCTGATGAGATCTGTGAGCAGAGTGTTCAAGTTCAT

TGACATGCCCACAGAGGGCAAGCCCACCAAGAGCACCAAGCCCTACAAGA

ATGGCCAGCTGAGCAAGGTGATGATCATTGAGAACAGCCATGTGAAGAAG

GATGACATCTGGCCCTCTGGAGGCCAGATGACAGTGAAGGACCTGACAGC

CAAGTACACAGAGGGGGGCAATGCCATCCTGGAGAACATCAGCTTCAGCA

TCAGCCCTGGCCAGAGGGTGGGCCTGCTGGGCAGAACAGGCTCTGGCAAG

AGCACCCTGCTGTCTGCCTTCCTGAGGCTGCTGAACACAGAGGGAGAGAT

CCAGATTGATGGGGTGAGCTGGGACAGCATCACCCTGCAGCAGTGGAGGA

AGGCCTTTGGGGTGATCCCCCAGAAGGTGTTCATCTTCTCTGGCACCTTC

AGGAAGAACCTGGACCCCTATGAGCAGTGGTCTGACCAGGAGATCTGGAA

GGTGGCCGATGAGGTGGGCCTGAGATCTGTGATTGAGCAGTTCCCTGGCA

AGCTGGACTTTGTGCTGGTGGATGGAGGCTGTGTGCTGAGCCATGGCCAC

AAGCAGCTGATGTGCCTGGCCAGATCTGTGCTGAGCAAGGCCAAGATCCT

GCTGCTGGATGAGCCCTCTGCCCACCTGGACCCTGTGACCTACCAGATCA

TCAGAAGAACCCTGAAGCAGGCCTTTGCCGACTGCACAGTGATCCTGTGT

GAGCACAGAATTGAGGCCATGCTGGAGTGCCAGCAGTTCCTGGTGATTGA

GGAGAACAAGGTGAGGCAGTATGACAGCATCCAGAAGCTGCTGAATGAGA

GAAGCCTGTTCAGACAGGCCATCAGCCCCTCTGACAGAGTGAAGCTGTTC

CCCCACAGGAACAGCAGCAAGTGCAAGAGCAAGCCCCAGATTGCCGCCCT

GAAGGAGGAGACAGAGGAGGAGGTGCAGGACACCAGACTGTGA.

In yet another embodiment, an exemplary codon-optimized CFTR mRNA sequence is:

(SEQ ID NO: 19)

ATGCAGAGGAGCCCCCTGGAGAAGGCCAGCGTGGTGAGCAAGCTGTTCTT

CAGCTGGACCAGGCCCATCCTGAGGAAGGGCTACAGGCAGAGGCTGGAGC

TGAGCGACATCTACCAGATCCCCAGCGTGGACAGCGCCGACAACCTGAGC

GAGAAGCTGGAGAGGGAGTGGGACAGGGAGCTGGCCAGCAAGAAGAACCC

CAAGCTGATCAACGCCCTGAGGAGGTGCTTCTTCTGGAGGTTCATGTTCT

ACGGCATCTTCCTGTACCTGGGCGAGGTGACCAAGGCCGTGCAGCCCCTG

CTGCTGGGCAGGATCATCGCCAGCTACGACCCCGACAACAAGGAGGAGAG

GAGCATCGCCATCTACCTGGGCATCGGCCTGTGCCTGCTGTTCATCGTGA

GGACCCTGCTGCTGCACCCCGCCATCTTCGGCCTGCACCACATCGGCATG

CAGATGAGGATCGCCATGTTCAGCCTGATCTACAAGAAGACCCTGAAGCT

GAGCAGCAGGGTGCTGGACAAGATCAGCATCGGCCAGCTGGTGAGCCTGC

TGAGCAACAACCTGAACAAGTTCGACGAGGGCCTGGCCCTGGCCCACTTC

GTGTGGATCGCCCCCCTGCAGGTGGCCCTGCTGATGGGCCTGATCTGGGA

-continued

```
GCTGCTGCAGGCCAGCGCCTTCTGCGGCCTGGGCTTCCTGATCGTGCTGG
CCCTGTTCCAGGCCGGCCTGGGCAGGATGATGATGAAGTACAGGGACCAG
AGGGCCGGCAAGATCAGCGAGAGGCTGGTGATCACCAGCGAGATGATCGA
GAACATCCAGAGCGTGAAGGCCTACTGCTGGGAGGAGGCCATGGAGAAGA
TGATCGAGAACCTGAGGCAGACCGAGCTGAAGCTGACCAGGAAGGCCGCC
TACGTGAGGTACTTCAACAGCAGCGCCTTCTTCTTCAGCGGCTTCTTCGT
GGTGTTCCTGAGCGTGCTGCCCTACGCCCTGATCAAGGGCATCATCCTGA
GGAAGATCTTCACCACCATCAGCTTCTGCATCGTGCTGAGGATGGCCGTG
ACCAGGCAGTTCCCCTGGGCCGTGCAGACCTGGTACGACAGCCTGGGCGC
CATCAACAAGATCCAGGACTTCCTGCAGAAGCAGGAGTACAAGACCCTGG
AGTACAACCTGACCACCACCGAGGTGGTGATGGAGAACGTGACCGCCTTC
TGGGAGGAGGGCTTCGGCGAGCTGTTCGAGAAGGCCAAGCAGAACAACAA
CAACAGGAAGACCAGCAACGGCGACGACAGCCTGTTCTTCAGCAACTTCA
GCCTGCTGGGCACCCCCGTGCTGAAGGACATCAACTTCAAGATCGAGAGG
GGCCAGCTGCTGGCCGTGGCCGGCAGCACCGGCGCCGGCAAGACCAGCCT
GCTGATGGTGATCATGGGCGAGCTGGAGCCCAGCGAGGGCAAGATCAAGC
ACAGCGGCAGGATCAGCTTCTGCAGCCAGTTCAGCTGGATCATGCCCGGC
ACCATCAAGGAGAACATCATCTTCGGCGTGAGCTACGACGAGTACAGGTA
CAGGAGCGTGATCAAGGCCTGCCAGCTGGAGGAGGACATCAGCAAGTTCG
CCGAGAAGGACAACATCGTGCTGGGCGAGGGCGGCATCACCCTGAGCGGC
GGCCAGAGGGCCAGGATCAGCCTGGCCAGGGCCGTGTACAAGGACGCCGA
CCTGTACCTGCTGGACAGCCCCTTCGGCTACCTGGACGTGCTGACCGAGA
AGGAGATCTTCGAGAGCTGCGTGTGCAAGCTGATGGCCAACAAGACCAGG
ATCCTGGTGACCAGCAAGATGGAGCACCTGAAGAAGGCCGACAAGATCCT
GATCCTGCACGAGGGCAGCAGCTACTTCTACGGCACCTTCAGCGAGCTGC
AGAACCTGCAGCCCGACTTCAGCAGCAAGCTGATGGGCTGCGACAGCTTC
GACCAGTTCAGCGCCGAGAGGAGGAACAGCATCCTGACCGAGACCCTGCA
CAGGTTCAGCCTGGAGGGCGACGCCCCCGTGAGCTGGACCGAGACCAAGA
AGCAGAGCTTCAAGCAGACCGGCGAGTTCGGCGAGAAGAGGAAGAACAGC
ATCCTGAACCCCATCAACAGCATCAGGAAGTTCAGCATCGTGCAGAAGAC
CCCCCTGCAGATGAACGGCATCGAGGAGGACAGCGACGAGCCCCTGGAGA
GGAGGCTGAGCCTGGTGCCCGACAGCGAGCAGGGCGAGGCCATCCTGCCC
AGGATCAGCGTGATCAGCACCGGCCCCACCCTGCAGGCCAGGAGGAGGCA
GAGCGTGCTGAACCTGATGACCCACAGCGTGAACCAGGGCCAGAACATCC
ACAGGAAGACCACCGCCAGCACCAGGAAGGTGAGCCTGGCCCCCCAGGCC
AACCTGACCGAGCTGGACATCTACAGCAGGAGGCTGAGCCAGGAGACCGG
CCTGGAGATCAGCGAGGAGATCAACGAGGAGGACCTGAAGGAGTGCTTCT
TCGACGACATGGAGAGCATCCCCGCCGTGACCACCTGGAACACCTACCTG
AGGTACATCACCGTGCACAAGAGCCTGATCTTCGTGCTGATCTGGTGCCT
GGTGATCTTCCTGGCCGAGGTGGCCGCCAGCCTGGTGGTGCTGTGGCTGC
```

-continued

```
TGGGCAACACCCCCCTGCAGGACAAGGGCAACAGCACCCACAGCAGGAAC
AACAGCTACGCCGTGATCATCACCAGCACCAGCAGCTACTACGTGTTCTA
CATCTACGTGGGCGTGGCCGACACCCTGCTGGCCATGGGCTTCTTCAGGG
GCCTGCCCCTGGTGCACACCCTGATCACCGTGAGCAAGATCCTGCACCAC
AAGATGCTGCACAGCGTGCTGCAGGCCCCCATGAGCACCCTGAACACCCT
GAAGGCCGGCGGCATCCTGAACAGGTTCAGCAAGGACATCGCCATCCTGG
ACGACCTGCTGCCCCTGACCATCTTCGACTTCATCCAGCTGCTGCTGATC
GTGATCGGCGCCATCGCCGTGGTGGCCGTGCTGCAGCCCTACATCTTCGT
GGCCACCGTGCCCGTGATCGTGGCCTTCATCATGCTGAGGGCCTACTTCC
TGCAGACCAGCCAGCAGCTGAAGCAGCTGGAGAGCGAGGGCAGGAGCCCC
ATCTTCACCCACCTGGTGACCAGCCTGAAGGGCCTGTGGACCCTGAGGGC
CTTCGGCAGGCAGCCCTACTTCGAGACCCTGTTCCACAAGGCCCTGAACC
TGCACACCGCCAACTGGTTCCTGTACCTGAGCACCCTGAGGTGGTTCCAG
ATGAGGATCGAGATGATCTTCGTGATCTTCTTCATCGCCGTGACCTTCAT
CAGCATCCTGACCACCGGCGAGGGCGAGGGCAGGGTGGGCATCATCCTGA
CCCTGGCCATGAACATCATGAGCACCCTGCAGTGGGCCGTGAACAGCAGC
ATCGACGTGGACAGCCTGATGAGGAGCGTGAGCAGGGTGTTCAAGTTCAT
CGACATGCCCACCGAGGGCAAGCCCACCAAGAGCACCAAGCCCTACAAGA
ACGGCCAGCTGAGCAAGGTGATGATCATCGAGAACAGCCACGTGAAGAAG
GACGACATCTGGCCCAGCGGCGGCCAGATGACCGTGAAGGACCTGACCGC
CAAGTACACCGAGGGCGGCAACGCCATCCTGGAGAACATCAGCTTCAGCA
TCAGCCCCGGCCAGAGGGTGGGCCTGCTGGGCAGGACCGGCAGCGGCAAG
AGCACCCTGCTGAGCGCCTTCCTGAGGCTGCTGAACACCGAGGGCGAGAT
CCAGATCGACGGCGTGAGCTGGGACAGCATCACCCTGCAGCAGTGGAGGA
AGGCCTTCGGCGTGATCCCCCAGAAGGTGTTCATCTTCAGCGGCACCTTC
AGGAAGAACCTGGACCCCTACGAGCAGTGGAGCGACCAGGAGATCTGGAA
GGTGGCCGACGAGGTGGGCCTGAGGAGCGTGATCGAGCAGTTCCCCGGCA
AGCTGGACTTCGTGCTGGTGGACGGCGGCTGCGTGCTGAGCCACGGCCAC
AAGCAGCTGATGTGCCTGGCCAGGAGCGTGCTGAGCAAGGCCAAGATCCT
GCTGCTGGACGAGCCCAGCGCCCACCTGGACCCCGTGACCTACCAGATCA
TCAGGAGGACCCTGAAGCAGGCCTTCGCCGACTGCACCGTGATCCTGTGC
GAGCACAGGATCGAGGCCATGCTGGAGTGCCAGCAGTTCCTGGTGATCGA
GGAGAACAAGGTGAGGCAGTACGACAGCATCCAGAAGCTGCTGAACGAGA
GGAGCCTGTTCAGGCAGGCCATCAGCCCCAGCGACAGGGTGAAGCTGTTC
CCCCACAGGAACAGCAGCAAGTGCAAGAGCAAGCCCCAGATCGCCGCCCT
GAAGGAGGAGACCGAGGAGGAGGTGCAGGACACCAGGCTGTGA.
```

In another embodiment, an exemplary codon-optimized CFTR mRNA sequence is:

(SEQ ID NO: 20)

```
ATGCAGAGATCCCCTCTGGAGAAGGCCTCAGTGGTGTCCAAGCTTTTCTT
CTCCTGGACCAGGCCCATTTTAAGAAAGGGCTACAGGCAGAGACTTGAGC
```

-continued

TGTCTGACATCTATCAGATCCCTTCTGTGGATTCTGCTGACAATCTTAGT
GAAAAATTGGAAAGGGAGTGGGACAGAGAGCTGGCAAGTAAAAAGAACCC
CAAGCTGATTAATGCCCTGAGGCGCTGCTTTTTTTGGAGATTCATGTTCT
ATGGCATATTCCTCTACCTTGGAGAAGTAACCAAAGCTGTACAGCCTCTC
CTCCTTGGCAGAATCATTGCCTCCTATGATCCTGATAACAAGGAGGAGAG
AAGCATAGCCATCTACCTGGGCATTGGGCTGTGCCTCTTGTTTATTGTGA
GGACCCTTCTCTTGCACCCTGCCATCTTTGGCCTTCATCACATTGGCATG
CAAATGAGAATAGCAATGTTTAGTCTTATTTACAAAAAAACATTAAAACT
CTCTTCCAGGGTGTTGGACAAGATCAGTATTGGACAACTGGTCAGCCTGC
TGAGCAACAACCTGAACAAGTTTGATGAAGGACTGGCCCTGGCCCACTTT
GTCTGGATTGCCCCCCTTCAGGTGGCTCTTTTGATGGGCCTGATCTGGGA
ACTCCTGCAGGCCTCTGCCTTCTGTGGGTTAGGCTTCCTGATAGTGCTAG
CTCTCTTTCAGGCAGGGTTGGGTAGAATGATGATGAAGTACAGAGACCAG
AGGGCTGGGAAGATATCTGAGAGGCTGGTCATTACTTCTGAAATGATAGA
AAACATCCAGTCTGTTAAAGCTTACTGCTGGGAGGAGGCTATGGAAAAGA
TGATTGAGAACTTGAGGCAAACAGAGCTCAAGCTGACTAGGAAGGCAGCC
TATGTCAGGTATTTCAACAGCAGTGCTTTCTTCTTCTCAGGCTTTTTCGT
GGTCTTCTTGAGTGTTCTGCCCTATGCCCTCATCAAGGGGATAATTTTGA
GAAAGATTTTCACCACTATTTCCTTTTGCATTGTCCTGAGGATGGCTGTC
ACCAGGCAATTCCCCTGGGCTGTGCAGACATGGTATGACTCTCTGGGGGC
CATCAACAAAATCCAAGATTTCCTGCAGAAGCAGGAGTACAAGACCCTGG
AATACAACCTCACCACCACAGAAGTTGTGATGGAGAATGTGACTGCATTC
TGGGAGGAAGGATTTGGGGAGCTGTTTGAGAAAGCAAAACAAAACAATAA
TAACAGGAAAACCAGCAATGGAGATGACTCCCTGTTCTTTTCCAACTTCT
CTTTGTTGGGCACCCCTGTCCTGAAAGATATAAACTTTAAAATTGAAAGA
GGGCAGCTGTTGGCAGTTGCTGGCTCCACAGGAGCTGGAAAAACTTCACT
ACTGATGGTGATCATGGGGGAGTTAGAACCCTCTGAAGGGAAAATAAAAC
ATTCTGGGAGGATTAGTTTCTGCAGCCAGTTCAGCTGGATCATGCCTGGG
ACCATTAAAGAAAATATTATATTTGGAGTGAGCTATGATGAATATAGATA
TAGGAGTGTCATCAAAGCCTGTCAGTTGGAGGAAGACATCAGCAAATTTG
CAGAGAAAGACAACATTGTTCTGGGTGAAGGTGGCATCACCCTGTCAGGA
GGGCAAAGGGCCAGGATCAGCTTGGCCAGAGCAGTCTATAAAGATGCTGA
TCTGTACCTCCTGGATAGCCCTTTTGGCTATCTGGATGTTTTGACAGAGA
AGGAAATTTTTGAGTCCTGTGTCTGCAAGTTAATGGCAAATAAAACAAGG
ATACTTGTGACCTCAAAAATGGAACACCTGAAGAAGGCTGACAAAATTCT
GATCCTGCATGAGGGCAGCAGCTACTTTTATGGAACATTTTCTGAACTGC
AGAATTTGCAACCAGACTTTTCATCAAAGCTCATGGGATGTGACAGTTTT
GATCAGTTTTCTGCAGAAAGGAGAAACTCCATTTTGACTGAGACCCTGCA
CAGGTTCAGTCTGGAGGGGGATGCCCCAGTGAGTTGGACTGAGACAAAGA
AACAGAGCTTCAAGCAGACTGGAGAGTTTGGAGAAAAGAGGAAAAACTCA

-continued

ATTCTCAATCCCATCAATAGCATCAGGAAGTTCAGCATAGTTCAGAAGAC
TCCTTTGCAGATGAATGGGATTGAAGAGGACTCAGATGAGCCCCTGGAAA
GGAGACTCTCCTTGGTGCCAGATTCAGAGCAGGGGGAAGCCATACTGCCA
AGGATCTCTGTGATTTCTACAGGGCCCACCCTCCAAGCAAGAAGGAGACA
GTCAGTTTTAAACCTGATGACCCACTCTGTCAACCAGGGACAGAACATTC
ATAGAAAGACAACAGCATCTACAAGAAAAGTTTCACTGGCCCCTCAAGCC
AATTTAACTGAACTAGATATCTACAGCAGGAGGCTCAGCCAAGAAACAGG
CCTGGAGATCTCAGAAGAAATAAATGAGGAGGATTTGAAGGAATGCTTCT
TTGATGATATGGAGAGCATCCCAGCTGTCACAACCTGGAACACCTACCTG
AGATACATCACAGTGCACAAATCCCTCATCTTTGTACTTATATGGTGCCT
TGTCATCTTCTTAGCTGAGGTGGCTGCTTCCCTGGTGGTGCTGTGGCTGC
TGGGAAACACACCCCTCCAGGATAAAGGGAACTCTACTCACAGCAGGAAC
AACAGTTATGCTGTGATCATCACCAGTACCTCCTCCTACTATGTGTTCTA
CATTTATGTTGGAGTTGCAGACACATTGCTTGCCATGGGTTTTTTTAGAG
GACTCCCCCTGGTGCATACTCTCATCACTGTTTCCAAAATCCTTCACCAC
AAGATGCTGCACAGTGTACTACAGGCTCCCATGAGCACCCTCAACACTCT
TAAAGCAGGAGGAATCTTGAACAGATTTAGCAAGGACATTGCAATTCTTG
ATGACCTGCTTCCACTGACCATCTTTGACTTCATCCAGCTTCTGCTCATT
GTAATTGGTGCCATTGCTGTGGTAGCAGTGCTCCAGCCATATATTTTTGT
GGCCACTGTGCCTGTTATTGTGGCCTTCATTATGTTGAGAGCCTACTTCC
TGCAGACCTCTCAGCAGCTCAAGCAACTTGAAAGTGAGGGCAGGAGCCCC
ATATTTACACACTTGGTCACTTCCCTCAAAGGCCTCTGGACACTCAGAGC
TTTTGGAAGACAACCTTATTTTGAAACTCTCTTCCACAAGGCTCTGAATC
TCCACACAGCCAACTGGTTTCTGTATCTTTCAACACTGCGCTGGTTCCAG
ATGAGGATTGAGATGATCTTTGTTATCTTCTTCATAGCTGTTACCTTCAT
CTCTATTCTGACAACTGGTGAGGGGGAAGGGAGAGTAGGCATCATCCTCA
CACTAGCCATGAACATAATGTCTACCTTACAATGGGCCGTGAACAGCTCC
ATAGATGTGGACAGCCTCATGAGAAGTGTGTCAAGAGTTTTCAAATTCAT
TGACATGCCCACAGAAGGCAAACCAACCAAGAGCACAAAACCCTACAAGA
ATGGCCAGCTGAGTAAGGTCATGATCATTGAAAATTCTCATGTGAAGAAG
GATGATATTTGGCCCAGTGGGGGCCAGATGACAGTCAAGGACCTCACTGC
CAAATACACAGAGGGTGGAAATGCTATCCTAGAGAACATCTCCTTCTCCA
TCTCCCCAGGCCAAAGAGTTGGCTTGCTGGGCAGGACTGGCAGTGGCAAG
TCCACCTTGCTCTCAGCATTTCTCAGGCTTTTAAATACAGAGGGAGAGAT
TCAAATTGATGGGGTGTCTTGGGATAGTATAACACTTCAACAGTGGAGGA
AAGCCTTTGGTGTGATTCCTCAGAAAGTGTTTATCTTCTCTGGCACTTTC
AGAAAAAATCTGGACCCCTATGAACAGTGGAGTGACCAGGAAATCTGGAA
GGTGGCAGATGAAGTGGGCCTAAGATCAGTCATAGAGCAGTTTCCTGGAA
AGTTGGATTTTGTGCTTGTAGATGGAGGCTGTGTGCTGTCCCATGGCCAT
AAACAGCTAATGTGCCTGGCTAGGTCAGTGCTGAGCAAGGCCAAGATCCT
GCTGTTAGATGAGCCTTCAGCCCATCTGGACCCTGTGACATACCAGATTA

-continued

TCAGAAGAACTCTGAAGCAGGCCTTTGCTGACTGCACTGTCATCCTGTGT

GAGCACAGAATTGAGGCCATGCTGGAGTGCCAGCAGTTCCTTGTTATAGA

AGAGAATAAGGTTAGGCAGTATGACAGCATTCAGAAACTGCTAAATGAAA

GATCTCTCTTCAGGCAAGCTATTTCACCATCTGATAGAGTGAAACTTTTT

CCCCACAGAAATTCCTCTAAATGTAAATCTAAGCCCCAGATAGCTGCCTT

GAAAGAGGAGACTGAAGAAGAAGTCCAGGACACCAGACTGTGA.

In another embodiment, an exemplary codon-optimized CFTR mRNA sequence is:

(SEQ ID NO: 21)

ATGCAGAGATCCCCGCTGGAGAAGGCATCTGTGGTGTCAAAACTGTTCTT

TAGCTGGACAAGGCCCATCCTTAGGAAAGGGTACAGACAGAGGTTGGAGC

TGTCAGACATATATCAGATCCCTTCAGTGGACTCTGCAGACAACCTCTCT

GAAAAGCTGGAGAGGGAATGGGACAGGGAACTGGCCAGCAAAAAAAACCC

TAAACTGATTAATGCCCTGAGGAGGTGCTTCTTTTGGAGATTCATGTTCT

ATGGGATCTTCCTTTACCTGGGGGAGGTGACTAAAGCTGTTCAGCCTCTT

CTTCTGGGGAGGATTATTGCCTCCTATGACCCAGACAACAAAGAAGAAAG

AAGCATAGCCATTTACTTAGGCATAGGCCTCTGCTTGCTCTTCATAGTTA

GAACCCTCCTACTCCACCCAGCCATCTTTGGTCTCCACCACATAGGTATG

CAGATGAGAATAGCAATGTTCTCCTTGATCTACAAGAAGACCCTCAAGCT

GTCCAGCAGGGTGCTGGACAAGATCTCCATAGGCCAGTTAGTCAGTCTAC

TGTCCAATAACTTAAATAAGTTTGATGAGGGACTGGCACTGGCACATTTT

GTGTGGATTGCCCCCCTCCAAGTGGCCCTTCTTATGGGCCTTATCTGGGA

GCTGTTGCAGGCCTCTGCTTTCTGTGGCCTGGGTTTCCTCATAGTCCTAG

CCTTATTCCAGGCTGGACTGGGCAGAATGATGATGAAGTATAGGGACCAA

AGAGCAGGGAAGATTTCTGAAAGGCTGGTTATAACTTCTGAGATGATTGA

GAACATTCAGTCAGTGAAAGCTTACTGCTGGGAAGAAGCTATGGAAAAAA

TGATTGAAAATCTCAGACAGACTGAATTAAAGTTGACCAGGAAAGCTGCT

TATGTCAGATACTTCAACTCCTCAGCCTTCTTTTTTTCTGGCTTCTTTGT

TGTATTCCTTTCAGTCCTCCCCTATGCCCTGATTAAGGGCATTATCTTGA

GGAAAATTTTCACAACCATCTCCTTTTGTATTGTCCTCAGGATGGCTGTT

ACAAGGCAATTTCCTTGGGCTGTGCAAACTTGGTATGATAGCCTTGGAGC

AATCAACAAGATCCAGGATTTCCTGCAAAAGCAGGAGTACAAGACATTGG

AATACAACCTTACCACCACTGAGGTGGTGATGGAAAATGTGACTGCCTTC

TGGGAGGAGGGGTTTGGAGAGCTGTTTGAGAAAGCCAAACAGAACAACAA

CAATAGAAAGACCTCTAATGGTGATGATTCCCTGTTCTTTTCTAACTTTA

GTCTTCTGGGGACCCCAGTTCTGAAAGATATTAACTTTAAAATTGAAAGG

GGACAGTTGCTGGCTGTGGCTGGGTCCACTGGGGCTGGGAAGACAAGCCT

GCTCATGGTGATCATGGGAGAGCTGGAACCCAGTGAAGGAAAGATCAAAC

ACTCAGGCAGGATCTCCTTCTGCAGCCAGTTCTCATGGATTATGCCAGGC

ACTATTAAAGAAAATATCATCTTTGGTGTAAGCTATGATGAGTACAGGTA

-continued

TAGATCTGTAATTAAAGCCTGCCAGCTGGAGGAAGACATCTCTAAGTTTG

CTGAGAAGGATAACATTGTGTTGGGGGAAGGGGGCATCACCCTTTCTGGT

GGGCAGAGGGCTAGGATCTCCCTTGCTAGGGCAGTATACAAGGATGCTGA

CTTGTACCTCTTGGATAGTCCTTTTGGCTACCTAGATGTGCTGACAGAGA

AAGAAATATTTGAAAGCTGTGTGTGTAAGCTCATGGCTAACAAGACCAGG

ATCCTGGTCACCAGTAAAATGGAACACCTCAAAAAAGCAGACAAGATCCT

TATTCTCCATGAGGGCTCCTCCTACTTCTATGGGACCTTCAGTGAGCTGC

AGAATCTGCAGCCAGACTTCTCCTCAAAACTTATGGGCTGTGACTCCTTT

GACCAATTCTCTGCAGAAAGAAGGAATAGCATACTGACAGAAACACTGCA

TAGATTCTCCCTGGAAGGAGATGCCCCAGTGAGTTGGACAGAAACCAAAA

AGCAGAGCTTCAAGCAGACTGGTGAGTTTGGTGAAAAGAGGAAGAATTCT

ATCCTGAACCCCATCAATAGCATCAGGAAATTTAGCATAGTCCAAAAGAC

CCCCCTCCAGATGAATGGAATAGAGGAGGATAGTGATGAGCCTCTTGAGA

GAAGGCTGTCCCTGGTTCCAGACAGTGAACAGGGTGAAGCCATTCTTCCG

AGGATCAGTGTCATCTCCACTGGGCCCACATTGCAGGCCAGAAGAAGACA

GTCTGTTCTGAATTTGATGACACATTCTGTGAATCAAGGCCAGAATATCC

ATAGAAAAACCACTGCCAGCACCAGAAAAGTTTCTCTAGCCCCCCAGGCT

AACCTGACTGAGTTAGACATCTACAGCAGAAGGCTGAGCCAAGAGACTGG

CTTGGAAATATCTGAGGAGATCAATGAGGAGGACCTCAAGGAGTGCTTCT

TTGATGACATGGAGTCAATCCCTGCAGTCACTACATGGAACACTTACCTA

AGGTACATCACAGTTCATAAGAGCCTCATCTTTGTCCTCATATGGTGTCT

GGTCATCTTTTTAGCAGAAGTGGCTGCCAGCCTAGTTGTGCTGTGGTTAC

TGGGCAATACACCTCTTCAGGACAAAGGCAATAGCACACACAGCAGAAAC

AACTCCTATGCAGTGATCATCACCTCTACAAGCTCTTACTATGTATTCTA

TATATATGTGGGAGTGGCAGATACTCTCCTGGCCATGGGATTCTTCAGGG

GATTACCTCTAGTTCACACATTGATCACAGTGTCAAAAATTCTCCACCAC

AAGATGTTACACAGTGTCCTGCAAGCCCCAATGTCTACTCTGAACACACT

TAAGGCAGGTGGAATTTTGAATAGGTTTAGCAAGGACATAGCTATCCTGG

ATGATCTCCTCCCTCTGACCATCTTTGACTTCATCCAGTTACTGCTCATT

GTAATTGGAGCCATTGCAGTGGTAGCAGTCCTACAGCCTTACATTTTTGT

GGCTACTGTTCCTGTTATTGTGGCCTTCATTATGCTAAGAGCTTACTTCC

TGCAAACAAGCCAACAGTTGAAACAGCTAGAAAGTGAGGGAAGGTCCCCC

ATCTTCACCCACCTGGTGACATCACTCAAGGGGCTATGGACTCTTAGGGC

TTTTGGGAGACAGCCGTACTTTGAGACCTTATTCCATAAGGCCCTTAACC

TCCATACAGCAAACTGGTTCTTATACCTGAGTACTCTGAGGTGGTTTCAA

ATGAGGATTGAAATGATTTTTGTGATCTTCTTCATTGCTGTGACCTTCAT

CTCAATCTTGACCACAGGAGAGGGGGAGGGCAGGGTGGGCATCATACTGA

CCTTGGCCATGAACATTATGTCAACCCTGCAGTGGGCTGTCAATAGCTCC

ATTGATGTGGACAGTCTGATGAGGAGTGTCTCCAGGGTCTTCAAGTTTAT

TGACATGCCAACTGAGGGCAAACCCACCAAAAGCACTAAGCCATATAAAA

ATGGCCAACTGTCCAAAGTGATGATCATTGAAAATTCACATGTAAAGAAG

-continued

GATGATATCTGGCCCTCTGGAGGACAGATGACAGTGAAAGACCTGACTGC
CAAGTACACAGAGGGTGGTAATGCCATTCTTGAGAACATTAGTTTCAGTA
TTTCCCCGGGGCAAAGGGTGGGCCTCCTTGGCAGAACAGGCTCTGGCAAG
AGTACCCTGCTGTCAGCCTTTTTAAGACTGTTGAACACTGAGGGAGAAAT
TCAGATTGATGGTGTCTCCTGGGATAGCATCACCCTCCAGCAGTGGAGAA
AAGCTTTTGGAGTGATCCCGCAAAAGGTTTTCATCTTTTCAGGCACCTTC
CGGAAGAACCTGGACCCCTATGAGCAGTGGTCTGACCAGGAAATATGGAA
GGTAGCTGATGAAGTTGGGCTTAGGTCAGTCATAGAGCAGTTCCCAGGCA
AACTGGACTTTGTCCTGGTGGATGGTGGATGTGTACTGAGTCATGGGCAC
AAACAGCTGATGTGCCTAGCCAGGTCTGTGCTCAGCAAGGCAAAGATATT
GCTGCTTGATGAACCCAGTGCCCATCTGGACCCAGTCACATATCAGATCA
TCAGAAGAACATTGAAGCAGGCCTTTGCTGATTGCACAGTTATCCTCTGT
GAGCACAGGATTGAGGCCATGCTGGAGTGCCAGCAGTTTCTGGTGATTGA
GGAGAATAAAGTAAGGCAGTATGACTCCATCCAGAAGCTGCTCAATGAAA
GAAGCCTCTTTAGACAAGCTATCTCCCCCTCAGACAGGGTCAAATTGTTC
CCTCACAGAAACAGCAGCAAGTGCAAGAGCAAGCCCCAAATTGCAGCCTT
GAAAGAGGAGACAGAGGAAGAGGTGCAGGACACCAGACTCTGA.

In another embodiment, an exemplary codon-optimized CFTR mRNA sequence is:

(SEQ ID NO: 22)

ATGCAGAGAAGCCCCCTGGAGAAGGCCAGCGTGGTGAGCAAGCTGTTCTT
CAGCTGGACCAGACCCATCCTGAGAAAGGGCTACAGACAGAGACTGGAGC
TGAGCGACATCTACCAGATCCCCAGCGTGGACAGCGCCGACAACCTGAGC
GAGAAGCTGGAGAGAGAGTGGGACAGAGAGCTGGCCAGCAAGAAGAACCC
CAAGCTGATCAACGCCCTGAGAAGATGCTTCTTCTGGAGATTCATGTTCT
ACGGCATCTTCCTGTACCTGGGCGAGGTGACCAAGGCCGTGCAGCCCCTG
CTGCTGGGCAGAATCATCGCCAGCTACGACCCCGACAACAAGGAGGAGAG
AAGCATCGCCATCTACCTGGGCATCGGCCTGTGCCTGCTGTTCATCGTGA
GAACCCTGCTGCTGCACCCCGCCATCTTCGGCCTGCACCACATCGGCATG
CAGATGAGAATCGCCATGTTCAGCCTGATCTACAAGAAGACCCTGAAGCT
GAGCAGCAGAGTGCTGGACAAGATCAGCATCGGCCAGCTGGTGAGCCTGC
TGAGCAACAACCTGAACAAGTTCGACGAGGGCCTGGCCCTGGCCCACTTC
GTGTGGATCGCCCCCCTGCAGGTGGCCCTGCTGATGGGCCTGATCTGGGA
GCTGCTGCAGGCCAGCGCCTTCTGCGGCCTGGGCTTCCTGATCGTGCTGG
CCCTGTTCCAGGCCGGCCTGGGCAGAATGATGATGAAGTACAGAGACCAG
AGAGCCGGCAAGATCAGCGAGAGACTGGTGATCACCAGCGAGATGATCGA
GAACATCCAGAGCGTGAAGGCCTACTGCTGGGAGGAGGCCATGGAGAAGA
TGATCGAGAACCTGAGACAGACCGAGCTGAAGCTGACCAGAAAGGCCGCC
TACGTGAGATACTTCAACAGCAGCGCCTTCTTCTTCAGCGGCTTCTTCGT
GGTGTTCCTGAGCGTGCTGCCCTACGCCCTGATCAAGGGCATCATCCTGA

-continued

GAAAGATCTTCACCACCATCAGCTTCTGCATCGTGCTGAGAATGGCCGTG
ACCAGACAGTTCCCCTGGGCCGTGCAGACCTGGTACGACAGCCTGGGCGC
CATCAACAAGATCCAGGACTTCCTGCAGAAGCAGGAGTACAAGACCCTGG
AGTACAACCTGACCACCACCGAGGTGGTGATGGAGAACGTGACCGCCTTC
TGGGAGGAGGGCTTCGGCGAGCTGTTCGAGAAGGCCAAGCAGAACAACAA
CAACAGAAAGACCAGCAACGGCGACGACAGCCTGTTCTTCAGCAACTTCA
GCCTGCTGGGCACCCCCGTGCTGAAGGACATCAACTTCAAGATCGAGAGA
GGCCAGCTGCTGGCCGTGGCCGGCAGCACCGGCGCCGGCAAGACCAGCCT
GCTGATGGTGATCATGGGCGAGCTGGAGCCCAGCGAGGGCAAGATCAAGC
ACAGCGGCAGAATCAGCTTCTGCAGCCAGTTCAGCTGGATCATGCCCGGC
ACCATCAAGGAGAACATCATCTTCGGCGTGAGCTACGACGAGTACAGATA
CAGAAGCGTGATCAAGGCCTGCCAGCTGGAGGAGGACATCAGCAAGTTCG
CCGAGAAGGACAACATCGTGCTGGGCGAGGGCGGCATCACCCTGAGCGGC
GGCCAGAGAGCCAGAATCAGCCTGGCCAGAGCCGTGTACAAGGACGCCGA
CCTGTACCTGCTGGACAGCCCCTTCGGCTACCTGGACGTGCTGACCGAGA
AGGAGATCTTCGAGAGCTGCGTGTGCAAGCTGATGGCCAACAAGACCAGA
ATCCTGGTGACCAGCAAGATGGAGCACCTGAAGAAGGCCGACAAGATCCT
GATCCTGCACGAGGGCAGCAGCTACTTCTACGGCACCTTCAGCGAGCTGC
AGAACCTGCAGCCCGACTTCAGCAGCAAGCTGATGGGCTGCGACAGCTTC
GACCAGTTCAGCGCCGAGAGAAGAAACAGCATCCTGACCGAGACCCTGCA
CAGATTCAGCCTGGAGGGCGACGCCCCCGTGAGCTGGACCGAGACCAAGA
AGCAGAGCTTCAAGCAGACCGGCGAGTTCGGCGAGAAGAGAAAGAACAGC
ATCCTGAACCCCATCAACAGCATCAGAAAGTTCAGCATCGTGCAGAAGAC
CCCCCTGCAGATGAACGGCATCGAGGAGGACAGCGACGAGCCCCTGGAGA
GAAGACTGAGCCTGGTGCCCGACAGCGAGCAGGGCGAGGCCATCCTGCCC
AGAATCAGCGTGATCAGCACCGGCCCCACCCTGCAGGCCAGAAGAAGACA
GAGCGTGCTGAACCTGATGACCCACAGCGTGAACCAGGGCCAGAACATCC
ACAGAAAGACCACCGCCAGCACCAGAAAGGTGAGCCTGGCCCCCCAGGCC
AACCTGACCGAGCTGGACATCTACAGCAGAAGACTGAGCCAGGAGACCGG
CCTGGAGATCAGCGAGGAGATCAACGAGGAGGACCTGAAGGAGTGCTTCT
TCGACGACATGGAGAGCATCCCCGCCGTGACCACCTGGAACACCTACCTG
AGATACATCACCGTGCACAAGAGCCTGATCTTCGTGCTGATCTGGTGCCT
GGTGATCTTCCTGGCCGAGGTGGCCGCCAGCCTGGTGGTGCTGTGGCTGC
TGGGCAACACCCCCCTGCAGGACAAGGGCAACAGCACCCACAGCAGAAAC
AACAGCTACGCCGTGATCATCACCAGCACCAGCAGCTACTACGTGTTCTA
CATCTACGTGGGCGTGGCCGACACCCTGCTGGCCATGGGCTTCTTCAGAG
GCCTGCCCCTGGTGCACACCCTGATCACCGTGAGCAAGATCCTGCACCAC
AAGATGCTGCACAGCGTGCTGCAGGCCCCCATGAGCACCCTGAACACCCT
GAAGGCCGGCGGCATCCTGAACAGATTCAGCAAGGACATCGCCATCCTGG
ACGACCTGCTGCCCCTGACCATCTTCGACTTCATCCAGCTGCTGCTGATC
GTGATCGGCGCCATCGCCGTGGTGGCCGTGCTGCAGCCCTACATCTTCGT

-continued

GGCCACCGTGCCCGTGATCGTGGCCTTCATCATGCTGAGAGCCTACTTCC

TGCAGACCAGCCAGCAGCTGAAGCAGCTGGAGAGCGAGGGCAGAAGCCCC

ATCTTCACCCACCTGGTGACCAGCCTGAAGGGCCTGTGGACCCTGAGAGC

CTTCGGCAGACAGCCCTACTTCGAGACCCTGTTCCACAAGGCCCTGAACC

TGCACACCGCCAACTGGTTCCTGTACCTGAGCACCCTGAGATGGTTCCAG

ATGAGAATCGAGATGATCTTCGTGATCTTCTTCATCGCCGTGACCTTCAT

CAGCATCCTGACCACCGGCGAGGGCGAGGGCAGAGTGGGCATCATCCTGA

CCCTGGCCATGAACATCATGAGCACCCTGCAGTGGGCCGTGAACAGCAGC

ATCGACGTGGACAGCCTGATGAGAAGCGTGAGCAGAGTGTTCAAGTTCAT

CGACATGCCCACCGAGGGCAAGCCCACCAAGAGCACCAAGCCCTACAAGA

ACGGCCAGCTGAGCAAGGTGATGATCATCGAGAACAGCCACGTGAAGAAG

GACGACATCTGGCCCAGCGGCGGCCAGATGACCGTGAAGGACCTGACCGC

CAAGTACACCGAGGGCGGCAACGCCATCCTGGAGAACATCAGCTTCAGCA

TCAGCCCCGGCCAGAGAGTGGGCCTGCTGGGCAGAACCGGCAGCGGCAAG

AGCACCCTGCTGAGCGCCTTCCTGAGACTGCTGAACACCGAGGGCGAGAT

CCAGATCGACGGCGTGAGCTGGGACAGCATCACCCTGCAGCAGTGGAGAA

AGGCCTTCGGCGTGATCCCCCAGAAGGTGTTCATCTTCAGCGGCACCTTC

AGAAAGAACCTGGACCCCTACGAGCAGTGGAGCGACCAGGAGATCTGGAA

GGTGGCCGACGAGGTGGGCCTGAGAAGCGTGATCGAGCAGTTCCCCGGCA

AGCTGGACTTCGTGCTGGTGGACGGCGGCTGCGTGCTGAGCCACGGCCAC

AAGCAGCTGATGTGCCTGGCCAGAAGCGTGCTGAGCAAGGCCAAGATCCT

GCTGCTGGACGAGCCCAGCGCCCACCTGGACCCCGTGACCTACCAGATCA

TCAGAAGAACCCTGAAGCAGGCCTTCGCCGACTGCACCGTGATCCTGTGC

GAGCACAGAATCGAGGCCATGCTGGAGTGCCAGCAGTTCCTGGTGATCGA

GGAGAACAAGGTGAGACAGTACGACAGCATCCAGAAGCTGCTGAACGAGA

GAAGCCTGTTCAGACAGGCCATCAGCCCCAGCGACAGAGTGAAGCTGTTC

CCCCACAGAAACAGCAGCAAGTGCAAGAGCAAGCCCCAGATCGCCGCCCT

GAAGGAGGAGACCGAGGAGGAGGTGCAGGACACCAGACTGTGA.

In another embodiment, an exemplary codon-optimized CFTR mRNA sequence is:

(SEQ ID NO: 23)

ATGCAGCGCAGCCCCCTGGAGAAGGCCAGCGTGGTGAGCAAGCTGTTCTT

CAGCTGGACCCGCCCCATCCTGCGCAAGGGCTACCGCCAGCGCCTGGAGC

TGAGCGACATCTACCAGATCCCCAGCGTGGACAGCGCCGACAACCTGAGC

GAGAAGCTGGAGCGCGAGTGGGACCGCGAGCTGGCCAGCAAGAAGAACCC

CAAGCTGATCAACGCCCTGCGCCGCTGCTTCTTCTGGCGCTTCATGTTCT

ACGGCATCTTCCTGTACCTGGGCGAGGTGACCAAGGCCGTGCAGCCCCTG

CTGCTGGGCCGCATCATCGCCAGCTACGACCCCGACAACAAGGAGGAGCG

CAGCATCGCCATCTACCTGGGCATCGGCCTGTGCCTGCTGTTCATCGTGC

GCACCCTGCTGCTGCACCCCGCCATCTTCGGCCTGCACCACATCGGCATG

-continued

CAGATGCGCATCGCCATGTTCAGCCTGATCTACAAGAAGACCCTGAAGCT

GAGCAGCCGCGTGCTGGACAAGATCAGCATCGGCCAGCTGGTGAGCCTGC

TGAGCAACAACCTGAACAAGTTCGACGAGGGCCTGGCCCTGGCCCACTTC

GTGTGGATCGCCCCCCTGCAGGTGGCCCTGCTGATGGGCCTGATCTGGGA

GCTGCTGCAGGCCAGCGCCTTCTGCGGCCTGGGCTTCCTGATCGTGCTGG

CCCTGTTCCAGGCCGGCCTGGGCCGCATGATGATGAAGTACCGCGACCAG

CGCGCCGGCAAGATCAGCGAGCGCCTGGTGATCACCAGCGAGATGATCGA

GAACATCCAGAGCGTGAAGGCCTACTGCTGGGAGGAGGCCATGGAGAAGA

TGATCGAGAACCTGCGCCAGACCGAGCTGAAGCTGACCCGCAAGGCCGCC

TACGTGCGCTACTTCAACAGCAGCGCCTTCTTCTTCAGCGGCTTCTTCGT

GGTGTTCCTGAGCGTGCTGCCCTACGCCCTGATCAAGGGCATCATCCTGC

GCAAGATCTTCACCACCATCAGCTTCTGCATCGTGCTGCGCATGGCCGTG

ACCCGCCAGTTCCCCTGGGCCGTGCAGACCTGGTACGACAGCCTGGGCGC

CATCAACAAGATCCAGGACTTCCTGCAGAAGCAGGAGTACAAGACCCTGG

AGTACAACCTGACCACCACCGAGGTGGTGATGGAGAACGTGACCGCCTTC

TGGGAGGAGGGCTTCGGCGAGCTGTTCGAGAAGGCCAAGCAGAACAACAA

CAACCGCAAGACCAGCAACGGCGACGACAGCCTGTTCTTCAGCAACTTCA

GCCTGCTGGGCACCCCCGTGCTGAAGGACATCAACTTCAAGATCGAGCGC

GGCCAGCTGCTGGCCGTGGCCGGCAGCACCGGCGCCGGCAAGACCAGCCT

GCTGATGGTGATCATGGGCGAGCTGGAGCCCAGCGAGGGCAAGATCAAGC

ACAGCGGCCGCATCAGCTTCTGCAGCCAGTTCAGCTGGATCATGCCCGGC

ACCATCAAGGAGAACATCATCTTCGGCGTGAGCTACGACGAGTACCGCTA

CCGCAGCGTGATCAAGGCCTGCCAGCTGGAGGAGGACATCAGCAAGTTCG

CCGAGAAGGACAACATCGTGCTGGGCGAGGGCGGCATCACCCTGAGCGGC

GGCCAGCGCGCCCGCATCAGCCTGGCCCGCGCCGTGTACAAGGACGCCGA

CCTGTACCTGCTGGACAGCCCCTTCGGCTACCTGGACGTGCTGACCGAGA

AGGAGATCTTCGAGAGCTGCGTGTGCAAGCTGATGGCCAACAAGACCCGC

ATCCTGGTGACCAGCAAGATGGAGCACCTGAAGAAGGCCGACAAGATCCT

GATCCTGCACGAGGGCAGCAGCTACTTCTACGGCACCTTCAGCGAGCTGC

AGAACCTGCAGCCCGACTTCAGCAGCAAGCTGATGGGCTGCGACAGCTTC

GACCAGTTCAGCGCCGAGCGCCGCAACAGCATCCTGACCGAGACCCTGCA

CCGCTTCAGCCTGGAGGGCGACGCCCCCGTGAGCTGGACCGAGACCAAGA

AGCAGAGCTTCAAGCAGACCGGCGAGTTCGGCGAGAAGCGCAAGAACAGC

ATCCTGAACCCCATCAACAGCATCCGCAAGTTCAGCATCGTGCAGAAGAC

CCCCCTGCAGATGAACGGCATCGAGGAGGACAGCGACGAGCCCCTGGAGC

GCCGCCTGAGCCTGGTGCCCGACAGCGAGCAGGGCGAGGCCATCCTGCCC

CGCATCAGCGTGATCAGCACCGGCCCCACCCTGCAGGCCCGCCGCCGCCA

GAGCGTGCTGAACCTGATGACCCACAGCGTGAACCAGGGCCAGAACATCC

ACCGCAAGACCACCGCCAGCACCCGCAAGGTGAGCCTGGCCCCCCAGGCC

AACCTGACCGAGCTGGACATCTACAGCCGCCGCCTGAGCCAGGAGACCGG

CCTGGAGATCAGCGAGGAGATCAACGAGGAGGACCTGAAGGAGTGCTTCT

-continued

TCGACGACATGGAGAGCATCCCCGCCGTGACCACCTGGAACACCTACCTG

CGCTACATCACCGTGCACAAGAGCCTGATCTTCGTGCTGATCTGGTGCCT

GGTGATCTTCCTGGCCGAGGTGGCCGCCAGCCTGGTGGTGCTGTGGCTGC

TGGGCAACACCCCCCTGCAGGACAAGGGCAACAGCACCCACAGCCGCAAC

AACAGCTACGCCGTGATCATCACCAGCACCAGCAGCTACTACGTGTTCTA

CATCTACGTGGGCGTGGCCGACACCCTGCTGGCCATGGGCTTCTTCCGCG

GCCTGCCCCTGGTGCACACCCTGATCACCGTGAGCAAGATCCTGCACCAC

AAGATGCTGCACAGCGTGCTGCAGGCCCCCATGAGCACCCTGAACACCCT

GAAGGCCGGCGGCATCCTGAACCGCTTCAGCAAGGACATCGCCATCCTGG

ACGACCTGCTGCCCCTGACCATCTTCGACTTCATCCAGCTGCTGCTGATC

GTGATCGGCGCCATCGCCGTGGTGGCCGTGCTGCAGCCCTACATCTTCGT

GGCCACCGTGCCCGTGATCGTGGCCTTCATCATGCTGCGCGCCTACTTCC

TGCAGACCAGCCAGCAGCTGAAGCAGCTGGAGAGCGAGGGCCGCAGCCCC

ATCTTCACCCACCTGGTGACCAGCCTGAAGGGCCTGTGGACCCTGCGCGC

CTTCGGCCGCCAGCCCTACTTCGAGACCCTGTTCCACAAGGCCCTGAACC

TGCACACCGCCAACTGGTTCCTGTACCTGAGCACCCTGCGCTGGTTCCAG

ATGCGCATCGAGATGATCTTCGTGATCTTCTTCATCGCCGTGACCTTCAT

CAGCATCCTGACCACCGGCGAGGGCGAGGGCCGCGTGGGCATCATCCTGA

CCCTGGCCATGAACATCATGAGCACCCTGCAGTGGGCCGTGAACAGCAGC

ATCGACGTGGACAGCCTGATGCGCAGCGTGAGCCGCGTGTTCAAGTTCAT

CGACATGCCCACCGAGGGCAAGCCCACCAAGAGCACCAAGCCCTACAAGA

ACGGCCAGCTGAGCAAGGTGATGATCATCGAGAACAGCCACGTGAAGAAG

GACGACATCTGGCCCAGCGGCGGCCAGATGACCGTGAAGGACCTGACCGC

CAAGTACACCGAGGGCGGCAACGCCATCCTGGAGAACATCAGCTTCAGCA

TCAGCCCCGGCCAGCGCGTGGGCCTGCTGGGCCGCACCGGCAGCGGCAAG

AGCACCCTGCTGAGCGCCTTCCTGCGCCTGCTGAACACCGAGGGCGAGAT

CCAGATCGACGGCGTGAGCTGGGACAGCATCACCCTGCAGCAGTGGCGCA

AGGCCTTCGGCGTGATCCCCCAGAAGGTGTTCATCTTCAGCGGCACCTTC

CGCAAGAACCTGGACCCCTACGAGCAGTGGAGCGACCAGGAGATCTGGAA

GGTGGCCGACGAGGTGGGCCTGCGCAGCGTGATCGAGCAGTTCCCCGGCA

AGCTGGACTTCGTGCTGGTGGACGGCGGCTGCGTGCTGAGCCACGGCCAC

AAGCAGCTGATGTGCCTGGCCCGCAGCGTGCTGAGCAAGGCCAAGATCCT

GCTGCTGGACGAGCCCAGCGCCCACCTGGACCCCGTGACCTACCAGATCA

TCCGCCGCACCCTGAAGCAGGCCTTCGCCGACTGCACCGTGATCCTGTGC

GAGCACCGCATCGAGGCCATGCTGGAGTGCCAGCAGTTCCTGGTGATCGA

GGAGAACAAGGTGCGCCAGTACGACAGCATCCAGAAGCTGCTGAACGAGC

GCAGCCTGTTCCGCCAGGCCATCAGCCCCAGCGACCGCGTGAAGCTGTTC

CCCCACCGCAACAGCAGCAAGTGCAAGAGCAAGCCCCAGATCGCCGCCCT

GAAGGAGGAGACCGAGGAGGAGGTGCAGGACACCCGCCTGTAA.

In yet another embodiment, an exemplary codon-optimized CFTR mRNA sequence is:

(SEQ ID NO: 24)

ATGCAGAGAAGCCCCCTGGAGAAGGCCAGCGTGGTGAGCAAGCTGTTCTT

CAGCTGGACCAGACCCATCCTGAGAAAGGGCTACAGACAGAGACTGGAGC

TGAGCGACATCTACCAGATCCCCAGCGTGGACAGCGCCGACAACCTGAGC

GAGAAGCTGGAGAGAGAGTGGGACAGAGAGCTGGCCAGCAAGAAGAACCC

CAAGCTGATCAACGCCCTGAGAAGATGCTTCTTCTGGAGATTCATGTTCT

ACGGCATCTTCCTGTACCTGGGCGAGGTGACCAAGGCCGTGCAGCCCCTG

CTGCTGGGCAGAATCATCGCCAGCTACGACCCCGACAACAAGGAGGAGAG

AAGCATCGCCATCTACCTGGGCATCGGCCTGTGCCTGCTGTTCATCGTGA

GAACCCTGCTGCTGCACCCCGCCATCTTCGGCCTGCACCACATCGGCATG

CAGATGAGAATCGCCATGTTCAGCCTGATCTACAAGAAGACCCTGAAGCT

GAGCAGCAGAGTGCTGGACAAGATCAGCATCGGCCAGCTGGTGAGCCTGC

TGAGCAACAACCTGAACAAGTTCGACGAGGGCCTGGCCCTGGCCCACTTC

GTGTGGATCGCCCCCCTGCAGGTGGCCCTGCTGATGGGCCTGATCTGGGA

GCTGCTGCAGGCCAGCGCCTTCTGCGGCCTGGGCTTCCTGATCGTGCTGG

CCCTGTTCCAGGCCGGCCTGGGCAGAATGATGATGAAGTACAGGGACCAG

AGAGCCGGCAAGATCAGCGAGAGACTGGTGATCACCAGCGAGATGATCGA

GAACATCCAGAGCGTGAAGGCCTACTGCTGGGAGGAGGCCATGGAGAAGA

TGATCGAGAACCTGAGACAGACCGAGCTGAAGCTGACCAGAAAGGCCGCC

TACGTGAGATACTTCAACAGCAGCGCCTTCTTCTTCAGCGGCTTCTTCGT

GGTGTTCCTGAGCGTGCTGCCCTACGCCCTGATCAAGGGCATCATCCTGA

GAAAGATCTTCACCACCATCAGCTTCTGCATCGTGCTGAGAATGGCCGTG

ACCAGACAGTTCCCCTGGGCCGTGCAGACCTGGTACGACAGCCTGGGCGC

CATCAACAAGATCCAGGACTTCCTGCAGAAGCAGGAGTACAAGACCCTGG

AGTACAACCTGACCACCACCGAGGTGGTGATGGAGAACGTGACCGCCTTC

TGGGAGGAGGGCTTCGGCGAGCTGTTCGAGAAGGCCAAGCAGAACAACAA

CAACAGAAAGACCAGCAACGGCGACGACAGCCTGTTCTTCAGCAACTTCA

GCCTGCTGGGCACCCCCGTGCTGAAGGACATCAACTTCAAGATCGAGAGA

GGCCAGCTGCTGGCCGTGGCCGGCAGCACCGGCGCCGGCAAGACCAGCCT

GCTGATGGTGATCATGGGCGAGCTGGAGCCCAGCGAGGGCAAGATCAAGC

ACAGCGGCAGAATCAGCTTCTGCAGCCAGTTCAGCTGGATCATGCCCGGC

ACCATCAAGGAGAACATCATCTTCGGCGTGAGCTACGACGAGTACAGATA

CAGAAGCGTGATCAAGGCCTGCCAGCTGGAGGAGGACATCAGCAAGTTCG

CCGAGAAGGACAACATCGTGCTGGGCGAGGGCGGCATCACCCTGAGCGGC

GGCCAGAGAGCCAGAATCAGCCTGGCCAGAGCCGTGTACAAGGACGCCGA

CCTGTACCTGCTGGACAGCCCCTTCGGCTACCTGGACGTGCTGACCGAGA

AGGAGATCTTCGAGAGCTGCGTGTGCAAGCTGATGGCCAACAAGACCAGA

ATCCTGGTGACCAGCAAGATGGAGCACCTGAAGAAGGCCGACAAGATCCT

GATCCTGCACGAGGGCAGCAGCTACTTCTACGGCACCTTCAGCGAGCTGC

AGAACCTGCAGCCCGACTTCAGCAGCAAGCTGATGGGCTGCGACAGCTTC

GACCAGTTCAGCGCCGAGAGAAGAAACAGCATCCTGACCGAGACCCTGCA

-continued

CAGATTCAGCCTGGAGGGCGACGCCCCCGTGAGCTGGACCGAGACCAAGA
AGCAGAGCTTCAAGCAGACCGGCGAGTTCGGCGAGAAGAGAAAGAACAGC
ATCCTGAACCCCATCAACAGCATCAGAAAGTTCAGCATCGTGCAGAAGAC
CCCCCTGCAGATGAACGGCATCGAGGAGGACAGCGACGAGCCCCTGGAGA
GAAGACTGAGCCTGGTGCCCGACAGCGAGCAGGGCGAGGCCATCCTGCCC
AGAATCAGCGTGATCAGCACCGGCCCCACCCTGCAGGCCAGAAGAAGACA
GAGCGTGCTGAACCTGATGACCCACAGCGTGAACCAGGGCCAGAACATCC
ACAGAAAGACCACCGCCAGCACCAGAAAGGTGAGCCTGGCCCCCCAGGCC
AACCTGACCGAGCTGGACATCTACAGCAGAAGACTGAGCCAGGAGACCGG
CCTGGAGATCAGCGAGGAGATCAACGAGGAGGACCTGAAGGAGTGCTTCT
TCGACGACATGGAGAGCATCCCCGCCGTGACCACCTGGAACACCTACCTG
AGATACATCACCGTGCACAAGAGCCTGATCTTCGTGCTGATCTGGTGCCT
GGTGATCTTCCTGGCCGAGGTGGCCGCCAGCCTGGTGGTGCTGTGGCTGC
TGGGCAACACCCCCCTGCAGGACAAGGGCAACAGCACCCACAGCAGAAAC
AACAGCTACGCCGTGATCATCACCAGCACCAGCAGCTACTACGTGTTCTA
CATCTACGTGGGCGTGGCCGACACCCTGCTGGCCATGGGCTTCTTCAGAG
GCCTGCCCCTGGTGCACACCCTGATCACCGTGAGCAAGATCCTGCACCAC
AAGATGCTGCACAGCGTGCTGCAGGCCCCCATGAGCACCCTGAACACCCT
GAAGGCCGGCGGCATCCTGAACAGATTCAGCAAGGACATCGCCATCCTGG
ACGACCTGCTGCCCCTGACCATCTTCGACTTCATCCAGCTGCTGCTGATC
GTGATCGGCGCCATCGCCGTGGTGGCCGTGCTGCAGCCCTACATCTTCGT
GGCCACCGTGCCCGTGATCGTGGCCTTCATCATGCTGAGAGCCTACTTCC
TGCAGACCAGCCAGCAGCTGAAGCAGCTGGAGAGCGAGGGCAGGAGCCCC
ATCTTCACCCACCTGGTGACCAGCCTGAAGGGCCTGTGGACCCTGAGAGC
CTTCGGCAGACAGCCCTACTTCGAGACCCTGTTCCACAAGGCCCTGAACC
TGCACACCGCCAACTGGTTCCTGTACCTGAGCACCCTGAGATGGTTCCAG
ATGAGAATCGAGATGATCTTCGTGATCTTCTTCATCGCCGTGACCTTCAT
CAGCATCCTGACCACCGGCGAGGGCGAGGGCAGAGTGGGCATCATCCTGA
CCCTGGCCATGAACATCATGAGCACCCTGCAGTGGGCCGTGAACAGCAGC
ATCGACGTGGACAGCCTGATGAGAAGCGTGAGCAGAGTGTTCAAGTTCAT
CGACATGCCCACCGAGGGCAAGCCCACCAAGAGCACCAAGCCCTACAAGA
ACGGCCAGCTGAGCAAGGTGATGATCATCGAGAACAGCCACGTGAAGAAG
GACGACATCTGGCCCAGCGGCGGCCAGATGACCGTGAAGGACCTGACCGC
CAAGTACACCGAGGGCGGCAACGCCATCCTGGAGAACATCAGCTTCAGCA
TCAGCCCCGGCCAGAGAGTGGGCCTGCTGGGCAGAACCGGCAGCGGCAAG
AGCACCCTGCTGAGCGCCTTCCTGAGACTGCTGAACACCGAGGGCGAGAT
CCAGATCGACGGCGTGAGCTGGGACAGCATCACCCTGCAGCAGTGGAGAA
AGGCCTTCGGCGTGATCCCCCAGAAGGTGTTCATCTTCAGCGGCACCTTC
AGAAAGAACCTGGACCCCTACGAGCAGTGGAGCGACCAGGAGATCTGGAA
GGTGGCCGACGAGGTGGGCCTGAGAAGCGTGATCGAGCAGTTCCCCGGCA
AGCTGGACTTCGTGCTGGTGGACGGCGGCTGCGTGCTGAGCCACGGCCAC
AAGCAGCTGATGTGCCTGGCCAGAAGCGTGCTGAGCAAGGCCAAGATCCT
GCTGCTGGACGAGCCCAGCGCCCACCTGGACCCCGTGACCTACCAGATCA
TCAGAAGAACCCTGAAGCAGGCCTTCGCCGACTGCACCGTGATCCTGTGC
GAGCACAGAATCGAGGCCATGCTGGAGTGCCAGCAGTTCCTGGTGATCGA
GGAGAACAAGGTGAGACAGTACGACAGCATCCAGAAGCTGCTGAACGAGA
GAAGCCTGTTCAGACAGGCCATCAGCCCCAGCGACAGAGTGAAGCTGTTC
CCCCACAGAAACAGCAGCAAGTGCAAGAGCAAGCCCCAGATCGCCGCCCT
GAAGGAGGAGACCGAGGAGGAGGTGCAGGACACCAGACTGTGA.

In another embodiment, an exemplary codon-optimized CFTR mRNA sequence is:

(SEQ ID NO: 25)

ATGCAGAGGTCACCTCTGGAAAAGGCTAGCGTGGTCAGCAAGCTATTTTT
TTCCTGGACCCGCCCGATACTCAGGAAGGGCTACCGACAGCGGCTGGAGC
TGAGTGACATTTATCAGATTCCCTCCGTCGATTCCGCTGACAACCTGTCT
GAGAAACTGGAGCGGGAATGGGATAGGGAACTGGCGTCCAAAAAAAACCC
CAAACTCATCAATGCACTCCGCAGATGCTTCTTCTGGCGGTTTATGTTTT
ATGGCATATTCCTGTATCTGGGGGAGGTGACGAAAGCCGTGCAGCCGCTG
CTGCTTGGTCGCATTATCGCGTCATACGATCCAGATAACAAGGAGGAAAG
AAGTATCGCTATCTATCTCGGGATAGGGCTGTGCCTGCTCTTCATTGTGC
GGACTCTTCTCTTGCACCCCGCCATTTTCGGTCTGCATCATATAGGTATG
CAGATGAGAATTGCGATGTTCTCATTGATTTACAAAAAAACGCTTAAGCT
AAGTTCAAGGGTGCTAGATAAGATATCGATCGGCCAGCTGGTGTCTCTGC
TTAGCAACAACCTCAATAAATTCGACGAAGGCCTTGCACTGGCCCACTTC
GTGTGGATCGCCCCTCTGCAGGTGGCTCTGCTGATGGGGTTAATATGGGA
GCTGTTGCAGGCCTCCGCTTTTTGTGGCCTGGGGTTTCTCATCGTGTTGG
CCTTGTTTCAGGCAGGGCTGGGACGTATGATGATGAAATATAGGGATCAG
AGGGCTGGCAAAATCTCTGAGCGCCTGGTTATTACGAGTGAAATGATTGA
GAACATCCAGTCAGTGAAGGCCTATTGCTGGGAGGAGGCCATGGAAAAAA
TGATTGAGAACCTACGCCAGACTGAGCTGAAGTTAACCAGAAAAGCCGCC
TATGTGCGCTACTTTAACAGTAGCGCATTTTTCTTCTCCGGTTTTTTCGT
GGTGTTTCTTAGTGTGTTGCCGTATGCCTTAATCAAGGGAATAATACTCC
GGAAGATTTTCACTACCATCAGCTTCTGTATCGTGTTGCGGATGGCCGTC
ACCCGGCAGTTTCCCTGGGCAGTACAGACTTGGTACGATTCTCTCGGAGC
AATTAACAAAATCCAAGACTTTCTACAAAAGCAGGAGTACAAGACCCTGG
AGTACAATCTGACCACCACAGAAGTCGTAATGGAGAATGTAACTGCCTTC
TGGGAAGAGGGCTTTGGCGAACTCTTTGAAAAGGCCAAGCAGAACAATAA
CAACCGGAAGACCTCCAACGGGGACGACAGCTTATTTTTCAGCAATTTTT
CTTTGCTCGGGACCCCTGTACTGAAAGATATTAACTTTAAGATCGAGCGC
GGACAACTCCTGGCTGTCGCCGGCAGCACTGGAGCTGGAAAAACATCACT
GCTTATGGTGATAATGGGAGAACTCGAACCAAGCGAGGGAAAAATAAAGC

-continued

ACTCTGGACGGATTAGTTTTTGCTCCCAGTTCTCGTGGATAATGCCTGGC

ACCATTAAGGAGAATATCATCTTTGGAGTGAGTTACGACGAATACCGGTA

CCGGTCCGTTATCAAGGCTTGTCAACTCGAGGAGGACATTTCTAAATTCG

CCGAAAAAGATAATATAGTGCTGGGCGAAGGAGGCATTACACTGAGCGGG

GGTCAGAGAGCTCGAATTAGCCTCGCCCGAGCAGTCTATAAAGACGCCGA

TCTTTACCTGCTGGATTCCCCTTTTGGGTATTTGGATGTTCTGACAGAGA

AGGAAATCTTTGAATCATGTGTCTGTAAACTGATGGCCAATAAGACTAGG

ATTCTAGTGACTTCGAAAATGGAGCACCTGAAAAAAGCGGACAAAATTCT

GATACTCCATGAAGGGTCTTCCTACTTCTACGGCACCTTCTCAGAGTTGC

AGAACTTACAACCTGATTTTTCATCTAAGCTTATGGGGTGCGACTCGTTT

GACCAGTTCTCCGCTGAAAGACGAAACAGCATCTTAACGGAAACTCTTCA

CAGGTTCTCATTAGAGGGAGATGCGCCGGTGTCCTGGACAGAGACAAAAA

AACAGTCTTTCAAACAGACAGGAGAGTTTGGCGAGAAGAGAAAAAACTCA

ATCCTCAATCCCATCAATTCTATTAGAAAGTTTAGCATCGTCCAAAAAAC

ACCATTGCAGATGAATGGGATTGAGGAGGACAGTGATGAGCCTTTGGAAC

GAAGACTGTCCCTGGTACCCGATAGCGAACAGGGTGAGGCCATCCTTCCT

AGGATCTCGGTCATAAGTACAGGGCCCACACTGCAGGCCAGGCGACGTCA

AAGTGTCCTCAATCTTATGACGCACAGTGTGAATCAGGGGCAGAACATCC

ATCGTAAGACGACAGCTTCAACTCGAAAGGTCAGTCTAGCTCCACAAGCC

AATCTTACAGAGCTGGACATTTATTCCCGCCGCCTCAGTCAGGAGACCGG

ATTGGAAATATCAGAGGAAATTAATGAAGAGGATCTGAAGGAATGCTTCT

TTGATGACATGGAATCGATCCCCGCTGTTACTACCTGGAACACATATCTG

AGATATATTACCGTCCATAAGAGCTTAATCTTTGTACTGATATGGTGCTT

GGTGATTTTCCTGGCAGAGGTTGCGGCGAGTTTGGTCGTGCTATGGCTCC

TTGGAAACACTCCCCTGCAGGATAAGGGGAACTCCACTCATAGCAGGAAT

AACAGCTATGCCGTGATCATCACCTCTACCTCCTCTTATTACGTGTTTTA

CATATACGTCGGTGTTGCGGATACCCTGTTGGCAATGGGGTTCTTTAGAG

GACTACCCCTAGTTCACACCCTGATCACCGTTTCGAAGATCTTGCACCAC

AAGATGCTTCATAGCGTTCTCCAAGCTCCTATGAGCACCCTTAATACACT

GAAAGCAGGAGGTATCCTTAACCGCTTTTCCAAAGACATCGCTATACTCG

ACGATTTGCTCCCATTGACCATCTTCGACTTCATTCAGCTGCTCCTCATT

GTGATCGGCGCCATTGCCGTGGTCGCAGTGTTACAGCCATATATTTTCGT

AGCCACCGTGCCCGTCATCGTGGCATTTATCATGCTGCGCGCATATTTCT

TACAGACATCTCAGCAACTGAAGCAGCTGGAATCTGAGGGCAGATCTCCT

ATTTTTACACACCTGGTTACCAGCCTGAAGGGCCTGTGGACCCTGCGTGC

TTTCGGTCGCCAACCCTACTTTGAGACTCTCTTCCATAAGGCTCTGAATT

TACATACTGCCAATTGGTTCCTATACCTTAGTACCCTTCGGTGGTTCCAG

ATGCGGATAGAAATGATCTTCGTGATTTTCTTCATCGCAGTCACTTTCAT

CTCTATTTTGACGACCGGTGAGGGCGAGGGCAGGGTGGGCATCATTCTGA

CTTTGGCCATGAACATTATGTCAACACTCCAGTGGGCCGTTAATTCAAGC

ATTGATGTGGATTCCTTGATGCGTTCCGTCAGCAGGGTATTTAAATTCAT

-continued

AGACATGCCCACCGAGGGCAAGCCAACAAAATCTACCAAGCCATACAAAA

ATGGCCAACTAAGCAAGGTCATGATTATCGAGAATTCTCATGTGAAAAAG

GACGACATTTGGCCTTCCGGGGGTCAAATGACTGTAAAGGACCTGACGGC

TAAATACACTGAGGGCGGTAATGCTATCTTGGAGAACATCTCTTTCAGCA

TCTCCCCTGGCCAGAGAGTGGGACTGCTCGGGCGGACAGGCTCCGGAAAG

TCTACGCTCCTTTCAGCATTCCTTAGACTTCTGAACACCGAAGGTGAGAT

TCAGATTGACGGGGTCTCTTGGGACTCCATCACACTTCAGCAATGGAGGA

AGGCATTCGGTGTAATCCCCCAAAAGGTTTTTATCTTCTCCGGAACATTT

CGTAAGAATCTGGACCCGTACGAGCAGTGGTCAGATCAGGAGATCTGGAA

AGTAGCAGACGAGGTCGGGCTACGGAGCGTTATTGAACAGTTTCCTGGCA

AACTGGACTTCGTTTTGGTGGACGGAGGCTGTGTGCTGAGTCACGGCCAT

AAACAACTGATGTGCTTAGCTAGGTCTGTTCTCAGCAAGGCAAAGATTTT

ACTGCTGGATGAACCAAGCGCCCACCTTGATCCAGTGACATATCAAATCA

TCAGAAGAACTCTTAAACAGGCGTTCGCCGACTGCACAGTGATCCTGTGT

GAGCACAGAATAGAAGCCATGCTGGAATGTCAACAGTTTCTCGTGATTGA

GGAGAACAAGGTGCGCCAGTACGATAGCATCCAGAAGTTACTCAATGAAA

GGTCACTCTTCAGGCAGGCCATCTCACCCAGCGACCGCGTTAAGCTGTTT

CCACACCGAAACAGTTCCAAGTGCAAAAGTAAGCCACAGATTGCTGCACT

GAAGGAAGAGACAGAAGAAGAAGTTCAGGACACTCGGCTCTGA.

In another embodiment, an exemplary codon-optimized CFTR mRNA sequence is:

(SEQ ID NO: 26)

ATGCAGAGGAGCCCACTGGAGAAAGCCTCCGTGGTGAGTAAACTCTTTTT

TAGTTGGACCAGACCCATCCTGCGAAAAGGATACAGGCAGCGCCTCGAGT

TGTCAGATATCTACCAGATTCCTTCTGTGGACTCAGCTGACAATTTGAGT

GAGAAGCTGGAGCGGGAGTGGGATAGAGAGCTGGCGAGCAAAAAAAACCC

CAAGCTTATCAATGCTCTGCGCCGCTGCTTTTTCTGGAGGTTCATGTTTT

ATGGGATCTTCCTGTACCTGGGGGAGGTCACCAAAGCTGTTCAGCCGCTC

CTTCTTGGCCGCATCATCGCCAGCTATGACCCTGATAATAAAGAAGAAAG

GTCTATTGCTATTTATCTGGGAATTGGCCTCTGCTTGCTCTTCATCGTCC

GCACCCTTCTGCTGCACCCTGCCATTTTTGGCCTTCACCACATCGGCATG

CAAATGAGAATTGCCATGTTCTCCCTCATTTACAAAAAGACCCTGAAACT

TTCCTCAAGAGTGTTAGATAAAATATCCATTGGTCAGCTGGTCAGCCTGC

TGTCCAACAATCTTAACAAATTTGATGAAGGCTTGGCGCTGGCCCACTTC

GTGTGGATTGCACCTCTGCAGGTGGCCCTGTTGATGGGACTTATATGGGA

GCTGCTTCAAGCCTCTGCTTTCTGTGGGCTGGGCTTTTTGATTGTACTGG

CACTTTTTCAGGCTGGGCTCGGAAGAATGATGATGAAATACAGAGATCAG

CGGGCCGGGAAGATATCAGAGCGACTTGTGATCACCAGTGAAATGATTGA

AAATATTCAGAGCGTGAAAGCCTACTGCTGGGAAGAAGCCATGGAGAAGA

TGATTGAGAACCTGAGGCAGACAGAGCTCAAGCTCACTCGGAAGGCTGCT

-continued

TATGTTCGCTATTTCAACAGCAGCGCCTTCTTCTTCAGTGGCTTCTTTGT
TGTCTTCCTGTCTGTTCTGCCATATGCACTGATAAAAGGCATTATTTTAC
GAAAGATCTTCACCACCATCAGTTTTTGCATCGTTCTCAGGATGGCCGTC
ACAAGACAGTTCCCCTGGGCTGTGCAGACCTGGTACGATTCCTTGGGGGC
CATCAACAAGATTCAAGATTTCTTGCAAAAACAAGAATATAAAACTTTAG
AATACAACCTCACCACCACTGAAGTGGTCATGGAAAATGTGACAGCCTTT
TGGGAGGAGGGTTTTGGAGAATTGTTCGAGAAGGCAAAGCAGAATAACAA
CAACAGGAAGACGAGCAATGGGGACGACTCTCTCTTCTTCAGCAACTTTT
CACTGCTCGGGACCCCTGTGTTGAAAGATATAAACTTCAAGATCGAGAGG
GGCCAGCTCTTGGCTGTGGCAGGCTCCACTGGAGCTGGTAAAACATCTCT
TCTCATGGTGATCATGGGGGAACTGGAGCCTTCCGAAGGAAAAATCAAGC
ACAGTGGGAGAATCTCATTCTGCAGCCAGTTTTCCTGGATCATGCCCGGC
ACCATTAAGGAAAACATCATATTTGGAGTGTCCTATGATGAGTACCGCTA
CCGGTCAGTCATCAAAGCCTGTCAGTTGGAGGAGGACATCTCCAAGTTTG
CAGAGAAAGACAACATTGTGCTTGGAGAGGGGGGTATCACTCTTTCTGGA
GGACAAAGAGCCAGGATCTCTTTGGCCCGGGCAGTCTACAAGGATGCAGA
CCTCTACTTGTTGGACAGTCCCTTCGGCTACCTCGACGTGCTGACTGAAA
AAGAAATTTTTGAAAGCTGTGTGTGCAAACTGATGGCAAACAAGACCAGG
ATTCTTGTCACCAGCAAGATGGAACATCTGAAGAAAGCGGACAAAATTCT
GATTCTGCATGAAGGGAGCTCCTACTTCTATGGAACATTTAGCGAGCTTC
AGAACCTACAGCCAGACTTCTCCTCCAAATTAATGGGCTGTGACTCCTTC
GACCAGTTCTCTGCAGAAAGAAGAAACTCTATACTCACAGAGACCCTCCA
CCGCTTCTCCCTTGAGGGAGATGCCCCAGTTTCTTGGACAGAAACCAAGA
AGCAGTCCTTTAAGCAGACTGGCGAGTTTGGTGAAAAGAGGAAAAATTCA
ATTCTCAATCCAATTAACAGTATTCGCAAGTTCAGCATTGTCCAGAAGAC
ACCCCTCCAGATGAATGGCATCGAAGAAGATAGTGACGAGCCGCTGGAGA
GACGGCTGAGTCTGGTGCCAGATTCAGAACAGGGGGAGGCCATCCTGCCC
CGGATCAGCGTCATTTCCACAGGCCCCACATTACAAGCACGGCGCCGGCA
GAGTGTTTTAAATCTCATGACCCATTCAGTGAACCAGGGCCAAAATATCC
ACAGGAAGACTACAGCTTCTACCCGGAAAGTGTCTCTGGCCCCTCAGGCC
AATCTGACCGAGCTGGACATCTACAGCAGGAGGCTCTCCCAGGAAACAGG
GCTGGAAATATCTGAAGAGATTAATGAAGAGGATCTTAAAGAGTGCTTCT
TTGATGACATGGAGAGCATCCCCGCGGTGACCACATGGAACACCTACCTT
AGATATATTACTGTCCACAAGAGCCTCATATTTGTCCTCATCTGGTGCCT
GGTTATTTTCCTCGCTGAGGTGGCGGCCAGTCTTGTTGTGCTCTGGCTGC
TGGGCAACACTCCTCTCCAGGACAAGGGCAATAGTACTCACAGCAGAAAT
AATTCTTATGCCGTCATCATTACAAGCACCTCCAGCTACTACGTGTTCTA
CATCTATGTGGGCGTGGCTGACACCCTCCTGGCCATGGGTTTCTTCCGGG
GCCTGCCTTTGGTGCACACCCTCATCACAGTGTCAAAAATTCTGCACCAT
AAAATGCTTCATTCTGTCCTGCAGGCACCCATGAGCACTTTGAACACATT
GAAGGCTGGCGGCATCCTCAACAGATTTTCTAAAGATATTGCTATCCTGG

-continued

ATGATCTCCTCCCCCTGACAATCTTTGACTTTATCCAGCTTCTGCTGATC
GTGATTGGAGCCATAGCAGTGGTTGCTGTCCTGCAGCCCTACATTTTTGT
GGCCACCGTGCCCGTGATTGTTGCCTTTATTATGCTCAGAGCTTACTTCC
TGCAAACTTCTCAACAGCTCAAACAGCTAGAATCTGAGGGCCGGAGCCCC
ATTTTTACCCACCTGGTGACTTCCCTGAAGGGACTGTGGACTCTGAGAGC
ATTCGGGCGACAGCCTTACTTTGAGACACTGTTCCACAAGGCCCTGAACT
TGCACACTGCCAACTGGTTTCTTTACCTGAGCACACTCCGCTGGTTCCAG
ATGCGGATAGAGATGATCTTCGTCATCTTTTTTATAGCTGTAACCTTCAT
TTCTATCCTTACAACAGGAGAAGGAGAGGGCAGGGTGGGAATCATCCTCA
CGCTGGCTATGAACATAATGTCCACCTTGCAGTGGGCCGTGAATTCCAGT
ATAGATGTGGATTCTCTAATGAGGAGTGTCTCCCGGGTGTTTAAATTCAT
TGATATGCCTACTGAGGGGAAACCCACCAAGTCAACAAAACCTTATAAGA
ATGGACAGCTGAGCAAGGTGATGATAATTGAGAACAGCCACGTGAAGAAG
GATGACATTTGGCCCAGCGGGGGCCAGATGACTGTGAAGGACCTGACGGC
CAAGTACACCGAAGGTGGAAATGCCATTTTGGAAAACATCAGCTTCTCAA
TCTCTCCTGGGCAGAGAGTTGGATTGCTGGGTCGCACGGGCAGCGGCAAA
TCAACCCTGCTCAGTGCCTTCCTTCGGCTCCTGAATACAGAAGGCGAAAT
CCAAATTGACGGGGTGAGCTGGGACAGCATCACCCTGCAGCAGTGGAGAA
AAGCATTTGGGGTCATTCCACAGAAAGTTTTCATCTTCTCTGGCACTTTC
AGAAAGAACCTGGACCCCTATGAGCAGTGGAGCGACCAGGAGATCTGGAA
GGTTGCAGATGAAGTTGGCCTGCGGAGTGTGATAGAACAATTTCCTGGCA
AGCTGGATTTTGTGCTGGTAGATGGAGGCTGCGTGCTGTCCCACGGCCAC
AAACAGCTGATGTGCCTCGCCCGCTCCGTTCTTTCAAAGGCCAAAATCTT
GCTTTTGGATGAGCCCAGTGCTCACCTCGACCCAGTGACCTATCAGATAA
TCCGCAGGACCTTAAAGCAAGCTTTTGCCGACTGCACCGTCATACTGTGT
GAGCACCGGATTGAAGCAATGCTGGAATGCCAGCAGTTTCTGGTGATCGA
GGAGAATAAGGTCCGGCAGTACGACAGCATCCAGAAGTTGTTGAATGAGC
GCAGCCTTTTCCGCCAGGCCATCTCCCCATCTGACAGAGTCAAGCTGTTT
CCACATAGGAACTCCTCTAAGTGCAAGTCCAAGCCCCAGATCGCTGCCCT
CAAGGAGGAAACTGAGGAAGAGGTGCAGGATACCCGCCTGTGA.

In another embodiment, an exemplary codon-optimized CFTR mRNA sequence is:

(SEQ ID NO: 27)

ATGCAACGGAGTCCTCTGGAAAAAGCCTCTGTCGTATCTAAGCTTTTCTT
CAGTTGGACACGCCCGATTTTGAGAAAGGGTTATCGGCAACGCTTGGAAC
TTAGTGACATCTACCAAATTCCAAGTGTAGACTCAGCCGATAACTTGAGC
GAAAAGCTCGAACGAGAGTGGGATCGAGAACTGGCTAGCAAAAAAAATCC
CAAACTCATAAATGCCCTGCGACGCTGTTTCTTTTGGCGATTTATGTTTT
ACGGTATTTTCCTTTATTTGGGTGAGGTCACGAAGGCTGTACAGCCACTG
CTGCTGGGTCGCATCATTGCCTCTTACGACCCTGACAACAAAGAGGAGCG

-continued

GTCAATAGCTATCTACCTTGGTATAGGACTTTGCTTGCTCTTCATAGTCC
GCACGTTGCTTCTCCACCCTGCTATATTTGGTCTCCATCACATTGGGATG
CAAATGCGGATCGCGATGTTCAGTCTTATATATAAAAAGACTCTTAAACT
TTCCAGCCGGGTTCTGGATAAGATCTCTATTGGTCAACTGGTATCTCTTT
TGTCTAACAACCTGAATAAGTTCGACGAGGGCCTTGCATTGGCCCATTTT
GTATGGATTGCCCCTTTGCAAGTCGCCCTCCTGATGGGATTGATCTGGGA
ACTCCTGCAAGCTAGTGCTTTTTGCGGATTGGGATTCCTCATAGTCCTTG
CGCTCTTTCAGGCGGGACTTGGACGCATGATGATGAAGTATCGCGACCAA
CGAGCTGGCAAGATCAGTGAACGGCTTGTAATAACCAGTGAAATGATAGA
GAACATCCAGAGCGTAAAAGCTTACTGTTGGGAAGAAGCGATGGAAAAGA
TGATTGAGAACCTTCGCCAGACAGAACTTAAACTTACACGAAAGGCCGCT
TATGTCCGGTACTTCAACTCTTCAGCATTTTTTTTAGTGGCTTCTTTGT
AGTGTTCCTGTCCGTCCTTCCGTATGCACTTATCAAGGGTATAAATACTTA
GGAAAATCTTCACAACAATCAGTTTTTGCATAGTCCTTCGCATGGCAGTA
ACTCGCCAATTTCCCTGGGCAGTTCAGACGTGGTACGACTCACTTGGCGC
AATTAACAAAATTCAAGATTTCCTCCAAAAGCAAGAGTATAAAACCTTGG
AATACAACCTTACCACCACAGAAGTTGTAATGGAAAATGTCACAGCCTTC
TGGGAGGAAGGTTTCGGCGAACTTTTTGAGAAGGCGAAGCAAAATAACAA
TAATCGGAAAACATCAAACGGTGACGATTCACTGTTCTTTTCTAACTTTA
GCCTTCTTGGGACGCCCGTCCTGAAGGACATAAACTTTAAGATTGAACGG
GGTCAACTTCTCGCGGTCGCAGGGAGTACTGGAGCGGGGAAAACGAGCCT
GCTGATGGTGATAATGGGGGAGTTGGAGCCCTCAGAAGGCAAGATCAAGC
ATAGTGGTAGAATTAGCTTCTGCAGTCAATTTAGTTGGATTATGCCGGGC
ACGATCAAAGAAAATATAATCTTTGGGGTATCCTACGATGAATACAGGTA
CCGATCAGTGATAAAAGCGTGCCAGCTTGAAGAAGACATTTCAAAGTTTG
CTGAGAAGGATAATATCGTACTTGGAGAAGGAGGTATCACCCTGTCTGGG
GGTCAACGAGCGAGGATCTCCCTGGCACGCGCCGTCTACAAGGACGCGGA
CCTCTATCTGTTGGATTCACCGTTCGGATATTTGGACGTGCTTACGGAGA
AAGAAATATTTGAGAGCTGTGTTTGCAAGCTCATGGCAAATAAAACCAGA
ATATTGGTTACAAGCAAGATGGAGCATCTTAAGAAAGCAGATAAAATCCT
GATATTGCACGAGGGCTCTTCATACTTCTACGGGACGTTTTCTGAGTTGC
AGAACCTCCAGCCGGATTTCAGCTCTAAGCTGATGGGCTGTGATTCCTTT
GATCAGTTTAGTGCGGAAAGACGAAACAGTATACTCACCGAAACACTGCA
CAGGTTCTCTCTGGAGGGCGACGCCCCGGTTTCCTGGACAGAGACGAAGA
AGCAGTCCTTCAAACAGACAGGCGAGTTTGGGGAGAAAAGGAAAAATAGC
ATACTCAACCCGATTAACAGCATTCGCAAGTTCAGTATAGTACAAAAGAC
CCCGTTGCAGATGAACGGTATAGAGGAAGATTCTGATGAGCCACTGGAAA
GACGGCTTTCTCTCGTTCCGGACAGTGAACAGGGAGAGGCAATACTGCCT
CGGATCAGCGTTATCTCTACAGGACCTACTTTGCAAGCTCGGCGCCGACA
GTCAGTCTTGAATCTTATGACTCATAGTGTTAATCAAGGCCAGAATATCC
ATCGCAAGACCACCGCAAGTACAAGGAAAGTGAGCTTGGCACCTCAAGCA

-continued

AACCTTACTGAACTTGATATCTACTCACGGCGACTTTCACAGGAGACCGG
ACTTGAAATTAGTGAAGAAATTAACGAGGAGGACCTCAAGGAGTGCTTCT
TCGATGACATGGAATCAATCCCCGCAGTCACAACCTGGAACACTTATCTG
AGGTATATAACAGTTCACAAGAGCCTCATTTTTGTACTTATTTGGTGTTT
GGTAATTTTCCTGGCGGAGGTTGCTGCTTCTTTGGTCGTCCTTTGGCTCC
TCGGGAATACACCGCTCCAAGACAAAGGCAACTCTACCCATAGTAGGAAC
AATTCATATGCAGTGATTATAACCAGTACATCATCTTATTACGTTTTCTA
TATTTATGTCGGGGTAGCTGACACGCTGTTGGCGATGGGCTTCTTTAGGG
GCCTCCCCTTGGTACACACCCTTATCACGGTGAGTAAAATCCTGCATCAC
AAAATGCTTCATTCTGTACTCCAAGCGCCGATGAGTACGCTTAATACGCT
GAAAGCAGGAGGGATACTGAATCGGTTCAGCAAGGACATCGCCATTCTGG
ATGACCTGCTTCCATTGACAATATTTGATTTCATTCAGCTCCTTCTCATA
GTTATTGGAGCCATAGCGGTGGTGGCTGTGCTTCAGCCTTATATATTCGT
TGCCACAGTTCCCGTTATAGTGGCATTTATAATGCTCAGGGCCTACTTTC
TCCAGACTTCCCAGCAGTTGAAGCAACTCGAATCAGAAGGAAGGTCACCT
ATTTTCACACATCTTGTGACTTCCTTGAAGGGCTTGTGGACGCTGCGGGC
CTTCGGAAGACAACCATATTTTGAAACTCTCTTCCACAAAGCTTTGAATC
TTCATACTGCGAACTGGTTCCTGTATTTGAGTACTTTGCGCTGGTTCCAG
ATGAGGATAGAAATGATATTCGTTATCTTCTTTATCGCGGTTACGTTCAT
AAGTATCCTCACTACGGGGGAGGGTGAGGGTAGAGTGGGCATAATACTGA
CCCTCGCCATGAACATTATGTCCACCCTGCAGTGGGCGGTAAACAGCAGC
ATAGATGTGGATTCTTTGATGCGCAGTGTGAGCAGGGTTTTTAAGTTTAT
CGATATGCCGACGGAAGGAAAGCCCACTAAAAGCACGAAACCCTATAAAA
ATGGACAGCTTAGCAAAGTAATGATAATCGAGAATAGCCATGTGAAAAAG
GATGACATATGGCCTTCCGGAGGCCAAATGACTGTTAAAGATCTGACCGC
TAAATATACCGAGGGCGGCAACGCAATACTCGAAAACATAAGCTTTTCCA
TAAGCCCCGGCCAACGCGTGGGTCTTCTGGGGAGGACTGGCTCCGGAAAA
TCAACGTTGCTTAGCGCGTTTTTGCGGCTCCTTAACACTGAAGGTGAGAT
CCAAATAGATGGCGTTAGTTGGGACTCTATAACACTGCAACAATGGCGGA
AAGCTTTCGGCGTCATACCTCAGAAGGTGTTCATCTTTAGCGGAACGTTC
AGGAAGAACTTGGATCCCTACGAACAATGGAGTGATCAAGAAATATGGAA
AGTGGCAGATGAGGTAGGCTTGCGCAGTGTCATTGAACAATTCCCAGGGA
AACTCGACTTTGTACTGGTGGACGGCGGTTGCGTCTTGTCACACGGGCAC
AAACAGTTGATGTGTTTGGCCCCGCAGTGTTTTGTCTAAGGCGAAGATTCT
GTTGCTCGACGAACCGAGTGCTCATCTTGATCCCGTCACCTACCAAATCA
TCAGAAGGACGTTGAAGCAAGCTTTCGCCGACTGCACTGTAATCCTTTGT
GAGCATAGGATCGAAGCAATGCTCGAGTGCCAACAGTTCTTGGTTATAGA
GGAGAATAAGGTTCGGCAATACGACTCAATACAGAAACTGCTTAATGAGC
GGTCACTCTTTCGACAAGCTATCTCTCCTAGTGACAGGGTAAAGCTTTTT

-continued

```
CCTCATCGGAATTCCAGCAAGTGTAAGAGTAAACCACAGATCGCCGCCCT

TAAAGAGGAGACCGAAGAAGAGGTGCAGGATACGAGACTTTAG.
```

In some embodiments, a codon-optimized CFTR mRNA sequence suitable for the present invention shares at least 60%, 65%, 70%, 75%, 80%, 85%, 90%, 95%, 96%, 97%, 98%, or 99% identity to SEQ ID NO:6 or SEQ ID NO:7 and encodes a CFTR protein having an amino acid sequence of SEQ ID NO:2.

In some embodiments, a suitable mRNA sequence may be an mRNA sequence encoding a homolog or an analog of human CFTR (hCFTR) protein. For example, a homolog or an analog of hCFTR protein may be a modified hCFTR protein containing one or more amino acid substitutions, deletions, and/or insertions as compared to a wild-type or naturally-occurring hCFTR protein while retaining substantial hCFTR protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 2. In some embodiments, an mRNA suitable for the present invention encodes a protein substantially identical to hCFTR protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 2. In some embodiments, an mRNA suitable for the present invention encodes a fragment or a portion of hCFTR protein. In some embodiments, an mRNA suitable for the present invention encodes a fragment or a portion of hCFTR protein, wherein the fragment or portion of the protein still maintains CFTR activity similar to that of the wild-type protein. Thus, in some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 6 or SEQ ID NO: 7.

In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to any one of SEQ ID NO: 8, SEQ ID NO: 29, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27.

In some embodiments, a suitable mRNA encodes a fusion protein comprising a full length, fragment or portion of an hCFTR protein fused to another protein (e.g., an N or C terminal fusion). In some embodiments, the protein fused to the mRNA encoding a full length, fragment or portion of an hCFTR protein encodes a signal or a cellular targeting sequence.

mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., mRNAs encoding CFTR) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

In some embodiments, mRNAs (e.g., mRNAs encoding CFTR) include a 3' tail structure. Typically, a tail structure includes a poly(A) and/or poly(C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

Modified mRNA

A CFTR mRNA may contain only naturally-occurring nucleotides (or unmodified nucleotides). In some embodiments, however, a suitable CFTR mRNA may contain backbone modifications, sugar modifications and/or base modifications. For example, modified nucleotides may include, but not be limited to, modified purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., mRNAs encoding CFTR) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., mRNAs encoding CFTR) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs encoding CFTR are unmodified.

Delivery Vehicles

According to the present invention, mRNA encoding a CFTR protein (e.g., a full length, fragment, or portion of a CFTR protein) as described herein may be delivered as naked mRNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

According to various embodiments, suitable delivery vehicles include, but are not limited to polymer based carriers, such as polyethyleneimine (PEI), lipid nanoparticles (LNPs) and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle (LNP) or liposome. In some embodiments, liposomes may comprise one or more cationic lipids. In some embodiments, a liposome comprises one or more cationic lipids, one or more non-cationic lipids, one or more cholesterol-based lipids and one or more PEG-modified lipids. In some embodiments, a liposome comprises one or more cationic lipids, one or more non-cationic lipids, and one or more PEG-modified lipids. In some embodiments, a liposome comprises no more than four distinct lipid components. In some embodiments, a liposome comprises no more than three distinct lipid components. In some embodiments, one distinct lipid component is a sterol-based cationic lipid.

As used herein, the term "cationic lipids" refers to any of a number of lipid and lipidoid species that have a net positive charge at a selected pH, such as at physiological pH. Several cationic lipids have been described in the literature, many of which are commercially available.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

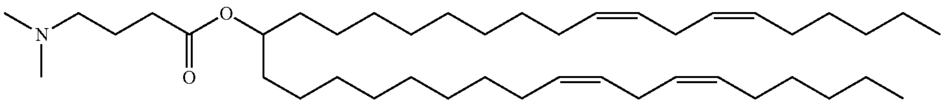 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

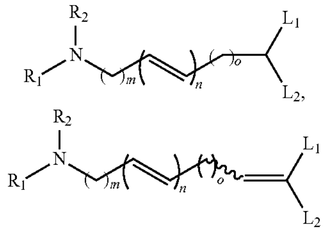

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z,18Z)—N,N-dimethyl-6-(9Z,12Z)-octadeca-9,12-dien-1-yl) tetracosa-15,18-dien-1-amine ("HGT5000"), having a compound structure of:

(HGT-5000)

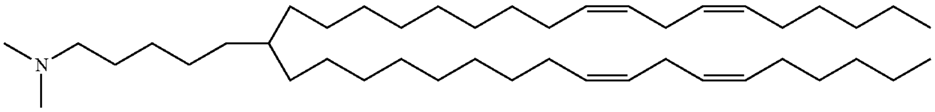

and pharmaceutically acceptable salts thereof. In certain embodiments, the compositions and methods of the present invention include the cationic lipid (15Z,18Z)—N,N-dimethyl-6-((9Z,12Z)-octadeca-9,12-dien-1-yl) tetracosa-4,15,18-trien-1-amine ("HGT5001"), having a compound structure of:

(HGT-5001)

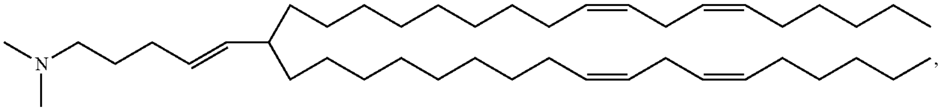

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

(HGT-5002)

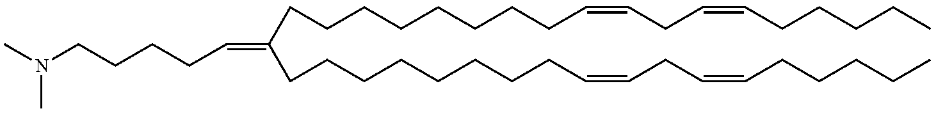

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

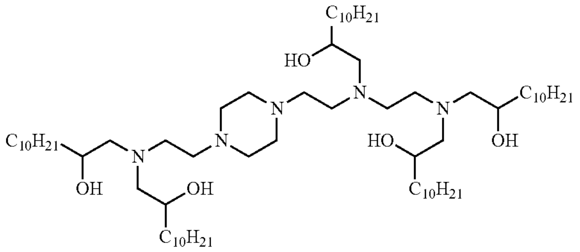

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

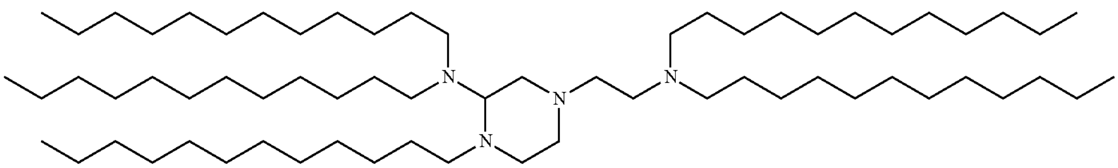 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

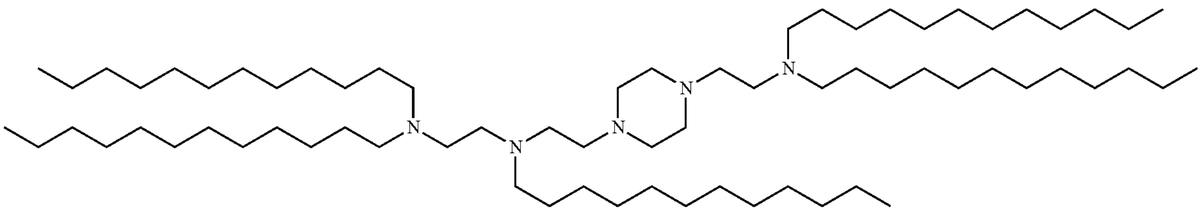 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

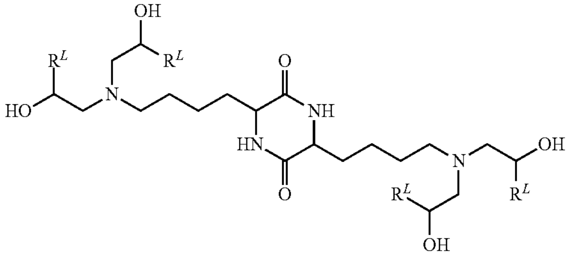

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

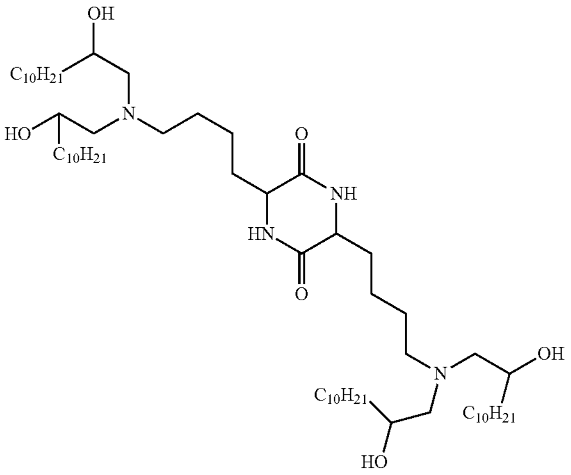

and pharmaceutically acceptable salts thereof. In certain embodiments, the compositions and methods of the present invention include a cationic lipid having a compound structure of:

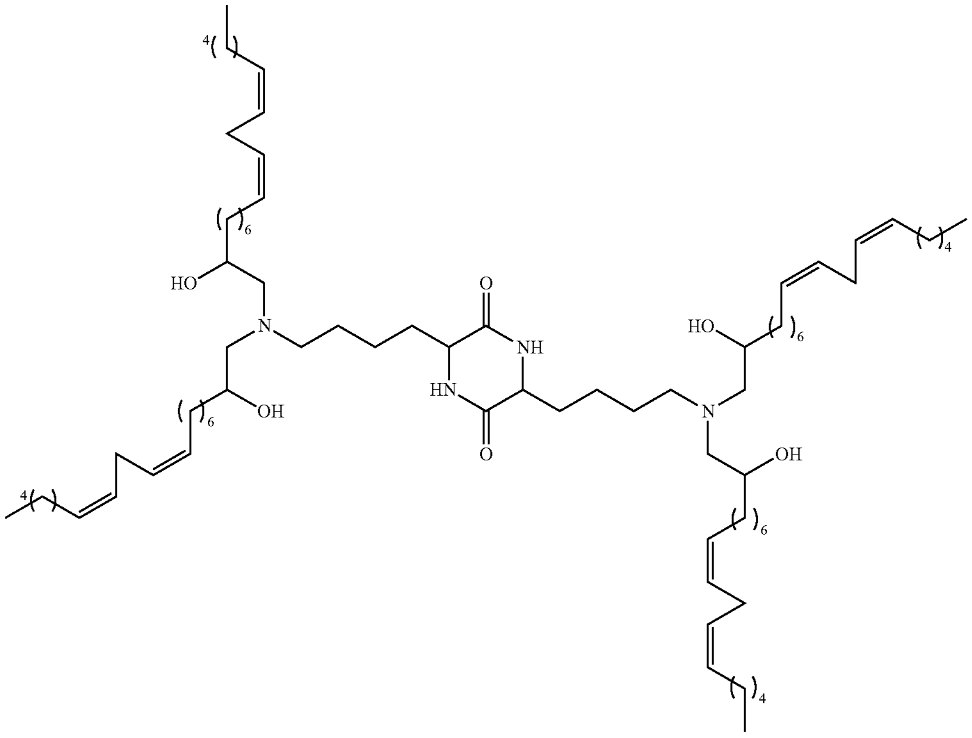

and pharmaceutically acceptable salts thereof. In certain embodiments, the compositions and methods of the present invention include a cationic lipid having a compound structure of:

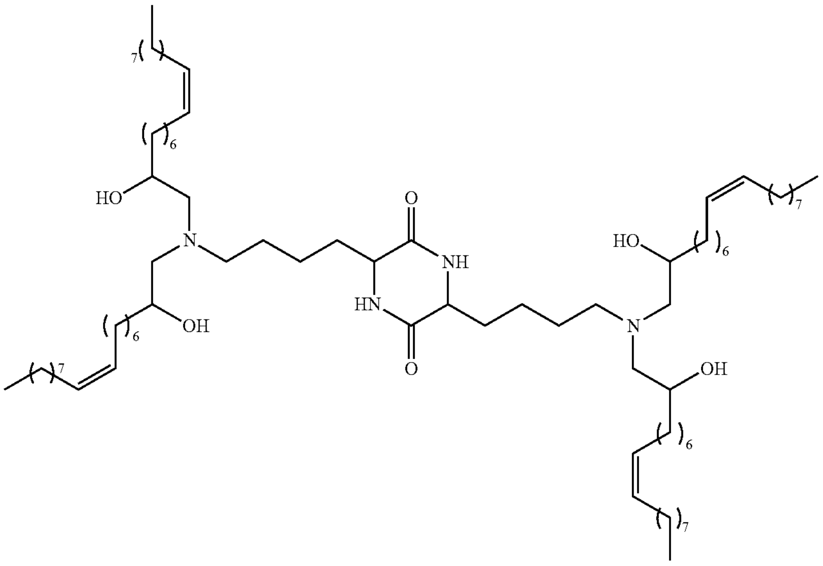

and pharmaceutically acceptable salts thereof. In certain embodiments, the compositions and methods of the present invention include a cationic lipid having a compound structure of:

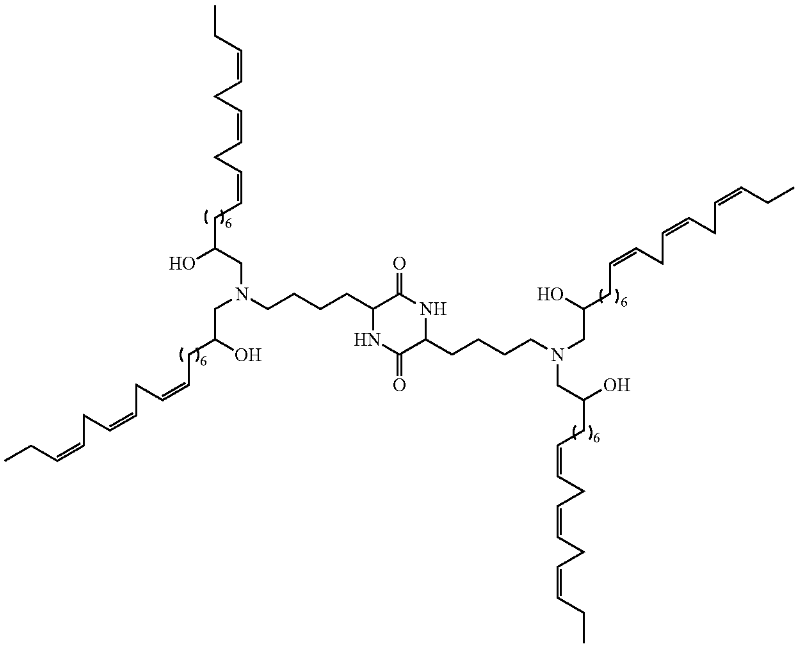

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

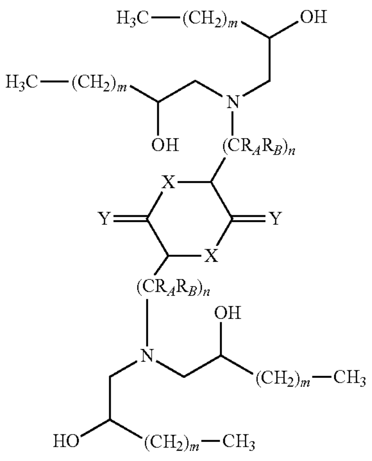

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

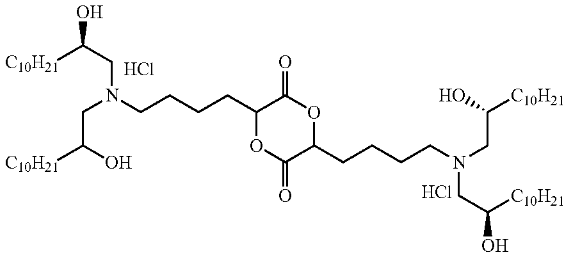

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

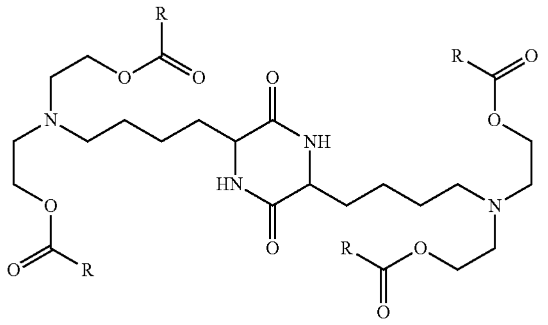

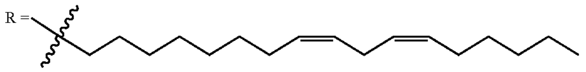

or a pharmaceutically acceptable salt thereof. In some embodiments, the compositions and methods of the present invention include a cationic lipid having the compound structure:

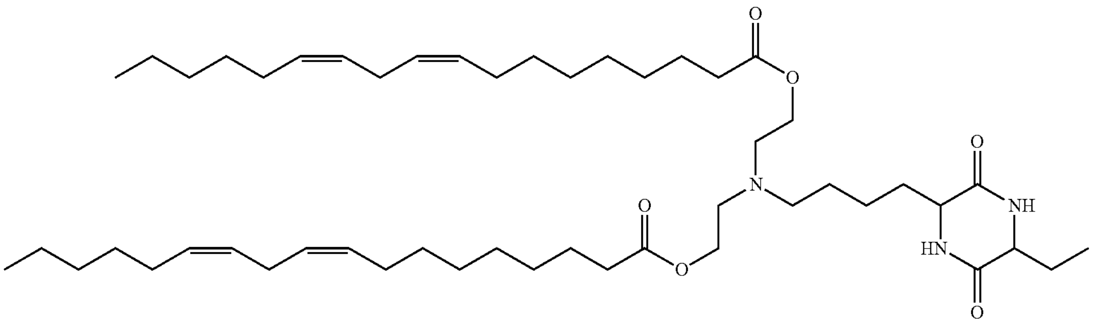 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof.

In some embodiments, the compositions and methods of the present invention include a cationic lipid having the compound structure:

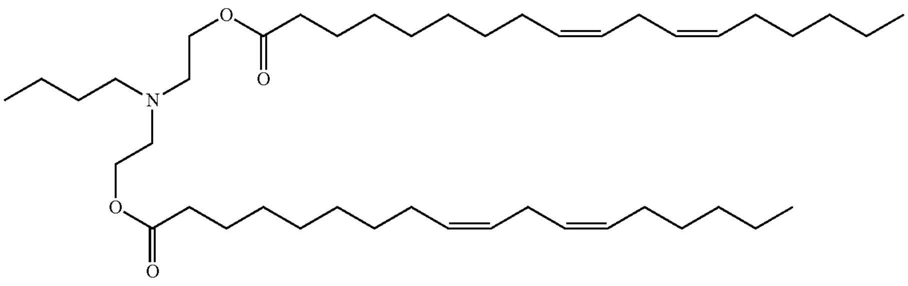 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

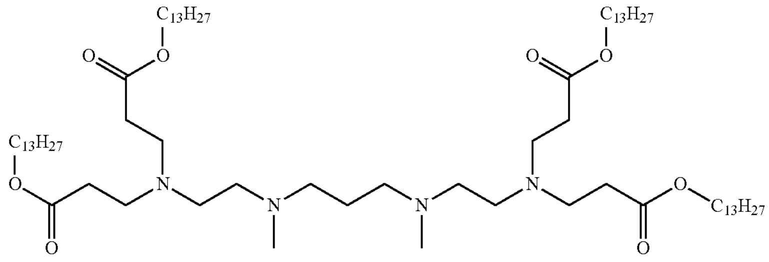

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

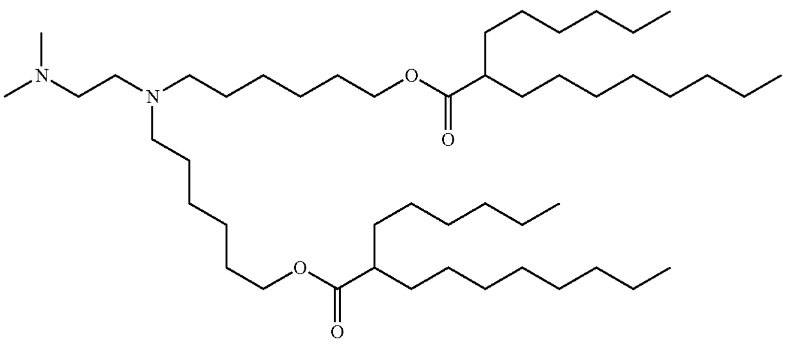 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

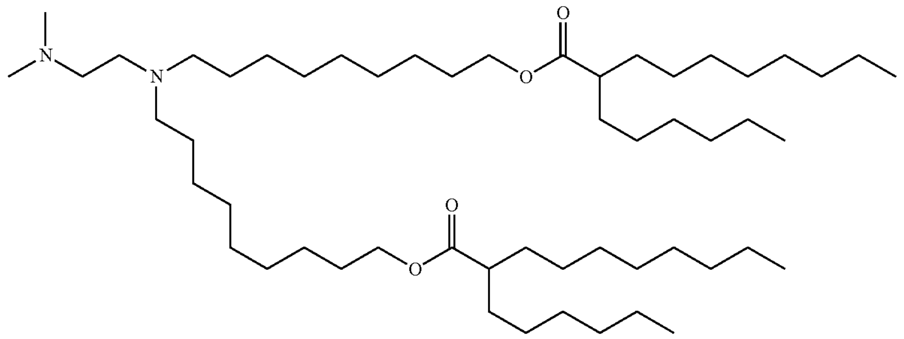 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

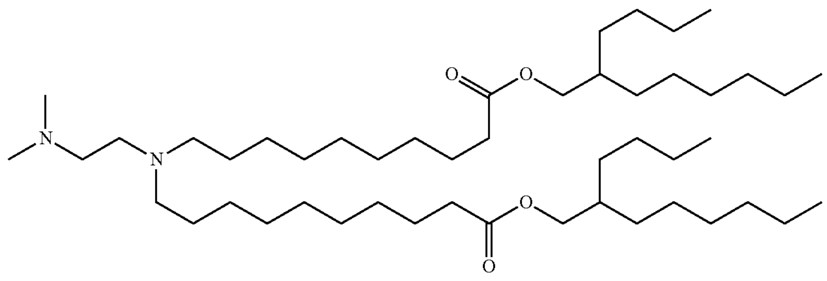 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

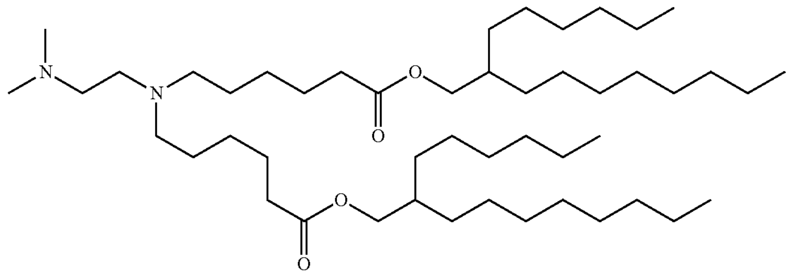 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

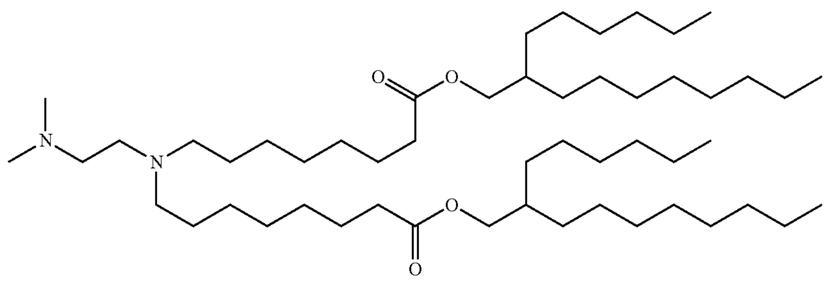 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

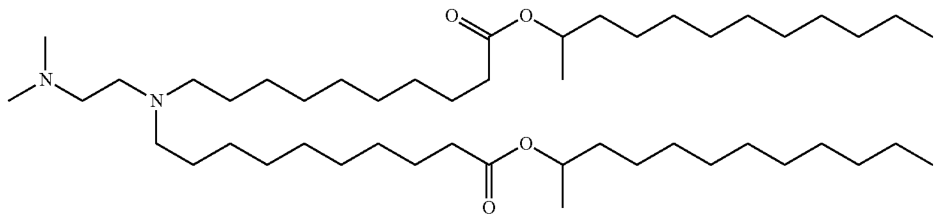 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

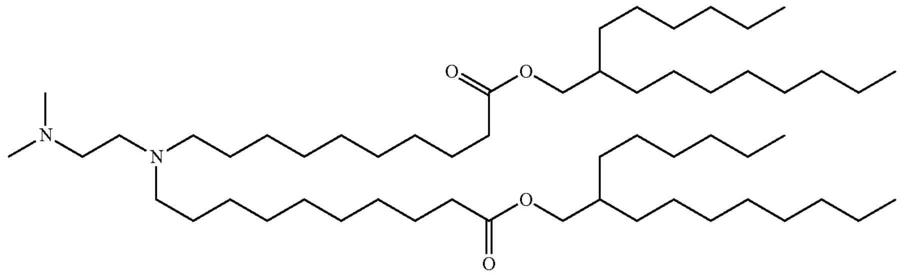 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

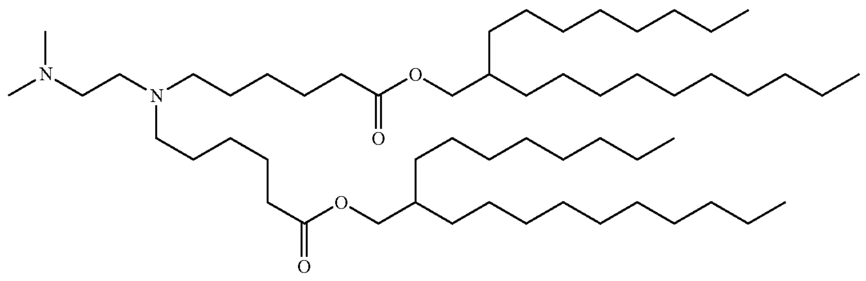 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

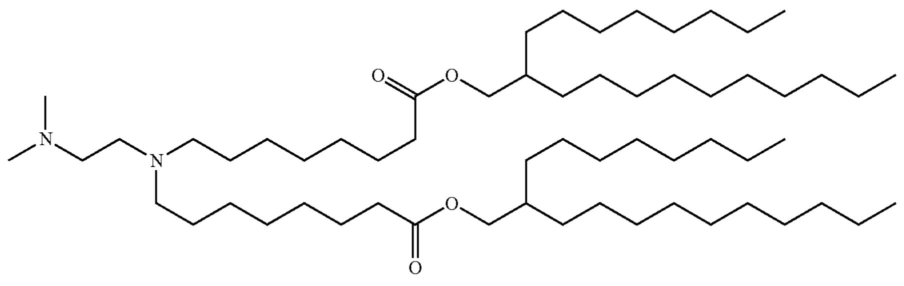 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

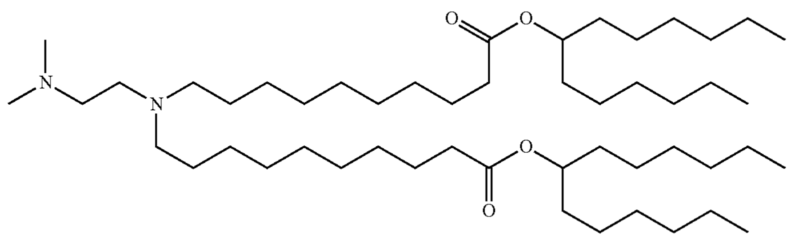 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

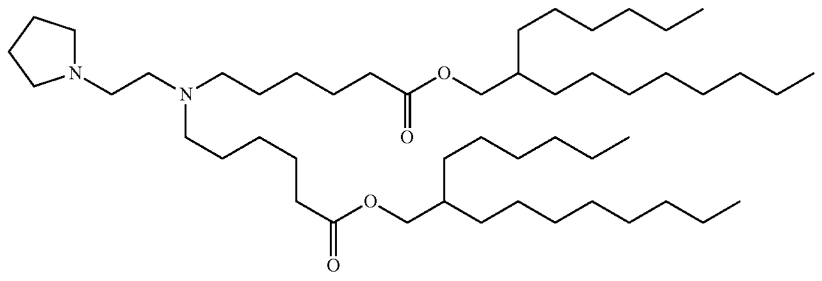 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

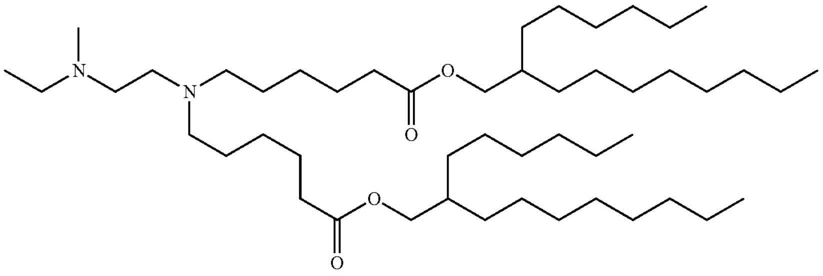 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

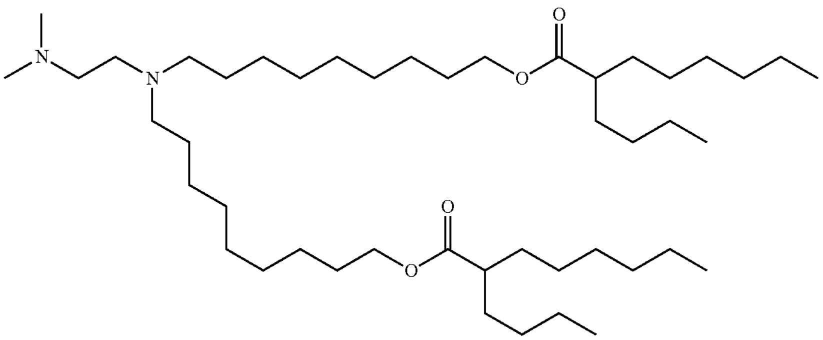 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

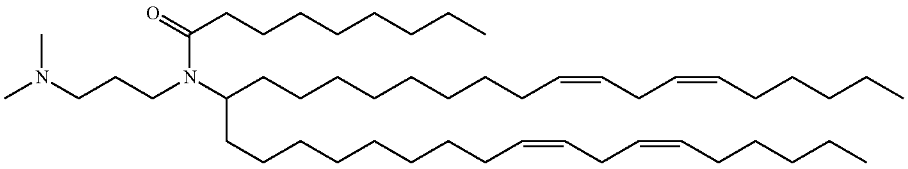 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

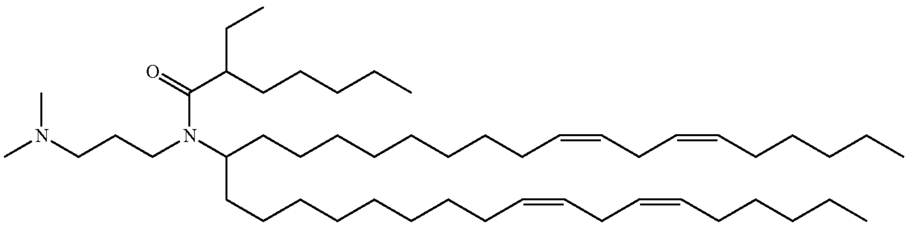 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

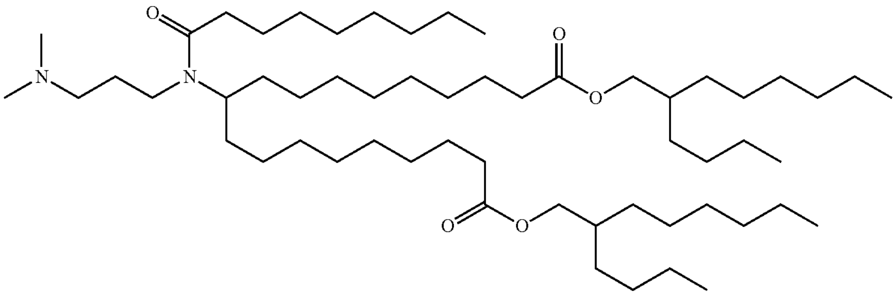 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

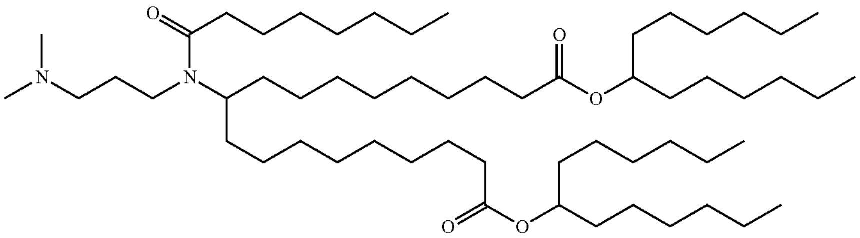 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

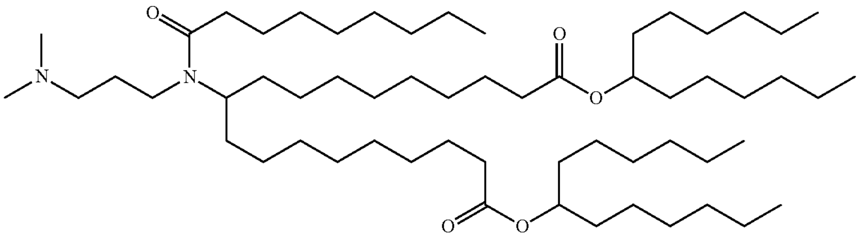 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

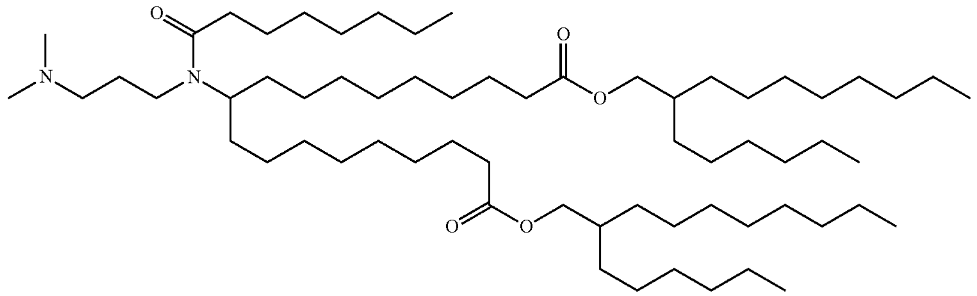 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

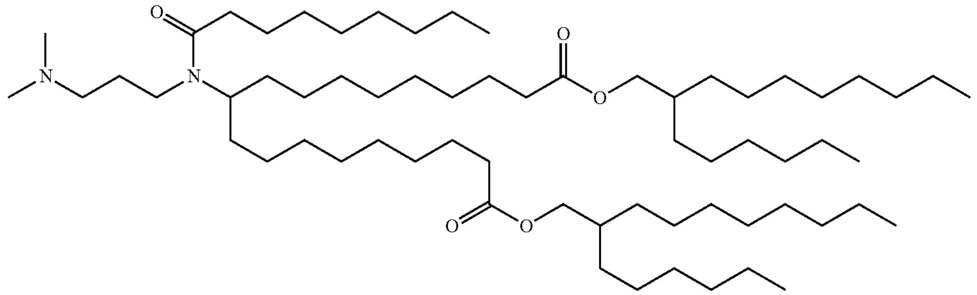 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

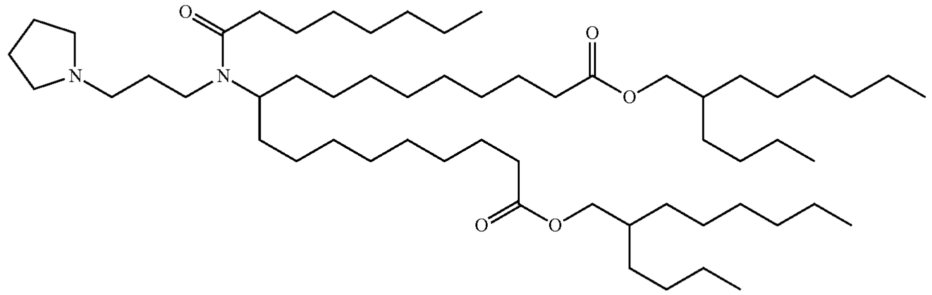 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

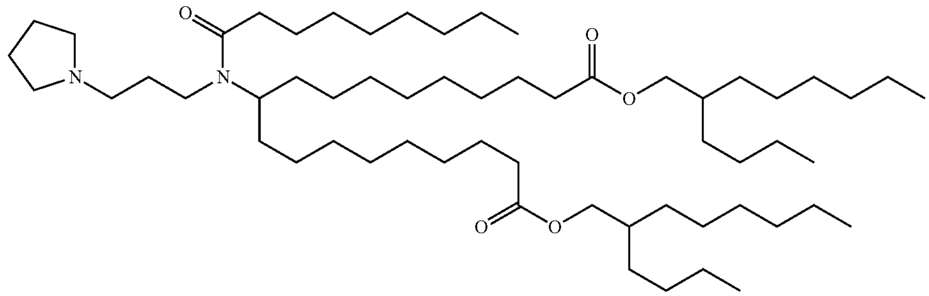 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

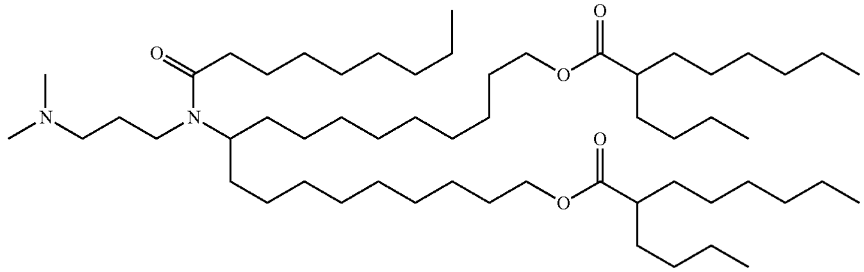 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

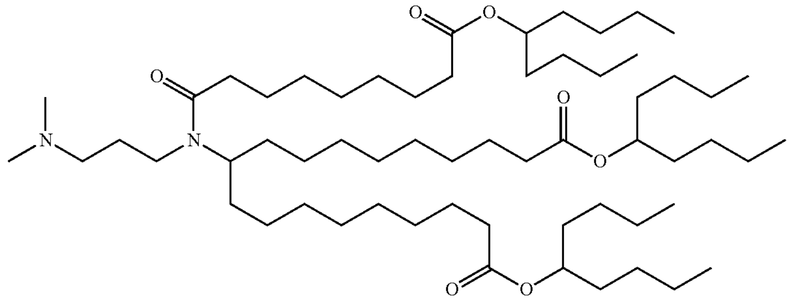 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

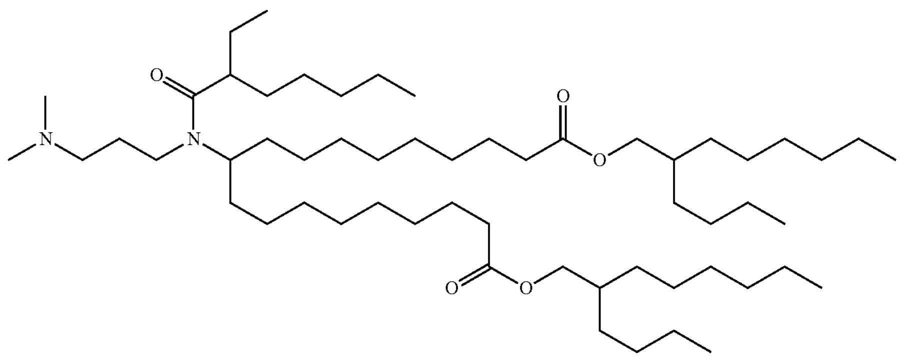 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

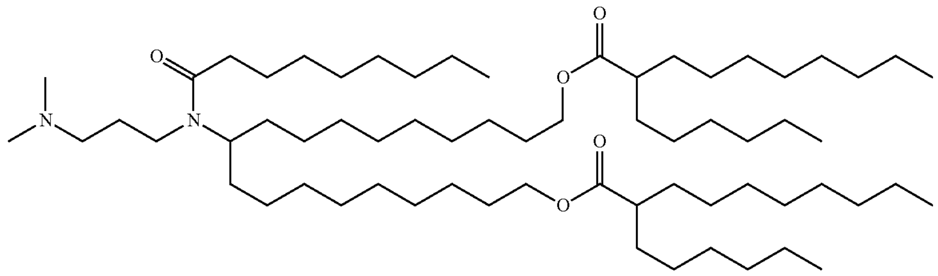 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

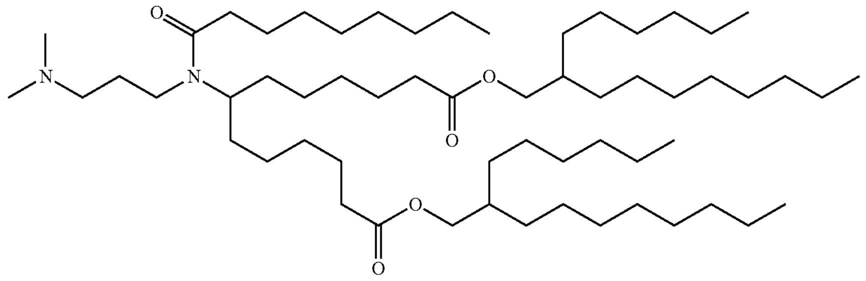 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

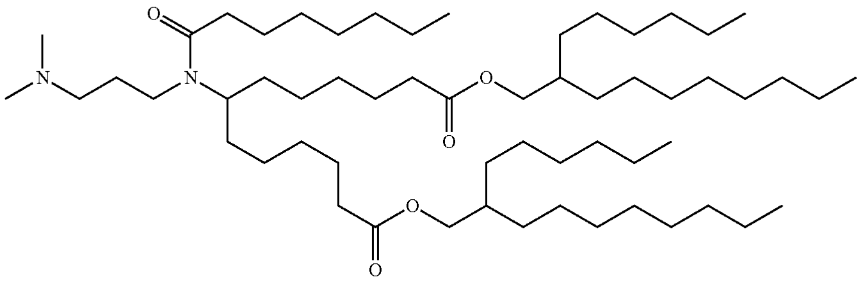 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

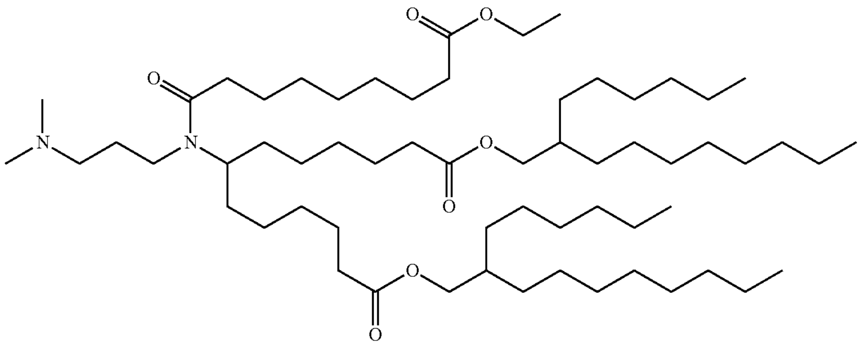 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

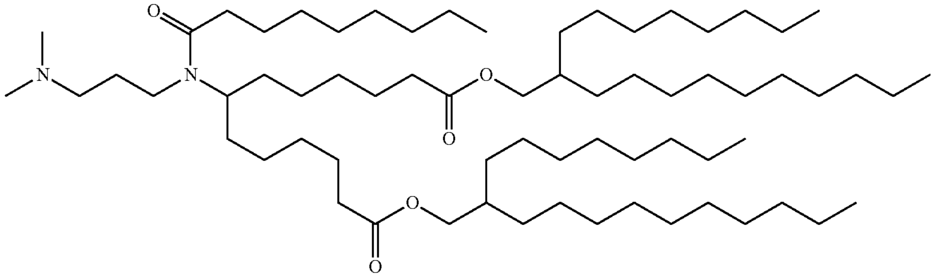 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

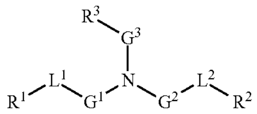

or a pharmaceutically acceptable salt thereof, wherein one of $L^1$ or $L^2$ is —O(C═O)—, —(C═O)O—, —C(═O)—, —O—, —S(O)$_x$, —S—S—, —C(═O)S—, —SC(═O)—, —$NR^aC$(═O)—, —C(═O)$NR^a$—, $NR^aC$(═O)$NR^a$—, —OC(═O)$NR^a$—, or —$NR^aC$(═O)O—; and the other of $L^1$ or $L^2$ is —O(C═O)—, —(C═O)O—, —C(═O)—, —O—, —$S(O)_x$, —S—S—, —C(═O)S—, SC(═O)—, —$NR^aC$(═O)—, —C(═O)$NR^a$—, $NR^aC$(═O)$NR^a$—, —OC(═O)$NR^a$— or —$NR^aC$(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)$OR^4$, —OC(═O)$R^4$ or —$NR^5C$(═O)$R^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

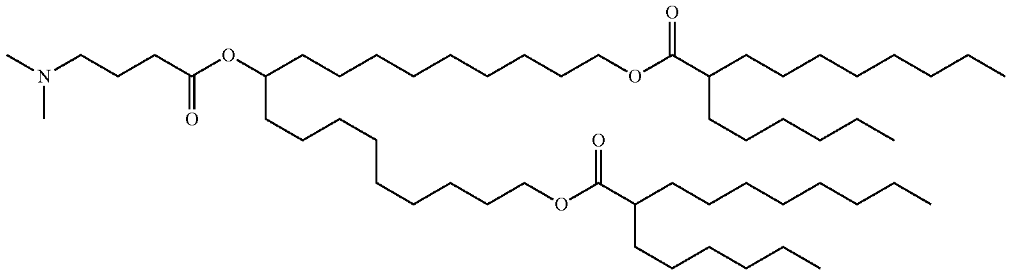 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

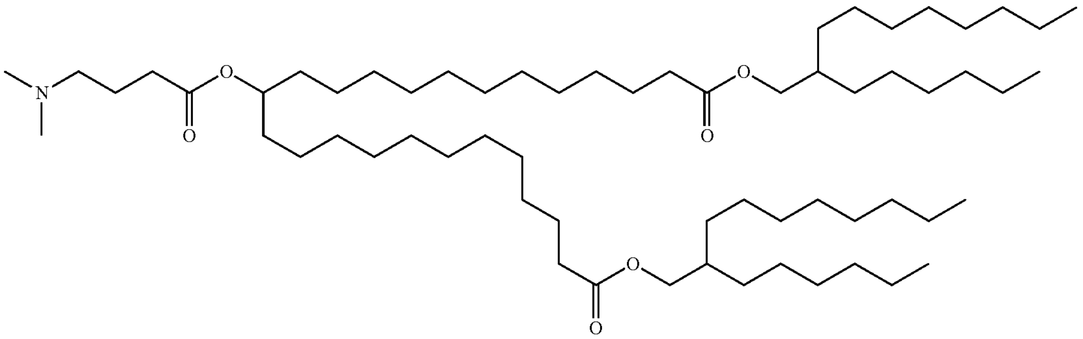 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

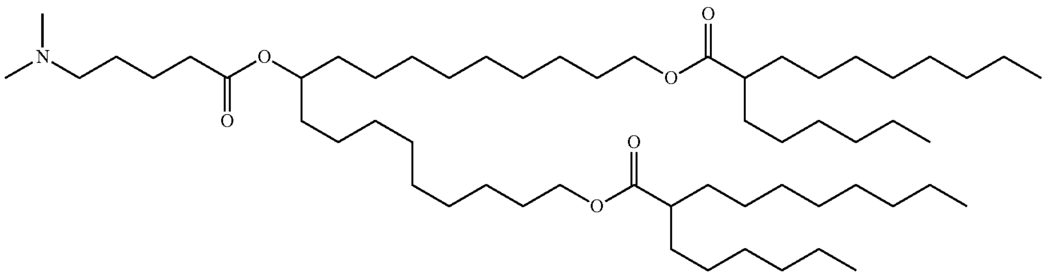 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

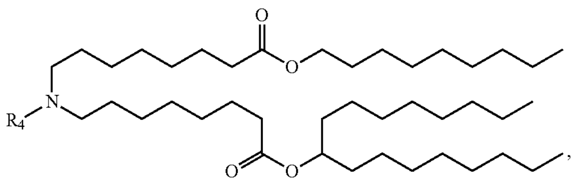

,

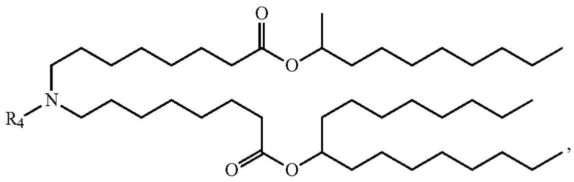

,

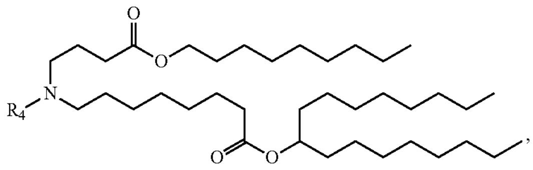

, and

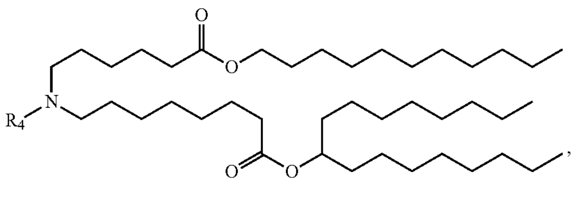

, and pharmaceutically acceptable salts thereof. For any one of these four formulas, $R_4$ is independently selected from $-(CH_2)_nQ$ and $-(CH_2)_nCHQR$; Q is selected from the group consisting of $-OR$, $-OH$, $-O(CH_2)_nN(R)_2$, $-OC(O)R$, $-CX_3$, $-CN$, $-N(R)C(O)R$, $-N(H)C(O)R$, $-N(R)S(O)_2R$, $-N(H)S(O)_2R$, $-N(R)C(O)N(R)_2$, $-N(H)C(O)N(R)_2$, $-N(H)C(O)N(H)(R)$, $-N(R)C(S)N(R)_2$, $-N(H)C(S)N(R)_2$, $-N(H)C(S)N(H)(R)$, and a heterocycle; and n is 1, 2, or 3. In certain embodiments, the compositions and methods of the present invention include a cationic lipid having a compound structure of:

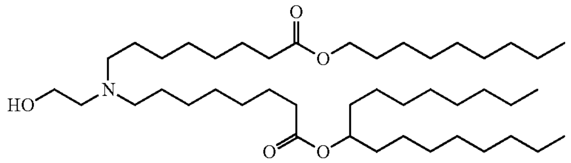 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

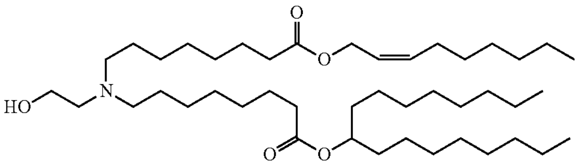 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

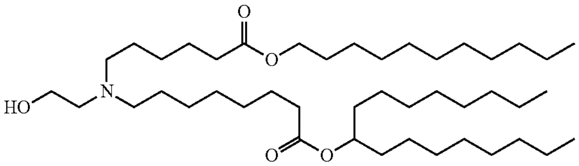 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

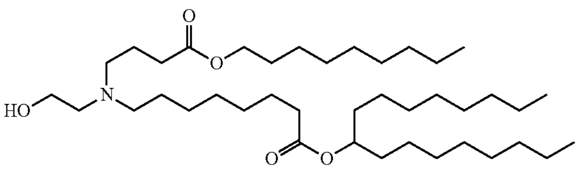 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

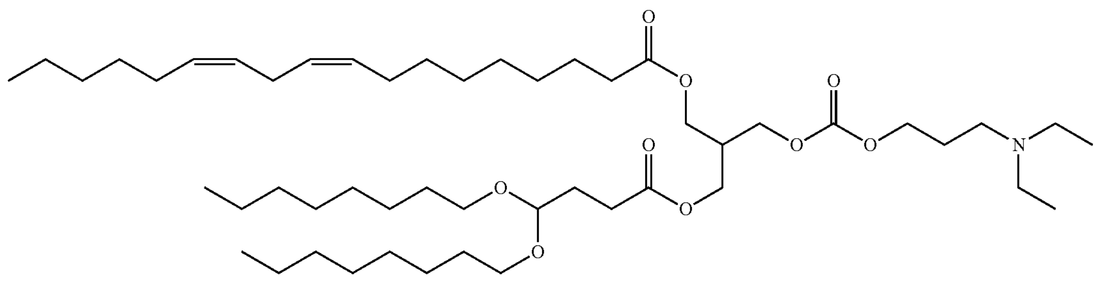 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

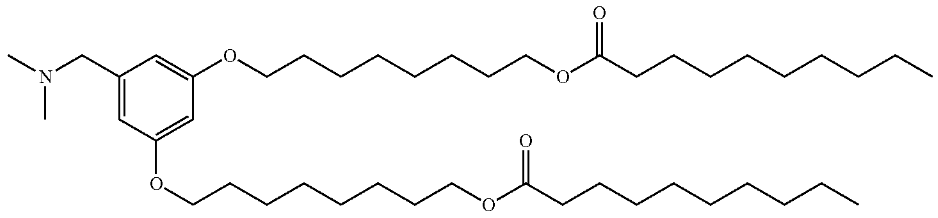 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

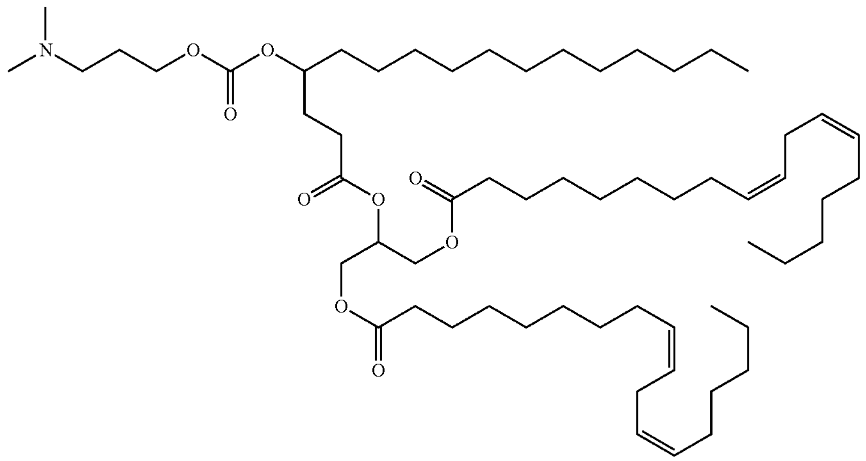 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

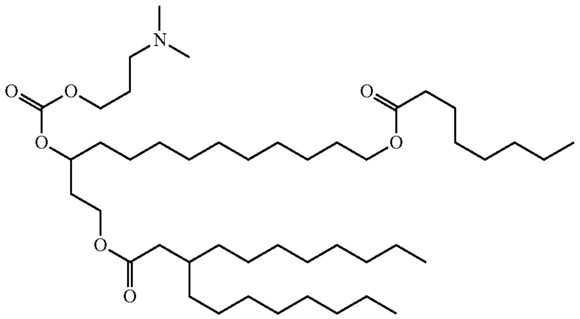 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

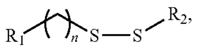

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

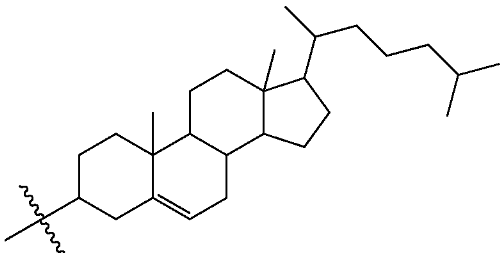

and

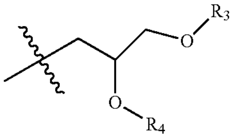

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

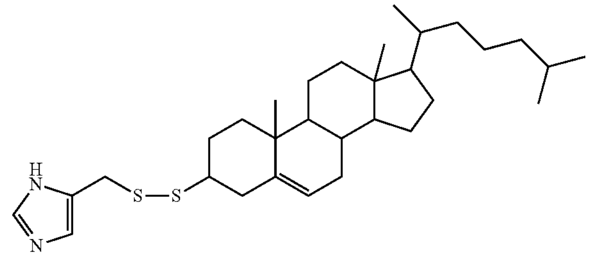

and pharmaceutically acceptable salts thereof. In certain embodiments, the compositions and methods of the present invention include a cationic lipid, "HGT4002", having a compound structure of:

(HGT4002)

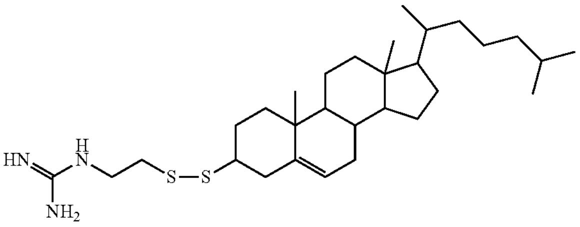

and pharmaceutically acceptable salts thereof. In certain embodiments, the compositions and methods of the present invention include a cationic lipid, "HGT4003", having a compound structure of:

(HGT4003)

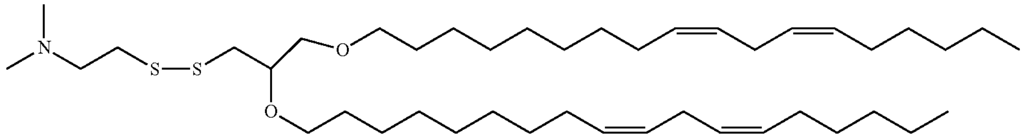

and pharmaceutically acceptable salts thereof. In certain embodiments, the compositions and methods of the present invention include a cationic lipid, "HGT4004", having a compound structure of:

(HGT4004)

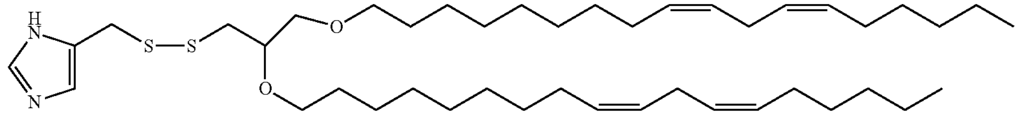

and pharmaceutically acceptable salts thereof. In certain embodiments, the compositions and methods of the present invention include a cationic lipid "HGT4005", having a compound structure of:

(HGT4005)

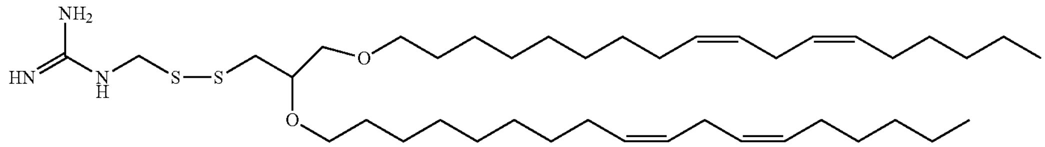

and pharmaceutically acceptable salts thereof.

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. No. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylarnrnonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9',1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z,12Z)-octadeca-9,12-dien-1-yloxy] propane-1-amine ("Octyl-CLinDMA"); (2R)-2-((8-[(3beta)-cholest-5-en-3-yloxy]octyl)oxy)-N,N-dimethyl-3-[(9Z,12Z)-octadeca-9,12-dien-1-yloxy]propan-1-amine ("Octyl-CLinDMA (2R)"); (2S)-2-((8-[(3P)-cholest-5-en-3-yloxy] octyl)oxy)-N,fsl-dimethyh3-[(9Z,12Z)-octadeca-9,12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z,12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate, as represented by the following structure:

(ICE)

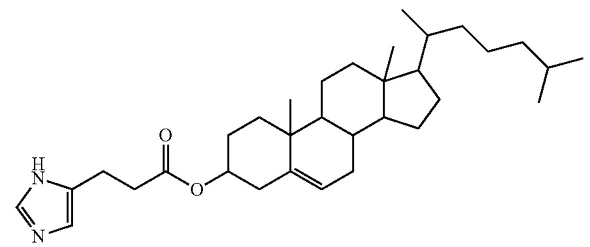

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5. In some embodiments, the ratio of sterol lipid(s) to non-cationic lipid(s) to PEG-modified lipid(s) is 50:45:5. In some embodiments, the ratio of sterol lipid(s) to non-cationic lipid(s) to PEG-modified lipid(s) is 50:40:10. In some embodiments, the ratio of sterol lipid(s) to non-cationic lipid(s) to PEG-modified lipid(s) is 55:40:5. In some embodiments, the ratio of sterol lipid(s) to non-cationic lipid(s) to PEG-modified lipid(s) is 55:35:10. In some embodiments, the ratio of sterol lipid(s) to non-cationic lipid(s) to PEG-modified lipid(s) is 60:35:5. In some embodiments, the ratio of sterol lipid(s) to non-cationic lipid(s) to PEG-modified lipid(s) is 60:30:10.

In some embodiments, a suitable liposome for the present invention comprises ICE and DOPE at an ICE:DOPE molar ratio of >1:1. In some embodiments, the ICE:DOPE molar ratio is <2.5:1. In some embodiments, the ICE:DOPE molar ratio is between 1:1 and 2.5:1. In some embodiments, the ICE:DOPE molar ratio is approximately 1.5:1. In some embodiments, the ICE:DOPE molar ratio is approximately 1.7:1. In some embodiments, the ICE:DOPE molar ratio is approximately 2:1. In some embodiments, a suitable liposome for the present invention comprises ICE and DMG-PEG-2K at an ICE:DMG-PEG-2K molar ratio of >10:1. In some embodiments, the ICE:DMG-PEG-2K molar ratio is <16:1. In some embodiments, the ICE:DMG-PEG-2K molar ratio is approximately 12:1. In some embodiments, the ICE:DMG-PEG-2K molar ratio is approximately 14:1. In some embodiments, a suitable liposome for the present invention comprises DOPE and DMG-PEG-2K at a DOPE: DMG-PEG-2K molar ratio of >5:1. In some embodiments, the DOPE: DMG-PEG-2K molar ratio is <11:1. In some embodiments, the DOPE: DMG-PEG-2K molar ratio is approximately 7:1. In some embodiments, the DOPE: DMG-PEG-2K molar ratio is approximately 10:1. In some embodiments, a suitable liposome for the present invention comprises ICE, DOPE and DMG-PEG-2K at an ICE:DOPE: DMG-PEG-2K molar ratio of 50:45:5. In some embodiments, a suitable liposome for the present invention comprises ICE, DOPE and DMG-PEG-2K at an ICE:DOPE: DMG-PEG-2K molar ratio of 50:40:10. In some embodiments, a suitable liposome for the present invention comprises ICE, DOPE and DMG-PEG-2K at an ICE:DOPE: DMG-PEG-2K molar ratio of 55:40:5. In some embodiments, a suitable liposome for the present invention comprises ICE, DOPE and DMG-PEG-2K at an ICE:DOPE: DMG-PEG-2K molar ratio of 55:35:10. In some embodiments, a suitable liposome for the present invention comprises ICE, DOPE and DMG-PEG-2K at an ICE:DOPE: DMG-PEG-2K molar ratio of 60:35:5. In some embodiments, a suitable liposome for the present invention comprises ICE, DOPE and DMG-PEG-2K at an ICE:DOPE: DMG-PEG-2K molar ratio of 60:30:10.

The liposomal transfer vehicles for use in the compositions of the invention can be prepared by various techniques which are presently known in the art. Various methods are described in published U.S. Application No. US 2011/0244026, published U.S. Application No. US 2016/0038432 and provisional U.S. Application No. 62/580,155, filed Nov. 1, 2017 and can be used to practice the present invention, all of which are incorporated herein by reference.

Briefly, the process of preparing CFTR-mRNA lipid nanoparticles includes a step of heating a first set of one or more solutions with a first set of one or more solutions (i.e., applying heat from a heat source to the solutions) to a temperature (or to maintain at a temperature) greater than ambient temperature. The first set of one more solutions can include a non-aqueous solution comprising the lipids used to form the lipid nanoparticle, and/or a solution comprising pre-formed lipid nanoparticles. The second set of one or more solutions can include an aqueous solution of the CFTR mRNA and/or a solution comprising the lipid nanoparticle encapsulated mRNA. In certain embodiments, the process includes a step of heating to a temperature (or to maintain at a temperature) greater than ambient temperature a first solution comprising pre-formed lipid nanoparticles with a second aqueous solution comprising CFTR mRNA In some embodiments, the process includes the step of heating one or both of the mRNA solution and the pre-formed lipid nanoparticle solution, prior to the mixing step. In some embodiments, the process includes heating one or more one or more of the solution comprising the pre-formed lipid nanoparticles, the solution comprising the mRNA and the solution comprising the lipid nanoparticle encapsulated mRNA, during the mixing step. In some embodiments, the process includes the step of heating the lipid nanoparticle encapsulated mRNA, after the mixing step. In some embodiments, the temperature to which one or more of the solutions is heated (or at which one or more of the solutions is maintained) is or is greater than about 30° C., 37° C., 40° C., 45° C., 50° C., 55° C., 60° C., 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature greater than ambient temperature to which one or more of the solutions is heated is about 65° C.

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating cystic fibrosis). For example, a therapeutically effective amount may be an amount sufficient to achieve a desired therapeutic and/or prophylactic effect.

In some embodiments, the composition comprising an mRNA encoding CFTR comprises mRNA at a concentration of at least 0.1 mg/mL. In some embodiments, the composition comprising an mRNA encoding CFTR comprises mRNA at a concentration of at least 0.2 mg/mL. In some embodiments, the composition comprising an mRNA encoding CFTR comprises mRNA at a concentration of at least 0.3 mg/mL. In some embodiments, the composition comprising an mRNA encoding CFTR comprises mRNA at a concentration of at least 0.4 mg/mL. In some embodiments, the mRNA encoding a CFTR protein is at a concentration of at least 0.5 mg/mL. In some embodiments, the mRNA encoding a CFTR protein is at a concentration of at least 0.6 mg/mL. In some embodiments, the mRNA encoding a CFTR protein is at a concentration of at least 0.7 mg/mL. In some embodiments, the mRNA encoding a CFTR protein is at a concentration of at least 0.8 mg/mL. In some embodiments, the mRNA encoding a CFTR protein is at a concentration of at least 0.9 mg/mL. In some embodiments, the mRNA encoding a CFTR protein is at a concentration of at least 1.0 mg/mL. In some embodiments, the mRNA encoding a CFTR protein is at a concentration of at least 2.0 mg/mL. In some embodiments, the mRNA encoding a CFTR protein is at a concentration of at least 3.0 mg/mL. In some embodiments, the mRNA encoding a CFTR protein is at a concentration of at least 4.0 mg/mL. In some embodiments, the mRNA encoding a CFTR protein is at a concentration of at least 5.0 mg/mL. In some embodiments, the mRNA encoding a CFTR protein is at a concentration of at least 6.0 mg/mL. In some embodiments, the mRNA encoding a CFTR protein is at a concentration of at least 7.0 mg/mL. In some embodiments, the mRNA encoding a CFTR protein is at a concentration of at least 8.0 mg/mL. In some embodiments, the mRNA encoding a CFTR protein is at a concentration of at least 9.0 mg/mL. In some embodiments, the mRNA encoding a CFTR protein is at a concentration of at least 10.0 mg/mL. In some embodiments, the mRNA encoding a CFTR protein is at a concentration ranging from 0.1 mg/mL to 10.0 mg/mL.

In some embodiments, the composition comprising an mRNA encoding CFTR is formulated with a diluent. In some embodiments, the diluent is selected from a group consisting of DMSO, ethylene glycol, glycerol, 2-Methyl-2,4-pentanediol (MPD), propylene glycol, sucrose, and trehalose. In some embodiments, the formulation comprises 1%, 2%, 3%, 4%, 5%, 6%, 7%, 8%, 9%, 10%, 11%, 12%, 13%, 14%, 15%, 16%, 17%, 18%, 19% or 20% diluent.

Pulmonary Delivery

A CFTR mRNA may be formulated for delivery via different administration routes including, but not limited to, oral, rectal, vaginal, transmucosal, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration. In some embodiments, a CFTR mRNA is formulated for pulmonary delivery. As used herein, pulmonary delivery refers to delivery to lung via, e.g., nasal cavity, trachea, bronchi, bronchioles, and/or other pulmonary system. In particular embodiments, a CFTR mRNA is formulated for nebulization. In these embodiments, the delivery vehicle may be in an aerosolized composition which can be inhaled.

In some embodiments, CFTR mRNA dry powder is formed by lyophilization of the mRNA-lipid complex. Applicant hereby fully incorporates by reference their earlier patent application U.S. Ser. No. 14/124,615 filed on Jun. 8, 2012, which was granted a U.S. Pat. No. 9,717,690 on 8 Jan. 2017. The lyophilized dry powder is suitable for long term storage. It can be reconstituted with purified water for administration to a subject in need thereof. In certain embodiments, upon reconstitution with an appropriate rehydration media (e.g., purified water, deionized water, 5% dextrose, 10% trehalose and/or normal saline, the reconstituted composition demonstrates pharmacological or biological activity comparable with that observed prior to lyophilization. For example, in certain embodiments, the pharmacological and biological activity of an encapsulated polynucleotide is equivalent to that observed prior to lyophilization of the composition; or alternatively demonstrates a negligible reduction in pharmacological and biological activity (e.g. less than about a 1%, 2%, 2.5%, 3%, 4%, 5%, 6%, 7%, 8% 9% or 10% reduction in the biological or pharmacological activity of an encapsulated polynucleotide).

In certain embodiments, the pharmaceutical compositions comprising lyophilized nanoparticles or lipid nanoparticle delivery vehicles are characterized as being stable (e.g., as stable as pharmaceutical compositions comprising an equivalent unlyophilized vehicles). Lyophilization of the lipid nanoparticles does not appreciably change or alter the particle size of the lipid nanoparticles following lyophilization and/or reconstitution. For example, disclosed herein are pharmaceutical compositions comprising lyophilized lipid delivery vehicles, wherein upon reconstitution (e.g., with purified water) the lipid nanoparticles do not flocculate or aggregate, or alternatively demonstrated limited or negligible flocculation or aggregation (e.g., as determined by the particle size of the reconstituted lipid nanoparticles).

Accordingly, in certain embodiments, upon reconstitution of a lyophilized lipid nanoparticle the lipid nanoparticles have a $Dv_{50}$ of less than about 500 nm (e.g., less than about 300 nm, 200 nm, 150 nm, 125 nm, 120 nm, 100 nm, 75 nm, 50 nm, 25 nm, or smaller). Similarly, in certain embodiments, upon reconstitution of a lyophilized lipid nanoparticle the lipid nanoparticles have a $Dv_{90}$ of less than about 750 nm (e.g., less than about 700 nm, 500 nm, 300 nm, 200 nm, 150 nm, 125 nm, 100 nm, 75 nm, 50 nm, 25 nm, or smaller).

In other embodiments, the pharmaceutical compositions comprising lyophilized lipid delivery vehicles are characterized as having a polydispersion index of less than about 1 (e.g., less than 0.95, 0.9, 0.8, 0.75, 0.7, 0.6, 0.5, 0.4, 0.3, 0.25, 0.2, 0.1, 0.05, or less). In some embodiments, the pharmaceutical compositions comprising lyophilized lipid delivery vehicles demonstrate a reduced tendency to flocculate or otherwise aggregate (e.g., during lyophilization or upon reconstitution). For example, upon reconstitution the lipid delivery vehicles may have an average particle size ($Z_{ave}$) of less than 500 nm (e.g., less than about 400 nm, 300 nm, 200 nm, 175 nm, 150 nm, 125 nm, 100 nm, 75 nm, 50 nm, 25 nm, or smaller in a PBS solution).

In some embodiments, the lyophilized lipid delivery vehicles (e.g., lyophilized lipid nanoparticles) further comprise or are alternatively prepared using one or more lyoprotectants (e.g., sugars and/or carbohydrates). In certain embodiments, the inclusion of one or more lyoprotectants in the lipid nanoparticle may improve or otherwise enhance the stability of the lyophilized lipid delivery vehicles (e.g., under normal storage conditions) and/or facilitate reconstitution of the lyophilized lipid delivery vehicles using a rehydration media, thereby preparing an aqueous formulation. For example, in certain embodiments the lipid nanoparticles are prepared and prior to lyophilization the buffer present in the liposomal formulation may be replaced (e.g., via centrifugation) with a lyoprotectant such as a sucrose solution or suspension (e.g., an aqueous solution comprising between about 1-50% or 10-25% sucrose). In some embodiments, the lyoprotectant in trehalose. In some embodiments, the lyoprotectant comprises 10-50%, or 10-25% or 10-20% or 10-15% trehalose. Other lyoprotectants that may be used to prepare the lyophilized compositions described herein include, for example, dextran (e.g., 1.5 kDa, 5 kDa and/or 40 kDa) and inulin (e.g., 1.8 kDa and/or 4 kDa). The lyophilized lipid delivery vehicles have an encapsulation efficiency of greater than about 80%.

A pharmaceutical composition comprising a lyophilized lipid nanoparticle comprising CFTR-encoding mRNA is stable at 4° C. for at least 1 month, at least 2 months, at least 3 months, at least 4 months, at least 5 months, at least 6 months, or for at least 1 year. In some embodiments, the lyophilized lipid delivery vehicles may be stored under refrigeration and remain stable (e.g., as demonstrated by minimal or no losses in their intended pharmaceutical or biological activity) for extended periods of time (e.g., stable for at least about 1, 2, 3, 4, 5, 6, 9, 12, 18, 24, 36 months or longer upon storage at about 4° C.). In other embodiments, the lyophilized lipid delivery vehicles may be stored without refrigeration and remain stable for extended periods of time (e.g., stable for at least about 1, 2, 3, 4, 5, 6, 9, 12, 18, 24, 36 months or longer upon storage at about 25° C.).

The pharmaceutical composition in lyophilized form can be stored in frozen condition for 1, 2, 3, 4, 5 or 10 years without loss of pharmacological or biological activity.

Accordingly, also provided herein are methods for treating disease in a subject by administering an effective amount of pharmaceutical compositions comprising lyophilized CFTR mRNA-lipid delivery vehicles to a subject (e.g., upon reconstitution with a rehydrating media such as sterile water for injection).

In some embodiments, the formulation is administered by a metered-dose inhaler.

In some embodiments, the formulation is administered by a nebulizer.

Suitable CFTR mRNA formulation for nebulization may be stored as a frozen liquid, or sterile liquid, or lyophilized or dry powder and reconstituted prior to nebulization. In some embodiments, the composition is stored in a single-use vial prior to nebulization. In some embodiments, the single-use vial comprises 50 mL or less of the composition. In some embodiments, the single-use vial comprises 40 mL or less of the composition. In some embodiments, the single-use vial comprises 30 mL or less of the composition. In some embodiments, the single-use vial comprises 20 mL or less of the composition. In some embodiments, the single-use vial comprises 10 mL or less of the composition. In some embodiments, the single-use vial comprises 9.0 mL or less of the composition. In some embodiments, the single-use vial comprises 8.0 mL or less of the composition. In some embodiments, the single-use vial comprises 7.0 mL or less of the composition. In some embodiments, the single-use vial comprises 6.0 mL or less of the composition. In some embodiments, the single-use vial comprises 5.0 mL or less of the composition. In some embodiments, the single-use vial comprises between 4.0 mL and 5.0 mL of the composition. In some embodiments, the single-use vial comprises 3.2 mL of the composition.

In some embodiments, pulmonary delivery involves inhalation (e.g., for nasal, tracheal, or bronchial delivery). In some embodiments, the CFTR mRNA formulation is nebulized prior to inhalation. Nebulization can be achieved by any nebulizer known in the art. A nebulizer transforms a liquid to a mist so that it can be inhaled more easily into the lungs. Nebulizers are effective for infants, children and adults. Nebulizers are able to nebulize large doses of inhaled medications. One type of nebulizer is a jet nebulizer, which comprises tubing connected to a compressor, which causes compressed air or oxygen to flow at a high velocity through a liquid medicine to turn it into an aerosol, which is then inhaled by the patient. Another type of nebulizer is the ultrasonic wave nebulizer, which comprises an electronic oscillator that generates a high frequency ultrasonic wave, which causes the mechanical vibration of a piezoelectric element, which is in contact with a liquid reservoir. The high frequency vibration of the liquid is sufficient to produce a vapor mist. Exemplary ultrasonic wave nebulizers are the Omron NE-U17 and the Beurer Nebulizer IH30. A third type of nebulizer comprises vibrating mesh technology (VMT). VMT comprises mesh/membrane with 1000-7000 holes that vibrates at the top of a liquid reservoir and thereby pressures out a mist of very fine droplets through the holes in the mesh/membrane. Exemplary VMT nebulizers include Pari eFlow, Respironics i-Neb, Beurer Nebulizer IH50, Aerogen Aeroneb and Philips InnoSpire Go.

In some embodiments, the nebulization volume is at a volume ranging from 13.0 mL to 42.0 mL. In some embodiments, the nebulization volume is at a volume less than or equal to 13.9 mL. In some embodiments, the nebulization volume is at a volume less than or equal to 16.0 mL. In some embodiments, the nebulization volume is at a volume less than or equal to 18.0 mL. In some embodiments, the nebulization volume is at a volume less than or equal to 20.0 mL. In some embodiments, the nebulization volume is at a volume less than or equal to 22.0 mL. In some embodiments, the nebulization volume is at a volume less than or equal to 24.0 mL. In some embodiments, the nebulization volume is at a volume less than or equal to 26.0 mL. In some embodiments, the nebulization volume is at a volume less than or equal to 27.9 mL. In some embodiments, the nebulization volume is at a volume less than or equal to 30.0 mL. In some embodiments, the nebulization volume is at a volume less than or equal to 32.0 mL. In some embodiments, the nebulization volume is at a volume less than or equal to 34.0 mL. In some embodiments, the nebulization volume is at a volume less than or equal to 36.0 mL. In some embodiments, the nebulization volume is at a volume less than or equal to 38.0 mL. In some embodiments, the nebulization volume is at a volume less than or equal to 40.0 mL. In some embodiments, the nebulization volume is at a volume less than or equal to 41.8 mL.

In some embodiments, the duration of nebulization ranges from 1 minute to 150 minutes. In some embodiments, the duration of nebulization is less than or equal to 1 minute. In some embodiments, the duration of nebulization is less than or equal to 2 minutes. In some embodiments, the duration of nebulization is less than or equal to 3 minutes. In some embodiments, the duration of nebulization is less than or equal to 6 minutes. In some embodiments, the duration of nebulization is less than or equal to 9 minutes. In some embodiments, the duration of nebulization is less than or equal to 12 minutes. In some embodiments, the duration of nebulization is less than or equal to 15 minutes. In some embodiments, the duration of nebulization is less than or equal to 18 minutes. In some embodiments, the duration of nebulization is less than or equal to 21 minutes. In some embodiments, the duration of nebulization is less than or equal to 24 minutes. In some embodiments, the duration of nebulization is less than or equal to 27 minutes. In some embodiments, the duration of nebulization is less than or equal to 30 minutes. In some embodiments, the duration of nebulization is less than or equal to 33 minutes. In some embodiments, the duration of nebulization is less than or equal to 36 minutes. In some embodiments, the duration of nebulization is less than or equal to 40 minutes. In some embodiments, the duration of nebulization is less than or equal to 45 minutes. In some embodiments, the duration of nebulization is less than or equal to 50 minutes. In some embodiments, the duration of nebulization is less than or equal to 55 minutes. In some embodiments, the duration of nebulization is less than or equal to 60 minutes. In some embodiments, the duration of nebulization is less than or equal to 67 minutes. In some embodiments, the duration of nebulization is less than or equal to 70 minutes. In some embodiments, the duration of nebulization is less than or equal to 80 minutes. In some embodiments, the duration of nebulization is less than or equal to 90 minutes. In some embodiments, the duration of nebulization is less than or equal to 100 minutes. In some embodiments, the duration of nebulization is less than or equal to 110 minutes. In some embodiments, the duration of nebulization is less than or equal to 120 minutes. In some embodiments, the duration of nebulization is less than or equal to 130 minutes. In some embodiments, the duration of nebulization is less than or equal to 140 minutes. In some embodiments, the duration of nebulization is less than or equal to 150 minutes.

In some embodiments, the number of nebulizers used during a single nebulization session ranges from 2-8. In some embodiments, 1 nebulizer is used during a single nebulization session. In some embodiments, 2 nebulizers are used during a single nebulization session. In some embodiments, 3 nebulizers are used during a single nebulization session. In some embodiments, 4 nebulizers are used during a single nebulization session. In some embodiments, 5 nebulizers are used during a single nebulization session. In some embodiments, 6 nebulizers are used during a single nebulization session. In some embodiments, 7 nebulizers are used during a single nebulization session. In some embodiments, 8 nebulizers are used during a single nebulization session.

Pharmacokinetics and Tissue Distribution

According to the present invention, administration of a formulation comprising a CFTR mRNA results in delivery of the mRNA and encoded CFTR protein in various targets tissues described herein. In particular, administration of a formulation comprising a CFTR mRNA according to the present invention results in a therapeutically or clinically effective level or activity of CFTR in the target tissue. In various embodiments, a target tissue includes lung, pancreas, kidney, liver, spleen, testes/ovaries, salivary glands, sweat glands, heart and brain. In some embodiments, a target tissue is lung. In some embodiments, a target tissue is the upper (i.e., superior) lobe of the right or left lung. In some embodiments, a target tissue is the lower (i.e., inferior) lobe of the right or left lung. In some embodiments, a target tissue is the middle lobe of the right lung.

In some embodiments, a target tissue is the apical segment of the right lung or the apicoposterior segment of the left lung. In some embodiments, a target tissue is the posterior segment of the right lung. In some embodiments, a target tissue is the anterior segment of the right or left lung. In some embodiments, a target tissue is the superior segment of the right or left lung. In some embodiments, a target tissue is the lateral basal segment of the right or left lung. In some embodiments, a target tissue is the anterior basal segment of the right lung. In some embodiments, a target tissue is the anteromedial basal segment of the left lung. In some embodiments, a target tissue is the lateral segment of the right lung. In some embodiments, a target tissue is the medial segment of the right lung. In some embodiments, a target tissue is the superior lingular segment of the left lung. In some embodiments, a target tissue is the inferior lingular segment of the left lung. In some embodiments, a target tissue is the posterior basal segment of the right or left lung. In some embodiments, a target tissue is the medial basal segment of the right lung.

In particular embodiments, a target tissue is epithelial cells in the lung. In some embodiments, a target tissue is smooth muscle cells in the lung. In some embodiment, a target tissue is pancreatic duct epithelial cells. In some embodiment, a target tissue is bile-duct epithelial cells. In some embodiment, a target tissue is epithelial cells of the salivary glands. In some embodiment, a target tissue is renal epithelial cells. In some embodiment, a target tissue is beta-S cells in sweat gland secretory coils of sweat glands. In some embodiment, a target tissue is epithelial cells of the reproductive tract.

In some embodiments, a CFTR mRNA delivered according to the present invention achieves a level of CFTR protein expression or activity that is at least 5%, 10%, 20%, 30%, 40%, 50%, 60%, 70%, 80%, 90%, or 95% of the normal level of CFTR protein expression or activity in a target tissue described herein. In some embodiments, a CFTR mRNA delivered according to the present invention achieves a level of CFTR protein expression or activity that is increased by at least 1-fold, 2-fold, 3-fold, 4-fold, 5-fold, 6-fold, 7-fold, 8-fold, 9-fold or 10-fold as compared to a control (e.g., endogenous level of protein or activity without or before the treatment according to the invention, or a historical reference level) in a target tissue described herein.

In general, a CFTR mRNA delivered according to the present invention have sufficiently long half time in a target tissue described herein. In some embodiments, a CFTR mRNA delivered according to the present invention has a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, 3 days, 7 days, 14 days, 21 days or a month. In some embodiments, a CFTR mRNA delivered according to the present invention results in detectable CFTR protein level or activity in a target tissue (e.g., the lung) or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, a week, two weeks, three weeks, or a month following administration. Detectable level or activity may be determined using various methods known in the art.

In some embodiments, a CFTR mRNA delivered according to the present invention results in increased CFTR protein level or activity in upper lobe lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in lower lobe lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in middle lobe lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in distal lung tissues by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 200-fold, 300-fold, 400-fold, or 500-fold as compared to a control (e.g., endogenous level of protein or activity without or before the treatment according to the invention, or a historical reference level).

In some embodiments, a CFTR mRNA delivered according to the present invention results in increased CFTR protein level or activity in distal peripheral lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 200-fold, or 300-fold as compared to a control (e.g., endogenous level of protein or activity without or before the treatment according to the invention, or a historical reference level).

In some embodiments, a CFTR mRNA delivered according to the present invention results in increased CFTR protein level or activity in lateral peripheral lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in medial peripheral lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, or 1000-fold as compared to a control (e.g., endogenous level of protein or activity without or before the treatment according to the invention, or a historical reference level).

In some embodiments, a CFTR mRNA delivered according to the present invention results in increased CFTR protein level or activity in middle lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 150-fold, 200-fold, 250-fold, 300-fold, 350-fold, 400-fold, 450-fold, or 500-fold as compared to a control (e.g., endogenous level of protein or activity without or before the treatment according to the invention, or a historical reference level).

In some embodiments, a CFTR mRNA delivered according to the present invention results in increased CFTR protein level or activity in proximal lung tissue by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in detectable CFTR protein or activity in the larynx, trachea, nasal turbinate, and/or bronchioalveolar lavage fluid (BALF). In some embodiments, a CFTR mRNA delivered according to the present invention results in detectable CFTR protein or activity in blood. In some embodiments, a CFTR mRNA delivered according to the present invention results in detectable CFTR protein or activity in lung, pancreas, kidney, liver, spleen, testes/ovaries, salivary glands, sweat glands, heart and brain.

In some embodiments, a CFTR mRNA delivered according to the present invention results in increased CFTR protein level or activity in larynx, trachea, tracheobronchial lymph node, and/or blood by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

The CFTR mRNA expression may be detected or quantified by qPCR on RNA purified from tissue samples. The CFTR protein expression may be determined by measuring immune responses to CFTR protein. In some embodiments, IgG antibody to CFTR protein is measured by an enzyme-linked immunosorbent assay in collected serum samples. In some embodiments, CFTR-specific T cell responses are assessed using collected peripheral blood mononuclear cells. In some embodiments, T cell responses to CFTR are measured by a human interferon-γ enzyme-linked immunospot assay as described by Calcedo et al. (Calcedo et al., *Hum Gene Ther Clin Dev.* (2013) 24:108-15). Qualitative assessment of CFTR protein may also be performed by Western blot analysis. The CFTR protein activity may be measured by CFTR chloride channel activity in appropriate tissue cells. A stable potential with the mean value of a 10 second scoring interval after perfusion of solution is recorded. CFTR activity is estimated by the change in potential difference following perfusion with chloride-free isoproterenol. Various other methods are known in the art and may be used to determine the CFTR mRNA and CFTR protein expression or activity.

Therapeutic Efficacy

According to the present invention, a CFTR mRNA is delivered to a CF patient in need of treatment at a therapeutically effective dose and an administration interval for a treatment period sufficient to improve, stabilize or reduce one or more symptoms of cystic fibrosis relative to a control. The terms "treat" or "treatment", as used in the context of cystic fibrosis herein, refers to amelioration of one or more symptoms associated with cystic fibrosis, prevention or delay of the onset of one or more symptoms of cystic fibrosis, and/or lessening of the severity or frequency of one or more symptoms of cystic fibrosis.

In some embodiments, a therapeutically effective dose of a CFTR mRNA is or greater than about 2 mg, 4 mg, 6 mg, 8 mg, 10 mg, 12 mg, 14 mg, 16 mg, 18 mg, 20 mg, 22 mg, 24 mg, 26 mg, 28 mg, 30 mg, 32 mg, 34 mg, 36 mg, 38 mg, or 40 mg per dose or equivalent thereof. In some embodiments, a therapeutically effective dose of a CFTR mRNA is or less than about 50 mg, 48 mg, 46 mg, 44 mg, 42 mg, 40 mg, 38 mg, 36 mg, 34 mg, 32 mg, 30 mg, 28 mg, 26 mg, 24 mg, 22 mg, 20 mg, 18 mg, 16 mg, 14 mg, 12 mg, 10 mg, 8 mg, 6 mg or 4 mg per dose or equivalent thereof. In some embodiments, a therapeutically effective dose of a CFTR mRNA is about 2-50 mg, 4-45 mg, 4-40 mg, 6-40 mg, 6-38 mg, 6-36 mg, 6-34 mg, 6-32 mg, 6-30 mg, 6-28 mg, 6-26 mg, 6-24 mg, 6-22 mg, 6-20 mg, 6-18 mg, 6-16 mg, 8-50 mg, 8-45 mg, 8-40 mg, 8-38 mg, 8-36 mg, 8-34 mg, 8-32 mg, 8-30 mg, 8-28 mg, 8-26 mg, 8-24 mg, 8-22 mg, or 8-20 mg per dose or equivalent thereof.

In some embodiments, a therapeutically effective dose of a CFTR mRNA is administered daily, twice a week, weekly, once every two weeks, once every three weeks, once every four weeks, monthly, once every two months, once every three months.

In some embodiments, a therapeutically effective dose of a CFTR mRNA is administered for a period of at least two weeks, three weeks, four weeks, a month, two months, three months, four months, five months, six months, seven months, eight months, nine months, ten months, eleven months, twelve months, 1 year, 2 years, 3 years, 4 years, 5 years, or 10 years.

Typically, the therapeutic effect of administration of a CFTR mRNA on a cystic fibrosis patient is measured relative to a control. In some embodiments, a control is the severity of one or more symptoms in the same patient before the treatment. In some embodiments, a control is indicative of a historical reference level of one or more symptoms in CF patients. In some embodiments, a control is indicative of a normal level of ability, physical conditions or biomarker corresponding to the one or more symptoms being measured.

In some embodiments, the therapeutic effect of administration of a CFTR mRNA according to the present invention is measured by a score on a Cystic Fibrosis Questionnaire Revise (CFQ-R) respiratory domain. In some embodiments, the therapeutic effect of administration of a CFTR mRNA according to the present invention is measured by a sweat chloride value. In some embodiments, the therapeutic effect of administration of a CFTR mRNA according to the present invention is measured by a body mass index and/or body weight. In some embodiments, the therapeutic effect of administration of a CFTR mRNA according to the present invention is measured by onset or severity of pulmonary exacerbation.

In some embodiments, the therapeutic effect of administration of a CFTR mRNA according to the present invention is measured by minute volume, respiratory rate, and/or tidal volume. In some embodiments, the therapeutic effect of administration of a CFTR mRNA according to the present invention on the respiratory system is determined by performing spirometry and assessing the following parameters: forced expiratory volume in 1 second ($FEV_1$): absolute volume (L) and percent based on the patient's age, gender, and height, forced vital capacity (FVC): absolute volume (L) and percent based on the patient's age, gender, and height, $FEV_1$/FVC: ratio and percent based on the patient's age, gender, and height, and/or forced expiratory flow over the middle one-half of the FVC ($FEF_{25-75\%}$): absolute volume (L) and percent based on the patient's age, gender, and height. In some embodiments, the parameters can be normalized using the ERS Global Lung Function Initiative (GLI) prediction equations. In some embodiments, the therapeutic effect of administration of a CFTR mRNA according to the present invention on the respiratory system is determined by chest x-ray.

In some embodiments, administration of a CFTR mRNA according to the present invention results in a change in the CFQ-R respiratory domain score by at least 1, at least 2, at least 3, at least 4, at least 5, at least 6, at least 7, at least 8, at least 9, at least 10, at least 11, at least 12, at least 13, at least 14, or at least 15 points relative to a control. In some embodiments, administration of a CFTR mRNA according to the present invention results in a change in the CFQ-R respiratory domain score by at least 1%, 2%, 3%, 4%, 5%, 6%, 7%, 8%, 9%, 10%, 11%, 12%, 13%, 14%, 15%, 16%, 17%, 18%, 19%, or 20% relative to a control.

In some embodiments, administration of a CFTR mRNA according to the present invention results in amelioration, prevention or delay in onset of pulmonary exacerbation. As used herein, pulmonary exacerbation refers to one or more of the following sino-pulmonary signs/symptoms: change in sputum, new or increased hemoptysis, increased cough, increased dyspnea, malaise/fatigue/lethargy, temperature >38° C. (~100.4° F.), anorexia/weight loss, sinus pain/tenderness, change in sinus discharge, change in physical chest exam, decrease in pulmonary function and radiographic indication of pulmonary infection.

In some embodiments, administration of a CFTR mRNA according to the present invention results in prevention or reduced inflammation associated with pulmonary exacerbation. For example, administration of a CFTR mRNA according to the present invention results in reduced expression of markers of inflammation and/or lung damage, including but not limited to, C-reactive protein, white cell counts, interleukin-8, neutrophil elastase alpha 1-antiprotease complexes and matrix metalloproteins, in blood or serum as compared to a control indicative of the corresponding level of relevant markers in a CF patient without treatment. Additionally or alternatively, administration of a CFTR mRNA according to the present invention results in reduced sputum concentrations of bioactive lipid mediators, such as the cysteinyl leukotrienes and prostaglandin-E2, or sputum cell counts as compared to a control indicative of the corresponding level of relevant markers in a CF patient without treatment.

In some embodiments, administration of a CFTR mRNA according to the present invention results in a weight gain of at least 1 pound, at least 2 pounds, at least 3 pounds, at least 4 pounds, at least 5 pounds, at least 6 pounds, at least 7 pounds, at least 8 pounds, at least 9 pounds, at least 10 pounds, at least 11 pounds, at least 12 pounds, at least 13 pounds, at least 14 pounds or at least 15 pounds as compared to pre-treatment body weight.

In some embodiments, a CFTR mRNA is administered in combination with one or more CFTR potentiators and/or correctors. In some embodiments, a CFTR mRNA is administered in combination with one or more CFTR potentiators. In some embodiments, a CFTR mRNA is administered in combination with one or more CFTR correctors. Suitable CFTR potentiators and/or correctors include ivacaftor (trade name Kalydeco), lumacaftor (in a combination with ivacaftor sold under the trade name Orkambi) or the combination of ivacaftor and lumacaftor. Additional suitable correctors include tezacaftor, VX-659 and VX-445. In some embodiments, a CFTR mRNA is administered in combination with one or more other CF treatment such as hormone replacement therapies, thyroid hormone replacement therapy, non-steroidal inflammatory drugs, and prescription dronabinol (Marinol) during treatment.

In some embodiments, CFTR potentiators and/or correctors and/or other cystic fibrosis treatments may be administered prior to, concurrently or subsequent to the administration of a CFTR mRNA according to the present invention. For example, CFTR potentiators and/or correctors and/or other cystic fibrosis treatments may be administered at 1 hour or longer, at 2 hours or longer, at 4 hours or longer, at 6 hours or longer, at 8 hours or longer, at 10 hours or longer, at 12 hours or longer, at 18 hours or longer, at 24 hours or longer, at 36 hours or longer, at 48 hours or longer, at 72 hours or longer, at 1 week or longer, at 2 weeks or longer, at 3 weeks or longer, or at 1 month or longer prior to or following administration of a CFTR mRNA according to the invention.

EXAMPLES

While certain compounds, compositions and methods of the present invention have been described with specificity in accordance with certain embodiments, the following examples serve only to illustrate the compounds of the invention and are not intended to limit the same.

Example 1. Formulation of mRNA/Liposome Composition

Codon-optimized Human Cystic Fibrosis Transmembrane Conductance Regulator (CFTR) messenger RNA was synthesized by in vitro transcription from a plasmid DNA template encoding the gene, which was followed by the addition of a 5' cap structure (Cap 1) (Fechter, P.; Brownlee, G. G. “Recognition of mRNA cap structures by viral and cellular proteins” J. Gen. Virology 2005, 86, 1239-1249) and a 3' poly(A) tail of approximately 250 nucleotides in length as determined by gel electrophoresis. The mRNA encoding CFTR protein also comprised 5' and 3' untranslated regions (UTRs).

An aqueous-based solution comprising the exemplary mRNA encoding CFTR protein was combined with an ethanol-based lipid solution, isolated and dialyzed into the final formulation appropriate for storage at −80° C. FIG. 1 shows an exemplary generalized schematic of the formulation.

The lipid solution contained three lipid components to form lipid nanoparticles. The three biodegradable components all contributed to the final drug product characteristics. The first component was the ionizable lipid, imidazole cholesterol ester (ICE). This afforded a positively charged environment at low pH which facilitates efficient encapsulation of the negatively charged mRNA. It may also play a key role in cell surface interaction to allow for cellular uptake. The second component of the LNP was 1,2-dioleoyl-sn-glycero-3-phosphoethanolamine (DOPE). DOPE is a zwitterionic lipid that has been reported to have fusogenic properties to enhance uptake and release of the drug payload. The final component was a PEGylated (i.e., PEG-modified) lipid known as 1,2-dimyristoyl-sn-glycerol, methoxypolyethylene glycol (DMG-PEG-2K). The addition of this PEGylated lipid provided control over particle size and stability of the nanoparticle and may provide enhanced mucopentrating properties for lung uptake. The nominal nitrogen/phosphorus (N/P) charge ratio of the LNP was 4 and the average particle size range for the mRNA encapsulated in the LNP was 40-60 nm.

Example 2. Dosing of CFTR mRNA/Liposome Composition

These studies evaluated a CFTR mRNA/liposome composition in a Sprague-Dawley rat model. No adverse effects on the central nervous system (CNS), cardiovascular (CV) system or respiration were observed.

CNS Evaluations

Neurobehavioral evaluations were performed on 6 males/group prior to dosing and on Day 1 (4 and 24 hours post-dosing). Temperature, humidity, noise level, and illumination of each room were measured and recorded to ensure that variations in environmental conditions were minimal during all evaluations. There were no effects on neurobehavior related to treatment with hCFTR mRNA-loaded ICE-based liposomes or ICE-based liposome vehicle control at inhaled doses up to 6.70 mg/kg hCFTR mRNA-loaded ICE-based liposomes.

Cardiovascular Evaluations

Male Sprague-Dawley rats (n=5/group), which had previously been implanted with telemetry devices, were dosed via nose-only inhalation with hCFTR mRNA-loaded ICE-based liposomes for up to 6 hours at target doses of 0 (0.9% Saline control) or 0.7, 3.75 or 6.4 mg/kg of hCFTR mRNA-loaded ICE-based liposomes or ICE-based liposome vehicle control (non-mRNA containing LNP suspended in a solution containing 10% trehalose) (achieved doses of 0, 0.86, 3.52, 6.02 or 0 mg/kg, respectively). For target doses at 0.7 and 3.75 mg/kg, air was administered following the end of exposure to make the total restrained time equivalent among all doses. Each dose day was followed by a minimum 7-day washout period. All animals were returned to the colony upon completion of all evaluations.

Telemetry parameters included cardiovascular parameters (systolic, diastolic, mean blood pressure, pulse pressure, heart rate and electrocardiographic parameters [PR, QRS, QT, QTc]), activity, and body temperature. Other parameters evaluated during the study were viability, clinical observations and body weight. Mean aerosol concentrations and estimated total delivered doses of hCFTR mRNA-loaded ICE-based liposomes and ICE-based liposome vehicle (total lipid) are summarized in Table 3.

TABLE 3

Mean hCFTR mRNA-Loaded Liposome and Liposome Aerosol Concentrations and Estimated Total Delivered Doses

| Treatment | hCFTR mRNA-loaded Liposome Aerosol Concentration (μg/L) Achieved | Exposure Duration (mins) | hCFTR mRNA-loaded Liposome Delivered Dose (mg/kg) Mean Achieved[a] |
|---|---|---|---|
| Control | 0 | 360 | 0 |
| Vehicle | 0 | 360 | 0 |
| Low | 30.5 | 40 | 0.86 |
| Mid | 23.7 | 210 | 3.52 |
| High | 23.7 | 360 | 6.02 |

[a]Overall mean of each individual animal for each treatment group. This dose reflects the total delivered dose of hCFTR mRNA.

In addition to this study in rats, similar cardiovascular evaluations were also performed as repeat-dose studies in rats and monkeys. In those repeat-dose studies, no test article-related effects were observed on any CV parameters evaluated up to the highest doses evaluated (6.7 mg/kg in rats and 0.691 mg/kg in monkeys).

Respiratory Evaluations

Respiratory effects of hCFTR mRNA-loaded ICE-based liposomes were evaluated as part of the single-dose and repeat-dose studies in rats and monkeys. An increase in minute volume was observed after inhalation administration of hCFTR mRNA-loaded ICE-based liposomes to Sprague Dawley rats, as well as respiratory rate and tidal volume, in all dose groups up to 6.4 mg/kg hCFTR mRNA-loaded ICE-based liposomes, as well as in 10% trehalose controls.

No effects were observed on respiratory parameters, including respiration rate, tidal volume and derived minute volume after inhalation administration of hCFTR mRNA-loaded ICE-based liposomes to Sprague-Dawley rats at repeat doses up to 6.7 mg/kg or cynomolgus monkeys at single or repeat doses up to 0.85 mg/kg or 0.691 mg/kg, respectively.

There is minimal toxicological concern regarding ICE, DOPE, and DMG-PEG 2000 as components of the composition developed for inhalation administration. In an in silico genotoxicity evaluation, ICE is predicted to be negative for bacterial mutagenicity. This is consistent with the negative mutagenicity/genotoxicity data that are available for imidazole and propionic acid, the 2 components of the imidazole-propionic acid moiety of ICE, and for cholesterol. DOPE is a variant of the glycerophospholipid, phosphatidylethanolamine, which is a component of lung surfactant. Degradation of DOPE would be expected to follow a similar path as for other glycerophospholipids, with the ultimate formation of ethanolamine and oleic acid, both of which are present in the circulation of infants and adults. DMG PEG 2000 is anticipated to have low toxicity based on information for the anticipated metabolic breakdown products PEG 2000 and myristic acid. There is minimal concern for local or systemic toxicity based on data from studies with PEGs of various sizes, while myristic acid is a fatty acid that is present in most animal and vegetable fats and is present in the circulation of infants and adults.

Example 3. Pharmacokinetics

In the study in this Example, Sprague-Dawley rats or monkeys were dosed for up to 6 hours (for rats) or for up to 2 hours (for monkeys) via inhalation with hCFTR mRNA-loaded ICE-based liposomes or with the ICE-based liposomes alone, and then sacrificed 24 hours later to measure the levels of hCFTR in various tissues. The target doses for are shown in Tables 4-6. The actual doses measured were 420, 630 and 850 μg/kg for hCFTR mRNA-loaded ICE-based liposomes administered to monkeys (corresponding to the target doses in the header of Table 4); 0.77, 4.05 and 6.70 mg/kg for hCFTR mRNA-loaded ICE-based liposomes administered to rats (corresponding to the target doses in the header of Table 5); and 0.77, 4.05 and 6.70 mg/kg for ICE-based liposomes administered to rats (corresponding to the target doses in the header of Table 6). Detailed tissue distribution results are presented below in Tables 4, 5, and 6.

TABLE 4

Mean Concentrations of hCFTR mRNA in Monkey Tissues and Blood 24 Hours Post-Inhalation of hCFTR mRNA-Loaded Liposomes

| | Males | | | | Females | | | |
|---|---|---|---|---|---|---|---|---|
| | | Target Inhaled Dose | | | | Target Inhaled Dose | | |
| Tissue [a] | Vehicle | 500 μg/kg | 750 μg/kg | 1000 μg/kg | Vehicle | 500 μg/kg | 750 μg/kg | 1000 μg/kg |
| Brain | BQL | 3.91 | 0.0968 | BQL | BQL | 2.05 | 0.110 | 1.18 |
| Heart | BQL | BQL | 0.165 | BQL | BQL | BQL | BQL | 0.537 |
| Kidney | BQL | BQL | BQL | 0.0523 | BQL | BQL | BQL | 0.231 |
| Larynx | 0.166 | BQL | 5.54 | 1.87 | BQL | 5.15 | 3.37 | 2.59 |
| Liver | BQL | BQL | 0.0670 | 1.27 | BQL | 0.917 | 0.147 | 8.48 |
| Lung (Average) | 0.110 | 208 | 67.2 | 82.1 | 0.426 | 819 | 1390 | 1880 |
| Spleen | BQL | 0.420 | BQL | BQL | BQL | BQL | 0.307 | 1.85 |
| Testis | BQL | BQL | BQL | 0.0912 | — | — | — | — |
| Ovary | — | — | — | — | BQL | 0.596 | BQL | 0.976 |
| Trachea | BQL | 0.176 | 0.993 | 1.65 | 0.0657 | 1.54 | 14.4 | 4.72 |
| Tracheobronchial LN | BQL | 30.9 | 0.284 | 70.3 | BQL | 0.147 | 468 | 5.28 |
| Blood | 0.0501 | BQL | 0.0433 | 0.0120 | 0.0188 | 0.00351 | 0.385 | 0.0121 |

BQL: Below limit of quantification

[a] Levels in tissue expressed as $10^6$ x copies/gm and levels in blood as $10^6$ x copies/mL, to express levels in comparable masses since 1 mL of blood ~1 gm.

TABLE 5

Mean hCFTR mRNA Concentrations in Rat Tissues and Blood 24 hours Post hCFTR mRNA-Loaded Liposome Doses of 0.7, 3.75 or 6.4 mg/kg

| | Males | | | | Females | | | |
|---|---|---|---|---|---|---|---|---|
| Tissue | Vehicle | 0.7 mg/kg | 3.75 mg/kg | 6.4 mg/kg | Vehicle | 0.7 mg/kg | 3.75 mg/kg | 6.4 mg/kg |
| Brain | BLQ | BLQ | BLQ | 55.4 | BLQ | BLQ | BLQ | 32.4 |
| Heart | BLQ | BLQ | BLQ | 17.0 | BLQ | BLQ | BLQ | 41.1 |
| Kidney | BLQ | BLQ | BLQ | 0.37 | BLQ | BLQ | BLQ | 0.95 |
| Larynx | 0.20 | BLQ | BLQ | 4178 | BLQ | BLQ | BLQ | 1410 |
| Liver | NC | BLQ | BLQ | 2.3 | BLQ | BLQ | BLQ | 9.75 |
| Lung | .061 | 2057 | 59,094 | 156130 | BLQ | 1361 | 33,649 | 180,000 |
| Nasal Turbinate | .12 | BLQ | BLQ | 792 | BLQ | BLQ | BLQ | 1450 |
| Spleen | BLQ | BLQ | BLQ | 3.8 | BLQ | BLQ | BLQ | 1.09 |
| Testis | 0.08 | BLQ | BLQ | 9.5 | BLQ | BLQ | BLQ | BLQ |
| Ovary | BLQ | BLQ | BLQ | BLQ | BLQ | BLQ | BLQ | 6.99 |
| Trachea | BLQ | BLQ | BLQ | 2980 | BLQ | BLQ | BLQ | 787 |
| Tracheobronchial LN | BLQ | BLQ | BLQ | 108 | BLQ | BLQ | BLQ | 1.48 |
| Blood | 0.076 | 0.68 | 14.7 | 0.20 | .016 | 0.29 | 133 | 1.48 |

BLQ: below level of quantitation
Concentrations in tissues (copies × 106/g)/concentrations in blood (copies × 106/mL), with the assumption that 1 mL of blood ≈ 1 g.

TABLE 6

Mean ICE Concentrations in Rat Tissues (μg/g) and Blood (μg/mL) 24 hours Post-Inhalation Dosing with hCFTR mRNA-Loaded Liposomes (Doses of 0.7, 3.75 or 6.4 mg/kg)

| | Males | | | | Females | | | |
|---|---|---|---|---|---|---|---|---|
| Tissue | Vehicle | 0.7 mg/kg | 3.75 mg/kg | 6.4 mg/kg | Vehicle | 0.7 mg/kg | 3.75 mg/kg | 6.4 mg/kg |
| Brain | BLQ | BLQ | BLQ | BLQ | BLQ | BLQ | BLQ | BLQ |
| Heart | BLQ | BLQ | BLQ | BLQ | BLQ | BLQ | BLQ | BLQ |
| Kidney | BLQ | BLQ | BLQ | BLQ | BLQ | BLQ | BLQ | BLQ |
| Larynx | 1.57 | 2.61 | BLQ | 1.57 | BLQ | BLQ | BLQ | 1.41 |
| Liver | BLQ | BLQ | BLQ | BLQ | BLQ | BLQ | BLQ | BLQ |
| Lung | 317 | 20.3 | 139 | 245 | 293 | 22.5 | 147 | 317 |
| Nasal Turbinate | 0.290 | BLQ | BLQ | 0.796 | BLQ | BLQ | BLQ | 0.724 |
| Spleen | NA | BLQ | BLQ | BLQ | BLQ | BLQ | BLQ | BLQ |
| Testis | BLQ | BLQ | BLQ | BLQ | BLQ | BLQ | BLQ | BLQ |
| Ovary | BLQ | BLQ | BLQ | BLQ | BLQ | BLQ | BLQ | BLQ |
| Trachea | 6.27 | BLQ | BLQ | 3.65 | BLQ | BLQ | BLQ | 2.40 |
| Tracheobronchial LN | BLQ | BLQ | BLQ | BLQ | BLQ | BLQ | BLQ | BLQ |
| Blood | BLQ | BLQ | BLQ | BLQ | BLQ | BLQ | BLQ | BLQ |

BLQ: below level of quantitation
Concentrations in tissues (copies × 106/g)/concentrations in blood (copies × 106/mL), with the assumption that 1 mL of blood ≈ 1 g.

These data show high levels of mRNA in lung tissue and associated respiratory tract issues such as larynx, trachea, tracheobronchial lymph nodes, and nasal turbinates with lower or background levels in heart, brain, liver, kidney, spleen, testis, and ovary, particularly at lower doses of administration, with the highest dose showing hCFTR mRNA distribution across various tissues. Lung levels were high and dose-responsive in both rats and NHP, with the highest levels seen at 6.4 mg/kg in rats.

Figure 2:
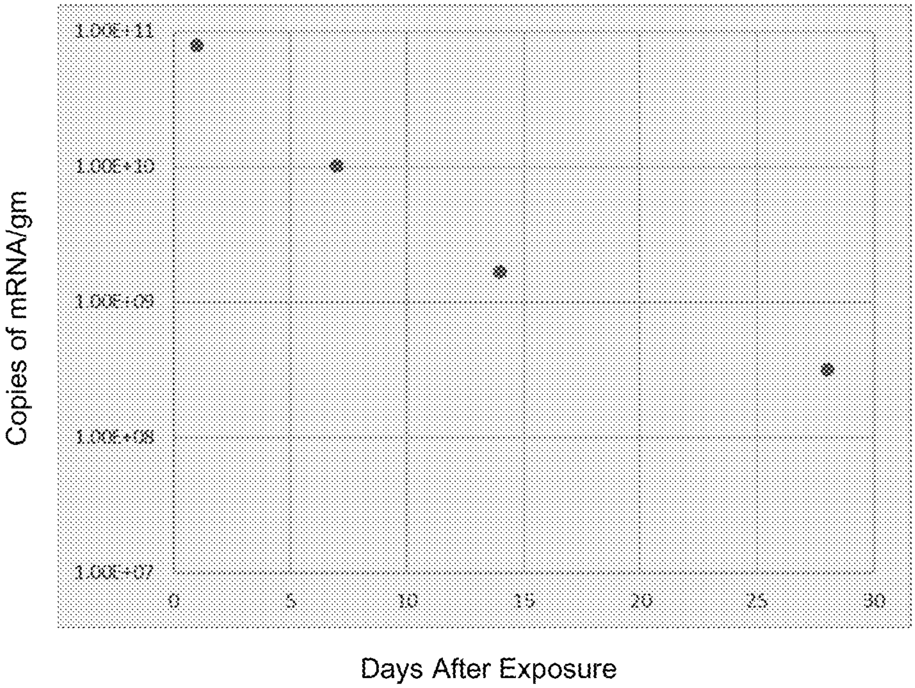
FIG. 2 depicts an exemplary graph of the number of copies of mRNA/gm in rat lung tissue after the rats were treated with hCFTR mRNA-loaded liposomes.
Figure 3:
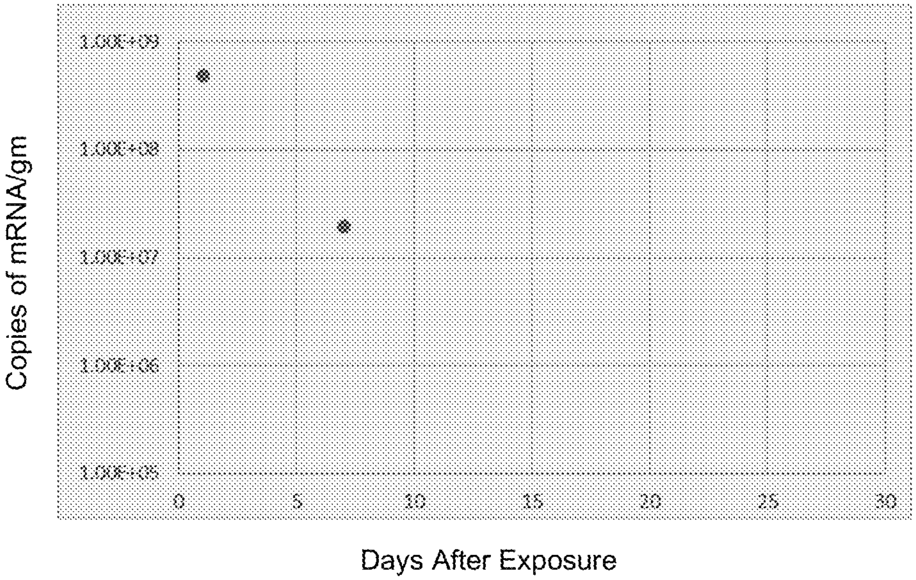
FIG. 3 depicts an exemplary graph of the number of copies of mRNA in primate (NHP) lung tissue after the NHPs were treated with hCFTR mRNA-loaded liposomes.

Kinetics of lung clearance of mRNA was measured reliably in rats since more sacrifice times could be used than for monkeys. FIG. 2 indicates a single component exponential decay with a half-life of approximately 2-3 days. Only two data points were available for NHP (FIG. 3) and these data appear consistent with the rat data in view of differences in dose.

As shown in Table 5, levels of mRNA in the lung were dose-dependent in a relatively linear manner. Lung tissue measurements made after a 28 day recovery period at the end of the 29-day study showed a decline in exposure of approximately 100-fold, similar to that seen 28 days after the single dose study.

The toxicokinetics of ICE liposomes were also examined. There were no measurable levels of ICE liposomes in whole blood. There were, however, measurable and dose-responsive levels of ICE liposomes in the lung tissue in rats (Table 6).

Example 4. In Vitro Activity of hCFTR in Human Bronchial Epithelial Cells

This Example illustrates a study where hCFTR mRNA was transfected into cultured human bronchial epithelial cells, whereupon the protein expressed from transfected hCFTR mRNA provided a significant increase in chloride transport across the bronchial epithelial cell membrane compared to buffer, thereby demonstrating the functional efficacy of the transfected mRNA. The changes in chloride transport across the bronchial epithelial cell membrane was measured by short circuit current output in an Ussing epithelial voltage clamp apparatus (i.e., a Ussing chamber). Specifically, using an established Ussing Chamber procedure (Charles River Laboratories), hCFTR mRNA encapsulated in a liposome comprising ICE, DOPE, and a PEG-modified lipid was incubated for 2 or 4 hours on the apical (mucosal) or basolateral (serosal) sides, or both sides, of human bronchial epithelial cells. A buffer blank also was included as a control, for example, to assess chloride transport by endogenous CFTR in the cells. Next, Forskolin-induced chloride channel activity was measured using the Ussing chamber assay. Following the measure of the current change as indicative of chloride transport across the bronchial epithelial cell membrane, a CFTR inhibitor was added to the samples to show that current change was due to CFTR activity.

Figure 4:
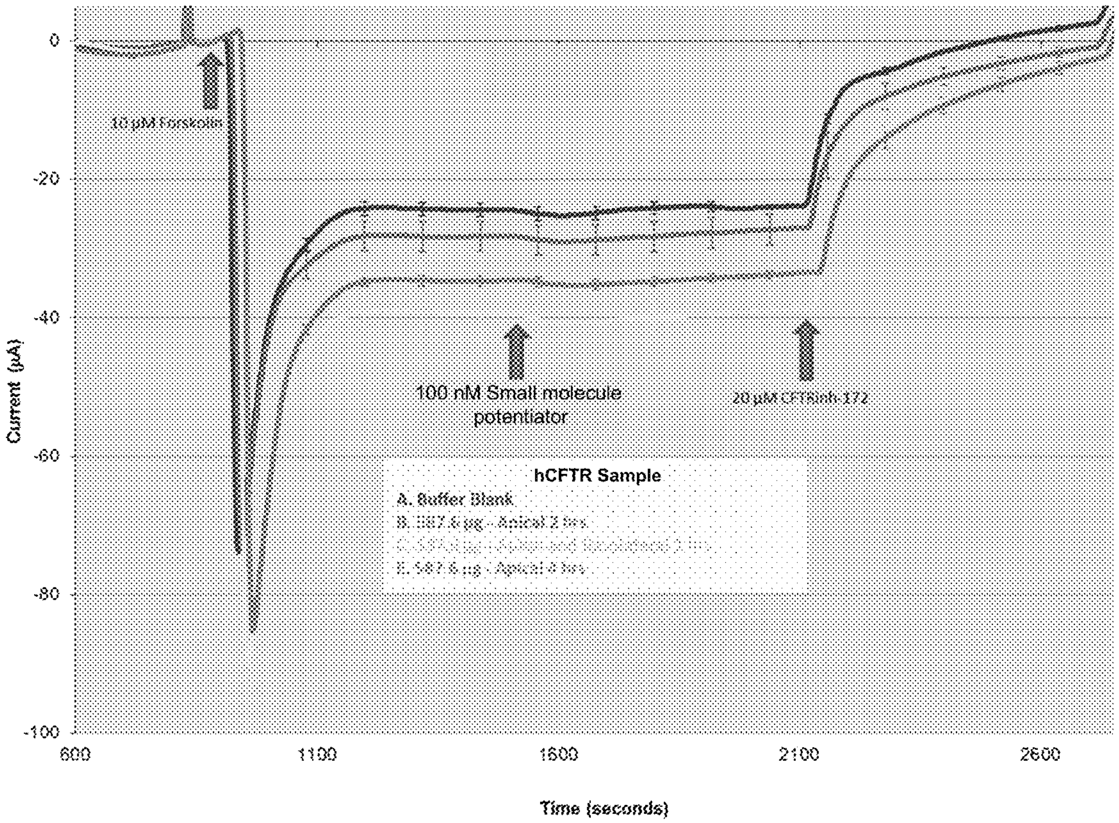
FIG. 4 depicts an exemplary graph showing increased chloride channel activity demonstrated after transfection with hCFTR mRNA-loaded liposomes.

As shown in FIG. 4, compared to the control group (A. Buffer Blank), treatment of the apical (mucosal) epithelial surface for 2 or 4 hours (Samples B and E, respectively) and the apical and basolateral (serosal) epithelial surfaces for 2 hours (Sample C) with hCFTR mRNA provided a significant increase in chloride channel activity. Additionally, the chloride activity in all groups was inhibited by the CFTR inhibitor-172. The results of this study show that the hCFTR mRNA delivered in a liposome to human bronchial epithelial cells produced active CFTR protein in those cells. It also shows that the active CFTR protein produced from the hCFTR mRNA provided significantly increased chloride transport, compared to endogenous CFTR protein, across the cell membranes of the transfected human bronchial epithelial cells.

Figure 5:
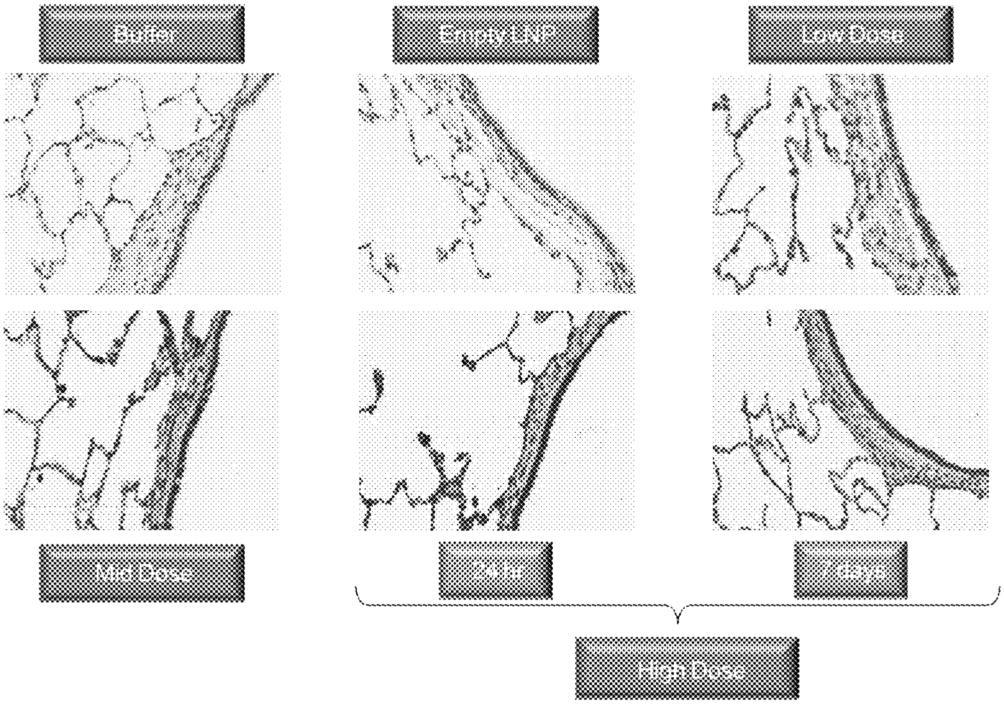
FIG. 5 depicts exemplary IHC of hCFTR protein in lung tissue from a primate after a single dose of a composition comprising an mRNA encoding a CFTR protein.
Figure 6:
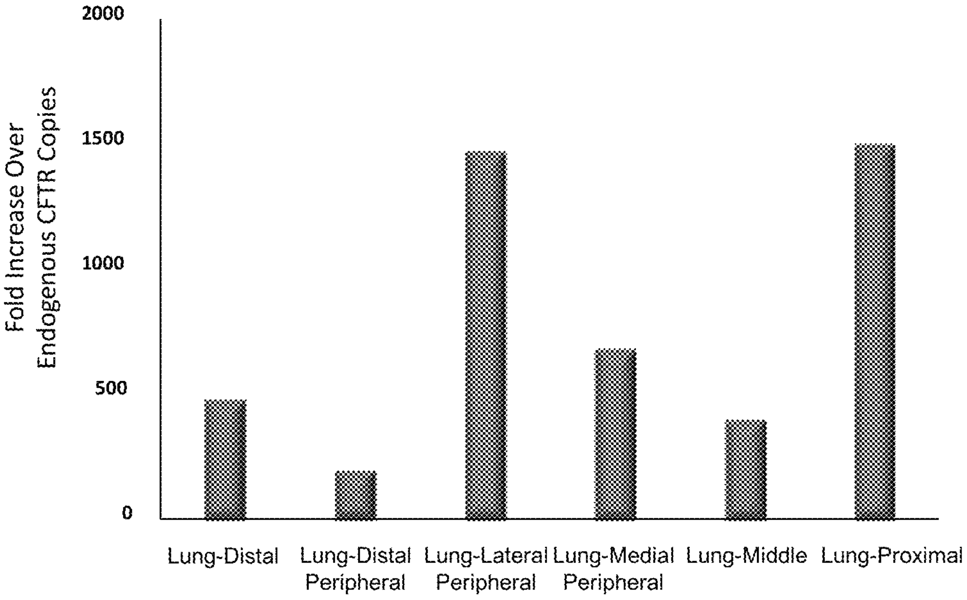
FIG. 6 depicts an exemplary graph of fold-increase of copies of CO-hCFTR mRNA over endogenous levels of CFTR mRNA in primate lung tissue after a single dose of a composition comprising an mRNA encoding a CFTR protein.
Figure 7:
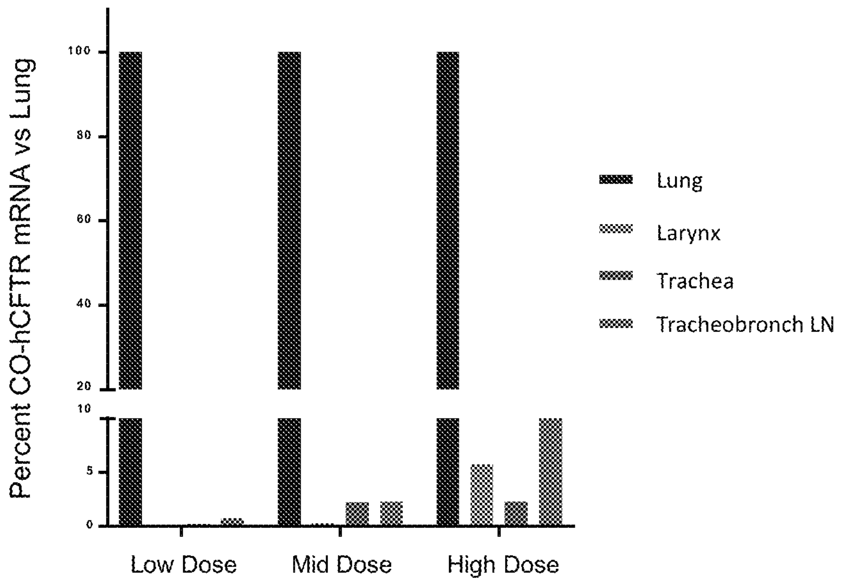
FIG. 7 depicts an exemplary graph of percent of CO-hCFTR mRNA delivered to primate lung tissue as compared to airway tissue after a single dose of a composition comprising an mRNA encoding a CFTR protein.

Example 5. Distribution of hCFTR after Single Dose of hCFTR mRNA/Liposome Composition in Primates In the study in this Example, non-human primates (NHPs) were treated with a single aerosol exposure of a CO-hCFTR mRNA/liposome composition. As shown in FIG. 5, immunohistochemistry (IHC) staining of lung cross-sections demonstrate a dose-dependent increase in intensity for positive hCFTR protein detection. Additionally, when hCFTR mRNA was detected and quantified in tissues from the NHPs, widespread distribution was found throughout the lungs of the monkeys, with CO-hCFTR levels orders of magnitude (>200-fold) over endogenous CFTR (FIG. 6). Additionally, the lungs of the monkeys, which were the target organs, received >90% of the CO-CFTR dose that entered the airway, when compared to other respiratory tract tissues that were tested (FIG. 7).

Example 6. Treatment of Cystic Fibrosis Subjects with CO-hCFTR mRNA/Liposome Composition The study in this example is designed to evaluate a CO-CFTR mRNA liposome composition in patients with cystic fibrosis.

A CO-hCFTR mRNA liposome composition (CO-hCFTR composition) is administered by nebulization to subjects with cystic fibrosis. The CO-hCFTR composition is dosed based on its content of CO-hCFTR mRNA. A nebulizer will be used to administer the CO-hCFTR composition by nebulization at a flow rate of approximately 0.3 mL/minute. The CO-hCFTR composition will be administered to subjects at the following 3 dose levels: 8.0, 16.0, or 24.0 mg of CO-hCFTR mRNA (nominal dose levels) either once or once per week for five weeks. Other subjects will be dosed with placebo control.

In order to receive treatment with administration of the CO-hCFTR composition, patients will have a confirmed diagnosis of CF as defined by all of the following: a sweat chloride value of ≥60 mmol/L by quantitative pilocarpine iontophoresis (documented in the subject's medical record), a confirmed disease-causing CFTR mutation (genotype confirmed at the screening visit), and chronic sinopulmonary disease and/or gastrointestinal/nutritional abnormalities consistent with CF disease; clinically stable CF disease, e.g., $FEV_1$≥50% and ≤90% of the predicted normal for age, gender, and height at screening, resting oxygen saturation ≥92% on room air (pulse oximetry), and body mass index ≥17.5 $kg/m^2$ and weight ≥40 kg. Subjects who are receiving lumacaftor/ivacaftor combination drug (ORKAMBI) will remain on it for the duration of the study preferably at a stable dose.

Procedures and tests that will be conducted both for screening subjects and during the study to evaluate the biological activity of the CO-CFTR mRNA liposome composition include: vital signs, pulse oximetry, physical examination, spirometry, clinical laboratory tests (serum chemistry, hematology, coagulation, urinalysis, CRP), ECG, chest x-ray, Cystic Fibrosis Questionnaire-Revised (CFQ-R), serum pregnancy test, AE and concomitant medication reporting, weight measurement, blood sampling for CO-hCFTR mRNA and ICE assays and blood sampling for immune response assays. Some subjects will also undergo bronchoscopy.

Bronchial epithelial cells obtained during bronchoscopies will be prepared for quantification of exogenous CO-hCFTR mRNA and endogenous CFTR mRNA by qPCR, and for a qualitative assessment of CFTR protein by Western blot analysis.

Additionally, during bronchoscopy, lower airway potential difference measurements will be performed to assess CFTR chloride channel activity in the bronchial epithelium. Potential difference measurements will be made at the lingula outlet of the left lung, as described by Dransfield et al. (Dransfield et al., Chest. (2013) 144:498-506). A stable potential with the mean value of a 10 second scoring interval after perfusion of each solution will recorded. CFTR activity will be estimated by the change in potential difference following perfusion with chloride-free isoproterenol.

The Cystic Fibrosis Questionnaire-Revised (CFQ-R; version for adolescents and adults [patients 14 years old and older]) will be completed subjects at in order to achieve both a baseline score and scores during the study for comparison. The results of the respiratory domain of the CFQ-R will be of primary interest; the minimal change from baseline representing a clinically important improvement in the respiratory domain was determined to be ≥4 (Quittner et al., *Chest.* (2009) 135:1610-8).

Example 7. CFTR Colocalization with Membrane Protein in Upper Airway Bronchial Cells This example demonstrates CFTR protein expression to various lung tissues, including upper bronchial epithelium, lower bronchial epithelium, and alveolar tissue after inhalation administration of CFTR mRNA formulated in a lipid nanoparticle. This example further demonstrates through colocalization with the endogenous membrane tight junction protein, ZO-1, which is found in the cell membrane, that the CFTR protein expressed from the administered CFTR mRNA is localized in the cell membrane of lung tissue, including lung epithelial cells, such as upper airway bronchial epithelial cells and lower airway bronchial epithelial cells, as well in the cell membranes of alveolar cells.

Colocalization Study Protocol:

The immunohistochemistry and colocalization study method described in this paragraph is common for Examples 7, 8 and 9. Lung delivery of the CFTR mRNA in primates was followed by immunohistochemistry to detect the protein expression and membrane colocalization in the upper airway bronchial cells and lower airway epithelial cells and deep alveolar lung. The primates in this study were grouped into five categories and were administered the following: (1) Control, Trehalose 10%; (2) Control, LNP vehicle; (3) CO-hCFTR low dose, 500 μg/kg, (4) CO-hCFTR medium dose, 750 μg/kg, (5) CO-hCFTR high dose, 1000 μg/kg. The mRNA-LNP formulation or controls (without mRNA) were administered daily. Accordingly, the animals were exposed for 60 minutes to the aerosol composition (Group 3, low dose, 500 μg/kg), 90 minutes of aerosol (Group 4, medium dose, 750 μg/kg), or 120 minutes of aerosol (Group 5, high dose) as described in Table 4. At the end of the study the animals were sacrificed and tissues collected for immunohistochemistry to detect the expression and localization of human CFTR protein in the lungs. For immunohistochemical detection of codon-optimized human CFTR protein, lung sections were incubated overnight at 4° C. with a 1:250 dilution of each of mouse monoclonal anti-CFTR antibody (MAB 25031, R & D Systems), and rabbit anti-ZO1 antibody (Ab214228, Abcam); or with anti-CFTR alone; and anti-ZO1 alone. Following overnight incubation, the sections were blocked with first blocking agent containing hydrogen peroxide, incubated with the secondary antibody (anti-mouse DyLight 594 for CFTR antibody, and anti-rabbit DyLight 488 antibody) and followed by second blocking in a solution containing 3% horse serum and 3% BSA and subjected to confocal microscopy for colocalization. DyLight 594 emits red signal, and DyLight 488 emits green, and upon colocalization of the two signals (and therefore the proteins each bind to), the optical merge yields yellow signal. (Color is not shown in the Figure).

Figure 8A:
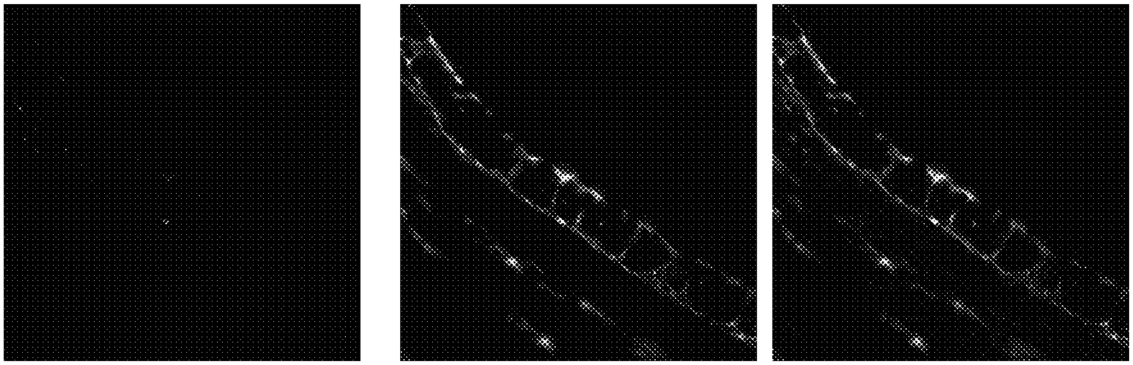
FIG. 8A-C depicts expression of CFTR mRNA-derived protein in primate upper bronchial epithelial cells colocalized with endogenous membrane tight junction protein, ZO1 (which is present in the cell membrane), following treatment with nebulized CFTR mRNA encapsulated in a lipid nanoparticle, delivered by inhalation.
Figure 8B:
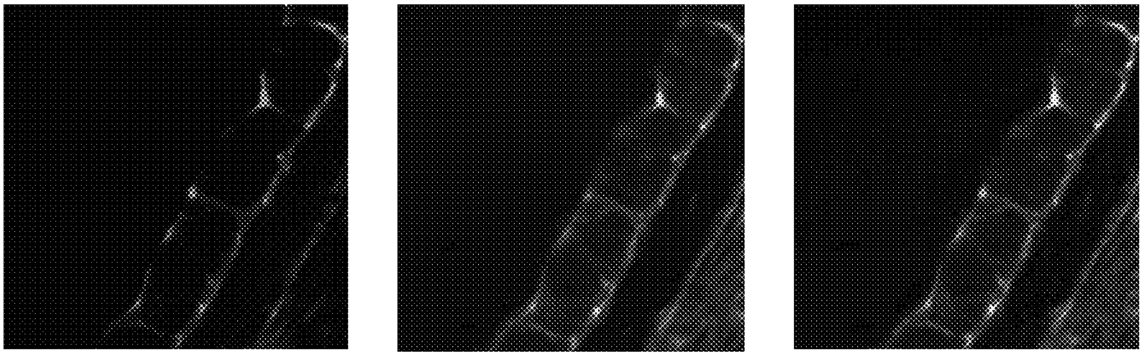
Figure 8C:
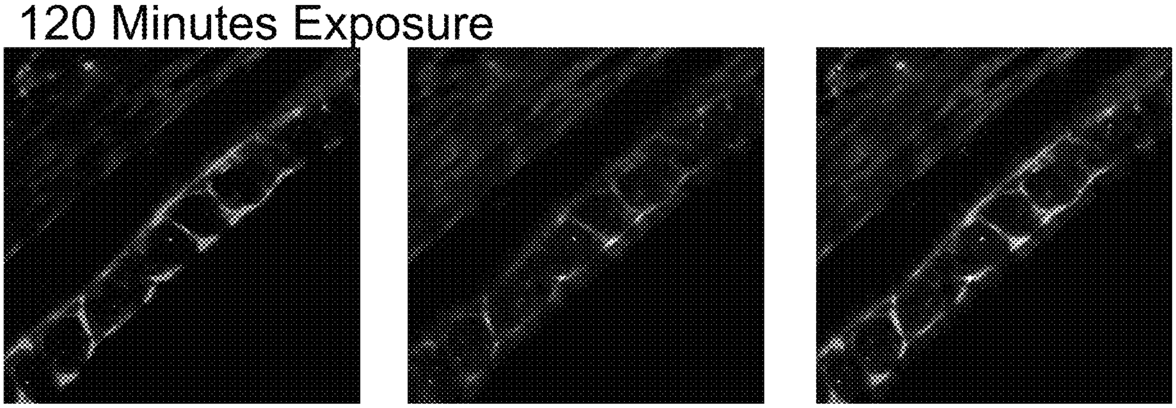

As shown in FIGS. 8A, 8B and 8C, CFTR protein translated from administered CFTR mRNA is expressed in the upper respiratory tract in bronchial epithelial cells. In the exemplary study, CFTR mRNA-derived protein exhibited a dose-dependent expression and colocalized with endogenous membrane tight junction protein ZO1 in upper bronchial epithelial cell membrane. FIG. 8A depicts representative microscopic images of bronchial epithelial cells from a control animal that received 10% trehalose alone, visualized for CFTR staining (left), ZO1 staining (middle) and optical merge of CFTR and ZO1 staining (right). FIG. 8B depicts representative microscopic images of bronchial epithelial cells of an animal that received low dose CFTR mRNA (500 μg/kg), visualized for CFTR staining (left), ZO1 staining (middle) and optical merge of CFTR and ZO1 staining (right). FIG. 8C depicts representative microscopic images of bronchial epithelial cells of an animal that received high dose CFTR mRNA (1000 μg/kg), visualized for CFTR staining (left), ZO1 staining (middle) and optical merge of CFTR and ZO1 staining (right). As indicated in the figure, the expression of CFTR was dose-dependent, that is, the immunostaining signal was stronger at the higher dose (FIG. 8C left image) than that of the low dose (FIG. 8B, left image). Also, as evident from the positioning of the CFTR and ZO1 signals, CFTR and ZO1 are expressed in the cell membrane of the epithelial cells. The two proteins colocalized yielding an intensified signal, which was yellow upon visual observation (FIGS. 8B and 8C right image). No red signal corresponding to CFTR was observed in FIG. 8A indicating the specificity of the staining. Also the merged optical signal was not intensified and monochromatic for ZO-1 signal alone. (Color is not shown in the Figure).

Figure 9A:
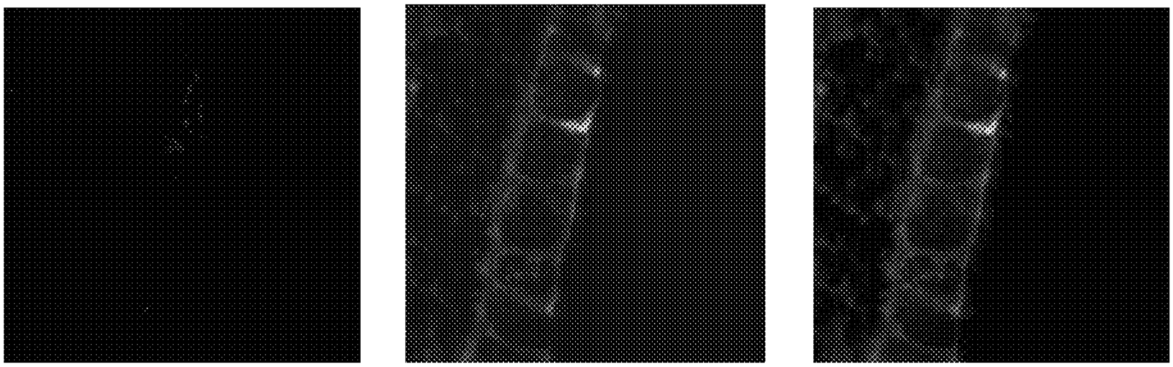
FIG. 9A-C depicts expression of CFTR mRNA-derived protein in primate lower airway epithelial cells colocalized with endogenous membrane tight junction protein, ZO1 (which is present in the cell membrane), following treatment with nebulized CFTR mRNA encapsulated in a lipid nanoparticle, delivered by inhalation.
Figure 9B:
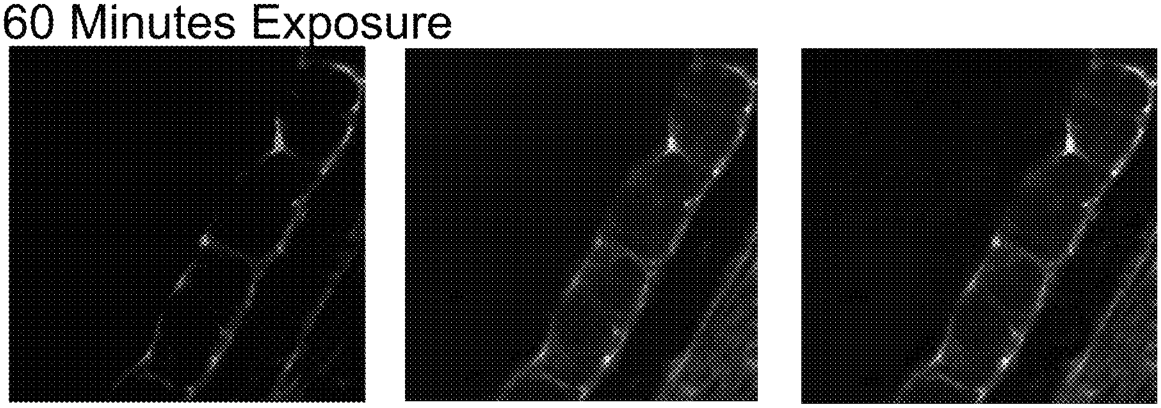
Figure 9C:
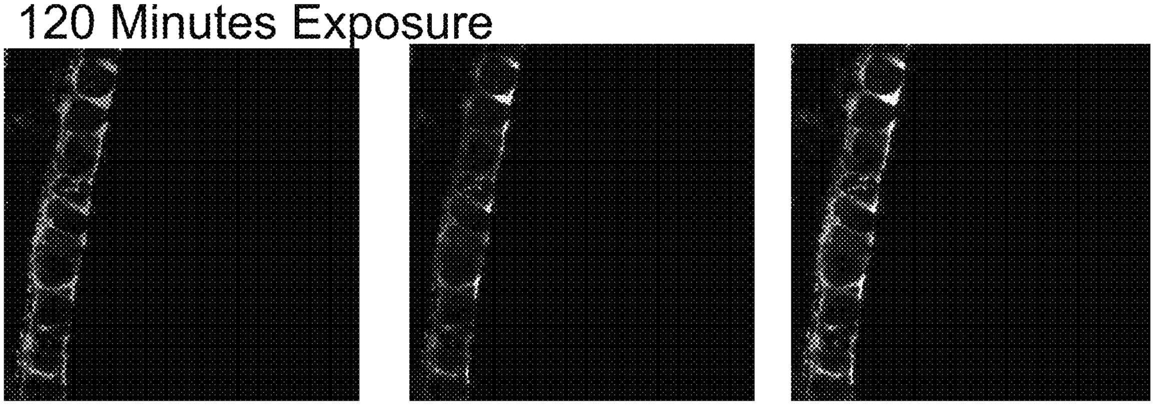

Example 8. CFTR Colocalization with Membrane Protein in Lower Airway Epithelial Cells For successful therapeutic effect, the administered CFTR mRNA has to be delivered to the lower lung. As shown in FIGS. 9A, 9B and 9C, CFTR protein translated from administered CFTR mRNA was expressed in lower respiratory tract epithelial cells. CFTR mRNA-derived protein exhibited a dose-dependent expression and colocalization with endogenous membrane tight junction protein ZO1 protein in lower airway epithelial cell membrane. FIG. 9A shows representative microscopic images of a tissue section from the lower airway epithelial cell membrane from a control animal that received 10% trehalose alone, visualized for CFTR staining (left), ZO1 staining (middle) and optical merge of CFTR and ZO1 staining (right). FIG. 9B shows representative microscopic images of a tissue section from the lower airway epithelial cell membrane of an animal that received low dose CFTR mRNA (500 μg/kg), visualized for CFTR staining (left), ZO1 staining (middle) and optical merge of CFTR and ZO1 staining (right). FIG. 9C shows representative microscopic images of a tissue section from the lower airway of an animal that received high dose CFTR mRNA (1000 μg/kg), visualized for CFTR staining (left), ZO1 staining (middle) and optical merge of CFTR and ZO1 staining (right). The intensity of the CFTR expression was higher in the high dose (FIG. 9C, left image) compared to low dose (FIG. 9B, left image). The merged image in FIG. 9C was yellow indicating that the proteins colocalized, whereas FIG. 9A had no signal for CFTR (left) as was expected of the control. (Color is not shown in the Figure).

Example 9. CFTR mRNA Derived Protein Expression in Alveolar Lung

Figure 10A:
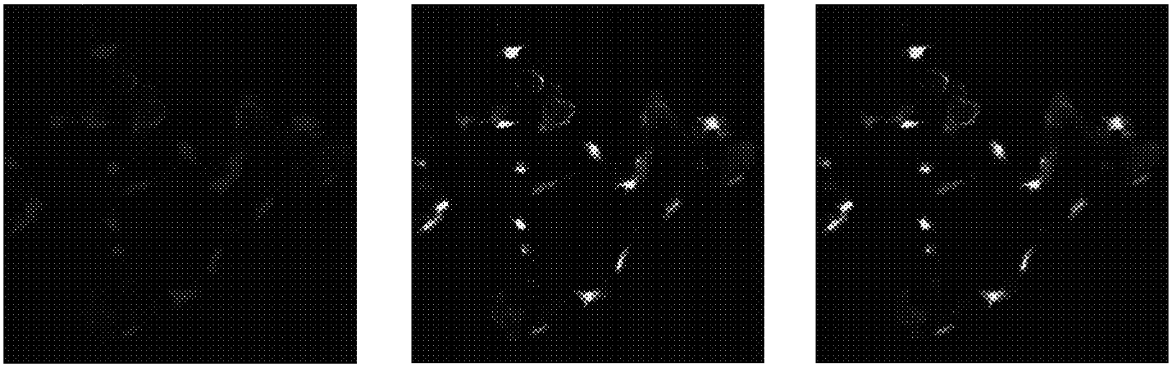
FIG. 10A-C depicts expression of CFTR mRNA-derived protein in cells of the alveolar region of a primate lung colocalized with endogenous membrane tight junction protein, ZO1 (which is present in the cell membrane), following treatment with nebulized CFTR mRNA encapsulated in a lipid nanoparticle, delivered by inhalation.
Figure 10B:
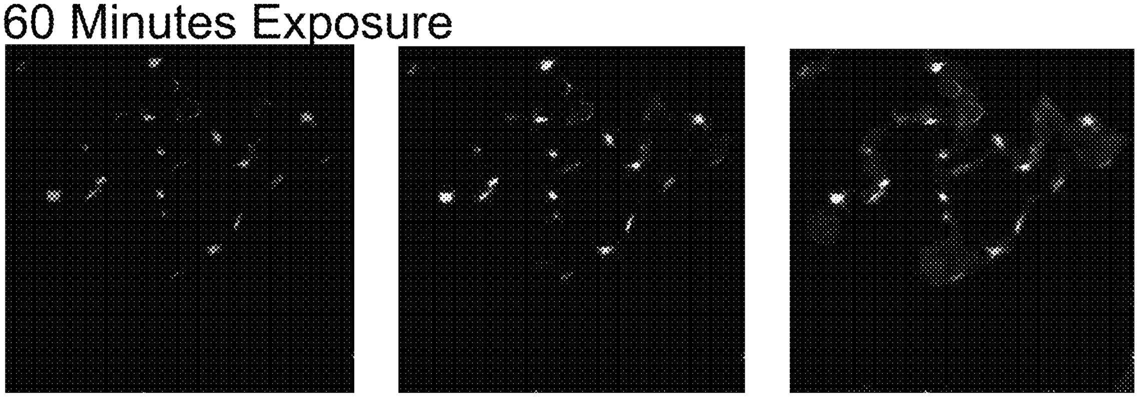
Figure 10C:
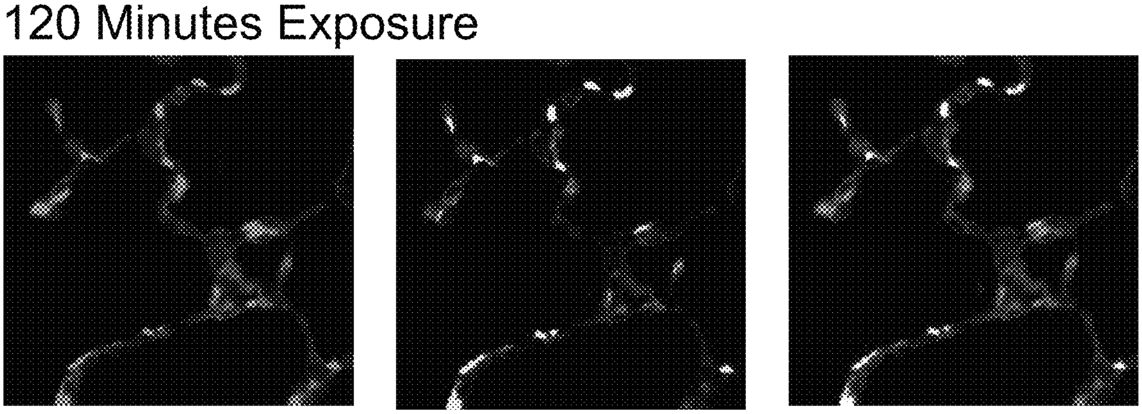

CFTR mRNA was successfully taken up by alveolar cells in the deep lung. As shown in FIGS. 10A, 10B and 10C, CFTR protein translated from administered CFTR mRNA was expressed in alveolar cell membranes and colocalized with endogenous membrane tight junction protein ZO1 protein in the alveolar cell membrane. FIG. 10A shows representative microscopic images of a tissue section from the lower airway epithelial cell membrane from a control animal that received 10% trehalose alone, visualized for CFTR staining (left), ZO1 staining (middle) and optical merge of CFTR and ZO1 staining (right). FIG. 10B shows representative microscopic images of a tissue section from the lower airway epithelial cell membrane of an animal that received low dose CFTR mRNA (500 μg/kg), visualized for CFTR staining (left), ZO1 staining (middle) and optical merge of CFTR and ZO1 staining (right). FIG. 10C shows representative microscopic images of a tissue section from the lower airway of an animal that received high dose CFTR mRNA (1000 μg/kg), visualized for CFTR staining (left), ZO1 staining (middle) and optical merge of CFTR and ZO1 staining (right). The intensity of the CFTR expression was higher in the high dose (FIG. 10C, left image) compared to low dose (FIG. 10B, left image). The merged image in FIG. 10C was yellow indicating that the proteins colocalized, whereas FIG. 10A had no signal for CFTR (left) as was expected for the control. (Color is not shown in the Figure).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating cystic fibrosis (CF), comprising a step of:

administering to a subject in need of treatment a composition comprising an mRNA encoding a Cystic Fibrosis Transmembrane Conductance Regulator (CFTR) protein, wherein the mRNA encoding the CFTR protein comprises a polynucleotide sequence at least 80% identical to SEQ ID NO: 1, wherein the mRNA is at a concentration of at least 0.4 mg/mL, and wherein the step of administering comprises inhalation.

2. The method of claim 1, wherein the mRNA is at a concentration ranging from 0.4 mg/mL to 0.8 mg/mL.

3. The method of claim 1, wherein the composition is nebulized prior to inhalation.

4. The method of claim 1, wherein the composition is stored as a frozen, sterile suspension prior to administering.

5. The method of claim 1, wherein the composition is stored in a single-use vial prior to administering.

6. The method of claim 5, wherein the single-use vial comprises less than 5.0 mL of the composition.

7. The method of claim 1, wherein the mRNA encoding the CFTR protein is at a dosage ranging from 8 mg to 24 mg.

8. The method of claim 1, wherein the mRNA encoding the CFTR protein further comprises a 5' untranslated region (UTR) sequence of SEQ ID NO: 3.

9. The method of claim 1, wherein the mRNA encoding the CFTR protein further comprises a 3' untranslated region (UTR) sequence of SEQ ID NO: 4 or SEQ ID NO: 5.

10. The method of claim 1, wherein the mRNA encoding the CFTR protein is encapsulated within a nanoparticle.

11. The method of claim 10, wherein the nanoparticle is a liposome.

12. The method of claim 11, wherein the liposome comprises one or more cationic lipids, one or more non-cationic lipids, and one or more PEG-modified lipids.

13. The method of claim 11, wherein the liposome has a size less than about 100 nm.

14. The method of claim 12, wherein the liposome comprises imidazole cholesterol ester (ICE), 1,2-dioleoyl-sn-glycero-3-phosphoethanolamine (DOPE), and 1,2-dimyristoyl-sn-glycerol, methoxypolyethylene glycol (DMG-PEG-2K).

15. The method of claim 1, wherein the mRNA encoding the CFTR protein comprises a polynucleotide sequence at least 85%, at least 90% or at least 91% or at least 92% or at least 93% or at least 94% or at least 95% or at least 96% or at least 97% or at least 98% or at least 99% or 100% identical to any one of SEQ ID NO: 6 to SEQ ID NO: 27.

16. The method of claim 1, where the pharmaceutical composition is stored in lyophilized dry powder form.

17. The method of claim 1, where the pharmaceutical composition in lyophilized form is stable in frozen condition for 1, 2, 3, 4, 5 or 10 years without loss of pharmacological or biological activity of the mRNA encoding CFTR protein.

* * * * *

SEQUENCE LISTING

```
<160> NUMBER OF SEQ ID NOS: 27

<210> SEQ ID NO 1
<211> LENGTH: 4443
<212> TYPE: RNA
<213> ORGANISM: Artificial Sequence
<220> FEATURE:
<223> OTHER INFORMATION: Chemically Synthesized Oligonucleotide

<400> SEQUENCE: 1

augcaacgcu cuccucuuga aaaggccucg guggugucca agcucuucuu cucguggacu      60

agacccaucc ugagaaaggg guacagacag cgcuuggagc uguccgauau cuaucaaauc     120

ccuuccgugg acuccgcgga caaccugucc gagaagcucg agagagaaug ggacagagaa     180

cucgccucaa agaagaaccc gaagcugauu aaugcgcuua ggcggugcuu uuucuggcgg     240

uucauguucu acggcaucuu ccucuaccug ggagagguca ccaaggccgu gcagccccug     300

uugcugggac ggauuauugc cuccuacgac cccgacaaca aggaagaaag aagcaucgcu     360

aucuacuugg gcaucggucu gugccugcuu uucaucgucc ggacccucuu guugcauccu     420

gcuauuuucg gccugcauca cauuggcaug cagaugagaa uugccauguu uucccugauc     480

uacaagaaaa cucugaagcu cucgagccgc gugcuugaca agauuuccau cggccagcuc     540

gugucccugc ucuccaacaa ucugaacaag uucgacgagg gccucgcccu ggcccacuuc     600

guguggaucg ccccucugca aguggcgcuu cugaugggcc ugaucuggga gcugcugcaa     660

gccucggcau ucugugggcu uggauuccug aucgugcugg cacuguucca ggccggacug     720

gggcggauga ugaugaagua cagggaccag agagccggaa agauuuccga acggcuggug     780

aucacuucgg aaaugaucga aaacauccag ucagugaagg ccuacugcug ggaagaggcc     840

auggaaaaga ugauugaaaa ccuccggcaa accgagcuga agcugacccg caaggccgcu     900

uacgugcgcu auuucaacuc guccgcuuuc uucuucuccg gguucuucgu ggguguuucuc     960

uccgugcucc ccuacgcccu gauuaaggga aucauccuca ggaagaucuu caccaccauu    1020

uccuucugua ucgugcuccg cauggccgug acccggcagu ucccaugggc cgugcagacu    1080

ugguacgacu cccugggagc cauuaacaag auccaggacu uccuucaaaa gcaggaguac    1140

aagacccucg aguacaaccu gacuacuacc gaggucguga uggaaaacgu caccgccuuu    1200

ugggaggagg gauuuggcga acuguucgag aaggccaagc agaacaacaa caaccgcaag    1260

accucgaacg gugacgacuc ccucuucuuu ucaaacuuca gccugcucgg gacgcccgug    1320

cugaaggaca uuaacuucaa gaucgaaaga ggacagcucc uggcgguggc cggaucgacc    1380

ggagccggaa agacuucccu gcugauggug aucaugggag agcuugaacc uagcgaggga    1440

aagaucaagc acuccggccg caucagcuuc uguagccagu uuuccuggau caugcccgga    1500

accauuaagg aaaacaucau cuucggcgug uccuacgaug aauaccgcua ccgguccgug    1560

aucaaagccu gccagcugga agaggauauu ucaaaguucg cggagaaaga uaacaucgug    1620

cugggcgaag gggguauuac cuugucgggg ggccagcggg cuagaaucuc gcuggccaga    1680

gccguguaua aggacgccga ccuguaucuc cuggacuccc ccuucggaua ccuggacguc    1740

cugaccgaaa aggagaucuu cgaaucgugc gugugcaagc ugauggcuaa caagacucgc    1800

auccucguga ccuccaaaau ggagcaccug aagaaggcag acaagauucu gauucugcau    1860
```

-continued

```
gaggggaucu ccuacuuuua cggcaccuuc ucggaguugc agaacuugca gcccgacuuc   1920
ucaucgaagc ugaugggguug cgacagcuuc gaccaguucu ccgccgaaag aaggaacucg   1980
auccugacgg aaaccuugca ccgcuucucu uuggaaggcg acgccccugu gucauggacc   2040
gagacuaaga agcagagcuu caagcagacc ggggaauucg gcgaaaagag gaagaacagc   2100
aucuugaacc ccauuaacuc cauccgcaag uucucaaucg ugcaaaagac gccacugcag   2160
augaacggca uugaggagga cuccgacgaa ccccuugaga ggcgccuguc ccuggugccg   2220
gacagcgagc agggagaagc cauccugccu cggauuuccg ugaucuccac ugguccgacg   2280
cuccaagccc ggcggcggca guccgugcug aaccugauga cccacagcgu gaaccagggc   2340
caaaacauuc accgcaagac uaccgcaucc acccggaaag ugucccuggc accucaagcg   2400
aaucuuaccg agcucgacau cuacucccgg agacugucgc aggaaaccgg gcucgaaauu   2460
uccgaagaaa ucaacgagga ggaucugaaa gagugcuucu ucgacgauau ggagucgaua   2520
cccgccguga cgacuuggaa cacuuaucug cgguacauca cugugcacaa gucauugauc   2580
uucgugcuga uuuggugccu ggugauuuuc cuggccgagg ucgcggccuc acugguggug   2640
cucuggcugu ugggaaacac gccucugcaa gacaagggaa acuccacgca cucgagaaac   2700
aacagcuaug ccgugauuau cacuuccacc uccucuuauu acguguucua caucuacguc   2760
ggaguggcgg auacccugcu cgcgaugggu uucuucagag gacugccgcu gguccacacc   2820
uugaucaccg ucagcaagau ucuucaccac aagauguugc auagcgugcu gcaggccccc   2880
auguccaccc ucaacacucu gaaggccgga ggcauucuga acagauucuc caaggacauc   2940
gcuauccugg acgaucuccu gccgcuuacc aucuuugacu ucauccagcu gcugcugauc   3000
gugauuggag caaucgcagu gguggcggug cugcagccuu acauuuucgu ggccacugug   3060
ccggucauug uggcguucau caugcugcgg gccuacuucc uccaaaccag ccagcagcug   3120
aagcaacugg aauccgaggg acgaucccccc aucuucacuc accuugugac gucguugaag   3180
ggacugugga cccuccgggc uuucggacgg cagcccuacu ucgaaacccu cuuccacaag   3240
gcccugaacc uccacaccgc caauugguuc cuguaccugu ccacccugcg gugguuccag   3300
augcgcaucg agaugauuuu cgucaucuuc uucaucgcgg ucacauucau cagcauccug   3360
acuaccggag agggagaggg acgggucgga auaauccuga cccucgccau gaacauuaug   3420
agcacccugc agugggcagu gaacagcucg aucgacgugg acagccugau gcgaagcguc   3480
agccgcgugu ucaaguucau cgacaugccu acugagggaa aacccacuaa guccacuaag   3540
cccuacaaaa auggccagcu gagcaagguc augaucaucg aaaacuccca cgugaagaag   3600
gacgauauuu ggcccuccgg aggucaaaug accgugaagg accugaccgc aaaguacacc   3660
gagggaggaa acgccauucu cgaaaacauc agcuucucca uuucgccggg acagcggguc   3720
ggccuucucg ggcggaccgg uuccgggaag ucaacucugc ugucggcuuu ccuccggcug   3780
cugaauaccg agggggaaau ccaaauugac ggcgugucuu gggauuccau uacucugcag   3840
caguggcgga aggccuucgg cgugaucccc cagaaggugu ucaucuucuc ggguaccuuc   3900
cggaagaacc uggauccuua cgagcagugg agcgaccaag aaaucuggaa ggucgccgac   3960
gaggucggcc ugcgcuccgu gauugaacaa uuuccuggaa agcuggacuu cgugcucguc   4020
gacgggggau guguccuguc gcacggacau aagcagcuca ugugccucgc acgguccgug   4080
cucuccaagg ccaagauucu gcugcuggac gaaccuucgg cccaccugga uccggucacc   4140
uaccagauca ucaggaggac ccugaagcag gccuuugccg auugcaccgu gauucucugc   4200
```

-continued gagcaccgca ucgaggccau gcuggagugc cagcaguucc uggucaucga ggagaacaag 4260
guccgccaau acgacuccau ucaaaagcuc cucaacgagc ggucgcuguu cagacaagcu 4320
auuucaccgu ccgauagagu gaagcucuuc ccgcaucgga acagcucaaa gugcaaaucg 4380
aagccgcaga ucgcagccuu gaaggaagag acugaggaag aggugcagga cacccggcuu 4440
uaa 4443

<210> SEQ ID NO 2
<211> LENGTH: 1480
<212> TYPE: PRT
<213> ORGANISM: Homo sapiens

<400> SEQUENCE: 2

Met Gln Arg Ser Pro Leu Glu Lys Ala Ser Val Val Ser Lys Leu Phe
1 5 10 15

Phe Ser Trp Thr Arg Pro Ile Leu Arg Lys Gly Tyr Arg Gln Arg Leu
20 25 30

Glu Leu Ser Asp Ile Tyr Gln Ile Pro Ser Val Asp Ser Ala Asp Asn
35 40 45

Leu Ser Glu Lys Leu Glu Arg Glu Trp Asp Arg Glu Leu Ala Ser Lys
50 55 60

Lys Asn Pro Lys Leu Ile Asn Ala Leu Arg Arg Cys Phe Phe Trp Arg
65 70 75 80

Phe Met Phe Tyr Gly Ile Phe Leu Tyr Leu Gly Glu Val Thr Lys Ala
85 90 95

Val Gln Pro Leu Leu Leu Gly Arg Ile Ile Ala Ser Tyr Asp Pro Asp
100 105 110

Asn Lys Glu Glu Arg Ser Ile Ala Ile Tyr Leu Gly Ile Gly Leu Cys
115 120 125

Leu Leu Phe Ile Val Arg Thr Leu Leu Leu His Pro Ala Ile Phe Gly
130 135 140

Leu His His Ile Gly Met Gln Met Arg Ile Ala Met Phe Ser Leu Ile
145 150 155 160

Tyr Lys Lys Thr Leu Lys Leu Ser Ser Arg Val Leu Asp Lys Ile Ser
165 170 175

Ile Gly Gln Leu Val Ser Leu Leu Ser Asn Asn Leu Asn Lys Phe Asp
180 185 190

Glu Gly Leu Ala Leu Ala His Phe Val Trp Ile Ala Pro Leu Gln Val
195 200 205

Ala Leu Leu Met Gly Leu Ile Trp Glu Leu Leu Gln Ala Ser Ala Phe
210 215 220

Cys Gly Leu Gly Phe Leu Ile Val Leu Ala Leu Phe Gln Ala Gly Leu
225 230 235 240

Gly Arg Met Met Met Lys Tyr Arg Asp Gln Arg Ala Gly Lys Ile Ser
245 250 255

Glu Arg Leu Val Ile Thr Ser Glu Met Ile Glu Asn Ile Gln Ser Val
260 265 270

Lys Ala Tyr Cys Trp Glu Glu Ala Met Glu Lys Met Ile Glu Asn Leu
275 280 285

Arg Gln Thr Glu Leu Lys Leu Thr Arg Lys Ala Ala Tyr Val Arg Tyr
290 295 300

Phe Asn Ser Ser Ala Phe Phe Phe Ser Gly Phe Phe Val Val Phe Leu
305 310 315 320

Ser Val Leu Pro Tyr Ala Leu Ile Lys Gly Ile Ile Leu Arg Lys Ile

-continued

```
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750
```

-continued

```
Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                1005

Ala Val  Leu Gln Pro Tyr Ile  Phe Val Ala Thr Val  Pro Val Ile
    1010                1015                1020

Val Ala  Phe Ile Met Leu Arg  Ala Tyr Phe Leu Gln  Thr Ser Gln
    1025                1030                1035

Gln Leu  Lys Gln Leu Glu Ser  Glu Gly Arg Ser Pro  Ile Phe Thr
    1040                1045                1050

His Leu  Val Thr Ser Leu Lys  Gly Leu Trp Thr Leu  Arg Ala Phe
    1055                1060                1065

Gly Arg  Gln Pro Tyr Phe Glu  Thr Leu Phe His Lys  Ala Leu Asn
    1070                1075                1080

Leu His  Thr Ala Asn Trp Phe  Leu Tyr Leu Ser Thr  Leu Arg Trp
    1085                1090                1095

Phe Gln  Met Arg Ile Glu Met  Ile Phe Val Ile Phe  Phe Ile Ala
    1100                1105                1110

Val Thr  Phe Ile Ser Ile Leu  Thr Thr Gly Glu Gly  Glu Gly Arg
    1115                1120                1125

Val Gly  Ile Ile Leu Thr Leu  Ala Met Asn Ile Met  Ser Thr Leu
    1130                1135                1140

Gln Trp  Ala Val Asn Ser Ser  Ile Asp Val Asp Ser  Leu Met Arg
    1145                1150                1155
```

-continued

```
Ser Val  Ser Arg Val Phe Lys  Phe Ile Asp Met Pro  Thr Glu Gly
    1160                 1165                 1170

Lys Pro  Thr Lys Ser Thr Lys  Pro Tyr Lys Asn Gly  Gln Leu Ser
    1175                 1180                 1185

Lys Val  Met Ile Ile Glu Asn  Ser His Val Lys Lys  Asp Asp Ile
    1190                 1195                 1200

Trp Pro  Ser Gly Gly Gln Met  Thr Val Lys Asp Leu  Thr Ala Lys
    1205                 1210                 1215

Tyr Thr  Glu Gly Gly Asn Ala  Ile Leu Glu Asn Ile  Ser Phe Ser
    1220                 1225                 1230

Ile Ser  Pro Gly Gln Arg Val  Gly Leu Leu Gly Arg  Thr Gly Ser
    1235                 1240                 1245

Gly Lys  Ser Thr Leu Leu Ser  Ala Phe Leu Arg Leu  Leu Asn Thr
    1250                 1255                 1260

Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350

Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480
```

<210> SEQ ID NO 3
<211> LENGTH: 140
<212> TYPE: RNA
<213> ORGANISM: Artificial Sequence
<220> FEATURE:
<223> OTHER INFORMATION: Chemically synthesized oligonucleotides

<400> SEQUENCE: 3
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg 140

<210> SEQ ID NO 4
<211> LENGTH: 105
<212> TYPE: RNA
<213> ORGANISM: Artificial Sequence
<220> FEATURE:
<223> OTHER INFORMATION: Chemically synthesized oligonucleotide

<400> SEQUENCE: 4
cggguggcau cccugugacc ccuccccagu gccucuccug gcccuggaag uugccacucc 60
agugcccacc agccuugucc uaauaaaauu aaguugcauc aagcu 105

<210> SEQ ID NO 5
<211> LENGTH: 105
<212> TYPE: RNA
<213> ORGANISM: Artificial Sequence
<220> FEATURE:
<223> OTHER INFORMATION: Chemically synthesized oligonucleotide

<400> SEQUENCE: 5
ggguggcauc ccugugaccc cuccccagug ccucuccugg cccuggaagu ugccacucca 60
gugcccacca gccuuguccu aauaaaauua aguugcauca aagcu 105

<210> SEQ ID NO 6
<211> LENGTH: 4688
<212> TYPE: RNA
<213> ORGANISM: Artificial Sequence
<220> FEATURE:
<223> OTHER INFORMATION: Chemically synthesized oligonucleotide

<400> SEQUENCE: 6
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcaacgcu cuccucuuga aaaggccucg guggugucca 180
agcucuucuu cucguggacu agacccaucc ugagaaaggg guacagacag cgcuuggagc 240
uguccgauau cuaucaaauc ccuuccgugg acuccgcgga caaccugucc gagaagcucg 300
agagagaaug ggacagagaa cucgccucaa agaagaaccc gaagcugauu aaugcgcuua 360
ggcggugcuu uuucuggcgg uucauguucu acggcaucuu ccucuaccug ggagagguca 420
ccaaggccgu gcagccccug uugcugggac ggauuauugc cuccuacgac cccgacaaca 480
aggaagaaag aagcaucgcu aucuacuugg gcaucggucu gugccugcuu uucaucgucc 540
ggacccucuu guugcauccu gcuauuuucg gccugcauca cauuggcaug cagaugagaa 600
uugccauguu uucccugauc uacaagaaaa cucugaagcu cucgagccgc gugcuugaca 660
agauuuccau cggccagcuc guguccuugc ucuccaacaa ucugaacaag uucgacgagg 720
gccucgcccu ggcccacuuc guguggaucg ccccucugca aguggcgcuu cugaugggcc 780
ugaucuggga gcugcugcaa gccucggcau ucugugggcu uggauuccug aucgugcugg 840
cacuguucca ggccggacug gggcggauga ugaugaagua cagggaccag agagccggaa 900
agauuuccga acggcuggug aucacuucgg aaaugaucga aaacauccag ucagugaagg 960
ccuacugcug ggaagaggcc auggaaaaga ugauugaaaa ccuccggcaa accgagcuga 1020
agcugacccg caaggccgcu uacgugcgcu auuucaacuc guccgcuuuc uucuucuccg 1080
gguucuucgu gguguuucuc uccgugcucc ccuacgcccu gauuaaggga aucauccuca 1140

-continued

```
ggaagaucuu caccaccauu uccuucugua ucgugcuccg cauggccgug acccggcagu   1200
ucccaugggc cgugcagacu ugguacgacu cccugggagc cauuaacaag auccaggacu   1260
uccuucaaaa gcaggaguac aagacccucg aguacaaccu gacuacuacc gaggucguga   1320
uggaaaacgu caccgccuuu ugggaggagg gauuuggcga acuguucgag aaggccaagc   1380
agaacaacaa caaccgcaag accucgaacg gugacgacuc ccucuucuuu ucaaacuuca   1440
gccugcucgg gacgcccgug cugaaggaca uuaacuucaa gaucgaaaga ggacagcucc   1500
uggcggugge cggaucgacc ggagccggaa agacuucccu gcugauggug aucaugggag   1560
agcuugaacc uagcgaggga aagaucaagc acuccggccg caucagcuuc uguagccagu   1620
uuuccuggau caugcccgga accauuaagg aaaacaucau cuucggcgug uccuacgaug   1680
aauaccgcua ccgguccgug aucaaagccu gccagcugga agaggauauu ucaaaguucg   1740
cggagaaaga uaacaucgug cugggcgaag ggguauuac cuugucgggg ggccagcggg   1800
cuagaaucuc gcuggccaga gccguguaua aggacgccga ccuguaucuc cuggacuccc   1860
ccuucggaua ccuggacguc cugaccgaaa aggagaucuu cgaaucgugc gugugcaagc   1920
ugauggcuaa caagacucgc auccucguga ccuccaaaau ggagcaccug aagaaggcag   1980
acaagauucu gauucugcau gaggggguccu ccuacuuuua cggcaccuuc ucggaguugc   2040
agaacuugca gcccgacuuc ucaucgaagc ugauggguug cgacagcuuc gaccaguucu   2100
ccgccgaaag aaggaacucg auccugacgg aaaccuugca ccgcuucucu uuggaaggcg   2160
acgccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg gacagcgagc agggagaagc cauccugccu cggauuuccg   2400
ugaucuccac ugguccgacg cuccaagccc ggcggcggca guccgugcug aaccugauga   2460
cccacagcgu gaaccagggc caaaacauuc accgcaagac uaccgcaucc acccggaaag   2520
ugucccuggc accucaagcg aaucuuaccg agcucgacau cuacucccgg agacugucgc   2580
aggaaaccgg gcucgaaauu uccgaagaaa ucaacgagga ggaucugaaa gagugcuucu   2640
ucgacgauau ggagucgaua cccgccguga cgacuuggaa cacuuaucug cgguacauca   2700
cugugcacaa gucauugauc uucgugcuga uuuggugccu ggugauuuuc cuggccgagg   2760
ucgcggccuc acuggguggug cucuggcugu ugggaaacac gccucugcaa gacaagggaa   2820
acuccacgca cucgagaaac aacagcuaug ccgugauuau cacuuccacc uccucuuauu   2880
acguguucua caucuacguc ggaguggcgg auacccugcu cgcgaugggu uucuucagag   2940
gacugccgcu gguccacacc uugaucaccg ucagcaagau ucuucaccac aagauguugc   3000
auagcgugcu gcaggccccc auguccaccc ucaacacucu gaaggccgga ggcauucuga   3060
acagauucuc caaggacauc gcuauccugg acgaucuccu gccgcuuacc aucuuugacu   3120
ucauccagcu gcugcugauc gugauuggag caaucgcagu ggugcggug cugcagccuu   3180
acauuuucgu ggccacugug ccggucauug uggcguucau caugcugcgg gccuacuucc   3240
uccaaaccag ccagcagcug aagcaacugg aauccgaggg acgauccccc aucuucacuc   3300
accuugugac gucguugaag ggacugugga cccuccgggc uuucggacgg cagcccuacu   3360
ucgaaacccu cuuccacaag gcccugaacc uccacaccgc caauugguuc cuguaccugu   3420
ccacccugcg gugguuccag augcgcaucg agaugauuuu cgucaucuuc uucaucgcgg   3480
ucacauucau cagcauccug acuaccggag agggagaggg acgggucgga auaauccuga   3540
```

cccucgccau gaacauuaug agcacccugc agugggcagu gaacagcucg aucgacgugg 3600
acagccugau gcgaagcguc agccgcgugu ucaaguucau cgacaugccu acugagggaa 3660
aacccacuaa guccacuaag cccuacaaaa auggccagcu gagcaagguc augaucaucg 3720
aaaacuccca cgugaagaag gacgauauuu ggcccuccgg aggucaaaug accgugaagg 3780
accugaccgc aaaguacacc gagggaggaa acgccauucu cgaaaacauc agcuucucca 3840
uuucgccggg acagcggguc ggccuucucg ggcggaccgg uuccgggaag ucaacucugc 3900
ugucggcuuu ccuccggcug cugaauaccg agggggaaau ccaaauugac ggcgugucuu 3960
gggauuccau uacucugcag caguggcgga aggccuucgg cgugaucccc cagaaggugu 4020
ucaucuucuc ggguaccuuc cggaagaacc uggauccuua cgagcagugg agcgaccaag 4080
aaaucuggaa ggucgccgac gaggucggcc ugcgcuccgu gauugaacaa uuuccuggaa 4140
agcuggacuu cgugcucguc gacgggggau guguccuguc gcacggacau aagcagcuca 4200
ugugccucgc acgguccgug cucuccaagg ccaagauucu gcugcuggac gaaccuucgg 4260
cccaccugga uccggucacc uaccagauca ucaggaggac ccugaagcag gccuuugccg 4320
auugcaccgu gauucucugc gagcaccgca ucgaggccau gcuggagugc cagcaguucc 4380
uggucaucga ggagaacaag guccgccaau acgacuccau ucaaaagcuc cucaacgagc 4440
ggucgcuguu cagacaagcu auuucaccgu ccgauagagu gaagcucuuc ccgcaucgga 4500
acagcucaaa gugcaaaucg aagccgcaga ucgcagccuu gaaggaagag acugaggaag 4560
aggugcagga cacccggcuu uaacgggugg caucccugug accccucccc agugccucuc 4620
cuggcccugg aaguugccac uccagugccc accagccuug uccuaauaaa auuaaguugc 4680
aucaagcu 4688

<210> SEQ ID NO 7
<211> LENGTH: 4688
<212> TYPE: RNA
<213> ORGANISM: Artificial Sequence
<220> FEATURE:
<223> OTHER INFORMATION: Chemically synthesized oligonucleotide

<400> SEQUENCE: 7
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcaacgcu cuccucuuga aaaggccucg guggugucca 180
agcucuucuu cucguggacu agacccaucc ugagaaaggg guacagacag cgcuuggagc 240
uguccgauau cuaucaaauc ccuuccgugg acuccgcgga caaccugucc gagaagcucg 300
agagagaaug ggacagagaa cucgccucaa agaagaaccc gaagcugauu aaugcgcuua 360
ggcggugcuu uuucuggcgg uucauguucu acggcaucuu ccucuaccug ggagagguca 420
ccaaggccgu gcagccccug uugcugggac ggauuauugc cuccuacgac cccgacaaca 480
aggaagaaag aagcaucgcu aucuacuugg gcaucggucu gugccugcuu uucaucgucc 540
ggacccucuu guugcauccu gcuauuuucg gccugcauca cauuggcaug cagaugagaa 600
uugccauguu uucccugauc uacaagaaaa cucugaagcu cucgagccgc gugcuugaca 660
agauuuccau cggccagcuc gugucccugc ucuccaacaa ucugaacaag uucgacgagg 720
gccucgcccu ggcccacuuc guguggaucg ccccucugca aguggcgcuu cugaugggcc 780
ugaucuggga gcugcugcaa gccucggcau ucugugggcu uggauuccug aucgugcugg 840

-continued

```
cacuguucca ggccggacug gggcggauga ugaugaagua cagggaccag agagccggaa    900
agauuuccga acggcuggug aucacuucgg aaaugaucga aaacauccag ucagugaagg    960
ccuacugcug ggaagaggcc auggaaaaga ugauugaaaa ccuccggcaa accgagcuga   1020
agcugacccg caaggccgcu uacgugcgcu auuucaacuc guccgcuuuc uucuucuccg   1080
gguucuucgu gguguuucuc uccgugcucc ccuacgcccu gauuaaggga aucauccuca   1140
ggaagaucuu caccaccauu uccuucugua ucgugcuccg cauggccgug acccggcagu   1200
ucccaugggc cgugcagacu ugguacgacu cccugggagc cauuaacaag auccaggacu   1260
uccuucaaaa gcaggaguac aagacccucg aguacaaccu gacuacuacc gaggucguga   1320
uggaaaacgu caccgccuuu ugggaggagg gauuuggcga acuguucgag aaggccaagc   1380
agaacaacaa caaccgcaag accucgaacg gugacgacuc ccucuucuuu ucaaacuuca   1440
gccugcucgg gacgcccgug cugaaggaca uuaacuucaa gaucgaaaga ggacagcucc   1500
uggcggugge cggaucgacc ggagccggaa agacuucccu gcugauggug aucaugggag   1560
agcuugaacc uagcgaggga aagaucaagc acuccggccg caucagcuuc uguagccagu   1620
uuuccuggau caugcccgga accauuaagg aaaacaucau cuucggcgug uccuacgaug   1680
aauaccgcua ccgguccgug aucaaagccu gccagcugga agaggauauu ucaaaguucg   1740
cggagaaaga uaacaucgug cugggcgaag ggggguauuac cuugucgggg ggccagcggg   1800
cuagaaucuc gcuggccaga gccguguaua aggacgccga ccuguaucuc cuggacuccc   1860
ccuucggaua ccuggacguc cugaccgaaa aggagaucuu cgaaucgugc gugugcaagc   1920
ugauggcuaa caagacucgc auccucguga ccuccaaaau ggagcaccug aagaaggcag   1980
acaagauucu gauucugcau gaggggucu ccuacuuuua cggcaccuuc ucggaguugc   2040
agaacuugca gcccgacuuc ucaucgaagc ugaugggguug cgacagcuuc gaccaguucu   2100
ccgccgaaag aaggaacucg auccugacgg aaaccuugca ccgcuucucu uuggaaggcg   2160
acgccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg gacagcgagc agggagaagc cauccugccu cggauuuccg   2400
ugaucuccac ugguccgacg cuccaagccc ggcggcggca guccgugcug aaccugauga   2460
cccacagcgu gaaccagggc caaaacauuc accgcaagac uaccgcaucc acccggaaag   2520
ugucccuggc accucaagcg aaucuuaccg agcucgacau cuacucccgg agacugucgc   2580
aggaaaccgg gcucgaaauu uccgaagaaa ucaacgagga ggaucugaaa gagugcuucu   2640
ucgacgauau ggagucgaua cccgccguga cgacuuggaa cacuuaucug cgguacauca   2700
cugugcacaa gucauugauc uucgugcuga uuuggugccu ggugauuuuc cuggccgagg   2760
ucgcggccuc acuggugg cucuggcugu ugggaaacac gccucugcaa gacaagggaa   2820
acuccacgca cucgagaaac aacagcuaug ccgugauuau cacuuccacc uccucuuauu   2880
acguguucua caucuacguc ggaguggcgg auacccugcu cgcgaugggu uucuucagag   2940
gacugccgcu gguccacacc uugaucaccg ucagcaagau ucuucaccac aagauguugc   3000
auagcgugcu gcaggccccc auguccaccc ucaacacucu gaaggccgga ggcauucuga   3060
acagauucuc caaggacauc gcuauccugg acgaucuccu gccgcuuacc aucuuugacu   3120
ucauccagcu gcugcugauc gugauuggag caaucgcagu gguggcggug cugcagccuu   3180
acauuuucgu ggccacugug ccggucauug uggcguucau caugcugcgg gccuacuucc   3240
```

uccaaaccag ccagcagcug aagcaacugg aauccgaggg acgaucccccc aucuucacuc 3300 accuugugac gucguugaag ggacugugga cccuccgggc uuucggacgg cagccccuacu 3360 ucgaaacccu cuuccacaag gcccugaacc uccacaccgc caauugguuc cuguaccugu 3420
ccacccugcg gugguuccag augcgcaucg agaugauuuu cgucaucuuc uucaucgcgg 3480
ucacauucau cagcauccug acuaccggag agggagaggg acgggucgga auaauccuga 3540
cccucgccau gaacauuaug agcacccugc agugggcagu gaacagcucg aucgacgugg 3600
acagccugau gcgaagcguc agccgcgugu ucaaguucau cgacaugccu acugagggaa 3660
aacccacuaa guccacuaag cccuacaaaa auggccagcu gagcaagguc augaucaucg 3720
aaaacuccca cgugaagaag gacgauauuu ggcccuccgg aggucaaaug accgugaagg 3780
accugaccgc aaaguacacc gagggaggaa acgccauucu cgaaaacauc agcuucucca 3840
uuucgccggg acagcggguc ggccuucucg ggcggaccgg uuccgggaag ucaacucugc 3900
ugucggcuuu ccuccggcug cugaauaccg agggggaaau ccaaauugac ggcgugucuu 3960
gggauuccau uacucugcag caguggcgga aggccuucgg cgugaucccc cagaaggugu 4020
ucaucuucuc ggguaccuuc cggaagaacc uggauccuua cgagcagugg agcgaccaag 4080
aaaucuggaa ggucgccgac gaggucggcc ugcgcuccgu gauugaacaa uuuccuggaa 4140
agcuggacuu cgugcucguc gacgggggau guguccuguc gcacggacau aagcagcuca 4200
ugugccucgc acgguccgug cucuccaagg ccaagauucu gcugcuggac gaaccuucgg 4260
cccaccugga uccggucacc uaccagauca ucaggaggac ccugaagcag gccuuugccg 4320
auugcaccgu gauucucugc gagcaccgca ucgaggccau gcuggagugc cagcaguucc 4380
uggucaucga ggagaacaag guccgccaau acgacuccau ucaaaagcuc cucaacgagc 4440
ggucgcuguu cagacaagcu auuucaccgu ccgauagagu gaagcucuuc ccgcaucgga 4500
acagcucaaa gugcaaaucg aagccgcaga ucgcagccuu gaaggaagag acugaggaag 4560
aggugcagga cacccggcuu uaagggugggc aucccuguga ccccucccca gugccucucc 4620
uggcccugga aguugccacu ccagugccca ccagccuugu ccuaauaaaa uuaaguugca 4680
ucaaagcu 4688

<210> SEQ ID NO 8
<211> LENGTH: 4443
<212> TYPE: DNA
<213> ORGANISM: Artificial Sequence
<220> FEATURE:
<223> OTHER INFORMATION: Artificially synthesized oligonucleotide

<400> SEQUENCE: 8
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg gggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540

-continued

```
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac accccctccag   2160
atgaatggca tcgaagaaga tagtgacgag ccgctggaga gacggctgag tctggtgcca   2220
gattcagaac aggggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc cccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
```

gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 9
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 9
atgcagagga gcccactgga gaaagcctcc gtggtgagta aactcttttt tagttggacc 60
agacccatcc tgcgaaaagg atacaggcag cgcctcgagt tgtctgatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg gggagaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480

-continued

```
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatttcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt ttcctggat catgcccggc    1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
```

atgagcactt tgaacacatt gaaggctggc ggcatcctca acagattttc taaagatatt 2940
gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcaccttga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 10
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 10
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg gggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420

-continued

```
gccattttttg gccttcacca catcggcatg caaatgagaa ttgccatgtt ctccctcatt     480
tacaaaaaga ccctgaaact ttcctcaaga gtgttagata aaatatccat tggtcagctg     540
gtcagcctgc tgtccaacaa tcttaacaaa tttgatgaag gcttggcgct ggcccacttc     600
gtgtggattg cacctctgca ggtggccctg ttgatgggac ttatatggga gctgcttcaa     660
gcctctgctt tctgtgggct gggctttttg attgtactgg cactttttca ggctgggctc     720
ggaagaatga tgatgaaata cagagatcag cgggccggga agatatcaga gcgacttgtg     780
atcaccagtg aaatgattga aaatattcag agcgtgaaag cctactgctg ggaagaagcc     840
atggagaaga tgattgagaa cctgaggcag acagagctca agctcactcg gaaggctgct     900
tatgttcgct atttcaacag cagcgccttc ttcttcagtg gcttctttgt tgtcttcctg     960
tctgttctgc catatgcact gataaaaggc attattttac gaaagatctt caccaccatc    1020
agtttttgca tcgttctcag gatggccgtc acaagacagt tcccctgggc tgtgcagacc    1080
tggtacgatt ccttgggggc catcaacaag attcaagatt tcttgcaaaa acaagaatat    1140
aaaactttag aatacaacct caccaccact gaagtggtca tggaaaatgt gacagccttt    1200
tgggaggagg gttttggaga attgttcgag aaggcaaagc agaataacaa caacaggaag    1260
acgagcaatg gggacgactc tctcttcttc agcaactttt cactgctcgg gacccctgtg    1320
ttgaaagata taaacttcaa gatcgagagg ggccagctct tggctgtggc aggctccact    1380
ggagctggta aaacatctct tctcatggtg atcatggggg aactggagcc ttccgaagga    1440
aaaatcaagc acagtgggag aatctcattc tgcagccagt ttcctggat catgcccggc    1500
accattaagg aaaacatcat atttggagtg tcctatgatg agtaccgcta ccggtcagtc    1560
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa aagaaatttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagacttc    1920
tcctccaaat taatgggctg tgactccttc gaccagttct ctgcagaaag aagaaactct    1980
atactcacag agaccctcca ccgcttctcc cttgagggag atgccccagt ttcttggaca    2040
gaaaccaaga agcagtcctt taagcagact ggcgagtttg gtgaaaagag gaaaaattca    2100
attctcaatc caattaacag tattcgcaag ttcagcattg tccagaagac acccctccag    2160
atgaatggca tcgaagaaga tagtgacgag ccgctggaga gacggctgag tctggtgcca    2220
gattcagaac agggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gcttgaaata    2460
tctgaagaga ttaatgaaga ggatcttaaa gagtgcttct ttgatgacat ggagagcatc    2520
cccgcggtga ccacatggaa cacctacctt agatatatta ctgtccacaa gagcctcata    2580
tttgtcctca tctggtgcct ggttatttttc ctcgctgagg tggcggccag tcttgttgtg    2640
ctctggctgc tgggcaacac tcctctccag gacaagggca atagtacaca cagcagaaat    2700
aattcttatg ccgtcatcat tacaagcacc tccagctact acgtgttcta catctatgtg    2760
ggcgtggctg acaccctcct ggccatgggt ttcttccggg gcctgccttt ggtgcacacc    2820
```

ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcaccttga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 11
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 11
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg ggggaggtca ccaaagctgt tcagccgctc 300
cttcttggcc gcatcatcgc cagctatgac cctgataata aagaagaaag gtctattgct 360

-continued

```
atttatctgg gaattggcct ctgcttgctc ttcatcgtcc gcacccttct gctgcaccct    420
gccattttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac accccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc cctcaggcc    2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
```

```
ggcgtggctg acaccctcct ggccatgggt ttcttccggg gcctgccttt ggtgcacacc   2820

ctcatcacag tgtcaaaaat tctgcaccat aaaatgcttc attctgtcct gcaggcaccc   2880

atgagcactt tgaacacatt gaaggctggc ggcatcctca acagattttc taaagatatt   2940

gctatcctgg atgatctcct ccccctgaca atctttgact ttatccagct tctgctgatc   3000

gtgattggag ccatagcagt ggttgctgtc ctgcagccct acatttttgt ggccaccgtg   3060

cccgtgattg ttgcctttat tatgctcaga gcttacttcc tgcaaacttc tcaacagctc   3120

aaacagctag aatctgaggg ccggagcccc atttttaccc acctggtgac ttccctgaag   3180

ggactgtgga ctctgagagc attcgggcga cagccttact ttgagacact gttccacaag   3240

gccctgaact tgcacactgc caactggttt ctttacctga gcacactccg ctggttccag   3300

atgcggatag agatgatctt cgtcatcttt tttatagctg taaccttcat ttctatcctt   3360

acaacaggag aaggagaggg cagggtggga atcatcctca cgctggctat gaacataatg   3420

tccaccttgc agtgggccgt gaattccagt atagatgtgg attctctaat gaggagtgtc   3480

tcccgggtgt ttaaattcat tgatatgcca actgagggga aacccaccaa gtcaacaaaa   3540

ccttataaga atggacagct gagcaaggtg atgataattg agaacagcca cgtgaagaag   3600

gatgacattt ggcccagcgg gggccagatg actgtgaagg acctgacggc caagtacacc   3660

gaaggtggaa atgccatttt ggaaaacatc agcttctcaa tctctcctgg gcagagagtt   3720

ggattgctgg gtcgcacggg cagcggcaaa tcaaccctgc tcagtgcctt ccttcggctc   3780

ctgaatacag aaggcgaaat ccaaattgac ggggtgagct gggacagcat caccctgcag   3840

cagtggagaa aagcatttgg ggtcattcca cagaaagttt tcatcttctc tggcactttc   3900

agaaagaacc tggaccccta tgagcagtgg agcgaccagg agatctggaa ggttgcagat   3960

gaagttggcc tgcggagtgt gatagaacaa tttcctggca agctggattt tgtgctggta   4020

gatggaggct gcgtgctgtc ccacggccac aaacagctga tgtgcctcgc ccgctccgtt   4080

ctttcaaagg ccaaaatctt gcttttggat gagcccagtg ctcacctcga cccagtgacc   4140

tatcagataa tccgcaggac cttaaagcaa gcttttgccg actgcaccgt catactgtgt   4200

gagcaccgga ttgaagcaat gctggaatgc cagcagtttc tggtgatcga ggagaataag   4260

gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

```
<210> SEQ ID NO 12
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 12

atgcagagga gcccactgga gaaagcctcc gtggtgagta aactcttttt tagttggacc     60

agacccatcc tgcgaaaagg atacaggcag cgcctcgagt tgtcagatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg gggaggtca ccaaagctgt tcagccgctc     300
```

-continued

```
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc ctattaacag tattcgcaag ttcagcattg tccagaagac accccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
```

aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 13
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 13
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240

-continued

```
ttcatgtttt atgggatctt cctgtacctg ggggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggcttttg attgtactgg cactttttca ggctgggctc    720
ggaagaatga tgatgaaata cagagatcag cgggccggga agatttcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc cctcaggcc    2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
```

```
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcca actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                 4443
```

<210> SEQ ID NO 14
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 14

```
atgcagagga gcccactgga gaaagcctcc gtggtgagta aactcttttt tagttggacc     60
agacccatcc tgcgaaaagg atacaggcag cgcctcgagt tgtctgatat ctaccagatt    120
ccttctgtgg actcagctga caatttgagt gagaagctgg agcgggagtg ggatagagag    180
```

-continued

```
ctggcgagca aaaaaaaccc caagcttatc aatgctctgc gccgctgctt tttctggagg    240
ttcatgtttt atgggatctt cctgtacctg ggggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtccgtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
```

```
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaag   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                  4443
```

<210> SEQ ID NO 15
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 15

```
atgcagagga gcccactgga gaaagcctcc gtggtgagta aactcttttt tagttggacc     60
agacccatcc tgcgaaaagg atacaggcag cgcctcgagt tgtcagatat ctaccagatt    120
```

-continued

```
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg gggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc ctattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
```

```
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtacaca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                  4443
```

<210> SEQ ID NO 16
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 16

```
atgcagagga gcccactgga gaaagcctcc gtggtgagta aactcttttt tagttggacc     60
```

```
agacccatcc tgcgaaaagg atacaggcag cgcctcgagt tgtcagatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg gggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt ttcctggat catgcccggc    1500
accattaagg aaaacatcat atttggagtg tcctatgatg agtaccgcta ccggtccgtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
```

tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttattttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct cccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag agtctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 17
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 17

-continued

```
atgcagagga gcccactgga gaaagcctcc gtggtgagta aactcttttt tagttggacc     60
agacccatcc tgcgaaaagg atacaggcag cgcctcgagt tgtctgatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg gggaggtca ccaaagctgt tcagccgctc     300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccattttg gccttcacca catcggcatg caaatgagaa ttgccatgtt ctccctcatt     480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatttcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg    1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc ctattaacag tattcgcaag ttcagcattg tccagaagac accccctccag  2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
```

-continued

```
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtacaca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                 4443
```

<210> SEQ ID NO 18
<211> LENGTH: 4443
<212> TYPE: DNA
<213> ORGANISM: Artificial Sequence
<220> FEATURE:
<223> OTHER INFORMATION: Artificially synthesized oligonucleotide -continued

<400> SEQUENCE: 18

```
atgcagagaa gccccctgga gaaggcctct gtggtgagca agctgttctt cagctggacc     60
agacccatcc tgagaaaggg ctacagacag agactggagc tgtctgacat ctaccagatc    120
ccctctgtgg actctgccga caacctgtct gagaagctgg agagagagtg ggacagagag    180
ctggccagca agaagaaccc caagctgatc aatgccctga gaagatgctt cttctggaga    240
ttcatgttct atggcatctt cctgtacctg ggagaggtga ccaaggccgt gcagcccctg    300
ctgctgggca ggatcattgc cagctatgac cctgacaaca aggaggagag aagcattgcc    360
atctacctgg gcattggcct gtgcctgctg ttcattgtga gaaccctgct gctgcaccct    420
gccatctttg gcctgcacca cattggcatg cagatgagaa ttgccatgtt cagcctgatc    480
tacaagaaga ccctgaagct gagcagcaga gtgctggaca agatcagcat tggccagctg    540
gtgagcctgc tgagcaacaa cctgaacaag tttgatgagg gcctggccct ggcccacttt    600
gtgtggattg ccccccctgca ggtggccctg ctgatgggcc tgatctggga gctgctgcag    660
gcctctgcct tctgtggcct gggcttcctg attgtgctgg ccctgttcca ggccggcctg    720
ggcagaatga tgatgaagta cagagaccag agagccggca agatctctga gagactggtg    780
atcacctctg agatgattga gaacatccag tctgtgaagg cctactgctg ggaggaggcc    840
atggagaaga tgattgagaa cctgagacag acagagctga agctgaccag gaaggccgcc    900
tatgtgagat acttcaacag ctctgccttc ttcttctctg gcttctttgt ggtgttcctg    960
tctgtgctgc cctatgccct gatcaagggc atcatcctga ggaagatctt caccaccatc   1020
agcttctgca ttgtgctgag gatggccgtg accaggcagt tcccctgggc cgtgcagacc   1080
tggtatgaca gcctgggggc catcaacaag atccaggact tcctgcagaa gcaggagtac   1140
aagaccctgg agtacaacct gaccaccaca gaggtggtga tggagaatgt gacagccttc   1200
tgggaggagg gctttggaga gctgtttgag aaggccaagc agaacaacaa caacagaaag   1260
accagcaatg gagatgacag cctgttcttc agcaacttca gcctgctggg caccccctgtg   1320
ctgaaggaca tcaacttcaa gattgagagg ggccagctgc tggccgtggc cggcagcaca   1380
ggagccggca agaccagcct gctgatggtg atcatgggag agctggagcc ctctgagggc   1440
aagatcaagc actctggcag aatcagcttc tgcagccagt tcagctggat catgcctggc   1500
accatcaagg agaacatcat ctttggggtg agctatgatg agtacaggta cagatctgtg   1560
atcaaggcct gccagctgga ggaggacatc tccaagtttg ccgagaagga caacattgtg   1620
ctgggggagg gaggcatcac cctgtctggg ggccagagag ccagaatcag cctggccaga   1680
gccgtgtaca aggatgccga cctgtacctg ctggacagcc cctttggcta cctggatgtg   1740
ctgacagaga aggagatctt tgagagctgt gtgtgcaagc tgatggccaa caagaccagg   1800
atcctggtga ccagcaagat ggagcacctg aagaaggccg acaagatcct gatcctgcat   1860
gagggcagca gctacttcta tggcaccttc tctgagctgc agaacctgca gcctgacttc   1920
agcagcaagc tgatgggctg tgacagcttt gaccagttct ctgctgagag aagaaacagc   1980
atcctgacag agaccctgca caggttcagc ctggaggggg atgcccctgt gagctggaca   2040
gagaccaaga agcagagctt caagcagaca ggagagtttg gggagaagag gaagaacagc   2100
atcctgaacc ccatcaacag catcaggaag ttcagcattg tgcagaagac ccccctgcag   2160
atgaatggca ttgaggagga ctctgatgag cccctggaga gaagactgag cctggtgcca   2220
gactctgagc agggagaggc catcctgccc aggatctctg tgatcagcac aggccccacc   2280
ctgcaggcca gaagaagaca gtctgtgctg aacctgatga cccactctgt gaaccagggc   2340
```

-continued

```
cagaatatcc acagaaagac cacagccagc accagaaagg tgagcctggc cccccaggcc   2400
aacctgacag agctggacat ctacagcaga aggctgagcc aggagacagg cctggagatc   2460
tctgaggaga tcaatgagga ggacctgaag gagtgcttct ttgatgacat ggagagcatc   2520
cctgccgtga ccacctggaa cacctacctg agatacatca cagtgcacaa gagcctgatc   2580
tttgtgctga tctggtgcct ggtgatcttc ctggccgagg tggccgccag cctggtggtg   2640
ctgtggctgc tgggcaacac ccccctgcag gacaagggca acagcaccca cagcagaaac   2700
aacagctatg ctgtgatcat caccagcacc agcagctact atgtgttcta catctatgtg   2760
ggagtggctg acaccctgct ggccatgggc ttcttcagag gcctgcccct ggtgcacacc   2820
ctgatcacag tgagcaagat cctgcaccac aagatgctgc actctgtgct gcaggccccc   2880
atgagcaccc tgaacaccct gaaggctgga ggcatcctga acagattcag caaggacatt   2940
gccatcctgg atgacctgct gcccctgacc atctttgact tcatccagct gctgctgatt   3000
gtgattggag ccattgccgt ggtggccgtg ctgcagccct acatctttgt ggccacagtg   3060
cctgtgattg tggccttcat catgctgagg gcctacttcc tgcagaccag ccagcagctg   3120
aagcagctgg agtctgaggg cagaagcccc atcttcaccc acctggtgac cagcctgaag   3180
ggcctgtgga ccctgagggc ctttggcaga cagccctact ttgagaccct gttccacaag   3240
gccctgaacc tgcacacagc caactggttc ctgtacctga gcaccctgag atggttccag   3300
atgaggattg agatgatctt tgtgatcttc ttcattgccg tgaccttcat cagcatcctg   3360
accacagggg agggcgaggg cagagtgggc atcatcctga ccctggccat gaacatcatg   3420
agcaccctgc agtgggccgt gaacagcagc attgatgtgg acagcctgat gagatctgtg   3480
agcagagtgt tcaagttcat tgacatgccc acagagggca agcccaccaa gagcaccaag   3540
ccctacaaga atggccagct gagcaaggtg atgatcattg agaacagcca tgtgaagaag   3600
gatgacatct ggccctctgg aggccagatg acagtgaagg acctgacagc caagtacaca   3660
gagggggggca atgccatcct ggagaacatc agcttcagca tcagccctgg ccagagggtg   3720
ggcctgctgg gcagaacagg ctctggcaag agcaccctgc tgtctgcctt cctgaggctg   3780
ctgaacacag agggagagat ccagattgat ggggtgagct gggacagcat caccctgcag   3840
cagtggagga aggcctttgg ggtgatcccc cagaaggtgt tcatcttctc tggcaccttc   3900
aggaagaacc tggaccccta tgagcagtgg tctgaccagg agatctggaa ggtggccgat   3960
gaggtgggcc tgagatctgt gattgagcag ttccctggca agctggactt tgtgctggtg   4020
gatggaggct gtgtgctgag ccatggccac aagcagctga tgtgcctggc cagatctgtg   4080
ctgagcaagg ccaagatcct gctgctggat gagccctctg cccacctgga ccctgtgacc   4140
taccagatca tcagaagaac cctgaagcag gcctttgccg actgcacagt gatcctgtgt   4200
gagcacagaa ttgaggccat gctggagtgc cagcagttcc tggtgattga ggagaacaag   4260
gtgaggcagt atgacagcat ccagaagctg ctgaatgaga gaagcctgtt cagacaggcc   4320
atcagcccct ctgacagagt gaagctgttc ccccacagga acagcagcaa gtgcaagagc   4380
aagccccaga ttgccgccct gaaggaggag acagaggagg aggtgcagga caccagactg   4440
tga                                                                 4443
```

<210> SEQ ID NO 19
<211> LENGTH: 4443
<212> TYPE: DNA
<213> ORGANISM: Artificial Sequence
<220> FEATURE:

-continued

<223> OTHER INFORMATION: Chemically synthesized oligonucleotide

<400> SEQUENCE: 19
atgcagagga gccccctgga gaaggccagc gtggtgagca agctgttctt cagctggacc 60
aggcccatcc tgaggaaggg ctacaggcag aggctggagc tgagcgacat ctaccagatc 120
cccagcgtgg acagcgccga caacctgagc gagaagctgg agagggagtg ggacagggag 180
ctggccagca agaagaaccc caagctgatc aacgccctga ggaggtgctt cttctggagg 240
ttcatgttct acggcatctt cctgtacctg ggcgaggtga ccaaggccgt gcagcccctg 300
ctgctgggca ggatcatcgc cagctacgac cccgacaaca aggaggagag gagcatcgcc 360
atctacctgg gcatcggcct gtgcctgctg ttcatcgtga ggaccctgct gctgcacccc 420
gccatcttcg gcctgcacca catcggcatg cagatgagga tcgccatgtt cagcctgatc 480
tacaagaaga ccctgaagct gagcagcagg gtgctggaca agatcagcat cggccagctg 540
gtgagcctgc tgagcaacaa cctgaacaag ttcgacgagg gcctggccct ggcccacttc 600
gtgtggatcg ccccccctgca ggtggccctg ctgatgggcc tgatctggga gctgctgcag 660
gccagcgcct tctgcggcct gggcttcctg atcgtgctgg ccctgttcca ggccggcctg 720
ggcaggatga tgatgaagta cagggaccag agggccggca agatcagcga gaggctggtg 780
atcaccagcg agatgatcga gaacatccag agcgtgaagg cctactgctg ggaggaggcc 840
atggagaaga tgatcgagaa cctgaggcag accgagctga agctgaccag gaaggccgcc 900
tacgtgaggt acttcaacag cagcgccttc ttcttcagcg gcttcttcgt ggtgttcctg 960
agcgtgctgc cctacgccct gatcaagggc atcatcctga ggaagatctt caccaccatc 1020
agcttctgca tcgtgctgag gatggccgtg accaggcagt tcccctgggc cgtgcagacc 1080
tggtacgaca gcctgggcgc catcaacaag atccaggact tcctgcagaa gcaggagtac 1140
aagaccctgg agtacaacct gaccaccacc gaggtggtga tggagaacgt gaccgccttc 1200
tgggaggagg gcttcggcga gctgttcgag aaggccaagc agaacaacaa caacaggaag 1260
accagcaacg gcgacgacag cctgttcttc agcaacttca gcctgctggg cacccccgtg 1320
ctgaaggaca tcaacttcaa gatcgagagg ggccagctgc tggccgtggc cggcagcacc 1380
ggcgccggca agaccagcct gctgatggtg atcatgggcg agctggagcc cagcgagggc 1440
aagatcaagc acagcggcag gatcagcttc tgcagccagt tcagctggat catgcccggc 1500
accatcaagg agaacatcat cttcggcgtg agctacgacg agtacaggta caggagcgtg 1560
atcaaggcct gccagctgga ggaggacatc agcaagttcg ccgagaagga caacatcgtg 1620
ctgggcgagg gcggcatcac cctgagcggc ggccagaggg ccaggatcag cctggccagg 1680
gccgtgtaca aggacgccga cctgtacctg ctggacagcc ccttcggcta cctggacgtg 1740
ctgaccgaga aggagatctt cgagagctgc gtgtgcaagc tgatggccaa caagaccagg 1800
atcctggtga ccagcaagat ggagcacctg aagaaggccg acaagatcct gatcctgcac 1860
gagggcagca gctacttcta cggcaccttc agcgagctgc agaacctgca gcccgacttc 1920
agcagcaagc tgatgggctg cgacagcttc gaccagttca gcgccgagag gaggaacagc 1980
atcctgaccg agaccctgca caggttcagc ctggagggcg acgcccccgt gagctggacc 2040
gagaccaaga agcagagctt caagcagacc ggcgagttcg gcgagaagag gaagaacagc 2100
atcctgaacc ccatcaacag catcaggaag ttcagcatcg tgcagaagac cccccctgcag 2160 atgaacggca tcgaggagga cagcgacgag cccctggaga ggaggctgag cctggtgccc 2220
gacagcgagc agggcgaggc catcctgccc aggatcagcg tgatcagcac cggccccacc 2280
ctgcaggcca ggaggaggca gagcgtgctg aacctgatga cccacagcgt gaaccagggc 2340
cagaacatcc acaggaagac caccgccagc accaggaagg tgagcctggc cccccaggcc 2400
aacctgaccg agctggacat ctacagcagg aggctgagcc aggagaccgg cctggagatc 2460
agcgaggaga tcaacgagga ggacctgaag gagtgcttct tcgacgacat ggagagcatc 2520
cccgccgtga ccacctggaa cacctacctg aggtacatca ccgtgcacaa gagcctgatc 2580
ttcgtgctga tctggtgcct ggtgatcttc ctggccgagg tggccgccag cctggtggtg 2640
ctgtggctgc tgggcaacac cccccctgcag gacaagggca acagcaccca cagcaggaac 2700
aacagctacg ccgtgatcat caccagcacc agcagctact acgtgttcta catctacgtg 2760
ggcgtggccg acaccctgct ggccatgggc ttcttcaggg gcctgcccct ggtgcacacc 2820
ctgatcaccg tgagcaagat cctgcaccac aagatgctgc acagcgtgct gcaggccccc 2880
atgagcaccc tgaacaccct gaaggccggc ggcatcctga acaggttcag caaggacatc 2940
gccatcctgg acgacctgct gcccctgacc atcttcgact tcatccagct gctgctgatc 3000
gtgatcggcg ccatcgccgt ggtggccgtg ctgcagccct acatcttcgt ggccaccgtg 3060
cccgtgatcg tggccttcat catgctgagg gcctacttcc tgcagaccag ccagcagctg 3120
aagcagctgg agagcgaggg caggagcccc atcttcaccc acctggtgac cagcctgaag 3180
ggcctgtgga ccctgagggc cttcggcagg cagccctact tcgagaccct gttccacaag 3240
gccctgaacc tgcacaccgc caactggttc ctgtacctga gcaccctgag gtggttccag 3300
atgaggatcg agatgatctt cgtgatcttc ttcatcgccg tgaccttcat cagcatcctg 3360
accaccggcg agggcgaggg cagggtgggc atcatcctga ccctggccat gaacatcatg 3420
agcaccctgc agtgggccgt gaacagcagc atcgacgtgg acagcctgat gaggagcgtg 3480
agcagggtgt tcaagttcat cgacatgccc accgagggca agcccaccaa gagcaccaag 3540
ccctacaaga acggccagct gagcaaggtg atgatcatcg agaacagcca cgtgaagaag 3600
gacgacatct ggcccagcgg cggccagatg accgtgaagg acctgaccgc caagtacacc 3660
gagggcggca acgccatcct ggagaacatc agcttcagca tcagccccgg ccagagggtg 3720
ggcctgctgg gcaggaccgg cagcggcaag agcaccctgc tgagcgcctt cctgaggctg 3780
ctgaacaccg agggcgagat ccagatcgac ggcgtgagct gggacagcat caccctgcag 3840
cagtggagga aggccttcgg cgtgatcccc cagaaggtgt tcatcttcag cggcaccttc 3900
aggaagaacc tggaccccta cgagcagtgg agcgaccagg agatctggaa ggtggccgac 3960
gaggtgggcc tgaggagcgt gatcgagcag ttccccggca agctggactt cgtgctggtg 4020
gacggcggct gcgtgctgag ccacggccac aagcagctga tgtgcctggc caggagcgtg 4080
ctgagcaagg ccaagatcct gctgctggac gagcccagcg cccacctgga ccccgtgacc 4140
taccagatca tcaggaggac cctgaagcag gccttcgccg actgcaccgt gatcctgtgc 4200
gagcacagga tcgaggccat gctggagtgc cagcagttcc tggtgatcga ggagaacaag 4260
gtgaggcagt acgacagcat ccagaagctg ctgaacgaga ggagcctgtt caggcaggcc 4320
atcagcccca gcgacagggt gaagctgttc cccccacagga acagcagcaa gtgcaagagc 4380
aagccccaga tcgccgccct gaaggaggag accgaggagg aggtgcagga caccaggctg 4440
tga 4443

<210> SEQ ID NO 20
<211> LENGTH: 4443
<212> TYPE: DNA

<213> ORGANISM: Artificial Sequence
<220> FEATURE:
<223> OTHER INFORMATION: Chemically synthesized oligonucleotide

<400> SEQUENCE: 20

```
atgcagagat cccctctgga gaaggcctca gtggtgtcca agcttttctt ctcctggacc      60
aggcccattt taagaaaggg ctacaggcag agacttgagc tgtctgacat ctatcagatc     120
ccttctgtgg attctgctga caatcttagt gaaaaattgg aaagggagtg ggacagagag     180
ctggcaagta aaaagaaccc caagctgatt aatgccctga ggcgctgctt tttttggaga     240
ttcatgttct atggcatatt cctctacctt ggagaagtaa ccaaagctgt acagcctctc     300
ctccttggca gaatcattgc ctcctatgat cctgataaca aggaggagag aagcatagcc     360
atctacctgg gcattgggct gtgcctcttg tttattgtga ggaccctgct cttgcaccct     420
gccatctttg gccttcatca cattggcatg caaatgagaa tagcaatgtt tagtcttatt     480
tacaaaaaaa cattaaaact ctcttccagg gtgttggaca agatcagtat tggacaactg     540
gtcagcctgc tgagcaacaa cctgaacaag tttgatgaag gactggccct ggcccacttt     600
gtctggattg ccccccttca ggtggctctt ttgatgggcc tgatctggga actcctgcag     660
gcctctgcct tctgtgggtt aggcttcctg atagtgctag ctctctttca ggcagggttg     720
ggtagaatga tgatgaagta cagagaccag agggctggga agatatctga gaggctggtc     780
attacttctg aaatgataga aaacatccag tctgttaaag cttactgctg ggaggaggct     840
atggaaaaga tgattgagaa cttgaggcaa acagagctca agctgactag gaaggcagcc     900
tatgtcaggt atttcaacag cagtgctttc ttcttctcag gcttttttcgt ggtcttcttg     960
agtgttctgc cctatgccct catcaagggg ataattttga gaaagatttt caccactatt    1020
tccttttgca ttgtcctgag gatggctgtc accaggcaat tcccctgggc tgtgcagaca    1080
tggtatgact ctctgggggc catcaacaaa atccaagatt tcctgcagaa gcaggagtac    1140
aagaccctgg aatacaacct caccaccaca gaagttgtga tggagaatgt gactgcattc    1200
tgggaggaag gatttgggga gctgtttgag aaagcaaaac aaaacaataa taacaggaaa    1260
accagcaatg gagatgactc cctgttcttt tccaacttct ctttgttggg cacccctgtc    1320
ctgaaagata taaactttaa aattgaaaga gggcagctgt tggcagttgc tggctccaca    1380
ggagctggaa aaacttcact actgatggtg atcatggggg agttagaacc ctctgaaggg    1440
aaaataaaac attctgggag gattagtttc tgcagccagt tcagctggat catgcctggg    1500
accattaaag aaaatattat atttggagtg agctatgatg aatatagata taggagtgtc    1560
atcaaagcct gtcagttgga ggaagacatc agcaaatttg cagagaaaga caacattgtt    1620
ctgggtgaag gtggcatcac cctgtcagga gggcaaaggg ccaggatcag cttggccaga    1680
gcagtctata aagatgctga tctgtacctc ctggatagcc cttttggcta tctggatgtt    1740
ttgacagaga aggaaatttt tgagtcctgt gtctgcaagt taatggcaaa taaaacaagg    1800
atacttgtga cctcaaaaat ggaacacctg aagaaggctg acaaaattct gatcctgcat    1860
gagggcagca gctactttta tggaacattt tctgaactgc agaatttgca accagacttt    1920
tcatcaaagc tcatgggatg tgacagtttt gatcagtttt ctgcagaaag gagaaactcc    1980
attttgactg agaccctgca caggttcagt ctggaggggg atgccccagt gagttggact    2040
gagacaaaga aacagagctt caagcagact ggagagtttg gagaaaagag gaaaaactca    2100
attctcaatc ccatcaatag catcaggaag ttcagcatag ttcagaagac tcctttgcag    2160
atgaatggga ttgaagagga ctcagatgag cccctggaaa ggagactctc cttggtgcca    2220
```

gattcagagc aggggggaagc catactgcca aggatctctg tgatttctac agggcccacc 2280
ctccaagcaa gaaggagaca gtcagtttta aacctgatga cccactctgt caaccaggga 2340
cagaacattc atagaaagac aacagcatct acaagaaaag tttcactggc ccctcaagcc 2400
aatttaactg aactagatat ctacagcagg aggctcagcc aagaaacagg cctggagatc 2460
tcagaagaaa taaatgagga ggatttgaag gaatgcttct ttgatgatat ggagagcatc 2520
ccagctgtca caacctggaa cacctacctg agatacatca cagtgcacaa atccctcatc 2580
tttgtactta tatggtgcct tgtcatcttc ttagctgagg tggctgcttc cctggtggtg 2640
ctgtggctgc tgggaaacac acccctccag gataaaggga actctactca cagcaggaac 2700
aacagttatg ctgtgatcat caccagtacc tcctcctact atgtgttcta catttatgtt 2760
ggagttgcag acacattgct tgccatgggt ttttttagag gactcccccct ggtgcatact 2820 ctcatcactg tttccaaaat ccttcaccac aagatgctgc acagtgtact acaggctccc 2880
atgagcaccc tcaacactct taaagcagga ggaatcttga acagatttag caaggacatt 2940
gcaattcttg atgacctgct tccactgacc atctttgact tcatccagct tctgctcatt 3000
gtaattggtg ccattgctgt ggtagcagtg ctccagccat atatttttgt ggccactgtg 3060
cctgttattg tggccttcat tatgttgaga gcctacttcc tgcagacctc tcagcagctc 3120
aagcaacttg aaagtgaggg caggagcccc atatttacac acttggtcac ttccctcaaa 3180
ggcctctgga cactcagagc ttttggaaga caaccttatt ttgaaactct cttccacaag 3240
gctctgaatc tccacacagc caactggttt ctgtatcttt caacactgcg ctggttccag 3300
atgaggattg agatgatctt tgttatcttc ttcatagctg ttaccttcat ctctattctg 3360
acaactggtg agggggaagg gagagtaggc atcatcctca cactagccat gaacataatg 3420
tctaccttac aatgggccgt gaacagctcc atagatgtgg acagcctcat gagaagtgtg 3480
tcaagagttt tcaaattcat tgacatgccc acagaaggca aaccaaccaa gagcacaaaa 3540
ccctacaaga atggccagct gagtaaggtc atgatcattg aaaattctca tgtgaagaag 3600
gatgatattt ggcccagtgg gggccagatg acagtcaagg acctcactgc caaatacaca 3660
gagggtggaa atgctatcct agagaacatc tccttctcca tctccccagg ccaaagagtt 3720
ggcttgctgg gcaggactgg cagtggcaag tccaccttgc tctcagcatt tctcaggctt 3780
ttaaatacag agggagagat tcaaattgat ggggtgtctt gggatagtat aacacttcaa 3840
cagtggagga aagcctttgg tgtgattcct cagaaagtgt ttatcttctc tggcactttc 3900
agaaaaaatc tggaccccta tgaacagtgg agtgaccagg aaatctggaa ggtggcagat 3960
gaagtgggcc taagatcagt catagagcag tttcctggaa agttggattt tgtgcttgta 4020
gatggaggct gtgtgctgtc ccatggccat aaacagctaa tgtgcctggc taggtcagtg 4080
ctgagcaagg ccaagatcct gctgttagat gagccttcag cccatctgga ccctgtgaca 4140
taccagatta tcagaagaac tctgaagcag gcctttgctg actgcactgt catcctgtgt 4200
gagcacagaa ttgaggccat gctggagtgc cagcagttcc ttgttataga agagaataag 4260
gttaggcagt atgacagcat tcagaaactg ctaaatgaaa gatctctctt caggcaagct 4320
atttcaccat ctgatagagt gaaacttttt ccccacagaa attcctctaa atgtaaatct 4380
aagccccaga tagctgcctt gaaagaggag actgaagaag aagtccagga caccagactg 4440
tga 4443

<210> SEQ ID NO 21

<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 21
atgcagagat ccccgctgga gaaggcatct gtggtgtcaa aactgttctt tagctggaca 60
aggcccatcc ttaggaaagg gtacagacag aggttggagc tgtcagacat atatcagatc 120
ccttcagtgg actctgcaga caacctctct gaaaagctgg agagggaatg ggacagggaa 180
ctggccagca aaaaaaaccc taaactgatt aatgccctga ggaggtgctt cttttggaga 240
ttcatgttct atgggatctt cctttacctg ggggaggtga ctaaagctgt tcagcctctt 300
cttctgggga ggattattgc ctcctatgac ccagacaaca aagaagaaag aagcatagcc 360
atttacttag gcataggcct ctgcttgctc ttcatagtta gaaccctcct actccaccca 420
gccatctttg gtctccacca cataggtatg cagatgagaa tagcaatgtt ctccttgatc 480
tacaagaaga ccctcaagct gtccagcagg gtgctggaca agatctccat aggccagtta 540
gtcagtctac tgtccaataa cttaaataag tttgatgagg gactggcact ggcacatttt 600
gtgtggattg ccccccctcca agtggccctt cttatgggcc ttatctggga gctgttgcag 660
gcctctgctt tctgtggcct gggtttcctc atagtcctag ccttattcca ggctggactg 720
ggcagaatga tgatgaagta tagggaccaa agagcaggga agatttctga aaggctggtt 780
ataacttctg agatgattga gaacattcag tcagtgaaag cttactgctg ggaagaagct 840
atggaaaaaa tgattgaaaa tctcagacag actgaattaa agttgaccag gaaagctgct 900
tatgtcagat acttcaactc ctcagccttc ttttttctg gcttctttgt tgtattcctt 960
tcagtcctcc cctatgccct gattaagggc attatcttga ggaaaatttt cacaaccatc 1020
tccttttgta ttgtcctcag gatggctgtt acaaggcaat ttccttgggc tgtgcaaact 1080
tggtatgata gccttggagc aatcaacaag atccaggatt tcctgcaaaa gcaggagtac 1140
aagacattgg aatacaacct taccaccact gaggtggtga tggaaaatgt gactgccttc 1200
tgggaggagg ggtttggaga gctgtttgag aaagccaaac agaacaacaa caatagaaag 1260
acctctaatg gtgatgattc cctgttcttt tctaacttta gtcttctggg gaccccagtt 1320
ctgaaagata ttaactttaa aattgaaagg ggacagttgc tggctgtggc tgggtccact 1380
ggggctggga agacaagcct gctcatggtg atcatgggag agctggaacc cagtgaagga 1440
aagatcaaac actcaggcag gatctccttc tgcagccagt tctcatggat tatgccaggc 1500
actattaaag aaaatatcat ctttggtgta agctatgatg agtacaggta tagatctgta 1560
attaaagcct gccagctgga ggaagacatc tctaagtttg ctgagaagga taacattgtg 1620
ttgggggaag gggcatcac cctttctggt gggcagaggg ctaggatctc ccttgctagg 1680
gcagtataca aggatgctga cttgtacctc ttggatagtc cttttggcta cctagatgtg 1740
ctgacagaga aagaaatatt tgaaagctgt gtgtgtaagc tcatggctaa caagaccagg 1800
atcctggtca ccagtaaaat ggaacacctc aaaaaagcag acaagatcct tattctccat 1860
gagggctcct cctacttcta tgggaccttc agtgagctgc agaatctgca gccagacttc 1920
tcctcaaaac ttatgggctg tgactccttt gaccaattct ctgcagaaag aaggaatagc 1980
atactgacag aaacactgca tagattctcc ctggaaggag atgccccagt gagttggaca 2040
gaaaccaaaa agcagagctt caagcagact ggtgagtttg gtgaaaagag gaagaattct 2100
atcctgaacc ccatcaatag catcaggaaa tttagcatag tccaaaagac ccccctccag 2160

```
atgaatggaa tagaggagga tagtgatgag cctcttgaga gaaggctgtc cctggttcca   2220
gacagtgaac agggtgaagc cattcttccg aggatcagtg tcatctccac tgggcccaca   2280
ttgcaggcca gaagaagaca gtctgttctg aatttgatga cacattctgt gaatcaaggc   2340
cagaatatcc atagaaaaac cactgccagc accagaaaag tttctctagc cccccaggct   2400
aacctgactg agttagacat ctacagcaga aggctgagcc aagagactgg cttggaaata   2460
tctgaggaga tcaatgagga ggacctcaag gagtgcttct ttgatgacat ggagtcaatc   2520
cctgcagtca ctacatggaa cacttaccta aggtacatca cagttcataa gagcctcatc   2580
tttgtcctca tatggtgtct ggtcatcttt ttagcagaag tggctgccag cctagttgtg   2640
ctgtggttac tgggcaatac acctcttcag gacaaaggca atagcacaca cagcagaaac   2700
aactcctatg cagtgatcat cacctctaca agctcttact atgtattcta tatatatgtg   2760
ggagtggcag atactctcct ggccatggga ttcttcaggg gattacctct agttcacaca   2820
ttgatcacag tgtcaaaaat tctccaccac aagatgttac acagtgtcct gcaagcccca   2880
atgtctactc tgaacacact taaggcaggt ggaattttga ataggtttag caaggacata   2940
gctatcctgg atgatctcct ccctctgacc atctttgact tcatccagtt actgctcatt   3000
gtaattggag ccattgcagt ggtagcagtc ctacagcctt acatttttgt ggctactgtt   3060
cctgttattg tggccttcat tatgctaaga gcttacttcc tgcaaacaag ccaacagttg   3120
aaacagctag aaagtgaggg aaggtccccc atcttcaccc acctggtgac atcactcaag   3180
gggctatgga ctcttagggc ttttgggaga cagccgtact ttgagacctt attccataag   3240
gcccttaacc tccatacagc aaactggttc ttatacctga gtactctgag gtggtttcaa   3300
atgaggattg aaatgatttt tgtgatcttc ttcattgctg tgaccttcat ctcaatcttg   3360
accacaggag agggggaggg cagggtgggc atcatactga ccttggccat gaacattatg   3420
tcaaccctgc agtgggctgt caatagctcc attgatgtgg acagtctgat gaggagtgtc   3480
tccagggtct tcaagtttat tgacatgcca actgagggca aacccaccaa aagcactaag   3540
ccatataaaa atggccaact gtccaaagtg atgatcattg aaaattcaca tgtaaagaag   3600
gatgatatct ggccctctgg aggacagatg acagtgaaag acctgactgc caagtacaca   3660
gagggtggta atgccattct tgagaacatt agtttcagta tttccccggg gcaaagggtg   3720
ggcctccttg gcagaacagg ctctggcaag agtaccctgc tgtcagcctt tttaagactg   3780
ttgaacactg agggagaaat tcagattgat ggtgtctcct gggatagcat caccctccag   3840
cagtggagaa aagcttttgg agtgatcccg caaaaggttt tcatcttttc aggcaccttc   3900
cggaagaacc tggaccccta tgagcagtgg tctgaccagg aaatatggaa ggtagctgat   3960
gaagttgggc ttaggtcagt catagagcag ttcccaggca aactggactt tgtcctggtg   4020
gatggtggat gtgtactgag tcatgggcac aaacagctga tgtgcctagc caggtctgtg   4080
ctcagcaagg caaagatatt gctgcttgat gaacccagtg cccatctgga cccagtcaca   4140
tatcagatca tcagaagaac attgaagcag gcctttgctg attgcacagt tatcctctgt   4200
gagcacagga ttgaggccat gctggagtgc cagcagtttc tggtgattga ggagaataaa   4260
gtaaggcagt atgactccat ccagaagctg ctcaatgaaa gaagcctctt tagacaagct   4320
atctccccct cagacagggt caaattgttc cctcacagaa acagcagcaa gtgcaagagc   4380
aagccccaaa ttgcagcctt gaaagaggag acagaggaag aggtgcagga caccagactc   4440
tga                                                                4443
```

<210> SEQ ID NO 22
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 22
atgcagagaa gccccctgga gaaggccagc gtggtgagca agctgttctt cagctggacc 60
agacccatcc tgagaaaggg ctacagacag agactggagc tgagcgacat ctaccagatc 120
cccagcgtgg acagcgccga caacctgagc gagaagctgg agagagagtg ggacagagag 180
ctggccagca agaagaaccc caagctgatc aacgccctga gaagatgctt cttctggaga 240
ttcatgttct acggcatctt cctgtacctg ggcgaggtga ccaaggccgt gcagcccctg 300
ctgctgggca gaatcatcgc cagctacgac cccgacaaca aggaggagag aagcatcgcc 360
atctacctgg gcatcggcct gtgcctgctg ttcatcgtga gaaccctgct gctgcacccc 420
gccatcttcg gcctgcacca catcggcatg cagatgagaa tcgccatgtt cagcctgatc 480
tacaagaaga ccctgaagct gagcagcaga gtgctggaca agatcagcat cggccagctg 540
gtgagcctgc tgagcaacaa cctgaacaag ttcgacgagg gcctggccct ggcccacttc 600
gtgtggatcg ccccctgca ggtggccctg ctgatgggcc tgatctggga gctgctgcag 660
gccagcgcct tctgcggcct gggcttcctg atcgtgctgg ccctgttcca ggccggcctg 720
ggcagaatga tgatgaagta cagagaccag agagccggca agatcagcga gagactggtg 780
atcaccagcg agatgatcga gaacatccag agcgtgaagg cctactgctg ggaggaggcc 840
atggagaaga tgatcgagaa cctgagacag accgagctga agctgaccag aaaggccgcc 900
tacgtgagat acttcaacag cagcgccttc ttcttcagcg gcttcttcgt ggtgttcctg 960
agcgtgctgc cctacgccct gatcaagggc atcatcctga gaaagatctt caccaccatc 1020
agcttctgca tcgtgctgag aatggccgtg accagacagt tcccctgggc cgtgcagacc 1080
tggtacgaca gcctgggcgc catcaacaag atccaggact tcctgcagaa gcaggagtac 1140
aagaccctgg agtacaacct gaccaccacc gaggtggtga tggagaacgt gaccgccttc 1200
tgggaggagg gcttcggcga gctgttcgag aaggccaagc agaacaacaa caacagaaag 1260
accagcaacg gcgacgacag cctgttcttc agcaacttca gcctgctggg cacccccgtg 1320
ctgaaggaca tcaacttcaa gatcgagaga ggccagctgc tggccgtggc cggcagcacc 1380
ggcgccggca agaccagcct gctgatggtg atcatgggcg agctggagcc cagcgagggc 1440
aagatcaagc acagcggcag aatcagcttc tgcagccagt tcagctggat catgcccggc 1500
accatcaagg agaacatcat cttcggcgtg agctacgacg agtacagata cagaagcgtg 1560
atcaaggcct gccagctgga ggaggacatc agcaagttcg ccgagaagga caacatcgtg 1620
ctgggcgagg gcggcatcac cctgagcggc ggccagagag ccagaatcag cctggccaga 1680
gccgtgtaca aggacgccga cctgtacctg ctggacagcc ccttcggcta cctggacgtg 1740
ctgaccgaga aggagatctt cgagagctgc gtgtgcaagc tgatggccaa caagaccaga 1800
atcctggtga ccagcaagat ggagcacctg aagaaggccg acaagatcct gatcctgcac 1860
gagggcagca gctacttcta cggcaccttc agcgagctgc agaacctgca gcccgacttc 1920
agcagcaagc tgatgggctg cgacagcttc gaccagttca gcgccgagag aagaaacagc 1980
atcctgaccg agaccctgca cagattcagc ctggagggcg acgcccccgt gagctggacc 2040
gagaccaaga agcagagctt caagcagacc ggcgagttcg gcgagaagag aaagaacagc 2100

-continued

```
atcctgaacc ccatcaacag catcagaaag ttcagcatcg tgcagaagac ccccctgcag   2160
atgaacggca tcgaggagga cagcgacgag cccctggaga gaagactgag cctggtgccc   2220
gacagcgagc agggcgaggc catcctgccc agaatcagcg tgatcagcac cggcccccacc   2280
ctgcaggcca gaagaagaca gagcgtgctg aacctgatga cccacagcgt gaaccagggc   2340
cagaacatcc acagaaagac caccgccagc accagaaagg tgagcctggc cccccaggcc   2400
aacctgaccg agctggacat ctacagcaga agactgagcc aggagaccgg cctggagatc   2460
agcgaggaga tcaacgagga ggacctgaag gagtgcttct tcgacgacat ggagagcatc   2520
cccgccgtga ccacctggaa cacctacctg agatacatca ccgtgcacaa gagcctgatc   2580
ttcgtgctga tctggtgcct ggtgatcttc ctggccgagg tggccgccag cctggtggtg   2640
ctgtggctgc tgggcaacac cccccctgcag gacaagggca acagcaccca cagcagaaac   2700
aacagctacg ccgtgatcat caccagcacc agcagctact acgtgttcta catctacgtg   2760
ggcgtggccg acaccctgct ggccatgggc ttcttcagag gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga acagattcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgaga gcctacttcc tgcagaccag ccagcagctg   3120
aagcagctgg agagcgaggg cagaagcccc atcttcaccc acctggtgac cagcctgaag   3180
ggcctgtgga ccctgagagc cttcggcaga cagccctact tcgagaccct gttccacaag   3240
gccctgaacc tgcacaccgc caactggttc ctgtacctga gcaccctgag atggttccag   3300
atgagaatcg agatgatctt cgtgatcttc ttcatcgccg tgaccttcat cagcatcctg   3360
accaccggcg agggcgaggg cagagtgggc atcatcctga ccctggccat gaacatcatg   3420
agcaccctgc agtgggccgt gaacagcagc atcgacgtgg acagcctgat gagaagcgtg   3480
agcagagtgt tcaagttcat cgacatgccc accgagggca agcccaccaa gagcaccaag   3540
ccctacaaga acggccagct gagcaaggtg atgatcatcg agaacagcca cgtgaagaag   3600
gacgacatct ggcccagcgg cggccagatg accgtgaagg acctgaccgc caagtacacc   3660
gagggcggca acgccatcct ggagaacatc agcttcagca tcagccccgg ccagagagtg   3720
ggcctgctgg gcagaaccgg cagcggcaag agcaccctgc tgagcgcctt cctgagactg   3780
ctgaacaccg agggcgagat ccagatcgac ggcgtgagct gggacagcat caccctgcag   3840
cagtggagaa aggccttcgg cgtgatcccc cagaaggtgt tcatcttcag cggcaccttc   3900
agaaagaacc tggaccccta cgagcagtgg agcgaccagg agatctggaa ggtggccgac   3960
gaggtgggcc tgagaagcgt gatcgagcag ttccccggca agctggactt cgtgctggtg   4020
gacggcggct gcgtgctgag ccacggccac aagcagctga tgtgcctggc cagaagcgtg   4080
ctgagcaagg ccaagatcct gctgctggac gagcccagcg cccacctgga ccccgtgacc   4140
taccagatca tcagaagaac cctgaagcag gccttcgccg actgcaccgt gatcctgtgc   4200
gagcacagaa tcgaggccat gctggagtgc cagcagttcc tggtgatcga ggagaacaag   4260
gtgagacagt acgacagcat ccagaagctg ctgaacgaga gaagcctgtt cagacaggcc   4320
atcagcccca gcgacagagt gaagctgttc cccccacagaa acagcagcaa gtgcaagagc   4380
aagccccaga tcgccgccct gaaggaggag accgaggagg aggtgcagga caccagactg   4440
```

tga 4443

<210> SEQ ID NO 23
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 23
atgcagcgca gccccctgga gaaggccagc gtggtgagca agctgttctt cagctggacc 60
cgccccatcc tgcgcaaggg ctaccgccag cgcctggagc tgagcgacat ctaccagatc 120
cccagcgtgg acagcgccga caacctgagc gagaagctgg agcgcgagtg ggaccgcgag 180
ctggccagca agaagaaccc caagctgatc aacgccctgc gccgctgctt cttctggcgc 240
ttcatgttct acggcatctt cctgtacctg ggcgaggtga ccaaggccgt gcagcccctg 300
ctgctgggcc gcatcatcgc cagctacgac cccgacaaca aggaggagcg cagcatcgcc 360
atctacctgg gcatcggcct gtgcctgctg ttcatcgtgc gcaccctgct gctgcacccc 420
gccatcttcg gcctgcacca catcggcatg cagatgcgca tcgccatgtt cagcctgatc 480
tacaagaaga ccctgaagct gagcagccgc gtgctggaca agatcagcat cggccagctg 540
gtgagcctgc tgagcaacaa cctgaacaag ttcgacgagg gcctggccct ggcccacttc 600
gtgtggatcg ccccccctgca ggtggccctg ctgatgggcc tgatctggga gctgctgcag 660
gccagcgcct tctgcggcct gggcttcctg atcgtgctgg ccctgttcca ggccggcctg 720
ggccgcatga tgatgaagta ccgcgaccag cgcgccggca agatcagcga gcgcctggtg 780
atcaccagcg agatgatcga gaacatccag agcgtgaagg cctactgctg ggaggaggcc 840
atggagaaga tgatcgagaa cctgcgccag accgagctga agctgacccg caaggccgcc 900
tacgtgcgct acttcaacag cagcgccttc ttcttcagcg gcttcttcgt ggtgttcctg 960
agcgtgctgc cctacgccct gatcaagggc atcatcctgc gcaagatctt caccaccatc 1020
agcttctgca tcgtgctgcg catggccgtg acccgccagt tcccctgggc cgtgcagacc 1080
tggtacgaca gcctgggcgc catcaacaag atccaggact tcctgcagaa gcaggagtac 1140
aagaccctgg agtacaacct gaccaccacc gaggtggtga tggagaacgt gaccgccttc 1200
tgggaggagg gcttcggcga gctgttcgag aaggccaagc agaacaacaa caaccgcaag 1260
accagcaacg gcgacgacag cctgttcttc agcaacttca gcctgctggg caccccccgtg 1320 ctgaaggaca tcaacttcaa gatcgagcgc ggccagctgc tggccgtggc cggcagcacc 1380
ggcgccggca agaccagcct gctgatggtg atcatgggcg agctggagcc cagcgagggc 1440
aagatcaagc acagcggccg catcagcttc tgcagccagt tcagctggat catgcccggc 1500
accatcaagg agaacatcat cttcggcgtg agctacgacg agtaccgcta ccgcagcgtg 1560
atcaaggcct gccagctgga ggaggacatc agcaagttcg ccgagaagga caacatcgtg 1620
ctgggcgagg gcggcatcac cctgagcggc ggccagcgcg cccgcatcag cctggcccgc 1680
gccgtgtaca aggacgccga cctgtacctg ctggacagcc ccttcggcta cctggacgtg 1740
ctgaccgaga aggagatctt cgagagctgc gtgtgcaagc tgatggccaa caagacccgc 1800
atcctggtga ccagcaagat ggagcacctg aagaaggccg acaagatcct gatcctgcac 1860
gagggcagca gctacttcta cggcaccttc agcgagctgc agaacctgca gcccgacttc 1920
agcagcaagc tgatgggctg cgacagcttc gaccagttca gcgccgagcg ccgcaacagc 1980
atcctgaccg agaccctgca ccgcttcagc ctggagggcg acgcccccgt gagctggacc 2040

```
gagaccaaga agcagagctt caagcagacc ggcgagttcg gcgagaagcg caagaacagc   2100
atcctgaacc ccatcaacag catccgcaag ttcagcatcg tgcagaagac ccccctgcag   2160
atgaacggca tcgaggagga cagcgacgag cccctggagc gccgcctgag cctggtgccc   2220
gacagcgagc agggcgaggc catcctgccc cgcatcagcg tgatcagcac cggccccacc   2280
ctgcaggccc gccgccgcca gagcgtgctg aacctgatga cccacagcgt gaaccagggc   2340
cagaacatcc accgcaagac caccgccagc acccgcaagg tgagcctggc cccccaggcc   2400
aacctgaccg agctggacat ctacagccgc cgcctgagcc aggagaccgg cctggagatc   2460
agcgaggaga tcaacgagga ggacctgaag gagtgcttct tcgacgacat ggagagcatc   2520
cccgccgtga ccacctggaa cacctacctg cgctacatca ccgtgcacaa gagcctgatc   2580
ttcgtgctga tctggtgcct ggtgatcttc ctggccgagg tggccgccag cctggtggtg   2640
ctgtggctgc tgggcaacac cccccctgcag gacaagggca acagcaccca cagccgcaac   2700
aacagctacg ccgtgatcat caccagcacc agcagctact acgtgttcta catctacgtg   2760
ggcgtggccg acaccctgct ggccatgggc ttcttccgcg gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga accgcttcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgcgc gcctacttcc tgcagaccag ccagcagctg   3120
aagcagctgg agagcgaggg ccgcagcccc atcttcaccc acctggtgac cagcctgaag   3180
ggcctgtgga ccctgcgcgc cttcggccgc cagccctact tcgagaccct gttccacaag   3240
gccctgaacc tgcacaccgc caactggttc ctgtacctga gcaccctgcg ctggttccag   3300
atgcgcatcg agatgatctt cgtgatcttc ttcatcgccg tgaccttcat cagcatcctg   3360
accaccggcg agggcgaggg ccgcgtgggc atcatcctga ccctggccat gaacatcatg   3420
agcaccctgc agtgggccgt gaacagcagc atcgacgtgg acagcctgat gcgcagcgtg   3480
agccgcgtgt tcaagttcat cgacatgccc accgagggca agcccaccaa gagcaccaag   3540
ccctacaaga acggccagct gagcaaggtg atgatcatcg agaacagcca cgtgaagaag   3600
gacgacatct ggcccagcgg cggccagatg accgtgaagg acctgaccgc caagtacacc   3660
gagggcggca acgccatcct ggagaacatc agcttcagca tcagccccgg ccagcgcgtg   3720
ggcctgctgg gccgcaccgg cagcggcaag agcaccctgc tgagcgcctt cctgcgcctg   3780
ctgaacaccg agggcgagat ccagatcgac ggcgtgagct gggacagcat caccctgcag   3840
cagtggcgca aggccttcgg cgtgatcccc cagaaggtgt tcatcttcag cggcaccttc   3900
cgcaagaacc tggaccccta cgagcagtgg agcgaccagg agatctggaa ggtggccgac   3960
gaggtgggcc tgcgcagcgt gatcgagcag ttccccggca agctggactt cgtgctggtg   4020
gacggcggct gcgtgctgag ccacggccac aagcagctga tgtgcctggc ccgcagcgtg   4080
ctgagcaagg ccaagatcct gctgctggac gagcccagcg cccacctgga ccccgtgacc   4140
taccagatca tccgccgcac cctgaagcag gccttcgccg actgcaccgt gatcctgtgc   4200
gagcaccgca tcgaggccat gctggagtgc cagcagttcc tggtgatcga ggagaacaag   4260
gtgcgccagt acgacagcat ccagaagctg ctgaacgagc gcagcctgtt ccgccaggcc   4320
atcagcccca gcgaccgcgt gaagctgttc ccccaccgca acagcagcaa gtgcaagagc   4380
```

-continued aagccccaga tcgccgccct gaaggaggag accgaggagg aggtgcagga cacccgcctg 4440
taa 4443

<210> SEQ ID NO 24
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 24
atgcagagaa gccccctgga gaaggccagc gtggtgagca agctgttctt cagctggacc 60
agacccatcc tgagaaaggg ctacagacag agactggagc tgagcgacat ctaccagatc 120
cccagcgtgg acagcgccga caacctgagc gagaagctgg agagagagtg ggacagagag 180
ctggccagca agaagaaccc caagctgatc aacgccctga gaagatgctt cttctggaga 240
ttcatgttct acggcatctt cctgtacctg ggcgaggtga ccaaggccgt gcagcccctg 300
ctgctgggca gaatcatcgc cagctacgac cccgacaaca aggaggagag aagcatcgcc 360
atctacctgg gcatcggcct gtgcctgctg ttcatcgtga gaaccctgct gctgcacccc 420
gccatcttcg gcctgcacca catcggcatg cagatgagaa tcgccatgtt cagcctgatc 480
tacaagaaga ccctgaagct gagcagcaga gtgctggaca agatcagcat cggccagctg 540
gtgagcctgc tgagcaacaa cctgaacaag ttcgacgagg gcctggccct ggcccacttc 600
gtgtggatcg ccccccctgca ggtggccctg ctgatgggcc tgatctggga gctgctgcag 660
gccagcgcct tctgcggcct gggcttcctg atcgtgctgg ccctgttcca ggccggcctg 720
ggcagaatga tgatgaagta cagggaccag agagccggca agatcagcga gagactggtg 780
atcaccagcg agatgatcga gaacatccag agcgtgaagg cctactgctg ggaggaggcc 840
atggagaaga tgatcgagaa cctgagacag accgagctga agctgaccag aaaggccgcc 900
tacgtgagat acttcaacag cagcgccttc ttcttcagcg gcttcttcgt ggtgttcctg 960
agcgtgctgc cctacgccct gatcaagggc atcatcctga gaaagatctt caccaccatc 1020
agcttctgca tcgtgctgag aatggccgtg accagacagt tcccctgggc cgtgcagacc 1080
tggtacgaca gcctgggcgc catcaacaag atccaggact tcctgcagaa gcaggagtac 1140
aagaccctgg agtacaacct gaccaccacc gaggtggtga tggagaacgt gaccgccttc 1200
tgggaggagg gcttcggcga gctgttcgag aaggccaagc agaacaacaa caacagaaag 1260
accagcaacg gcgacgacag cctgttcttc agcaacttca gcctgctggg caccccccgtg 1320 ctgaaggaca tcaacttcaa gatcgagaga ggccagctgc tggccgtggc cggcagcacc 1380
ggcgccggca agaccagcct gctgatggtg atcatgggcg agctggagcc cagcgagggc 1440
aagatcaagc acagcggcag aatcagcttc tgcagccagt tcagctggat catgcccggc 1500
accatcaagg agaacatcat cttcggcgtg agctacgacg agtacagata cagaagcgtg 1560
atcaaggcct gccagctgga ggaggacatc agcaagttcg ccgagaagga caacatcgtg 1620
ctgggcgagg gcggcatcac cctgagcggc ggccagagag ccagaatcag cctggccaga 1680
gccgtgtaca aggacgccga cctgtacctg ctggacagcc ccttcggcta cctggacgtg 1740
ctgaccgaga aggagatctt cgagagctgc gtgtgcaagc tgatggccaa caagaccaga 1800
atcctggtga ccagcaagat ggagcacctg aagaaggccg acaagatcct gatcctgcac 1860
gagggcagca gctacttcta cggcaccttc agcgagctgc agaacctgca gcccgacttc 1920
agcagcaagc tgatgggctg cgacagcttc gaccagttca gcgccgagag aagaaacagc 1980

-continued atcctgaccg agaccctgca cagattcagc ctggagggcg acgcccccgt gagctggacc 2040
gagaccaaga agcagagctt caagcagacc ggcgagttcg gcgagaagag aaagaacagc 2100
atcctgaacc ccatcaacag catcagaaag ttcagcatcg tgcagaagac ccccctgcag 2160
atgaacggca tcgaggagga cagcgacgag cccctggaga gaagactgag cctggtgccc 2220
gacagcgagc agggcgaggc catcctgccc agaatcagcg tgatcagcac cggccccacc 2280
ctgcaggcca gaagaagaca gagcgtgctg aacctgatga cccacagcgt gaaccagggc 2340
cagaacatcc acagaaagac caccgccagc accagaaagg tgagcctggc cccccaggcc 2400
aacctgaccg agctggacat ctacagcaga agactgagcc aggagaccgg cctggagatc 2460
agcgaggaga tcaacgagga ggacctgaag gagtgcttct tcgacgacat ggagagcatc 2520
cccgccgtga ccacctggaa cacctacctg agatacatca ccgtgcacaa gagcctgatc 2580
ttcgtgctga tctggtgcct ggtgatcttc ctggccgagg tggccgccag cctggtggtg 2640
ctgtggctgc tgggcaacac cccccctgcag gacaagggca acagcaccca cagcagaaac 2700
aacagctacg ccgtgatcat caccagcacc agcagctact acgtgttcta catctacgtg 2760
ggcgtggccg acaccctgct ggccatgggc ttcttcagag gcctgcccct ggtgcacacc 2820
ctgatcaccg tgagcaagat cctgcaccac aagatgctgc acagcgtgct gcaggccccc 2880
atgagcaccc tgaacaccct gaaggccggc ggcatcctga acagattcag caaggacatc 2940
gccatcctgg acgacctgct gcccctgacc atcttcgact tcatccagct gctgctgatc 3000
gtgatcggcg ccatcgccgt ggtggccgtg ctgcagccct acatcttcgt ggccaccgtg 3060
cccgtgatcg tggccttcat catgctgaga gcctacttcc tgcagaccag ccagcagctg 3120
aagcagctgg agagcgaggg caggagcccc atcttcaccc acctggtgac cagcctgaag 3180
ggcctgtgga ccctgagagc cttcggcaga cagccctact tcgagaccct gttccacaag 3240
gccctgaacc tgcacaccgc caactggttc ctgtacctga gcaccctgag atggttccag 3300
atgagaatcg agatgatctt cgtgatcttc ttcatcgccg tgaccttcat cagcatcctg 3360
accaccggcg agggcgaggg cagagtgggc atcatcctga ccctggccat gaacatcatg 3420
agcaccctgc agtgggccgt gaacagcagc atcgacgtgg acagcctgat gagaagcgtg 3480
agcagagtgt tcaagttcat cgacatgccc accgagggca agcccaccaa gagcaccaag 3540
ccctacaaga acggccagct gagcaaggtg atgatcatcg agaacagcca cgtgaagaag 3600
gacgacatct ggcccagcgg cggccagatg accgtgaagg acctgaccgc caagtacacc 3660
gagggcggca acgccatcct ggagaacatc agcttcagca tcagccccgg ccagagagtg 3720
ggcctgctgg gcagaaccgg cagcggcaag agcaccctgc tgagcgcctt cctgagactg 3780
ctgaacaccg agggcgagat ccagatcgac ggcgtgagct gggacagcat caccctgcag 3840
cagtggagaa aggccttcgg cgtgatcccc cagaaggtgt tcatcttcag cggcaccttc 3900
agaaagaacc tggaccccta cgagcagtgg agcgaccagg agatctggaa ggtggccgac 3960
gaggtgggcc tgagaagcgt gatcgagcag ttccccggca agctggactt cgtgctggtg 4020
gacggcggct gcgtgctgag ccacggccac aagcagctga tgtgcctggc cagaagcgtg 4080
ctgagcaagg ccaagatcct gctgctggac gagcccagcg cccacctgga ccccgtgacc 4140
taccagatca tcagaagaac cctgaagcag gccttcgccg actgcaccgt gatcctgtgc 4200
gagcacagaa tcgaggccat gctggagtgc cagcagttcc tggtgatcga ggagaacaag 4260
gtgagacagt acgacagcat ccagaagctg ctgaacgaga gaagcctgtt cagacaggcc 4320

-continued atcagcccca gcgacagagt gaagctgttc ccccacagaa acagcagcaa gtgcaagagc 4380
aagccccaga tcgccgccct gaaggaggag accgaggagg aggtgcagga caccagactg 4440
tga 4443

<210> SEQ ID NO 25
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 25
atgcagaggt cacctctgga aaaggctagc gtggtcagca agctattttt ttcctggacc 60
cgcccgatac tcaggaaggg ctaccgacag cggctggagc tgagtgacat ttatcagatt 120
ccctccgtcg attccgctga caacctgtct gagaaactgg agcgggaatg ggatagggaa 180
ctggcgtcca aaaaaaaccc caaactcatc aatgcactcc gcagatgctt cttctggcgg 240
tttatgtttt atggcatatt cctgtatctg ggggaggtga cgaaagccgt gcagccgctg 300
ctgcttggtc gcattatcgc gtcatacgat ccagataaca aggaggaaag aagtatcgct 360
atctatctcg ggatagggct gtgcctgctc ttcattgtgc ggactcttct cttgcacccc 420
gccattttcg gtctgcatca tataggtatg cagatgagaa ttgcgatgtt ctcattgatt 480
tacaaaaaaa cgcttaagct aagttcaagg gtgctagata agatatcgat cggccagctg 540
gtgtctctgc ttagcaacaa cctcaataaa ttcgacgaag gccttgcact ggcccacttc 600
gtgtggatcg cccctctgca ggtggctctg ctgatggggt taatatggga gctgttgcag 660
gcctccgctt tttgtggcct ggggtttctc atcgtgttgg ccttgtttca ggcagggctg 720
ggacgtatga tgatgaaata tagggatcag agggctggca aaatctctga gcgcctggtt 780
attacgagtg aaatgattga gaacatccag tcagtgaagg cctattgctg ggaggaggcc 840
atggaaaaaa tgattgagaa cctacgccag actgagctga agttaaccag aaaagccgcc 900
tatgtgcgct actttaacag tagcgcattt ttcttctccg gtttttttcgt ggtgtttctt 960 agtgtgttgc cgtatgcctt aatcaaggga ataatactcc ggaagatttt cactaccatc 1020
agcttctgta tcgtgttgcg gatggccgtc acccggcagt ttccctgggc agtacagact 1080
tggtacgatt ctctcggagc aattaacaaa atccaagact ttctacaaaa gcaggagtac 1140
aagaccctgg agtacaatct gaccaccaca gaagtcgtaa tggagaatgt aactgccttc 1200
tgggaagagg gctttggcga actctttgaa aaggccaagc agaacaataa caaccggaag 1260
acctccaacg gggacgacag cttatttttc agcaattttt ctttgctcgg gacccctgta 1320
ctgaaagata ttaactttaa gatcgagcgc ggacaactcc tggctgtcgc cggcagcact 1380
ggagctggaa aaacatcact gcttatggtg ataatgggag aactcgaacc aagcgaggga 1440
aaaataaagc actctggacg gattagtttt tgctcccagt tctcgtggat aatgcctggc 1500
accattaagg agaatatcat ctttggagtg agttacgacg aataccggta ccggtccgtt 1560
atcaaggctt gtcaactcga ggaggacatt tctaaattcg ccgaaaaaga taatatagtg 1620
ctgggcgaag gaggcattac actgagcggg ggtcagagag ctcgaattag cctcgcccga 1680
gcagtctata aagacgccga tctttacctg ctggattccc cttttgggta tttggatgtt 1740
ctgacagaga aggaaatctt tgaatcatgt gtctgtaaac tgatggccaa taagactagg 1800
attctagtga cttcgaaaat ggagcacctg aaaaaagcgg acaaaattct gatactccat 1860
gaagggtctt cctacttcta cggcaccttc tcagagttgc agaacttaca acctgatttt 1920

-continued

```
tcatctaagc ttatggggtg cgactcgttt gaccagttct ccgctgaaag acgaaacagc   1980
atcttaacgg aaactcttca caggttctca ttagagggag atgcgccggt gtcctggaca   2040
gagacaaaaa aacagtcttt caaacagaca ggagagtttg gcgagaagag aaaaaactca   2100
atcctcaatc ccatcaattc tattagaaag tttagcatcg tccaaaaaac accattgcag   2160
atgaatggga ttgaggagga cagtgatgag cctttggaac gaagactgtc cctggtaccc   2220
gatagcgaac agggtgaggc catccttcct aggatctcgg tcataagtac agggcccaca   2280
ctgcaggcca ggcgacgtca aagtgtcctc aatcttatga cgcacagtgt gaatcagggg   2340
cagaacatcc atcgtaagac gacagcttca actcgaaagg tcagtctagc tccacaagcc   2400
aatcttacag agctggacat ttattcccgc cgcctcagtc aggagaccgg attggaaata   2460
tcagaggaaa ttaatgaaga ggatctgaag gaatgcttct ttgatgacat ggaatcgatc   2520
cccgctgtta ctacctggaa cacatatctg agatatatta ccgtccataa gagcttaatc   2580
tttgtactga tatggtgctt ggtgattttc ctggcagagg ttgcggcgag tttggtcgtg   2640
ctatggctcc ttggaaacac tcccctgcag gataagggga actccactca tagcaggaat   2700
aacagctatg ccgtgatcat cacctctacc tcctcttatt acgtgtttta catatacgtc   2760
ggtgttgcgg ataccctgtt ggcaatgggg ttctttagag gactacccct agttcacacc   2820
ctgatcaccg tttcgaagat cttgcaccac aagatgcttc atagcgttct ccaagctcct   2880
atgagcaccc ttaatacact gaaagcagga ggtatcctta accgcttttc caaagacatc   2940
gctatactcg acgatttgct cccattgacc atcttcgact tcattcagct gctcctcatt   3000
gtgatcggcg ccattgccgt ggtcgcagtg ttacagccat atattttcgt agccaccgtg   3060
cccgtcatcg tggcatttat catgctgcgc gcatatttct tacagacatc tcagcaactg   3120
aagcagctgg aatctgaggg cagatctcct atttttacac acctggttac cagcctgaag   3180
ggcctgtgga ccctgcgtgc tttcggtcgc caaccctact ttgagactct cttccataag   3240
gctctgaatt tacatactgc caattggttc ctataccta gtacccttcg gtggttccag   3300
atgcggatag aaatgatctt cgtgattttc ttcatcgcag tcactttcat ctctattttg   3360
acgaccggtg agggcgaggg cagggtgggc atcattctga ctttggccat gaacattatg   3420
tcaacactcc agtgggccgt taattcaagc attgatgtgg attccttgat gcgttccgtc   3480
agcagggtat ttaaattcat agacatgccc accgagggca agccaacaaa atctaccaag   3540
ccatacaaaa atggccaact aagcaaggtc atgattatcg agaattctca tgtgaaaaag   3600
gacgacattt ggccttccgg gggtcaaatg actgtaaagg acctgacggc taaatacact   3660
gagggcggta atgctatctt ggagaacatc tctttcagca tctcccctgg ccagagagtg   3720
ggactgctcg ggcggacagg ctccggaaag tctacgctcc tttcagcatt ccttagactt   3780
ctgaacaccg aaggtgagat tcagattgac ggggtctctt gggactccat cacacttcag   3840
caatggagga aggcattcgg tgtaatcccc caaaaggttt ttatcttctc cggaacattt   3900
cgtaagaatc tggacccgta cgagcagtgg tcagatcagg agatctggaa agtagcagac   3960
gaggtcgggc tacggagcgt tattgaacag tttcctggca aactggactt cgttttggtg   4020
gacggaggct gtgtgctgag tcacggccat aaacaactga tgtgcttagc taggtctgtt   4080
ctcagcaagg caaagatttt actgctggat gaaccaagcg cccaccttga tccagtgaca   4140
tatcaaatca tcagaagaac tcttaaacag gcgttcgccg actgcacagt gatcctgtgt   4200
gagcacagaa tagaagccat gctggaatgt caacagtttc tcgtgattga ggagaacaag   4260
```

gtgcgccagt acgatagcat ccagaagtta ctcaatgaaa ggtcactctt caggcaggcc 4320
atctcaccca gcgaccgcgt taagctgttt ccacaccgaa acagttccaa gtgcaaaagt 4380
aagccacaga ttgctgcact gaaggaagag acagaagaag aagttcagga cactcggctc 4440
tga 4443

<210> SEQ ID NO 26
<211> LENGTH: 4443
<212> TYPE: DNA
<213> ORGANISM: Artificial Sequence
<220> FEATURE:
<223> OTHER INFORMATION: Chemically synthesized oligonucleotide

<400> SEQUENCE: 26
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg ggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatatcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg ggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860

-continued gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc caattaacag tattcgcaag ttcagcattg tccagaagac acccctccag 2160
atgaatggca tcgaagaaga tagtgacgag ccgctggaga gacggctgag tctggtgcca 2220
gattcagaac agggggaggc catcctgccc cggatcagcg tcatttccac aggcccccaca 2280
ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gctggaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttattttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct cccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200

-continued

```
gagcaccgga ttgaagcaat gctggaatgc cagcagtttc tggtgatcga ggagaataag   4260

gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

<210> SEQ ID NO 27
<211> LENGTH: 4443
<212> TYPE: DNA
<213> ORGANISM: Artificial Sequence
<220> FEATURE:
<223> OTHER INFORMATION: Chemically synthesized oligonucelotide

<400> SEQUENCE: 27

```
atgcaacgga gtcctctgga aaaagcctct gtcgtatcta agcttttctt cagttggaca     60

cgccccgattt tgagaaaggg ttatcggcaa cgcttggaac ttagtgacat ctaccaaatt    120

ccaagtgtag actcagccga taacttgagc gaaaagctcg aacgagagtg ggatcgagaa    180

ctggctagca aaaaaaatcc caaactcata aatgccctgc gacgctgttt cttttggcga    240

tttatgtttt acggtatttt cctttatttg ggtgaggtca cgaaggctgt acagccactg    300

ctgctgggtc gcatcattgc ctcttacgac cctgacaaca aagaggagcg gtcaatagct    360

atctaccttg gtataggact ttgcttgctc ttcatagtcc gcacgttgct tctccaccct    420

gctatatttg gtctccatca cattgggatg caaatgcgga tcgcgatgtt cagtcttata    480

tataaaaaga ctcttaaact ttccagccgg gttctggata agatctctat tggtcaactg    540

gtatctcttt tgtctaacaa cctgaataag ttcgacgagg gccttgcatt ggcccatttt    600

gtatggattg cccctttgca agtcgccctc ctgatgggat tgatctggga actcctgcaa    660

gctagtgctt tttgcggatt gggattcctc atagtccttg cgctctttca ggcgggactt    720

ggacgcatga tgatgaagta tcgcgaccaa cgagctggca agatcagtga acggcttgta    780

ataaccagtg aaatgataga gaacatccag agcgtaaaag cttactgttg ggaagaagcg    840

atggaaaaga tgattgagaa ccttcgccag acagaactta aacttacacg aaaggccgct    900

tatgtccggt acttcaactc ttcagcattt ttttttagtg gcttctttgt agtgttcctg    960

tccgtccttc cgtatgcact tatcaagggt ataatactta ggaaaatctt cacaacaatc   1020

agtttttgca tagtccttcg catggcagta actcgccaat ttccctgggc agttcagacg   1080

tggtacgact cacttggcgc aattaacaaa attcaagatt tcctccaaaa gcaagagtat   1140

aaaaccttgg aatacaacct taccaccaca gaagttgtaa tggaaaatgt cacagccttc   1200

tgggaggaag gtttcggcga actttttgag aaggcgaagc aaaataacaa taatcggaaa   1260

acatcaaacg gtgacgattc actgttcttt tctaacttta gccttcttgg gacgcccgtc   1320

ctgaaggaca taaactttaa gattgaacgg ggtcaacttc tcgcggtcgc agggagtact   1380

ggagcgggga aaacgagcct gctgatggtg ataatggggg agttggagcc ctcagaaggc   1440

aagatcaagc atagtggtag aattagcttc tgcagtcaat ttagttggat tatgccgggc   1500

acgatcaaag aaaatataat ctttggggta tcctacgatg aatacaggta ccgatcagtg   1560

ataaaagcgt gccagcttga agaagacatt tcaaagtttg ctgagaagga taatatcgta   1620

cttggagaag gaggtatcac cctgtctggg ggtcaacgag cgaggatctc cctggcacgc   1680

gccgtctaca aggacgcgga cctctatctg ttggattcac cgttcggata tttggacgtg   1740

cttacggaga aagaaatatt tgagagctgt gtttgcaagc tcatggcaaa taaaaccaga   1800
```

-continued

```
atattggtta caagcaagat ggagcatctt aagaaagcag ataaaatcct gatattgcac   1860
gagggctctt catacttcta cgggacgttt tctgagttgc agaacctcca gccggatttc   1920
agctctaagc tgatgggctg tgattccttt gatcagttta gtgcggaaag acgaaacagt   1980
atactcaccg aaacactgca caggttctct ctggagggcg acgccccggt ttcctggaca   2040
gagacgaaga agcagtcctt caaacagaca ggcgagtttg gggagaaaag gaaaaatagc   2100
atactcaacc cgattaacag cattcgcaag ttcagtatag tacaaaagac cccgttgcag   2160
atgaacggta tagaggaaga ttctgatgag ccactggaaa gacggctttc tctcgttccg   2220
gacagtgaac agggagaggc aatactgcct cggatcagcg ttatctctac aggacctact   2280
ttgcaagctc ggcgccgaca gtcagtcttg aatcttatga ctcatagtgt taatcaaggc   2340
cagaatatcc atcgcaagac caccgcaagt acaaggaaag tgagcttggc acctcaagca   2400
aaccttactg aacttgatat ctactcacgg cgactttcac aggagaccgg acttgaaatt   2460
agtgaagaaa ttaacgagga ggacctcaag gagtgcttct tcgatgacat ggaatcaatc   2520
cccgcagtca caacctggaa cacttatctg aggtatataa cagttcacaa gagcctcatt   2580
tttgtactta tttggtgttt ggtaattttc ctggcggagg ttgctgcttc tttggtcgtc   2640
ctttggctcc tcgggaatac accgctccaa gacaaaggca actctaccca tagtaggaac   2700
aattcatatg cagtgattat aaccagtaca tcatcttatt acgttttcta tatttatgtc   2760
ggggtagctg acacgctgtt ggcgatgggc ttctttaggg gcctcccctt ggtacacacc   2820
cttatcacgg tgagtaaaat cctgcatcac aaaatgcttc attctgtact ccaagcgccg   2880
atgagtacgc ttaatacgct gaaagcagga gggatactga atcggttcag caaggacatc   2940
gccattctgg atgacctgct tccattgaca atatttgatt tcattcagct ccttctcata   3000
gttattggag ccatagcggt ggtggctgtg cttcagcctt atatattcgt tgccacagtt   3060
cccgttatag tggcatttat aatgctcagg gcctactttc tccagacttc ccagcagttg   3120
aagcaactcg aatcagaagg aaggtcacct attttcacac atcttgtgac ttccttgaag   3180
ggcttgtgga cgctgcgggc cttcggaaga caaccatatt ttgaaactct cttccacaaa   3240
gctttgaatc ttcatactgc gaactggttc ctgtatttga gtactttgcg ctggttccag   3300
atgaggatag aaatgatatt cgttatcttc tttatcgcgg ttacgttcat aagtatcctc   3360
actacggggg agggtgaggg tagagtgggc ataatactga ccctcgccat gaacattatg   3420
tccaccctgc agtgggcggt aaacagcagc atagatgtgg attctttgat gcgcagtgtg   3480
agcagggttt ttaagtttat cgatatgccg acggaaggaa agcccactaa aagcacgaaa   3540
ccctataaaa atggacagct tagcaaagta atgataatcg agaatagcca tgtgaaaaag   3600
gatgacatat ggccttccgg aggccaaatg actgttaaag atctgaccgc taaatatacc   3660
gagggcggca acgcaatact cgaaaacata agcttttcca taagccccgg ccaacgcgtg   3720
ggtcttctgg ggaggactgg ctccggaaaa tcaacgttgc ttagcgcgtt tttgcggctc   3780
cttaacactg aaggtgagat ccaaatagat ggcgttagtt gggactctat aacactgcaa   3840
caatggcgga aagctttcgg cgtcatacct cagaaggtgt tcatctttag cggaacgttc   3900
aggaagaact tggatcccta cgaacaatgg agtgatcaag aaatatggaa agtggcagat   3960
gaggtaggct tgcgcagtgt cattgaacaa ttcccaggga aactcgactt tgtactggtg   4020
gacggcggtt gcgtcttgtc acacgggcac aaacagttga tgtgtttggc ccgcagtgtt   4080
ttgtctaagg cgaagattct gttgctcgac gaaccgagtg ctcatcttga tcccgtcacc   4140
```

-continued

| | | | | | | |
|---|---|---|---|---|---|---|
| taccaaatca | tcagaaggac | gttgaagcaa | gctttcgccg | actgcactgt | aatcctttgt | 4200 |
| gagcatagga | tcgaagcaat | gctcgagtgc | caacagttct | tggttataga | ggagaataag | 4260 |
| gttcggcaat | acgactcaat | acagaaactg | cttaatgagc | ggtcactctt | tcgacaagct | 4320 |
| atctctccta | gtgacagggt | aaagcttttt | cctcatcgga | attccagcaa | gtgtaagagt | 4380 |
| aaaccacaga | tcgccgccct | taaagaggag | accgaagaag | aggtgcagga | tacgagactt | 4440 |
| tag | | | | | | 4443 |